US012583815B2

(12) United States Patent
Zhang et al.

(10) Patent No.: US 12,583,815 B2
(45) Date of Patent: Mar. 24, 2026

(54) INHIBITORS OF YAP/TAZ-TEAD ONCOPROTEINS, SYNTHESIS AND USE THEREOF

(71) Applicant: BRIDGENE BIOSCIENCES, INC., San Jose, CA (US)

(72) Inventors: Chao Zhang, Monterey Park, CA (US); Michael J. Bishop, San Diego, CA (US); Hang Chen, San Jose, CA (US); Ping Cao, San Jose, CA (US)

(73) Assignee: BRIDGENE BIOSCIENCES, INC., San Jose, CA (US)

( * ) Notice: Subject to any disclaimer, the term of this patent is extended or adjusted under 35 U.S.C. 154(b) by 389 days.

(21) Appl. No.: 18/013,431

(22) PCT Filed: Jul. 2, 2021

(86) PCT No.: PCT/US2021/040361
§ 371 (c)(1),
(2) Date: Dec. 28, 2022

(87) PCT Pub. No.: WO2022/006548
PCT Pub. Date: Jan. 6, 2022

(65) Prior Publication Data

US 2023/0286904 A1 Sep. 14, 2023

Related U.S. Application Data

(60) Provisional application No. 63/047,736, filed on Jul. 2, 2020.

(51) Int. Cl.

| | |
|---|---|
| ***C07C 233/25*** | (2006.01) |
| ***A61K 45/06*** | (2006.01) |
| ***C07C 233/23*** | (2006.01) |
| ***C07C 233/27*** | (2006.01) |
| ***C07C 251/42*** | (2006.01) |
| ***C07D 205/04*** | (2006.01) |
| ***C07D 213/40*** | (2006.01) |
| ***C07D 213/64*** | (2006.01) |
| ***C07D 213/643*** | (2006.01) |
| ***C07D 215/38*** | (2006.01) |
| ***C07D 217/24*** | (2006.01) |
| ***C07D 231/12*** | (2006.01) |
| ***C07D 231/54*** | (2006.01) |
| ***C07D 237/08*** | (2006.01) |
| ***C07D 249/06*** | (2006.01) |
| ***C07D 261/08*** | (2006.01) |
| ***C07D 261/12*** | (2006.01) |
| ***C07D 261/20*** | (2006.01) |
| ***C07D 271/06*** | (2006.01) |
| ***C07D 275/02*** | (2006.01) |
| ***C07D 309/14*** | (2006.01) |
| ***C07D 311/68*** | (2006.01) |
| ***C07D 333/32*** | (2006.01) |
| ***C07D 333/36*** | (2006.01) |

(52) U.S. Cl.
CPC ............ *C07C 233/25* (2013.01); *A61K 45/06* (2013.01); *C07C 233/23* (2013.01); *C07C 233/27* (2013.01); *C07C 251/42* (2013.01); *C07D 205/04* (2013.01); *C07D 213/40* (2013.01); *C07D 213/64* (2013.01); *C07D 213/643* (2013.01); *C07D 215/38* (2013.01); *C07D 217/24* (2013.01); *C07D 231/12* (2013.01); *C07D 231/54* (2013.01); *C07D 237/08* (2013.01); *C07D 249/06* (2013.01); *C07D 261/08* (2013.01); *C07D 261/12* (2013.01); *C07D 261/20* (2013.01); *C07D 271/06* (2013.01); *C07D 275/02* (2013.01); *C07D 309/14* (2013.01); *C07D 311/68* (2013.01); *C07D 333/32* (2013.01); *C07D 333/36* (2013.01); *C07C 2602/08* (2017.05); *C07C 2602/10* (2017.05); *C07C 2602/50* (2017.05)

(58) Field of Classification Search
None
See application file for complete search history.

(56) References Cited

U.S. PATENT DOCUMENTS

| | | | | |
|---|---|---|---|---|
| 4,684,398 A | 8/1987 | Dunbar et al. | | |
| 11,458,149 B1 * | 10/2022 | Castro | .................... | A61K 31/47 |

FOREIGN PATENT DOCUMENTS

| | | |
|---|---|---|
| EP | 2361248 B1 | 9/2018 |
| JP | 2007-506785 A | 3/2007 |
| JP | 2013-541561 A | 11/2013 |
| WO | WO-2005/066156 A1 | 7/2005 |
| WO | WO-2008/092199 A1 | 8/2008 |

(Continued)

OTHER PUBLICATIONS

Cancer [online], [retrieved on Jul. 6, 2007] Retrieved from the Internet, URL: http://www.nim.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
PubChem, "AKOS013284208," SID 149423563 (Jun. 2, 2019), accessed Feb. 20, 2025, <https://pubchem.ncbi.nlm.nih.gov/substance/149423563> (5 pages).

(Continued)

*Primary Examiner* — Kristin A Vajda
(74) *Attorney, Agent, or Firm* — Clark & Elbing LLP

(57) ABSTRACT

Disclosed herein are synthesis and use of covalent inhibitors selective for Transcriptional Enhancer Factor TEF-1 (TEAD1), which can be used for treatment of cancers such as glioblastoma, gastric cancer, colorectal cancer, pancreatic ductal adenocarcinoma (PDAC), and malignant pleural mesothelioma (MPM). Further disclosed herein are pharmaceutical compositions including the TEAD1 inhibitor and methods of treating cancers using the same.

8 Claims, 1 Drawing Sheet

(56) References Cited

FOREIGN PATENT DOCUMENTS

| | | | |
|---|---|---|---|
| WO | WO-2011/060321 | A1 | 5/2011 |
| WO | WO-2018/093569 | A1 | 5/2018 |
| WO | WO-2020/081572 | A1 | 4/2020 |

OTHER PUBLICATIONS

Ismayilov et al., "New versatile ligand family, pyrazine-modulated oligo-α-pyridylamino ligands, from coordination polymer to extended metal atom chains," Dalton Trans. (27):2898-907 (Jul. 2007).
Bloch et al., "Silver(I) coordination polymers of the 'hinged' pyrazine containing ligand di-2-pyrazinylmethane," Supramolecular Chemistry. 27(11-12):807-819 (38 pages) (Nov. 2015).
Ren et al., "Design and synthesis of boron-containing diphenylpyrimidines as potent BTL and JAK3 dual inhibitors," Bioorg Med Chem. 28(2):1152326 (Dec. 2019) (12 pages).
Syassi et al., "Nouvelle méthode de synthèse des 4,5-dihydroisoxazoles en milieu biphasique solide-liquide et par activation ultrasonique," Tetrahedron Letters. 40(40):7205-7206 (1999) (English Abstract Included).
Savateev et al., "Potassium Poly(Heptazine Imide): Transition Metal-Free Solid-State Triplet Sensitizer in Cascade Energy Transfer and [3+2]-cycloadditions," Angew Chem Int Ed Engl. 59(35):15061-15068 (includes supporting information) (Aug. 2020) (112 pages).
Jiang et al. "Design and synthesis of neolamellarin a derivatives targeting heat shock protein 90," Eur J Med Chem. 135:24-33 (Jul. 2017).
Coutouli-Argyropouloi et al. "1,3-Dipolar cycloaddition approach to isoxazole, isoxazoline and isoxazolidine analogues of C-nucleosides related to pseudouridine," Tetrahedron. 62(7):1494-1501 (Feb. 2006).
Gogoi et al. "Surfactant/I2/Water:An Efficient System for Deprotection of Oximes and Imines to Carbonyls under Neutral Conditions in Water," J Org Chem. 70(5):1934-1936 (Mar. 2005).
Pinna et al., "Addition Reactions of Acetylenic Esters Upon 6-Substituted-α-Tetralone Ketoximes and Conversion of the Adducts into 4,5-Dihydro-1H-Benzo[g]indoles," Journal of Chemical Research, Miniprint. 11:2777-2795 (Jan. 1990).
Novaes et al., "Formal Total Synthesis of Actinoranone: Synthesis Approaches and Cytoxic Studies," J Org Chem. 83(9):5160-5176 (May 2018).
Upare et al., "Catalyst free synthesis of mono- and disubstituted pyrimidines from O-acyl oximes," Tetrahedron Letters. 59(25):2430-2433 (Jun. 2018).
Pobbati, & Hong. "Emerging roles of TEAD transcription factors and its coactivators in cancers." Cancer biology & therapy, May 2013, 14(5), 390-398 (9 Pages).
Zhang, et al. "Expression and Yes-Associated Protein in Gastric Adenocarcinoma and Inhibitory Effects of its Knockdown on Gastric Cancer Cell Proliferation and Metastasis." International Journal of Immunopathology and Pharmacology. May 2012;25(3):583-590 (8 Pages).
Wang, et al. "The HIPPO pathway in gynecological malignancies." American journal of cancer research, 10(2), Feb. 2020, 610-629 (20 Pages).
Martin, et al. "Assembly and activation of the Hippo signalome by FAT1 tumor suppressor." Nat Commun 9, 2372, Jul. 2018 (13 Pages).
Woodard, et al., "Drug development against the hippo pathway in mesothelioma." Translational lung cancer research, Jun. 2017, 6(3), 335-342 (8 Pages).
Miyanaga, et al., "Hippo pathway gene mutations in malignant mesothelioma: revealed by RNA and targeted exon sequencing." Journal of thoracic oncology : official publication of the International Association for the Study of Lung Cancer, 10(5), 844-851, 2015.

* cited by examiner

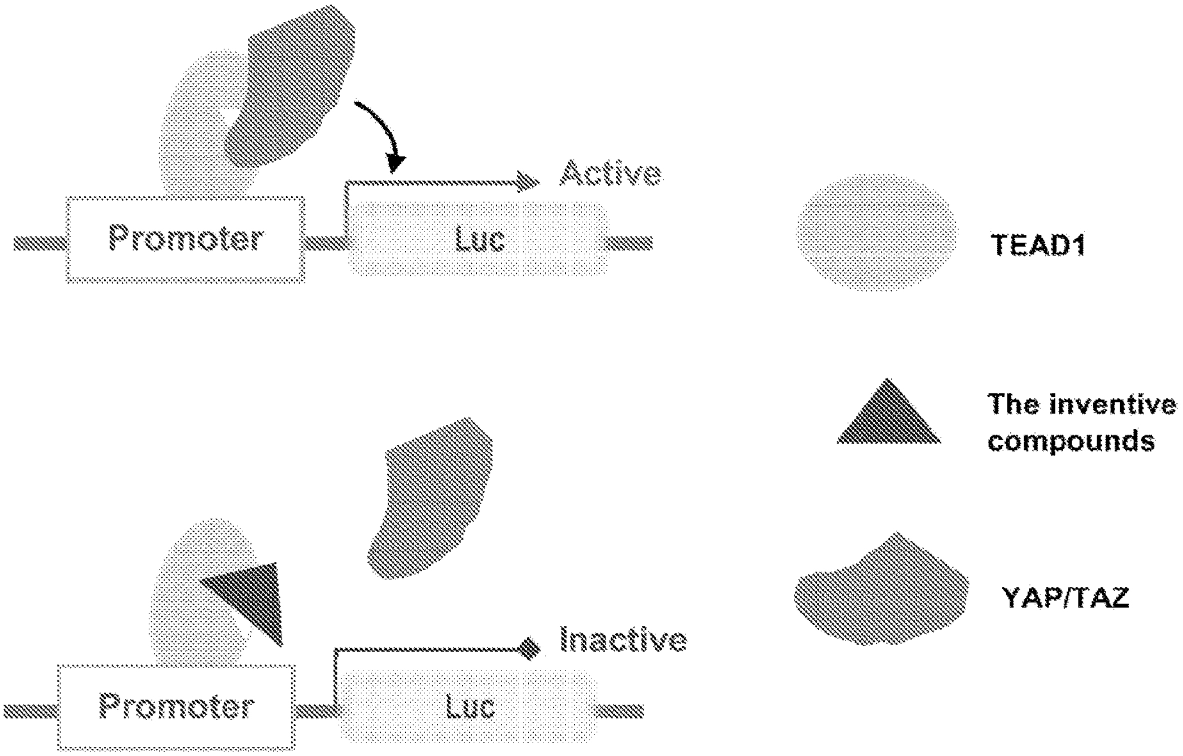
Active
Promoter
Luc
Inactive
Promoter
Luc
TEAD1
The inventive compounds
YAP/TAZ

INHIBITORS OF YAP/TAZ-TEAD ONCOPROTEINS, SYNTHESIS AND USE THEREOF

CROSS-REFERENCE TO RELATED APPLICATIONS

This application is a national phase entry of PCT/US2021/040361, filed on Jul. 2, 2021, which claims the benefit under 35 U.S.C. § 119(e) to U.S. Provisional Application No. 63/047,736, filed on Jul. 2, 2020. The contents of these applications are hereby incorporated herein by reference in their entireties.

BACKGROUND OF THE INVENTION

Field of the Invention

The present invention relates generally to cancer therapy, and more specifically to the synthesis of covalent inhibitors of YAP/TAZ-TEAD oncoproteins and use thereof for the treatment of cancers.

BACKGROUND INFORMATION

The interaction between Yes Associated Protein 65 (YAP), TAZ, a transcriptional coactivator paralog to YAP, and all TEAD proteins was demonstrated both in vitro and in vivo. In both cases the interaction of the proteins leads to increased TEAD transcriptional activity. YAP/TAZ are effectors of the Hippo tumor suppressor pathway that restricts organ growth by keeping in check cell proliferation and promoting apoptosis. The Cancer Genome Atlas (TCGA) database indicates that certain types of cancers show aberrant TEAD1 gene with gaining copy number. Accordingly, inhibitors of TEAD, specifically those selective for TEAD1, can have great potential in the application of cancer therapy.

SUMMARY OF THE INVENTION

The present invention is based on the seminal discovery of a class of small molecule compounds effective as covalent inhibitors of YAP/TAZ-TEAD oncoproteins. These compounds can be used in cancer therapy.

In one embodiment, the invention provides a compound according to Formula (I) or an optically pure stereoisomer, solvate, or pharmaceutically acceptable salt thereof.

Formula (I)

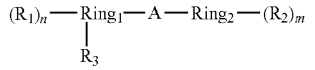

or an optically pure stereoisomer, pharmaceutically acceptable salt, or solvate thereof.

In some embodiments, $Ring_1$ is selected from the group consisting of phenyl, naphthyl, anthracene,

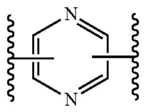,
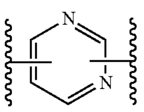,
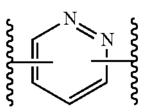,

-continued

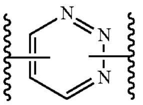,
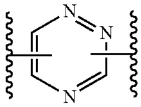,
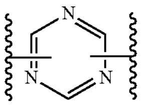,
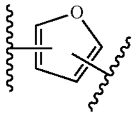,
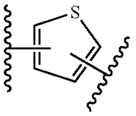,
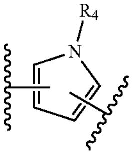,
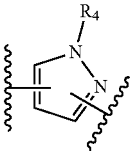,
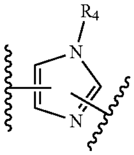,
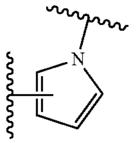,
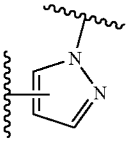,
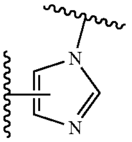,
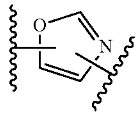,
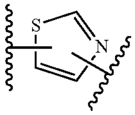,
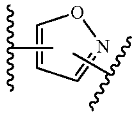,
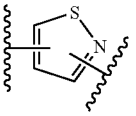,
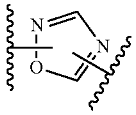,
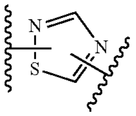,
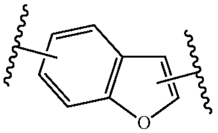,
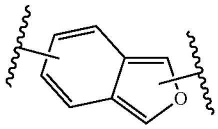,
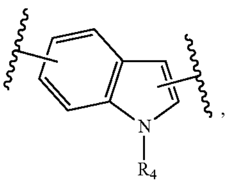,
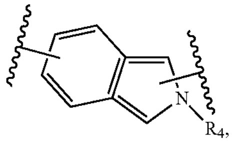,
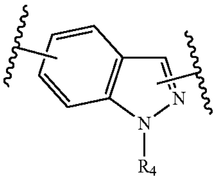,
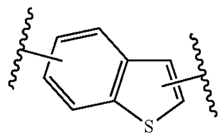,
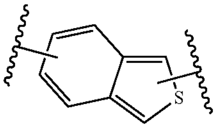,
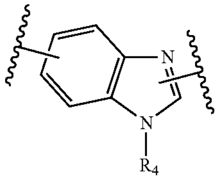,
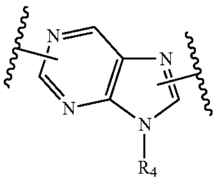,
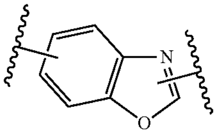, -continued
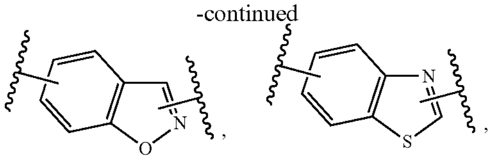
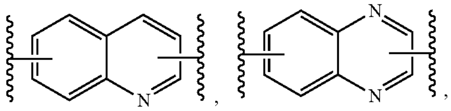
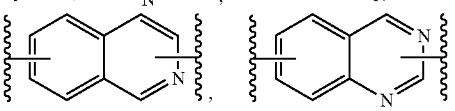
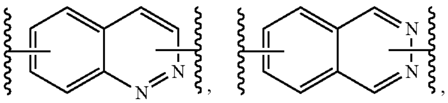
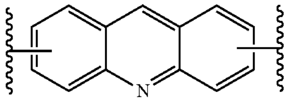
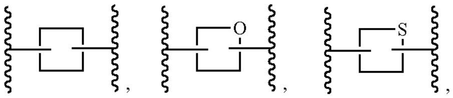
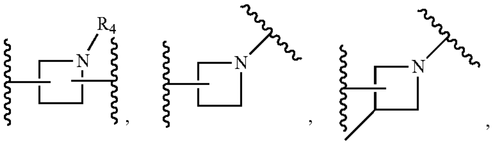
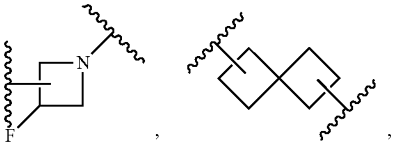
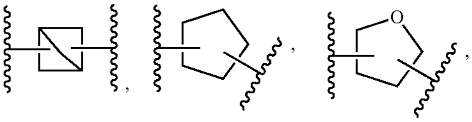
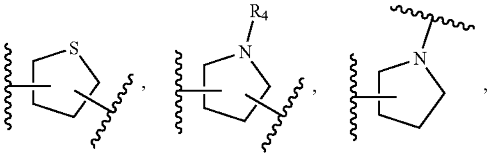
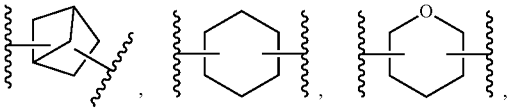
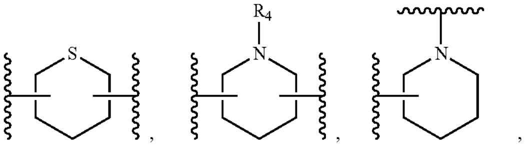
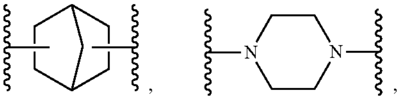 and
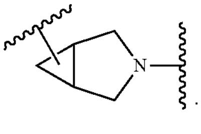.
In some embodiments, $Ring_2$ is selected from the group consisting of naphthyl, anthracene,
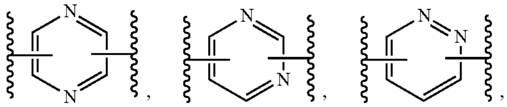
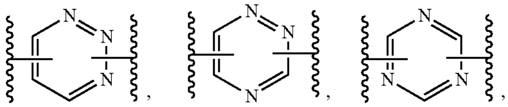
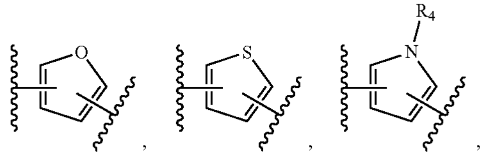
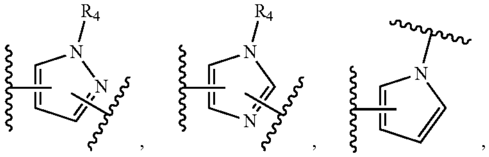
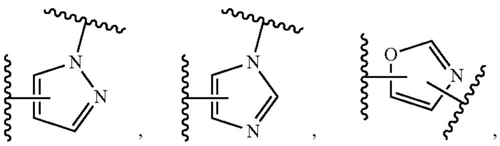
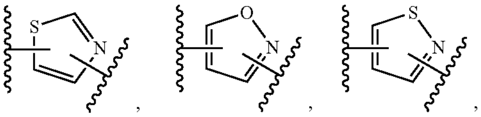
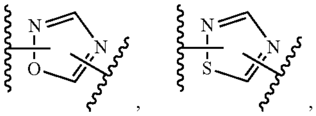
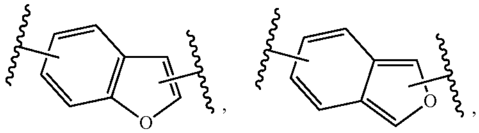
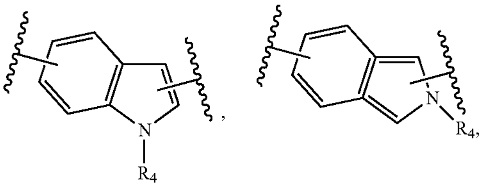
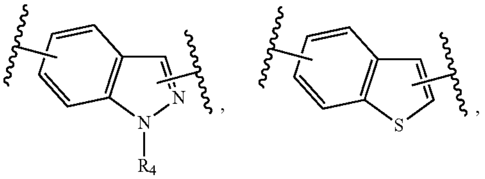
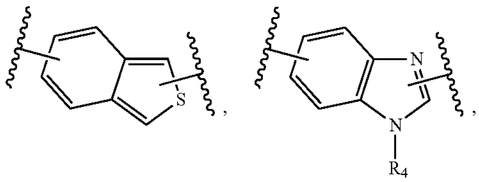

-continued

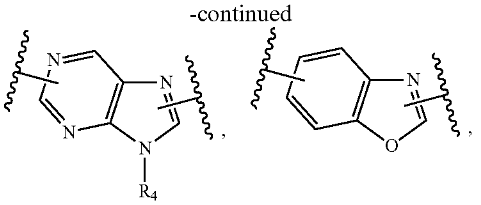

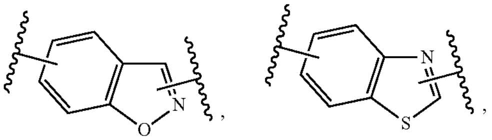

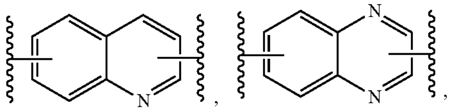

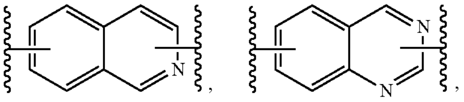

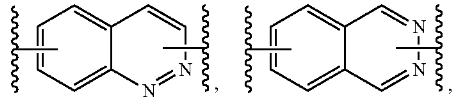

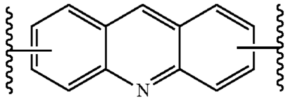

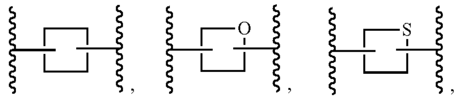

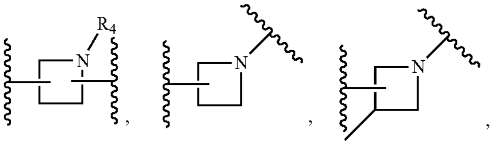

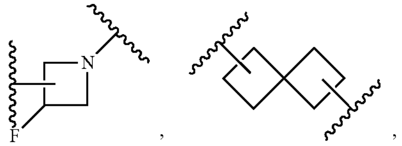

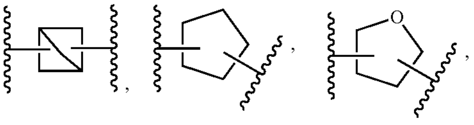

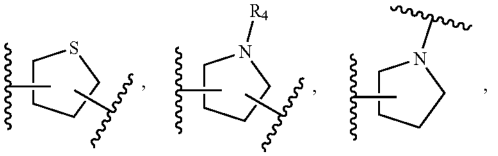

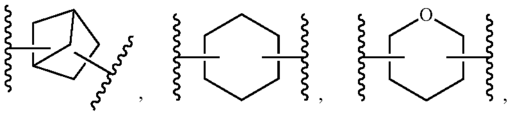

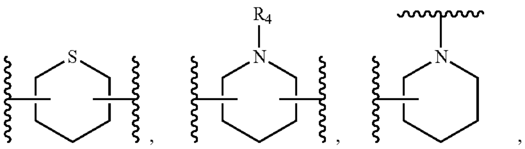

-continued

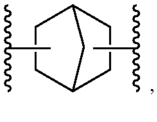, 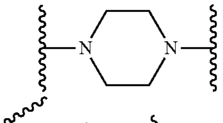, and

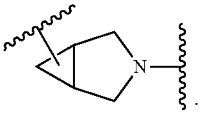.

In some embodiments, A is —O—$(CH_2)$p-, —CO—$(CH_2)$p-, —CO—O—$(CH_2)$p-, —S—$(CH_2)$p-, —SO—$(CH_2)$p-, —$SO_2$—$(CH_2)$p-, —$NR_4$—$(CH_2)$p-, —CO—$NR_4$—$(CH_2)$p-, —$NR_4$—CO—$NR_4$—$(CH_2)$p-, —OPO—$(CH_2)$p-, —$OPO_2$—$(CH_2)$p-, or —$(CR_6R_7)_p$—.

In some embodiments, $R_1$ is selected from the group consisting of

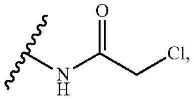 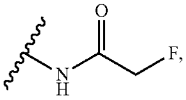

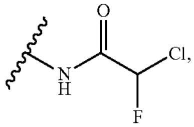 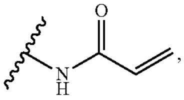

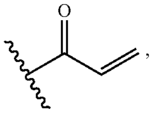 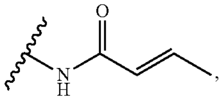

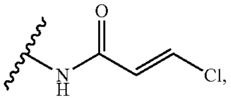 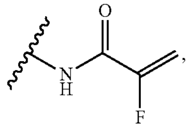

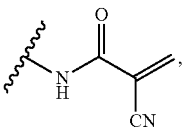 and 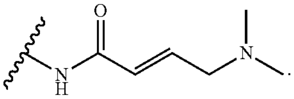

Each $R_2$ can be independently F, Br, Cl, $CF_3$, CN, $N_3$, $NH_2$, $NO_2$, OH, $OCH_3$, $CO(CH_2)_{0-5}CH_3$, $O(CH_2)_{0-5}CH_3$, $(CH_2)_{0-9}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH{=}CH_2$, $(CH_2)_{0-5}CH{=}CHCH_3$, $(CH_2)_{0-5}C{\equiv}CH$, $(CH_2)_{0-5}C{\equiv}CCH_3$, $NHCO(CH_2)_{0-5}CH{=}CH_2$, $NHCO(CH_2)_{0-5}CH{=}CHCH_3$, $NHCONH(CH_2)_{0-5}CH{=}CH_2$, $NHCONH(CH_2)_{0-5}CH{=}CHCH_3$, $O(CH_2)_{0-5}CH{=}CH_2$, $O(CH_2)_{0-5}CH{=}CHCH_3$, $CO(CH_2)_{0-5}CH{=}CH_2$, $CO(CH_2)_{0-5}CH{=}CHCH_3$, $OCO(CH_2)_{0-5}CH{=}CH_2$, $OCO(CH_2)_{0-5}CH{=}CHCH_3$, $SO_2(CH_2)_{0-5}CH{=}CH_2$, $SO_2(CH_2)_{0-5}CH{=}CHCH_3$, $NHCO(CH_2)_{0-5}C{\equiv}CH$, $NHCO(CH_2)_{0-5}C{\equiv}CCH_3$, $NHCONH(CH_2)_{0-5}C{\equiv}CH$, $NHCONH(CH_2)_{0-5}C{\equiv}CCH_3$, $O(CH_2)_{0-5}C{\equiv}CH$, $O(CH_2)_{0-5}C{\equiv}CCH_3$, $SO_2(CH_2)_{0-5}C{\equiv}CH$, $SO_2(CH_2)_{0-5}C{\equiv}CCH_3$, $CO(CH_2)_{0-5}C{\equiv}CH$, $CO(CH_2)_{0-5}C{\equiv}CCH_3$, $OCO(CH_2)_{0-5}C{\equiv}CH$, or $OCO(CH_2)_{0-5}C{\equiv}CCH_3$, each of these groups is optionally substituted by one, two, three, or four $R_5$.

In some embodiments, $R_3$ is selected from the group consisting of H, F, Br, Cl, $CF_3$, CN, $N_3$, $NH_2$, $NO_2$, OH, and $OCH_3$. n is an integer selected from 0 to 5. m is an integer selected from 0 to 5.

In some embodiments, each $R_4$ is independently H or $C_{1-3}$alkyl optionally substituted by one, two, three, or four $R_5$, Each $R_5$ is independently selected from the group consisting of H, methyl, ethyl, propyl, isopropyl, cyclopropyl, cyclobutyl, F, Br, Cl, $CF_3$, $NO_2$, OH, $OCH_3$, CN, and amino group unsubstituted or substituted with methyl, ethyl, or propyl. p is an integer selected from 0 to 3. Each $R_6$ and $R_7$ is independently H, methyl, ethyl, F, Br, Cl, $CF_3$, $NO_2$, OH, $OCH_3$, or CN.

In another embodiment, the invention provides a compound according to Formula (III) or an optically pure stereoisomer, solvate, or pharmaceutically acceptable salt thereof.

Formula (III)

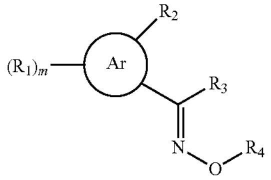

In one aspect, Ar is selected from the group consisting of phenyl, naphthyl, anthracene, pyridyl

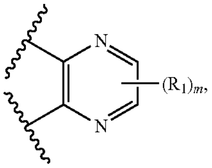
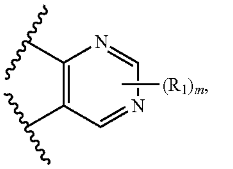
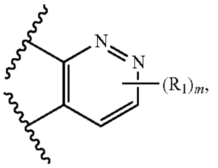
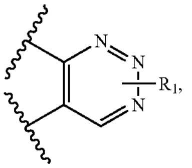
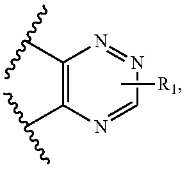
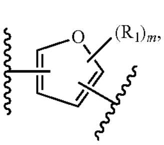
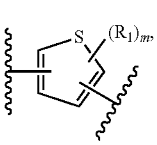
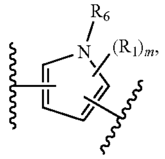
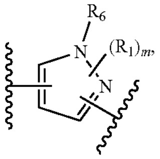
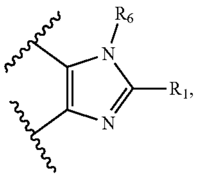
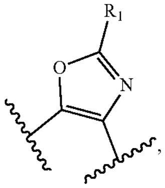
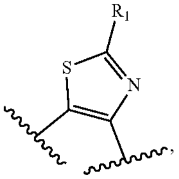
and
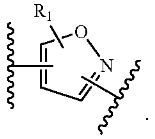

In another aspect, each $R_1$ can be independently $CO(CH_2)_{0-5}CH_3$, $O(CH_2)_{0-5}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH{=}CH_2$, $(CH_2)_{0-5}CH{=}CHCH_3$, $(CH_2)_{0-5}C{\equiv}CH$, $(CH_2)_{0-5}C{\equiv}CCH_3$, $NHCO(CH_2)_{0-5}CH{=}CH_2$, $NHCO(CH_2)_{0-5}CH{=}CHCH_3$, $NHCONH(CH_2)_{0-5}CH{=}CH_2$, $NHCONH(CH_2)_{0-5}CH{=}CHCH_3$, $O(CH_2)_{0-5}CH{=}CH_2$, $O(CH_2)_{0-5}CH{=}CHCH_3$, $CO(CH_2)_{0-5}CH{=}CH_2$, $CO(CH_2)_{0-5}CH{=}CHCH_3$, $OCO(CH_2)_{0-5}CH{=}CH_2$, $OCO(CH_2)_{0-5}CH{=}CHCH_3$, $SO_2(CH_2)_{0-5}CH{=}CH_2$, $SO_2(CH_2)_{0-5}CH{=}CHCH_3$, $NHCO(CH_2)_{0-5}C{\equiv}CH$, $NHCO(CH_2)_{0-5}C{\equiv}CCH_3$, $NHCONH(CH_2)_{0-5}C{\equiv}CH$, $NHCONH(CH_2)_{0-5}C{\equiv}CCH_3$, $O(CH_2)_{0-5}C{\equiv}CH$, $O(CH_2)_{0-5}C{\equiv}CCH_3$, $SO_2(CH_2)_{0-5}C{\equiv}CH$, $SO_2(CH_2)_{0-5}C{\equiv}CCH_3$, $CO(CH_2)_{0-5}C{\equiv}CH$, $CO(CH_2)_{0-5}C{\equiv}CCH_3$, $OCO(CH_2)_{0-5}C{\equiv}CH$, or $OCO(CH_2)_{0-5}C{\equiv}CCH_3$, each of which can be optionally substituted by one, two, three, or four $R_5$.

In yet another aspect, m can be an integer selected from 1 to 4. In some aspects, m can be 1.

In certain aspects, each $R_2$ can be independently F, Br, Cl, $CF_3$, CN, $N_3$, $NH_2$, $NO_2$, OH, $OCH_3$, $CO(CH_2)_{0-5}CH_3$, $O(CH_2)_{0-5}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH{=}CH_2$, $(CH_2)_{0-5}CH{=}CHCH_3$, $(CH_2)_{0-5}C{\equiv}CH$, $(CH_2)_{0-5}C{\equiv}CCH_3$, $NHCO(CH_2)_{0-5}CH{=}CH_2$, $NHCO(CH_2)_{0-5}CH{=}CHCH_3$, $NHCONH(CH_2)_{0-5}CH{=}CH_2$, $NHCONH(CH_2)_{0-5}CH{=}CHCH_3$, $O(CH_2)_{0-5}CH{=}CH_2$, $O(CH_2)_{0-5}CH{=}CHCH_3$, $CO(CH_2)_{0-5}CH{=}CH_2$, $CO(CH_2)_{0-5}CH{=}CHCH_3$, $OCO(CH_2)_{0-5}CH{=}CH_2$, $OCO(CH_2)_{0-5}CH{=}CHCH_3$, $SO_2(CH_2)_{0-5}CH{=}CH_2$, $SO_2(CH_2)_{0-5}CH{=}CHCH_3$, $NHCO(CH_2)_{0-5}C{\equiv}CH$, $NHCO(CH_2)_{0-5}C{\equiv}CCH_3$, $NHCONH(CH_2)_{0-5}C{\equiv}CH$, $NHCONH(CH_2)_{0-5}C{\equiv}CCH_3$, $O(CH_2)_{0-5}C{\equiv}CH$, $O(CH_2)_{0-5}C{\equiv}CCH_3$, $SO_2(CH_2)_{0-5}C{\equiv}CH$, $SO_2(CH_2)_{0-5}C{\equiv}CCH_3$, $CO(CH_2)_{0-5}C{\equiv}CH$, $CO(CH_2)_{0-5}C{\equiv}CCH_3$, $OCO(CH_2)_{0-5}C{\equiv}CH$, or $OCO(CH_2)_{0-5}C{\equiv}CCH_3$, each of these groups can be optionally substituted by one, two, three, or four $R_5$.

In certain aspects, each $R_1$ or $R_2$ can be independently selected from the group consisting of

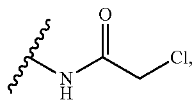
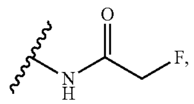
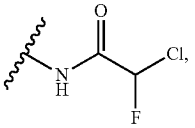
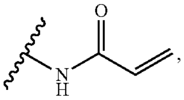
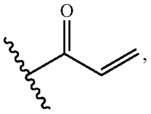
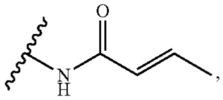
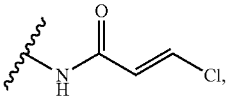
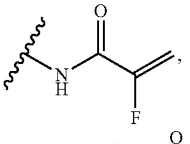
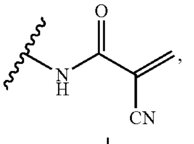
and
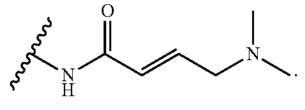

In various aspects, $R_3$ can be H or $C_{1-8}$alkyl optionally substituted by one, two, three, or four $R_5$.

In some aspects, $R_2$ and $R_3$ together can form a bicyclic structure with Ar, the cyclic moiety between $R_2$ and $R_3$ can include $-(CR_7R_8)_n-$, wherein n can be an integer selected from 1 to 5. In some aspects, n can be 2, 3, or 4.

In certain aspects, $R_4$ can be H, $C_{1-8}$alkyl, $CH_2CH_2(OCH_2CH_2)_1$-s, $CO(CH_2)_{0-5}CH_3$, $(CH_2)_{0-5}CH{=}CH_2$, $(CH_2)_{0-5}C{\equiv}CH$, $CONH(CH_2)_{0-5}CH{=}CH_2$, $CO(CH_2)_{0-5}CH{=}CH_2$, $SO_2(CH_2)_{0-5}CH{=}CH_2$, $CONH(CH_2)_{0-5}C{\equiv}CH$, $CO(CH_2)_{0-5}C{\equiv}CH$, or $SO_2(CH_2)_{0-5}C{\equiv}CH$, each of which can be optionally substituted by one, two, three, or four $R_5$.

Each $R_5$ can be independently selected from the group consisting of H, methyl, ethyl, propyl, isopropyl, cyclopropyl, cyclobutyl, F, Br, Cl, $CF_3$, $NO_2$, OH, $OCH_3$, CN, and amino group unsubstituted or substituted with methyl, ethyl, or propyl.

Each $R_6$ can be independently H or $C_{1-3}$alkyl. Each $R_7$ and $R_8$ can be independently H, methyl, ethyl, F, Br, Cl, $CF_3$, or CN.

In yet another embodiment, the invention provides a compound according to Formula (IV) or an optically pure stereoisomer, solvate, or pharmaceutically acceptable salt thereof.

Formula (IV)

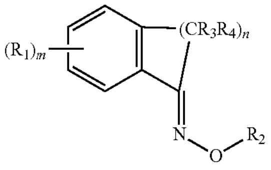

In one aspect, each $R_1$ can be independently $CO(CH_2)_{0-5}CH_3$, $O(CH_2)_{0-5}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH{=}CH_2$, $(CH_2)_{0-5}CH{=}CHCH_3$, $(CH_2)_{0-5}C{\equiv}H$, $(CH_2)_{0-5}C{\equiv}CCH_3$, $NHCO(CH_2)_{0-5}CH{=}CH_2$, $NHCO(CH_2)_{0-5}CH{=}CHCH_3$, $NHCONH(CH_2)_{0-5}CH{=}CH_2$, $NHCONH(CH_2)_{0-5}CH{=}CHCH_3$, $O(CH_2)_{0-5}CH{=}CH_2$, $O(CH_2)_{0-5}CH{=}CHCH_3$, $CO(CH_2)_{0-5}CH{=}CH_2$, $CO(CH_2)_{0-5}CH{=}CHCH_3$, $OCO(CH_2)_{0-5}CH{=}CH_2$, $OCO(CH_2)_{0-5}CH{=}CHCH_3$, $SO_2(CH_2)_{0-5}CH{=}CH_2$, $SO_2(CH_2)_{0-5}CH{=}CHCH_3$, $NHCO(CH_2)_{0-5}C{\equiv}CH$, $NHCO(CH_2)_{0-5}C{\equiv}CCH_3$, $NHCONH(CH_2)_{0-5}C{\equiv}CH$, $NHCONH(CH_2)_{0-5}C{\equiv}CCH_3$, $O(CH_2)_{0-5}C{\equiv}CH$, $O(CH_2)_{0-5}C{\equiv}CCH_3$, $SO_2(CH_2)_{0-5}C{\equiv}CH$, $SO_2(CH_2)_{0-5}C{\equiv}CCH_3$, $CO(CH_2)_{0-5}C{\equiv}CH$, $CO(CH_2)_{0-5}C{\equiv}CCH_3$, $OCO(CH_2)_{0-5}C{\equiv}CH$, or $OCO(CH_2)_{0-5}C{\equiv}CCH_3$, each of which can be optionally substituted by one, two, three, or four $R_5$.

In certain aspects, each $R_1$ can be independently

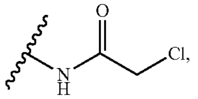

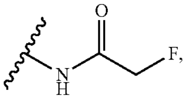

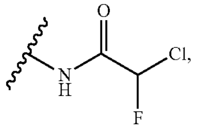

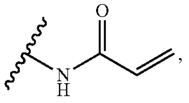

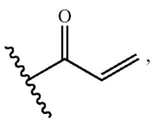

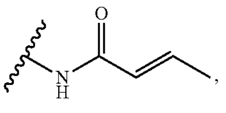

-continued

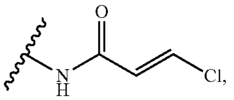

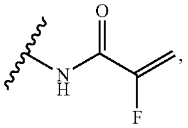

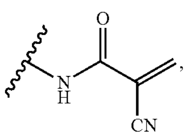

or

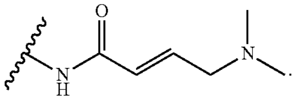

In another aspect, n can be an integer selected from 1 to 5. In some aspects, n can be 2, 3, or 4.

In yet another aspect, m can be an integer selected from 1 to 4. In some aspects, m can be 1.

In certain aspects, $R_2$ can be H, $C_{1-8}$alkyl, $CH_2CH_2(OCH_2CH_2)_1$-s, $CO(CH_2)_{0-5}CH_3$, $(CH_2)_{0-5}CH{=}CH_2$, $(CH_2)_{0-5}C{\equiv}CH$, $CONH(CH_2)_{0-5}CH{=}CH_2$, $CO(CH_2)_{0-5}CH{=}CH_2$, $SO_2(CH_2)_{0-5}CH{=}CH_2$, $CONH(CH_2)_{0-5}C{\equiv}CH$, $CO(CH_2)_{0-5}C{\equiv}CH$, or $SO_2(CH_2)_{0-5}C{\equiv}CH$, each of which can be optionally substituted by one, two, three, or four $R_5$.

In various aspects, each $R_3$ and $R_4$ can be independently H, methyl, ethyl, F, Br, Cl, $CF_3$, or CN. Each $R_5$ can be independently selected from the group consisting of H, methyl, ethyl, propyl, isopropyl, cyclopropyl, cyclobutyl, F, Br, Cl, $CF_3$, $NO_2$, OH, $OCH_3$, CN, and amino group unsubstituted or substituted with methyl, ethyl, or propyl. $R_6$ can be $(CH_2)_{0-5}CH{=}CH_2$, $(CH_2)_{0-5}C{\equiv}CH$, $NHCO(CH_2)_{0-5}CH{=}CH_2$, $OCO(CH_2)_{0-5}CH{=}CH_2$, $NHCO(CH_2)_{0-5}C{\equiv}CH$, or $OCO(CH_2)_{0-5}C{\equiv}CH$.

In certain aspects, the compound of the present disclosure can have a structure selected from the group consisting of

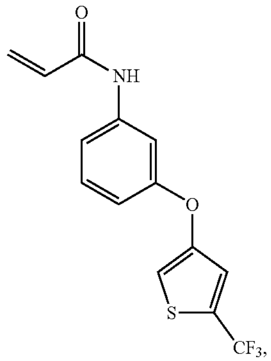

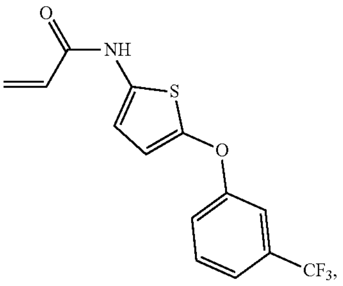

-continued
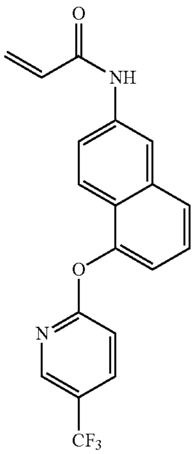,
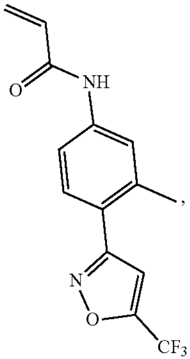,
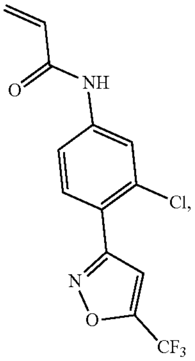
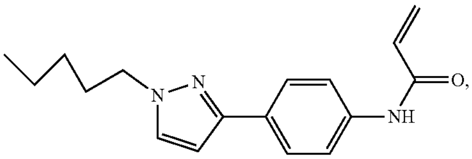
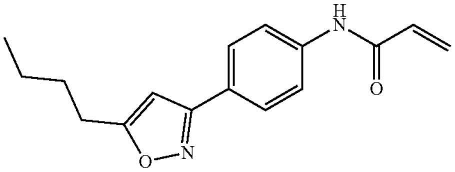,
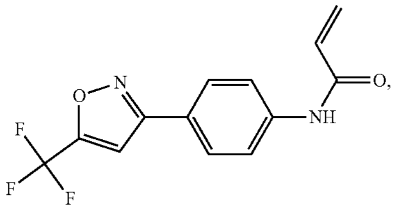
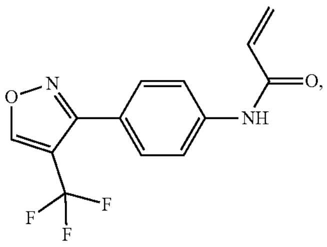
-continued
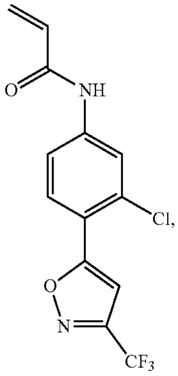
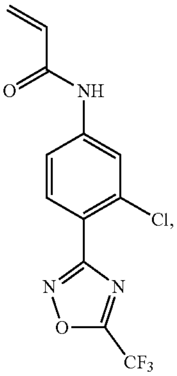
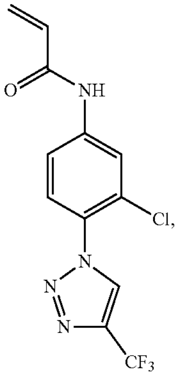
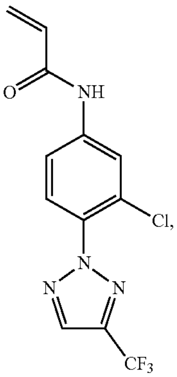
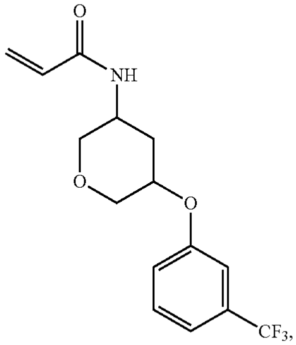
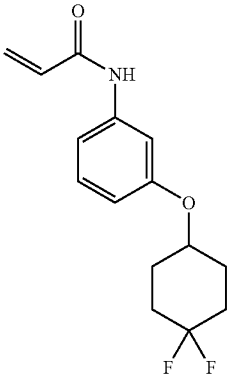, -continued

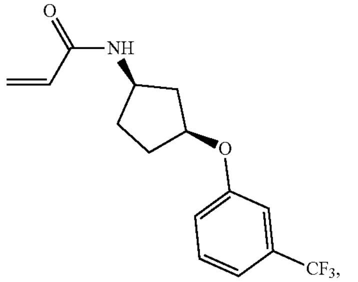

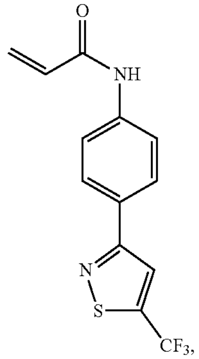

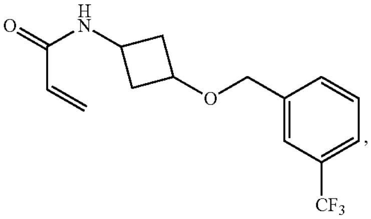

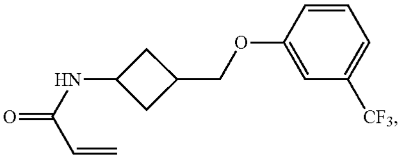

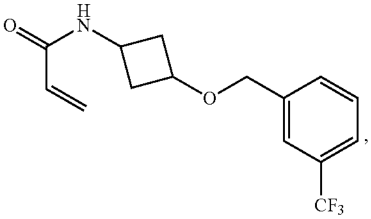

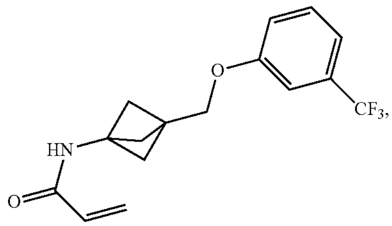

-continued

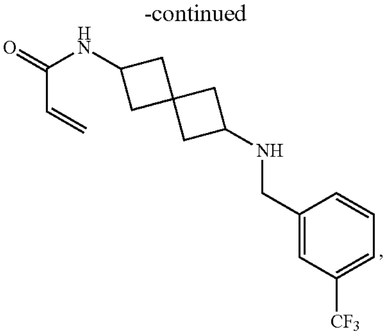

or stereoisomer thereof.

In some embodiments, the invention provides a compound according to Formula (VI) or an optically pure stereoisomer, solvate, or pharmaceutically acceptable salt thereof.

$(R_1)_n$-$Ring_1$-$Ring_2$-$(R_2)_m$ Formula (VI)

Wherein each $Ring_1$ and $Ring_2$ can be independently selected from the group consisting of phenyl, naphthyl, anthracene,

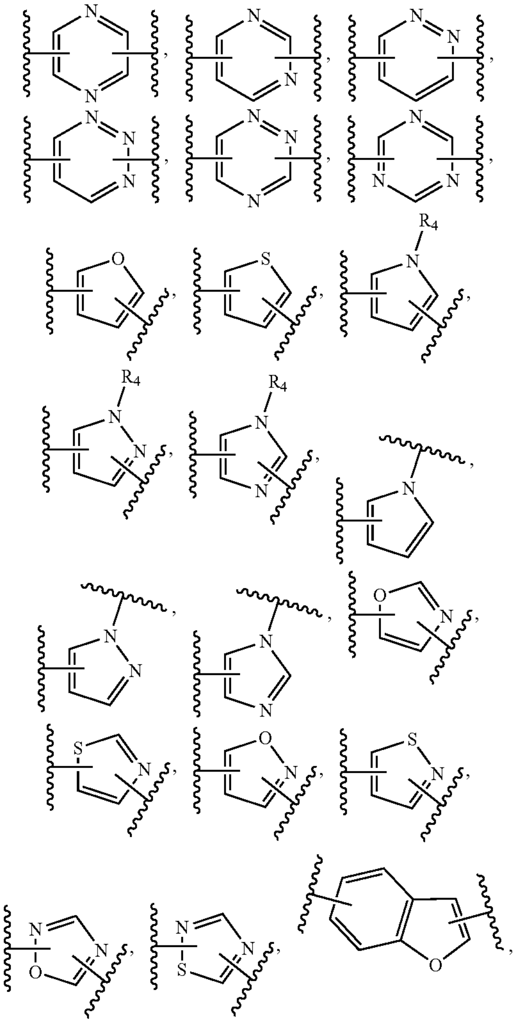

-continued

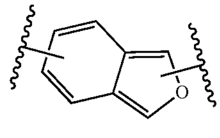, 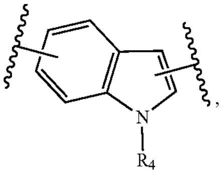,

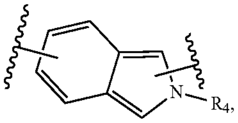 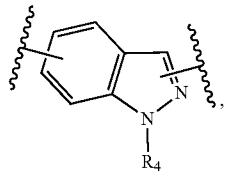,

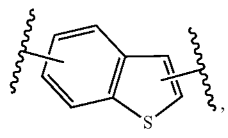, 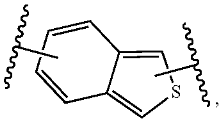,

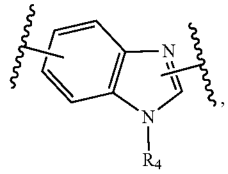, 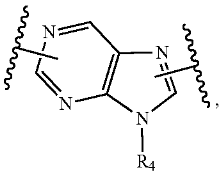,

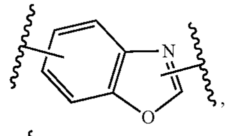, 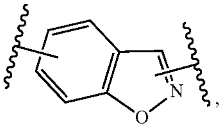,

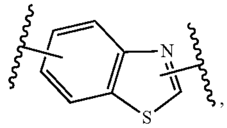, 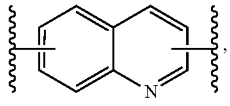,

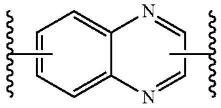, 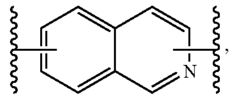,

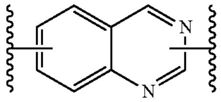, 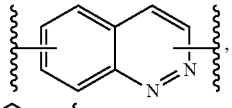,

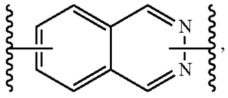, and

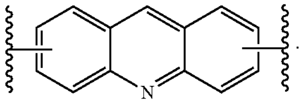.

Each $R_1$ can be independently $CO(CH_2)_{0-5}CH_3$, $O(CH_2)_{0-5}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH{=}CH_2$, $(CH_2)_{0-5}CH{=}CHCH_3$, $(CH_2)_{0-5}C{\equiv}CH$, $(CH_2)_{0-5}C{\equiv}CCH_3$, $NHCO(CH_2)_{0-5}CH{=}CH_2$, $NHCO(CH_2)_{0-5}CH{=}CHCH_3$, $NHCONH(CH_2)_{0-5}CH{=}CH_2$, $NHCONH(CH_2)_{0-5}CH{=}CHCH_3$, $O(CH_2)_{0-5}CH{=}CH_2$, $O(CH_2)_{0-5}CH{=}CHCH_3$, $CO(CH_2)_{0-5}CH{=}CH_2)$ $CO(CH_2)$, $CH{=}CHCH_3$, $OCO(CH_2){-}CH{=}CH_2$, $OCO(CH_2)_{0-5}CH{=}CHCH_3$, $SO_2(CH_2)_{0-5}CH{=}CH_2$, $SO_2(CH_2)_{0-5}CH{=}CHCH_3$, $NHCO(CH_2)_{0-5}C{\equiv}CH$, $NHCO(CH_2)_{0-5}C{\equiv}CCH_3$, $NHCONH(CH_2)_{0-5}C{\equiv}CH$, $NHCONH(CH_2)_{0-5}C{\equiv}CCH_3$, $O(CH_2)_{0-5}C{\equiv}CH$, $O(CH_2)_{0-5}C\ {\equiv}CCH_3$, $SO_2(CH_2)_{0-5}C{\equiv}CH$, $SO_2(CH_2)_{0-5}C{\equiv}CCH_3$, $CO(CH_2)_{0-5}C{\equiv}CH$, $CO(CH_2)_{0-5}C\ {\equiv}CCH_3$, $OCO(CH_2)_{0-5}C{\equiv}CH$, or $OCO(CH_2)_{0-5}C{\equiv}CCH_3$, each of which can be optionally substituted by one, two, three, or four $R_3$.

Each $R_2$ can be independently F, Br, Cl, $CF_3$, CN, $N_3$, $NH_2$, $NO_2$, OH, $OCH_3$, $CO(CH_2)_{0-5}CH_3$, $O(CH_2)_{0-5}CH_3$, $(CH_2)_{0-9}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH{=}CH_2$, $(CH_2)_{0-5}CH{=}CHCH_3$, $(CH_2)_{0-5}C{\equiv}CH$, $(CH_2)_{0-5}C{\equiv}CCH_3$, $NHCO(CH_2)_{0-5}CH{=}CH_2$, $NHCO(CH_2)_{0-5}CH{=}CHCH_3$, $NHCONH(CH_2)_{0-5}CH{=}CH_2$, $NHCONH(CH_2)_{0-5}CH{=}CHCH_3$, $O(CH_2)_{0-5}CH{=}CH_2$, $O(CH_2)_{0-5}CH{=}CHCH_3$, $CO(CH_2)_{0-5}CH{=}CH_2$, $CO(CH_2)_{0-5}CH{=}CHCH_3$, $OCO(CH_2)_{0-5}CH{=}CH_2$, $OCO(CH_2)_{0-5}CH{=}CHCH_3$, $SO_2(CH_2)_{0-5}CH{=}CH_2$, $SO_2(CH_2)_{0-5}CH{=}CHCH_3$, $NHCO(CH_2)_{0-5}C{\equiv}CH$, $NHCO(CH_2)_{0-5}C{\equiv}CCH_3$, $NHCONH(CH_2)_{0-5}C{\equiv}CH$, $NHCONH(CH_2)_{0-5}C{\equiv}CCH_3$, $O(CH_2)_{0-5}C{\equiv}CH$, $O(CH_2)_{0-5}C{\equiv}CCH_3$, $SO_2(CH_2)_{0-5}C{\equiv}CH$, $SO_2(CH_2)_{0-5}C{\equiv}CCH_3$, $CO(CH_2)_{0-5}C{\equiv}CH$, $CO(CH_2)_{0-5}C{\equiv}CCH_3$, $OCO(CH_2)_{0-5}C\ {\equiv}CH$, or $OCO(CH_2)_{0-5}C{\equiv}CCH_3$, each of these groups can be optionally substituted by one, two, three, or four $R_3$.

In certain aspects, each $R_1$ or $R_2$ can be independently selected from the group consisting of

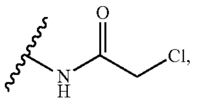, 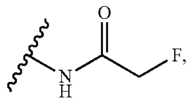,

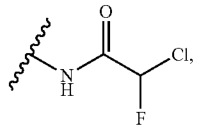, 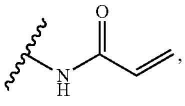, 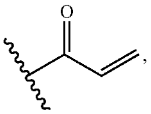,

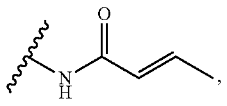, 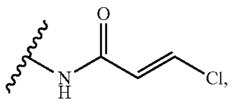,

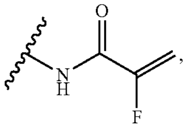, 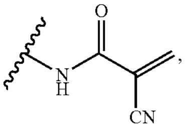, and

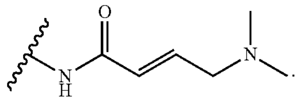.

Each $R_3$ can be independently selected from the group consisting of H, methyl, ethyl, propyl, isopropyl, cyclopropyl, cyclobutyl, F, Br, Cl, $CF_3$, $NO_2$, OH, $OCH_3$, CN, and amino group unsubstituted or substituted with methyl, ethyl, or propyl.

Each $R_4$ can be independently H or $C_{1-3}$alkyl optionally substituted by one, two, three, or four $R_3$.

n can be an integer selected from 0 to 5. In some aspects, n can be 1, 2, 3, or 4. In some aspects, n can be 1.

m can be an integer selected from 0 to 5. In some aspects, m can be 1, 2, 3, or 4. In some aspects, m can be 1.

In some embodiments, the compound of the present disclosure can be selected from the group consisting of consisting of

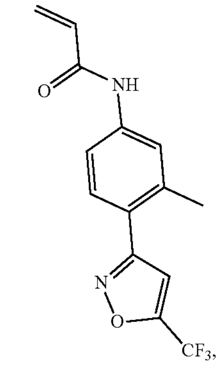
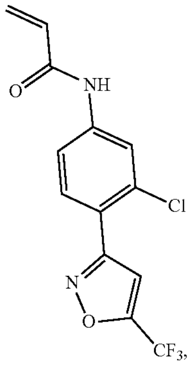
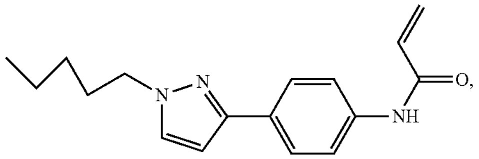
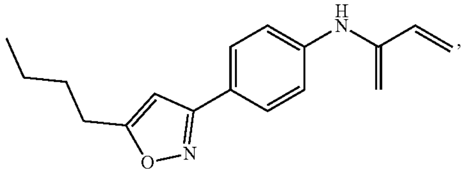
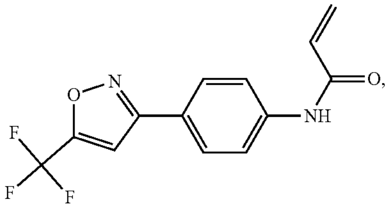
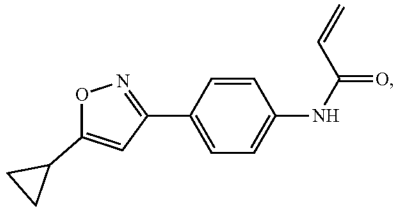
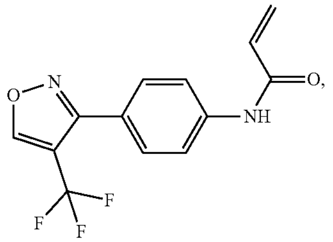
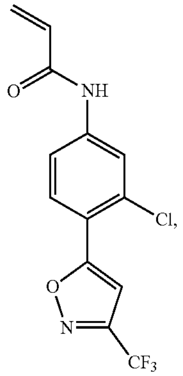
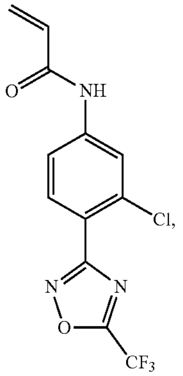
-continued
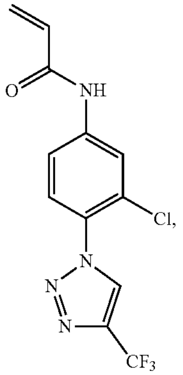
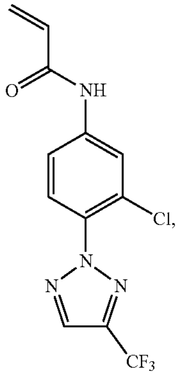
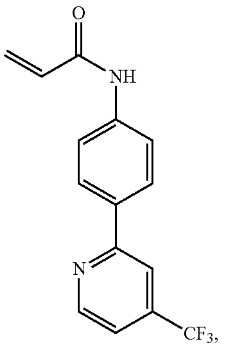
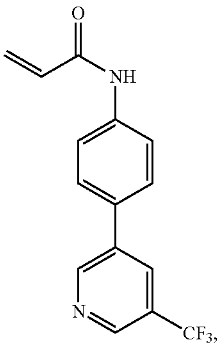
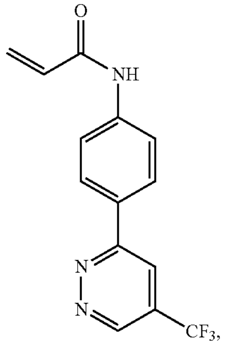
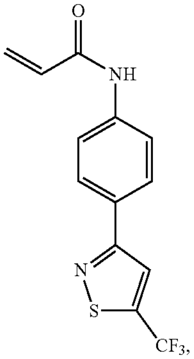
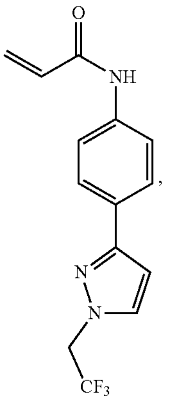
or stereoisomer thereof.
In some embodiments, the invention provides a compound according to Formula (VII) or an optically pure stereoisomer, solvate, or pharmaceutically acceptable salt thereof.

Formula (VII)

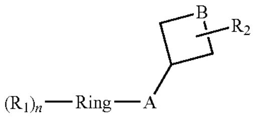

n can be an integer selected from 0 to 5. In some aspects, n can be 1, 2, 3, or 4. In some aspects, n can be 1.

A can be $-O-(CH_2)_m-$, $-CO-(CH_2)_m-$, $-CO-O-(CH_2)_m-$, $-S-(CH_2)_m-$, $-SO-(CH_2)_m-$, $-SO_2-(CH_2)_m-$, $-NR_4-(CH_2)_m-$, $-CO-NR_4-(CH_2)_m-$, $-NR_4-CO-NR_4-(CH_2)_m-$, $-OPO-(CH_2)_m-$, $-OPO_2-(CH_2)_m-$, or $-(CR_5R_6)_m-$.

Each m can be independently an integer selected from 0 to 5.

Wherein Ring can be independently selected from the group consisting of phenyl, naphthyl, anthracene,

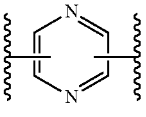, 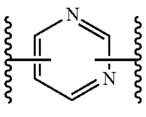, 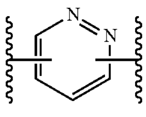,

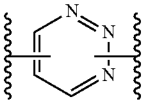, 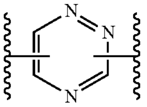, 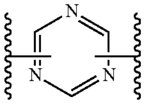,

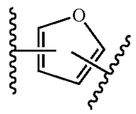, 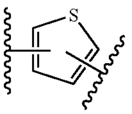, 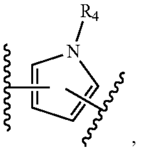,

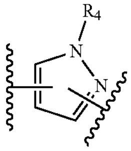, 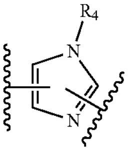, 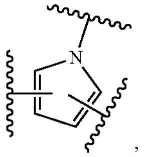,

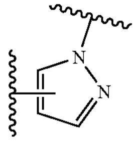, 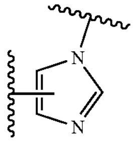,

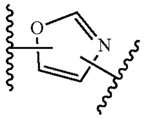, 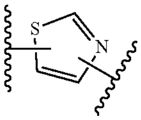, 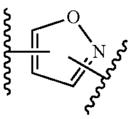,

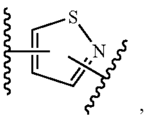, 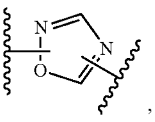, 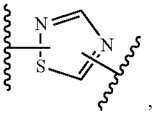,

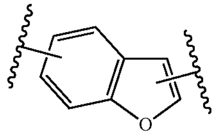, 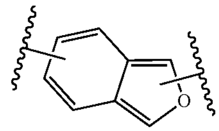,

-continued

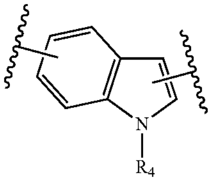, 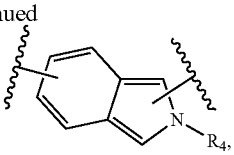

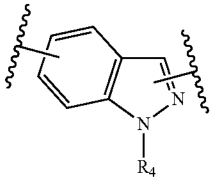, 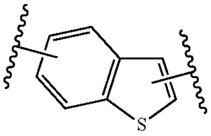,

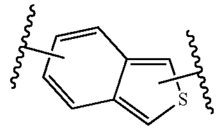, 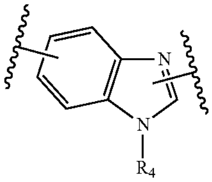,

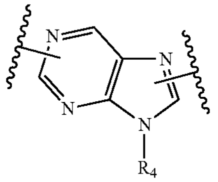, 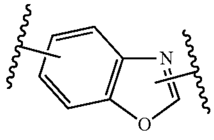,

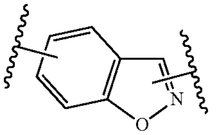, 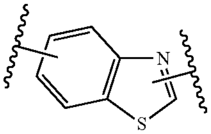,

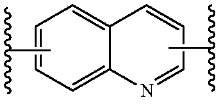, 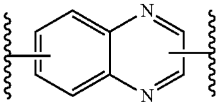,

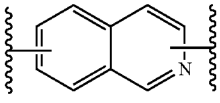, 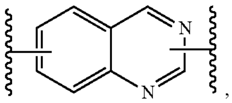,

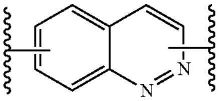,

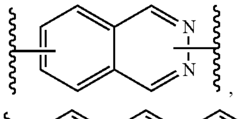, and

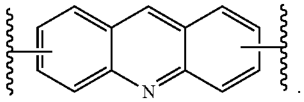.

Each $R_1$ can be independently $CO(CH_2)_{0-5}CH_3$, $O(CH_2)_{0-5}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH{=}CH_2$, $(CH_2)_{0-5}CH{=}CHCH_3$, $(CH_2)_{0-5}C{\equiv}CH$, $(CH_2)_{0-5}C{\equiv}CCH_3$, $NHCO(CH_2)_{0-5}CH{=}CH_2$, $NHCO(CH_2)_{0-5}CH{=}CHCH_3$, $NHCONH(CH_2)_{0-5}CH{=}CH_2$, $NHCONH(CH_2)_{0-5}CH{=}CHCH_3$, $O(CH_2)_{0-5}CH{=}CH_2$, $O(CH_2)_{0-5}CH{=}CHCH_3$, $CO(CH_2)_{0-5}CH{=}CH_2$, $CO(CH_2)_{0-5}CH{=}CHCH_3$, $OCO(CH_2)_{0-5}CH{=}CH_2$, $OCO(CH_2)_{0-5}CH{=}CHCH_3$, $SO_2(CH_2)_{0-5}CH{=}CH_2$, $SO_2(CH_2)_{0-5}CH{=}CHCH_3$, $NHCO(CH_2)_{0-5}C{\equiv}CH$, $NHCO(CH_2)_{0-5}C{\equiv}CCH_3$, NHCONH $(CH_2)_{0-5}C\equiv CH$, $NHCONH(CH_2)_{0-5}C\equiv CCH_3$, $O(CH_2)_{0-5}C\equiv CH$, $O(CH_2)_{0-5}C\equiv CCH_3$, $SO_2(CH_2)_{0-5}C\equiv CH$, $SO_2(CH_2)_{0-5}C\equiv CCH_3$, $CO(CH_2)_{0-5}C\equiv CH$, $CO(CH_2)_{0-5}C\equiv CCH_3$, $OCO(CH_2)_{0-5}C\equiv CH$, or $OCO(CH_2)_{0-5}C\equiv CCH_3$, each of which can be optionally substituted by one, two, three, or four $R_3$.

In some embodiments, B is carbon or nitrogen.

When B is carbon, $R_2$ can be selected from the group consisting of

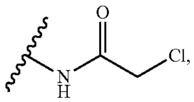
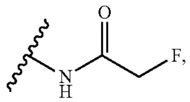
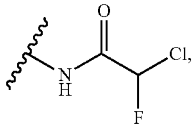
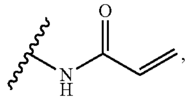
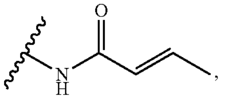
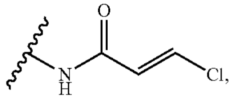
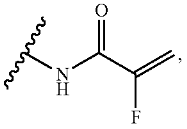
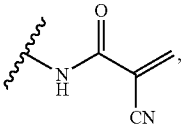
and
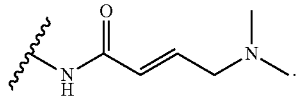

When B is nitrogen, $R_2$ can be connected to B to form

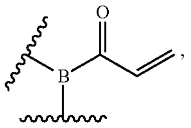
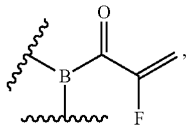
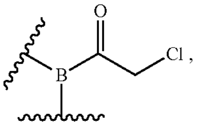
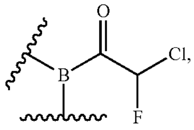
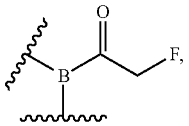
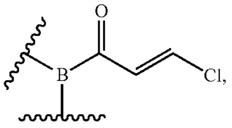
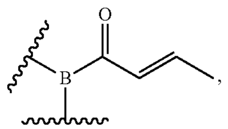
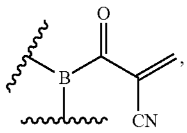
and
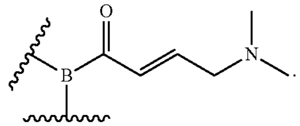

Each $R_3$ can be independently selected from the group consisting of H, methyl, ethyl, propyl, isopropyl, cyclopropyl, cyclobutyl, F, Br, Cl, $CF_3$, $NO_2$, OH, $OCH_3$, CN, and amino group unsubstituted or substituted with methyl, ethyl, or propyl.

Each $R_4$ can be independently H or $C_{1-3}$alkyl optionally substituted by one, two, three, or four $R_3$.

Each $R_5$ and $R_6$ can be independently H, methyl, ethyl, F, Br, Cl, $CF_3$, $NO_2$, OH, $OCH_3$, or CN.

In some embodiments, the compound of the present disclosure can be selected from the group consisting of

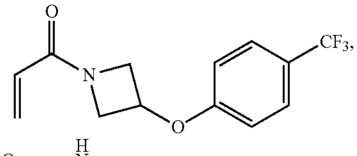
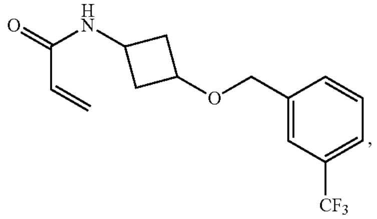
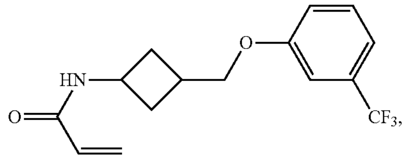
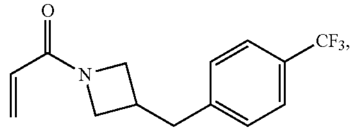
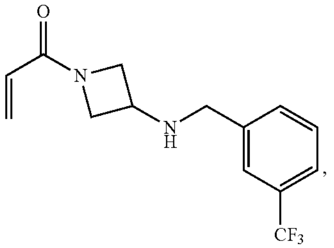
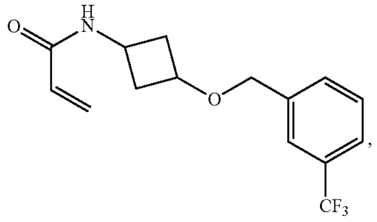

or stereoisomer thereof.

In various aspects, disclosed herein is pharmaceutical formulation including the compound with a structure of Formula (II), Formula (III), Formula (IV), Formula (V), Formula (VI), Formula (VII), or a pharmaceutically acceptable carrier.

In one aspect, the present disclosure is directed to a method of treating cancer in a subject, which can include administering an effective amount of the compound with a structure of Formula (II), Formula (III), Formula (IV), Formula (V), Formula (VI), OR Formula (VII).

In another aspect, the cancer that can be treated by the presently-disclosed compounds can be selected from the group consisting of bladder cancer, breast cancer, ovarian cancer, pancreatic ductal adenocarcinoma (PDAC), glioblastoma, gastric cancer, cervical cancer, colon cancer, endometrial cancer, head and neck cancer, lung cancer, melanoma, multiple myeloma, leukemia, non-Hodgkin's lymphoma, prostate cancer, rectal cancer, malignant melanomas, alimentary/gastrointestinal tract cancer, liver cancer, skin cancer, lymphoma, malignant pleural mesothelioma (MPM), kidney cancer, muscle cancer, bone cancer, brain cancer, eye or ocular cancer, rectal cancer, colorectal cancer, cervical cancer, oral cancer, benign and malignant tumors, stomach cancer, corpus uteri, testicular cancer, renal cancer, throat cancer, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, neurofibromatosis, tuberous sclerosis, hemangiomas, and lymphangiogenesis. In certain aspects, the cancer can be glioblastoma, gastric cancer, colorectal cancer, pancreatic ductal adenocarcinoma (PDAC), or malignant pleural mesothelioma (MPM).

In some aspects, the cancer treatment method can further include administering chemotherapeutic agent. The disclosed compound can be administered prior to, simultaneously with or following the administration of the chemotherapeutic agent. In some aspects, the disclosed compound can be administered orally or intravenously.

BRIEF DESCRIPTION OF THE DRAWINGS

FIG. 1 is a schematic illustration of how the disclosed compounds function as covalent TEAD1 inhibitors.

DETAILED DESCRIPTION OF THE INVENTION

The present invention is based on the seminal discovery that a class of small molecule compounds can selectively inhibit TEAD1 activity, which exhibits great potential in the treatment of certain types of cancers. TEAD1 belongs to TEADs family, which regulates cell growth and proliferation via TEAD1/YAP/TAZ complex. TEAD regulates glioblastoma sternness and invasiveness by regulating EGFR and AQP4 expression, via the pathway of TEAD-EGFR/AQP4. Further via the pathway of Hippo-YAP/TAZ-TEAD, YAP/TAZ-TEAD activation induces transcription of cell cycle-promoting genes; TEAD1 regulates expression of cytoskeleton remodeling gene; TEAD1 increases expression of other transcription factor like Myc and SP1; YAP/TAZ-TEAD1 axis regulates cell apoptosis; blocking TEAD1 aberrant activities will down regulates gene expression of MYC, KRAS, BRAF, NF2, LKB1 and PD-L1, etc. As a result, inhibitor compounds selective for TEAD1 have great potential in the treatment of cancers such as glioblastoma, gastric cancer, colorectal cancer, pancreatic ductal adenocarcinoma (PDAC), and malignant pleural mesothelioma (MPM).

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The preferred methods and materials are now described.

The term "about" will be understood by persons of ordinary skill in the art. Whether the term "about" is used explicitly or not, every quantity given herein refers to the actual given value, and it is also meant to refer to the approximation to such given value that would be reasonably inferred based on the ordinary skill in the art.

Alkyl groups refer to univalent groups derived from alkanes by removal of a hydrogen atom from any carbon atom, which include straight chain and branched chain with from 1 to 12 carbon atoms, and typically from 1 to about 10 carbons or in some embodiments, from 1 to about 6 carbon atoms, or in other embodiments having 1, 2, 3 or 4 carbon atoms. Examples of straight chain alkyl groups include, but are not limited to, methyl, ethyl, n-propyl, n-butyl, n-pentyl, and n-hexyl groups. Examples of branched chain alkyl groups include, but are not limited to isopropyl, isobutyl, sec-butyl and tert-butyl groups. Alkyl groups may be substituted or unsubstituted. Representative substituted alkyl groups may be mono-substituted or substituted more than once, such as, but not limited to, mono-, di-, or tri-substituted. As used herein, the term alkyl, unless otherwise stated, refers to both cyclic and noncyclic groups.

The terms "cyclic alkyl" or "cycloalkyl" refer to univalent groups derived from cycloalkanes by removal of a hydrogen atom from a ring carbon atom. Cycloalkyl groups are saturated or partially saturated non-aromatic structures with a single ring or multiple rings including isolated, fused, bridged, and spiro ring systems, having 3 to 14 carbon atoms, or in some embodiments, from 3 to 12, or 3 to 10, or 3 to 8, or 3, 4, 5, 6 or 7 carbon atoms. Cycloalkyl groups may be substituted or unsubstituted. Representative substituted cycloalkyl groups may be mono-substituted or substituted more than once, such as, but not limited to, mono-, di-, or tri-substituted. Examples of monocyclic cycloalkyl groups include, but are not limited to cyclopropyl, cyclobutyl, cyclopentyl, and cyclohexyl groups. Examples of multicyclic ring systems include, but are not limited to, bicycle [4.4.0]decane, bicycle[2.2.1]heptane, spiro[2.2]pentane, and the like.

Alkenyl groups refer to straight and branched chain and cycloalkyl groups as defined above, with one or more double bonds between two carbon atoms. Alkenyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkenyl groups may be substituted or unsubstituted. Representative substituted alkenyl groups may be mono-substituted or substituted more than once, such as, but not limited to, mono-, di-, or tri-substituted. Examples of alkenyl groups include, but are not limited to, vinyl, allyl, —CH═CH($CH_3$), —CH═C($CH_3$)$_2$, —C($CH_3$)═$CH_2$, cyclopentenyl, cyclohexenyl, butadienyl, pentadienyl, and hexadienyl, among others.

Alkynyl groups refer to straight and branched chain and cycloalkyl groups as defined above, with one or more triple bonds between two carbon atoms. Alkynyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkynyl groups may be substituted or unsubstituted. Representative substituted alkynyl groups may be mono-substituted or substituted more than once, such as, but not limited to, mono-, di-, or tri-substituted. Exemplary alkynyl groups include, but are not limited to, ethynyl, propargyl, and —C≡C($CH_3$), among others.

Aryl groups are cyclic aromatic hydrocarbons that include single and multiple ring compounds, including multiple ring compounds that contain separate and/or fused aryl groups. Aryl groups may contain from 6 to about 18 ring carbons, or in some embodiments from 6 to 14 ring carbons or even 6 to 10 ring carbons in other embodiments. Aryl group also includes heteroaryl groups, which are aromatic ring compounds containing 5 or more ring members, one or more ring carbon atoms of which are replaced with heteroatom such as, but not limited to, N, O, and S. Aryl groups may be substituted or unsubstituted. Representative substituted aryl groups may be mono-substituted or substituted more than once, such as, but not limited to, mono-, di-, or tri-substituted. Aryl groups include, but are not limited to, phenyl, biphenylenyl, triphenylenyl, naphthyl, anthryl, and pyrenyl groups.

Suitable heterocyclyl groups include cyclic groups with atoms of at least two different elements as members of its rings, of which one or more is a heteroatom such as, but not limited to, N, O, or S. Heterocyclyl groups may include 3 to about 20 ring members, or 3 to 18 in some embodiments, or about 3 to 15, 3 to 12, 3 to 10, or 3 to 6 ring members. The ring systems in heterocyclyl groups may be unsaturated, partially saturated, and/or saturated. Heterocyclyl groups may be substituted or unsubstituted. Representative substituted heterocyclyl groups may be mono-substituted or substituted more than once, such as, but not limited to, mono-, di-, or tri-substituted. Exemplary heterocyclyl groups include, but are not limited to, pyrrolidinyl, tetrahydrofuryl, dihydrofuryl, tetrahydrothienyl, tetrahydrothiopyranyl, piperidyl, morpholinyl, thiomorpholinyl, thioxanyl, piperazinyl, azetidinyl, aziridinyl, imidazolidinyl, pyrazolidinyl, thiazolidinyl, tetrahydrothiophenyl, tetrahydrofuranyl, dioxolyl, furanyl, thiophenyl, pyrrolyl, imidazolyl, pyrazolyl, pyrazolinyl, triazolyl, tetrazolyl, oxazolyl, isoxazolyl, thiazolyl, thiazolinyl, oxetanyl, thietanyl, homopiperidyl, oxepanyl, thiepanyl, oxazepinyl, diazepinyl, thiazepinyl, 1,2,3,6-tetrahydropyridyl, indolinyl, 2H-pyranyl, 4H-pyranyl, dioxolanyl, dioxanyl, purinyl, quinolizinyl, cinnolinyl, phthalazinyl, pteridinyl, and benzothiazolyl groups.

Polycyclic or polycyclyl groups refer to two or more rings in which two or more carbons are common to the two adjoining rings, wherein the rings are "fused rings"; if the rings are joined by one common carbon atom, these are "spiro" ring systems. Rings that are joined through non-adjacent atoms are "bridged" rings. Polycyclic groups may be substituted or unsubstituted. Representative polycyclic groups may be substituted one or more times.

Halogen groups include F, Cl, Br, and I; nitro group refers to —$NO_2$; cyano group refers to —CN; isocyano group refers to —N≡C; epoxy groups encompass structures in which an oxygen atom is directly attached to two adjacent or non-adjacent carbon atoms of a carbon chain or ring system, which is essentially a cyclic ether structure. An epoxide is a cyclic ether with a three-atom ring.

An alkoxy group is a substituted or unsubstituted alkyl group, as defined above, singular bonded to oxygen. Alkoxy groups may be substituted or unsubstituted. Representative substituted alkoxy groups may be substituted one or more times. Exemplary alkoxy groups include, but are not limited to, methoxy, ethoxy, propoxy, butoxy, pentoxy, hexoxy, isopropoxy, sec-butoxy, tert-butoxy, cyclopropyloxy, cyclobutyloxy, cyclopentyloxy, and cyclohexyloxy groups.

The terms "amine" and "amino" refer to derivatives of ammonia, wherein one of more hydrogen atoms have been replaced by a substituent which include, but are not limited to alkyl, alkenyl, aryl, and heterocyclyl groups. Carbamate groups refers to —O(C═O)$NR_1R_2$, where $R_1$ and $R_2$ are independently hydrogen, aliphatic groups, aryl groups, or heterocyclyl groups.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, C(O)$CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

As used herein, the term "isomer" or "isomers" means chemical compounds that have identical number of atoms of each element and have the same atoms or isotopes connected by bonds of the same type but differ in their relative positions in space, apart from rotations. For this disclosure, isomer[s], diastereomer[s] and enantiomer[s] have the same meaning and may be used interchangeably. Centers of asymmetry that are present in the disclosed compounds can all independently of one another have (R) configuration or (S) configuration. When bonds to the chiral carbon are depicted as straight lines in the structural formulas, it is understood that both the (R) and (S) configurations of the chiral carbon, and hence both enantiomers and mixtures thereof, are embraced within the formula. Similarly, when a compound name is recited without a chiral designation for a chiral carbon, it is understood that both the (R) and (S) configurations of the chiral carbon, and hence individual enantiomers and mixtures thereof, are embraced by the name. If a compound disclosed herein contains a double bond, the substituent may be in the E or Z configuration. If a compound disclosed herein contains a disubstituted cycloalkyl, the cycloalkyl substituent may have a cis- or trans-configuration. All tautomeric forms are also intended to be included.

Pharmaceutically acceptable salts of compounds described herein include conventional nontoxic salts or quaternary ammonium salts of a compound, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. In other cases, described compounds may contain one or more acidic functional groups and, thus, are capable of forming pharmaceutically acceptable salts with pharmaceutically acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

In one embodiment, the invention provides a compound according to Formula (I) or an optically pure stereoisomer, solvate, or pharmaceutically acceptable salt thereof.

Formula (I)

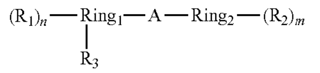

Wherein each $Ring_1$ and $Ring_2$ can be independently selected from the group consisting of phenyl, naphthyl, anthracene,

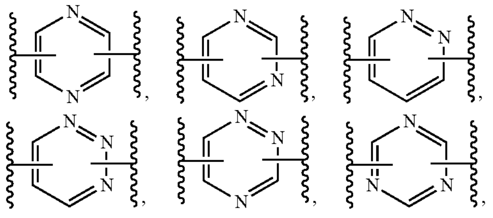

-continued

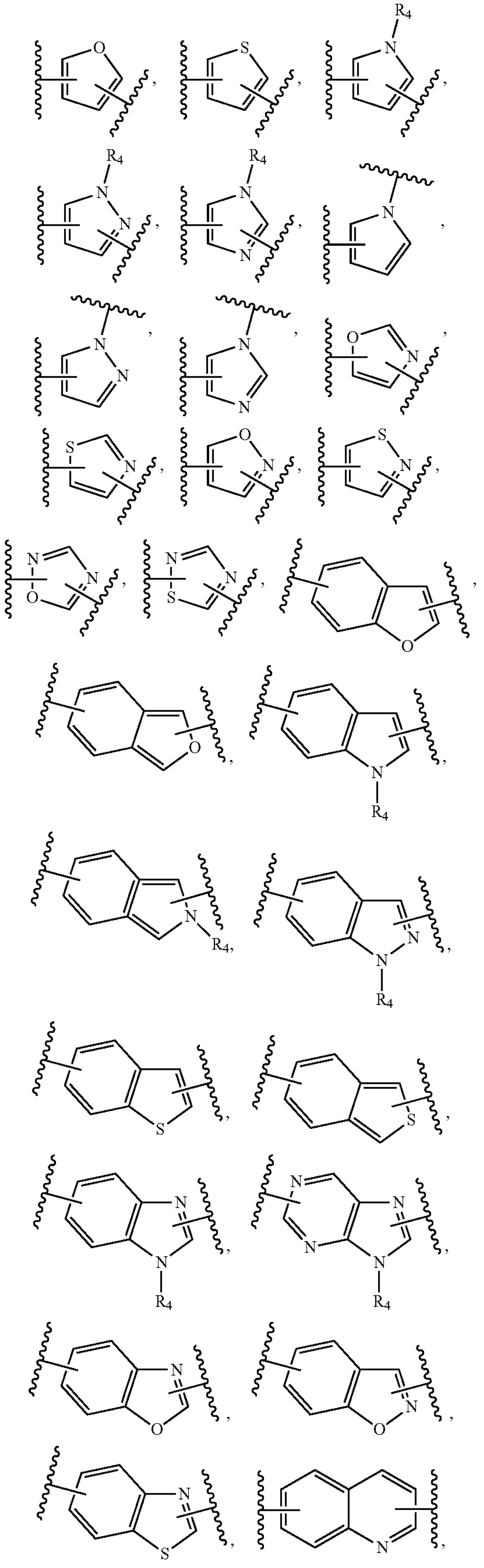

-continued

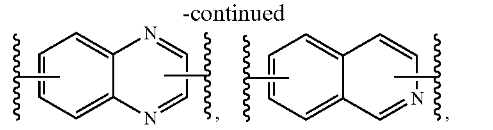

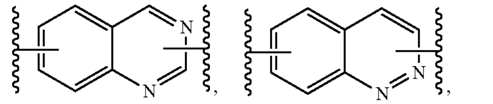

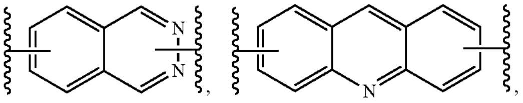

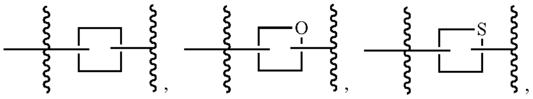

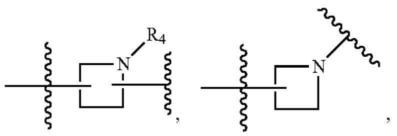

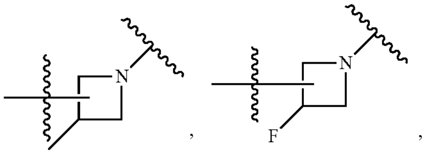

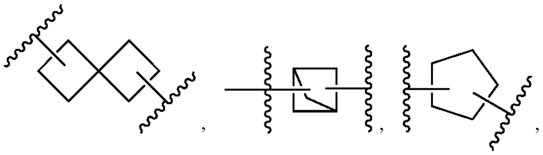

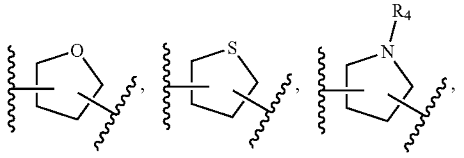

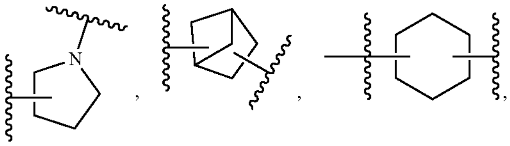

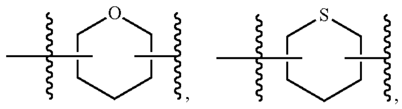

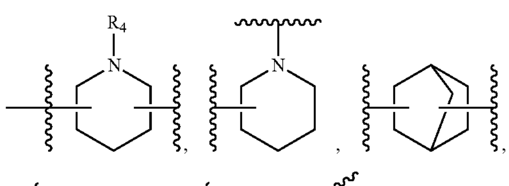

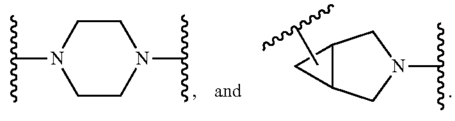

In some aspects, both $Ring_1$ and $Ring_2$ are

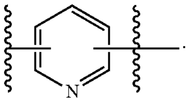

In some aspects, $Ring_1$ can be phenyl, $Ring_2$ can be

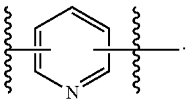

The illustration for $Ring_1$ refers to connections with A and $R_1$.

A can be —O—$(CH_2)$p-, —CO—$(CH_2)$p-, —CO—O—$(CH_2)$p-, —S—$(CH_2)$p-, —SO—$(CH_2)$p-, —$SO_2$—$(CH_2)$p-, —$NR_4$—$(CH_2)$p-, —CO—$NR_4$—$(CH_2)$p-, —$NR_4$—CO—$NR_4$—$(CH_2)$p-, —OPO—$(CH_2)$p-, —$OPO_2$—$(CH_2)$p-, or —$(CR_6R_7)_p$—.

n can be an integer selected from 0 to 5. In some aspects, n can be 1, 2, 3, or 4. In some aspects, n can be 1.

m can be an integer selected from 0 to 5. In some aspects, m can be 1, 2, 3, or 4. In some aspects, m can be 1.

Each p can be independently an integer selected from 0 to 3. In some aspects, p can be 0.

Each $R_1$ can be independently $CO(CH_2)_{0-5}CH_3$, $O(CH_2)_{0-5}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH{=}CH_2$, $(CH_2)_{0-5}CH{=}CHCH_3$, $(CH_2)_{0-5}C{\equiv}CH$, $(CH_2)_{0-5}C{\equiv}CCH_3$, $NHCO(CH_2)_{0-5}CH{=}CH_2$, $NHCO(CH_2)_{0-5}CH{=}CHCH_3$, $NHCONH(CH_2)_{0-5}CH{=}CH_2$, $NHCONH(CH_2)_{0-5}CH{=}CHCH_3$, $O(CH_2)_{0-5}CH{=}CH_2$, $O(CH_2)_{0-5}CH{=}CHCH_3$, $CO(CH_2)_{0-5}CH{=}CH_2$, $CO(CH_2)_{0-5}CH{=}CHCH_3$, $OCO(CH_2)_{0-5}CH{=}CH_2$, $OCO(CH_2)_{0-5}CH{=}CHCH_3$, $SO_2(CH_2)_{0-5}CH{=}CH_2$, $SO_2(CH_2)_{0-5}CH{=}CHCH_3$, $NHCO(CH_2)_{0-5}C{\equiv}CH$, $NHCO(CH_2)_{0-5}C{\equiv}CCH_3$, $NHCONH(CH_2)_{0-5}C{\equiv}CH$, $NHCONH(CH_2)_{0-5}C{\equiv}CCH_3$, $O(CH_2)_{0-5}C{\equiv}CH$, $O(CH_2)_{0-5}C{\equiv}CCH_3$, $SO_2(CH_2)_{0-5}C{\equiv}CH$, $SO_2(CH_2)_{0-5}C{\equiv}CCH_3$, $CO(CH_2)_{0-5}C{\equiv}CH$, $CO(CH_2)_{0-5}C{\equiv}CCH_3$, $OCO(CH_2)_{0-5}C{\equiv}CH$, or $OCO(CH_2)_{0-5}C{\equiv}CCH_3$, each of which can be optionally substituted by one, two, three, or four $R_5$.

Each $R_2$ can be independently F, Br, Cl, $CF_3$, CN, $N_3$, $NH_2$, $NO_2$, OH, $OCH_3$, $CO(CH_2)_{0-5}CH_3$, $O(CH_2)_{0-5}CH_3$, $(CH_2)_{0-9}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH{=}CH_2$, $(CH_2)_{0-5}CH{=}CHCH_3$, $(CH_2)_{0-5}C{\equiv}CH$, $(CH_2)_{0-5}C{\equiv}CCH_3$, $NHCO(CH_2)_{0-5}CH{=}CH_2$, $NHCO(CH_2)_{0-5}CH{=}CHCH_3$, $NHCONH(CH_2)_{0-5}CH{=}CH_2$, $NHCONH(CH_2)_{0-5}CH{=}CHCH_3$, $O(CH_2)_{0-5}CH{=}CH_2$, $O(CH_2)_{0-5}CH{=}CHCH_3$, $CO(CH_2)_{0-5}CH{=}CH_2$, $CO(CH_2)_{0-5}CH{=}CHCH_3$, $OCO(CH_2)_{0-5}CH{=}CH_2$, $OCO(CH_2)_{0-5}CH{=}CHCH_3$, $SO_2(CH_2)_{0-5}CH{=}CH_2$, $SO_2(CH_2)_{0-5}CH{=}CHCH_3$, $NHCO(CH_2)_{0-5}C{\equiv}CH$, $NHCO(CH_2)_{0-5}C{\equiv}CCH_3$, $NHCONH(CH_2)_{0-5}C{\equiv}CH$, $NHCONH(CH_2)_{0-5}C{\equiv}CCH_3$, $O(CH_2)_{0-5}C{\equiv}CH$, $O(CH_2)_{0-5}C{\equiv}CCH_3$, $SO_2(CH_2)_{0-5}C{\equiv}CH$, $SO_2(CH_2)_{0-5}C{\equiv}CCH_3$, $CO(CH_2)_{0-5}C{\equiv}CH$, $CO(CH_2)_{0-5}C{\equiv}CCH_3$, $OCO(CH_2)_{0-5}C{\equiv}CH$, or $OCO(CH_2)_{0-5}C{\equiv}CCH_3$, each of these groups can be optionally substituted by one, two, three, or four $R_5$.

In certain aspects, each $R_1$ or $R_2$ can be independently selected from the group consisting of

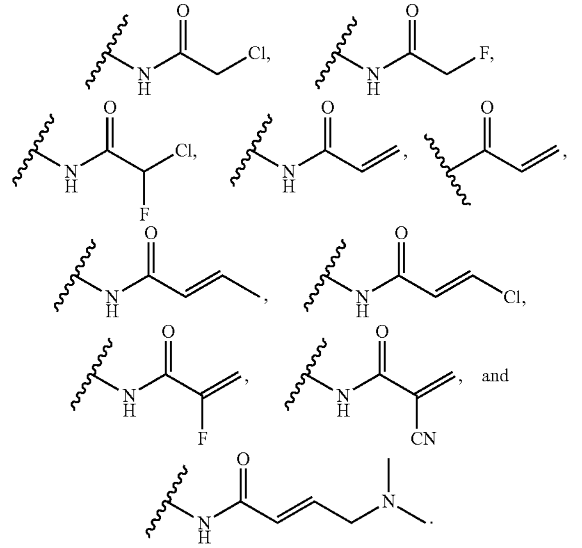

and $R_3$ can be selected from the group consisting of H, F, Br, Cl, $CF_3$, CN, $N_3$, $NH_2$, $NO_2$, OH, and $OCH_3$.

Each $R_4$ can be independently H or $C_{1-3}$alkyl optionally substituted by one, two, three, or four $R_5$.

Each $R_5$ can be independently selected from the group consisting of H, methyl, ethyl, propyl, isopropyl, cyclopropyl, cyclobutyl, F, Br, Cl, $CF_3$, $NO_2$, OH, $OCH_3$, CN, and amino group unsubstituted or substituted with methyl, ethyl, or propyl.

p can be 1, 2, or 3.

Each $R_6$ and $R_7$ can be independently H, methyl, ethyl, F, Br, Cl, $CF_3$, $NO_2$, OH, $OCH_3$, or CN.

In another embodiment, the invention provides a compound according to Formula (II) or an optically pure stereoisomer, solvate, or pharmaceutically acceptable salt thereof.

Formula (II)

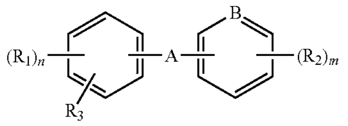

Wherein A can be —O—, —CO—, —$NR_4$—, —CO—$NR_4$—, or $SO_2$. B can be N or CH.

n can be an integer selected from 0 to 5. In some aspects, n can be 1, 2, 3, or 4. In some aspects, n can be 1. In some aspects, when n is 1, $R_1$ can be placed at ortho, meta, or para position on the phenyl ring.

m can be an integer selected from 0 to 5. In some aspects, m can be 1, 2, 3, or 4. In some aspects, m can be 1. In some aspects, when m is 1, $R_2$ can be placed at ortho, meta, or para position on the phenyl ring.

Each $R_1$ can be independently $CO(CH_2)_{0-5}CH_3$, $O(CH_2)_{0-5}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH{=}CH_2$, $(CH_2)_{0-5}CH{=}CHCH_3$, $(CH_2)_{0-5}C{\equiv}CH$, $(CH_2)_{0-5}C{\equiv}CCH_3$, $NHCO(CH_2)_{0-5}CH{=}CH_2$, $NHCO(CH_2)_{0-5}CH{=}CHCH_3$, $NHCONH(CH_2)_{0-5}CH{=}CH_2$, $NHCONH(CH_2)_{0-5}CH{=}CHCH_3$, $O(CH_2)_{0-5}CH{=}CH_2$, $O(CH_2)_{0-5}CH{=}CHCH_3$, $CO(CH_2)_{0-5}CH{=}CH_2$, $CO(CH_2)_{0-5}CH{=}CHCH_3$, $OCO(CH_2)_{0-5}CH{=}CH_2$, $OCO(CH_2)_{0-5}CH{=}CHCH_3$, $SO_2(CH_2)_{0-5}CH{=}CH_2$, $SO_2(CH_2)_{0-5}CH{=}CHCH_3$, $NHCO(CH_2)_{0-5}C{\equiv}CH$, $NHCO(CH_2)_{0-5}C{\equiv}CCH_3$, $NHCONH(CH_2)_{0-5}C{\equiv}CH$, $NHCONH(CH_2)_{0-5}C{\equiv}CCH_3$, $O(CH_2)_{0-5}C{\equiv}CH$, $O(CH_2)_{0-5}C{\equiv}CCH_3$, $SO_2(CH_2)_{0-5}C{\equiv}CH$, $SO_2(CH_2)_{0-5}C{\equiv}CCH_3$, $CO(CH_2)_{0-5}C{\equiv}CH$, $CO(CH_2)_{0-5}C{\equiv}CCH_3$, $OCO(CH_2)_{0-5}C{\equiv}CH$, or $OCO(CH_2)_{0-5}C{\equiv}CCH_3$, each of which can be optionally substituted by one, two, three, or four $R_5$.

Each $R_2$ can be independently F, Br, Cl, $CF_3$, CN, $N_3$, $NH_2$, $NO_2$, OH, $OCH_3$, $CO(CH_2)_{0-5}CH_3$, $O(CH_2)_{0-5}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH{=}CH_2$, $(CH_2)_{0-5}CH{=}CHCH_3$, $(CH_2)_{0-5}C{\equiv}CH$, $(CH_2)_{0-5}C{\equiv}CCH_3$, $NHCO(CH_2)_{0-5}CH{=}CH_2$, $NHCO(CH_2)_{0-5}CH{=}CHCH_3$, $NHCONH(CH_2)_{0-5}CH{=}CH_2$, $NHCONH(CH_2)_{0-5}CH{=}CHCH_3$, $O(CH_2)_{0-5}CH{=}CH_2$, $O(CH_2)_{0-5}CH{=}CHCH_3$, $CO(CH_2)_{0-5}CH{=}CH_2$, $CO(CH_2)_{0-5}CH{=}CHCH_3$, $OCO(CH_2)_{0-5}CH{=}CH_2$, $OCO(CH_2)_{0-5}CH{=}CHCH_3$, $SO_2(CH_2)_{0-5}CH{=}CH_2$, $SO_2(CH_2)_{0-5}CH{=}CHCH_3$, $NHCO(CH_2)_{0-5}C{\equiv}CH$, $NHCO(CH_2)_{0-5}C{\equiv}CCH_3$, $NHCONH(CH_2)_{0-5}C{\equiv}CH$, $NHCONH(CH_2)_{0-5}C{\equiv}CCH_3$, $O(CH_2)_{0-5}C{\equiv}CH$, $O(CH_2)_{0-5}C{\equiv}CCH_3$, $SO_2(CH_2)_{0-5}C{\equiv}CH$, $SO_2(CH_2)_{0-5}C{\equiv}CCH_3$, $CO(CH_2)_{0-5}C{\equiv}CH$, $CO(CH_2)_{0-5}C{\equiv}CCH_3$, $OCO(CH_2)_{0-5}C{\equiv}CH$, or $OCO(CH_2)_{0-5}C{\equiv}CCH_3$, each of these groups can be optionally substituted by one, two, three, or four $R_5$.

In certain aspects, each $R_1$ or $R_2$ can be independently selected from the group consisting of

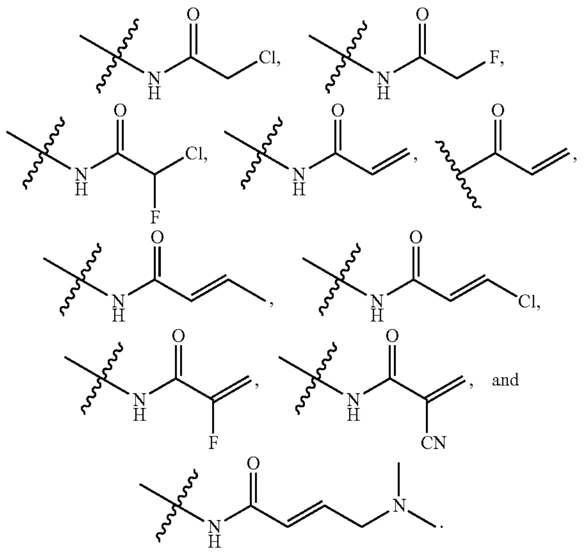

and $R_3$ can be selected from the group consisting of H, F, Br, Cl, $CF_3$, CN, $N_3$, $NH_2$, $NO_2$, OH, and $OCH_3$.

Each $R_4$ can be independently H or $C_{1-3}$alkyl optionally substituted by one, two, three, or four $R_5$.

Each $R_5$ can be independently selected from the group consisting of H, methyl, ethyl, propyl, isopropyl, cyclopropyl, cyclobutyl, F, Br, Cl, $CF_3$, $NO_2$, OH, $OCH_3$, CN, and amino group unsubstituted or substituted with methyl, ethyl, or propyl.

In yet another embodiment, the invention provides a compound according to Formula (III) or an optically pure stereoisomer, solvate, or pharmaceutically acceptable salt thereof.

Formula (III)

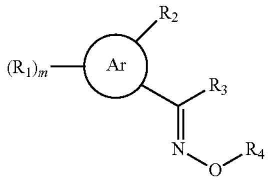

Wherein Ar is selected from the group consisting of phenyl, naphthyl, anthracene, pyridyl,

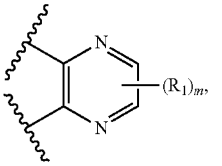, 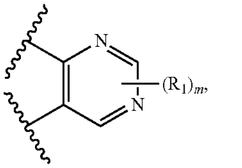, 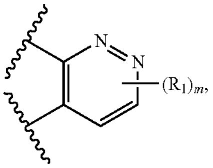, 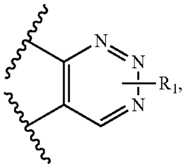, 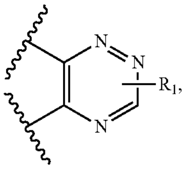, 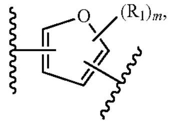, 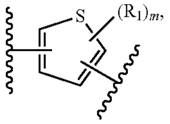, 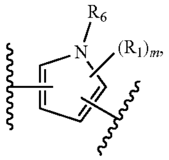, 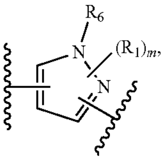, 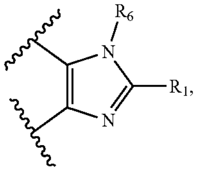, 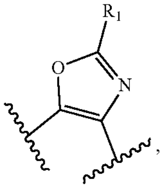, 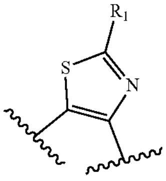, and 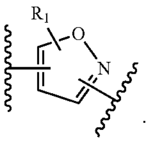.

Each $R_1$ can be independently $CO(CH_2)_{0\text{-}5}CH_3$, $O(CH_2)_{0\text{-}5}CH_3$, $OCO(CH_2)_{0\text{-}5}CH_3$, $NHCO(CH_2)_{0\text{-}5}CH_3$, $NHCONH(CH_2)_{0\text{-}5}CH_3$, $NH(CH_2)_{0\text{-}5}CH_3$, $(CH_2)_{0\text{-}5}CH{=}CH_2$, $(CH_2)_{0\text{-}5}CH{=}CHCH_3$, $(CH_2)_{0\text{-}5}C{\equiv}CH$, $(CH_2)_{0\text{-}5}C{\equiv}CCH_3$, $NHCO(CH_2)_{0\text{-}5}CH{=}CH_2$, $NHCO(CH_2)_{0\text{-}5}CH{=}CHCH_3$, $NHCONH(CH_2)_{0\text{-}5}CH{=}CH_2$, $NHCONH(CH_2)_{0\text{-}5}CH{=}CHCH_3$, $O(CH_2)_{0\text{-}5}CH{=}CH_2$, $O(CH_2)_{0\text{-}5}CH{=}CHCH_3$, $CO(CH_2)_{0\text{-}5}CH{=}CH_2$, $CO(CH_2)_{0\text{-}5}CH{=}CHCH_3$, $OCO(CH_2)_{0\text{-}5}CH{=}CH_2$, $OCO(CH_2)_{0\text{-}5}CH{=}CHCH_3$, $SO_2(CH_2)_{0\text{-}5}CH{=}CH_2$, $SO_2(CH_2)_{0\text{-}5}CH{=}CHCH_3$, $NHCO(CH_2)_{0\text{-}5}C{\equiv}CH$, $NHCO(CH_2)_{0\text{-}5}C{\equiv}CCH_3$, $NHCONH(CH_2)_{0\text{-}5}C{\equiv}CH$, $NHCONH(CH_2)_{0\text{-}5}C{\equiv}CCH_3$, $O(CH_2)_{0\text{-}5}C{\equiv}CH$, $O(CH_2)_{0\text{-}5}C{\equiv}CCH_3$, $SO_2(CH_2)_{0\text{-}5}C{\equiv}CH$, $SO_2(CH_2)_{0\text{-}5}C{\equiv}CCH_3$, $CO(CH_2)_{0\text{-}5}C{\equiv}CH$, $CO(CH_2)_{0\text{-}5}C{\equiv}CCH_3$, $OCO(CH_2)_{0\text{-}5}C{\equiv}CH$, or $OCO(CH_2)_{0\text{-}5}C{\equiv}CCH_3$, each of which can be optionally substituted by one, two, three, or four $R_5$.

Each m can be independently an integer selected from 0 to 4. In some aspects, m can be 1, 2, or 3.

Each $R_2$ can be independently F, Br, Cl, $CF_3$, CN, $N_3$, $NH_2$, $NO_2$, OH, $OCH_3$, $CO(CH_2)_{0\text{-}5}CH_3$, $O(CH_2)_{0\text{-}5}CH_3$, $OCO(CH_2)_{0\text{-}5}CH_3$, $NHCO(CH_2)_{0\text{-}5}CH_3$, $NHCONH(CH_2)_{0\text{-}5}CH_3$, $NH(CH_2)_{0\text{-}5}CH_3$, $(CH_2)_{0\text{-}5}CH{=}CH_2$, $(CH_2)_{0\text{-}5}CH{=}CHCH_3$, $(CH_2)_{0\text{-}5}C{\equiv}CH$, $(CH_2)_{0\text{-}5}C{\equiv}CCH_3$, $NHCO(CH_2)_{0\text{-}5}CH{=}CH_2$, $NHCO(CH_2)_{0\text{-}5}CH{=}CHCH_3$, $NHCONH(CH_2)_{0\text{-}5}CH{=}CH_2$, $NHCONH(CH_2)_{0\text{-}5}CH{=}CHCH_3$, $O(CH_2)_{0\text{-}5}CH{=}CH_2$, $O(CH_2)_{0\text{-}5}CH{=}CHCH_3$, $CO(CH_2)_{0\text{-}5}CH{=}CH_2$, $CO(CH_2)_{0\text{-}5}CH{=}CHCH_3$, $OCO(CH_2)_{0\text{-}5}CH{=}CH_2$, $OCO(CH_2)_{0\text{-}5}CH{=}CHCH_3$, $SO_2(CH_2)_{0\text{-}5}CH{=}CH_2$, $SO_2(CH_2)_{0\text{-}5}CH{=}CHCH_3$, $NHCO(CH_2)_{0\text{-}5}C{\equiv}CH$, $NHCO(CH_2)_{0\text{-}5}C{\equiv}CCH_3$, $NHCONH(CH_2)_{0\text{-}5}C{\equiv}CH$, $NHCONH(CH_2)_{0\text{-}5}C{\equiv}CCH_3$, $O(CH_2)_{0\text{-}5}C{\equiv}CH$, $O(CH_2)_{0\text{-}5}C{\equiv}CCH_3$, $SO_2(CH_2)_{0\text{-}5}C{\equiv}CH$, $SO_2(CH_2)_{0\text{-}5}C{\equiv}CCH_3$, $CO(CH_2)_{0\text{-}5}C{\equiv}CH$, $CO(CH_2)_{0\text{-}5}C{\equiv}CCH_3$, $OCO(CH_2)_{0\text{-}5}C{\equiv}CH$, or $OCO(CH_2)_{0\text{-}5}C{\equiv}CCH_3$, each of these groups can be optionally substituted by one, two, three, or four $R_5$.

In certain aspects, each $R_1$ or $R_2$ can be independently selected from the group consisting of

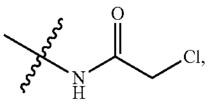, 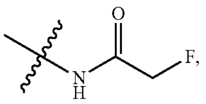, 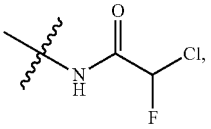, 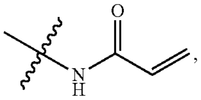, 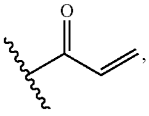, 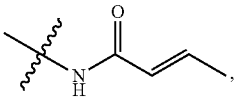, 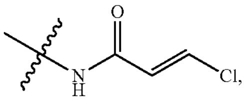, 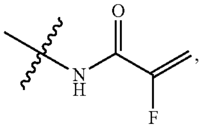, 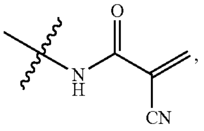, and 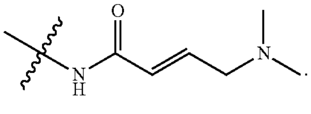.

$R_3$ can be H or $C_{1\text{-}8}$alkyl optionally substituted by one, two, three, or four $R_5$.

In some aspects, $R_2$ and $R_3$ together can form a bicyclic structure with Ar, the cyclic moiety between $R_2$ and $R_3$ can include $-(CR_7R_8)_n-$, wherein n can be an integer selected from 1 to 5. In some aspects, n can be 2, 3, or 4.

$R_4$ can be H, $C_{1\text{-}8}$alkyl, $CH_2CH_2(OCH_2CH_2)_l$-s, $CO(CH_2)_{0\text{-}5}CH_3$, $(CH_2)_{0\text{-}5}CH{=}CH_2$, $(CH_2)_{0\text{-}5}C{\equiv}CH$, $CONH(CH_2)_{0\text{-}5}CH{=}CH_2$, $CO(CH_2)_{0\text{-}5}CH{=}CH_2$, $SO_2(CH_2)_{0\text{-}5}CH{=}CH_2$, $CONH(CH_2)_{0\text{-}5}C{\equiv}CH$, $CO(CH_2)_{0\text{-}5}C{\equiv}CH$, or $SO_2(CH_2)_{0\text{-}5}C{\equiv}CH$, each of which can be optionally substituted by one, two, three, or four $R_5$.

Each $R_5$ can be independently selected from the group consisting of H, methyl, ethyl, propyl, isopropyl, cyclopropyl, cyclobutyl, F, Br, Cl, $CF_3$, $NO_2$, OH, $OCH_3$, CN, and amino group unsubstituted or substituted with methyl, ethyl, or propyl.

Each $R_6$ can be independently H or $C_{1-3}$alkyl.

Each $R_7$ and $R_8$ can be independently H, methyl, ethyl, F, Br, Cl, $CF_3$, or CN.

In some embodiments, the invention provides a compound according to Formula (IV) or an optically pure stereoisomer, solvate, or pharmaceutically acceptable salt thereof.

Formula (IV)

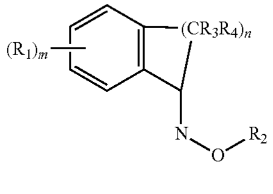

Each $R_1$ can be independently $CO(CH_2)_{0-5}CH_3$, $O(CH_2)_{0-5}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH{=}CH_2$, $(CH_2)_{0-5}CH{=}CHCH_3$, $(CH_2)_{0-5}C{\equiv}CH$, $(CH_2)_{0-5}C{\equiv}CCH_3$, $NHCO(CH_2)_{0-5}CH{=}CH_2$, $NHCO(CH_2)_{0-5}CH{=}CHCH_3$, $NHCONH(CH_2)_{0-5}CH{=}CH_2$, $NHCONH(CH_2)_{0-5}CH{=}CHCH_3$, $O(CH_2)_{0-5}CH{=}CH_2$, $O(CH_2)_{0-5}CH{=}CHCH_3$, $CO(CH_2)_{0-5}CH{=}CH_2$, $CO(CH_2)_{0-5}CH{=}CHCH_3$, $OCO(CH_2)_{0-5}CH{=}CH_2$, $OCO(CH_2)_{0-5}CH{=}CHCH_3$, $SO_2(CH_2)_{0-5}CH{=}CH_2$, $SO_2(CH_2)_{0-5}CH{=}CHCH_3$, $NHCO(CH_2)_{0-5}C{\equiv}CH$, $NHCO(CH_2)_{0-5}C{\equiv}CCH_3$, $NHCONH(CH_2)_{0-5}C{\equiv}CH$, $NHCONH(CH_2)_{0-5}C{\equiv}CCH_3$, $O(CH_2)_{0-5}C{\equiv}CH$, $O(CH_2)_{0-5}C{\equiv}CCH_3$, $SO_2(CH_2)_{0-5}C{\equiv}CH$, $SO_2(CH_2)_{0-5}C{\equiv}CCH_3$, $CO(CH_2)_{0-5}C{\equiv}CH$, $CO(CH_2)_{0-5}C{\equiv}CCH_3$, $OCO(CH_2)_{0-5}C{\equiv}CH$, or $OCO(CH_2)_{0-5}C{\equiv}CCH_3$, each of which can be optionally substituted by one, two, three, or four $R_5$.

In certain aspects, each $R_1$ can be independently selected from the group consisting of

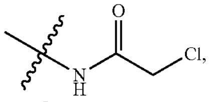, 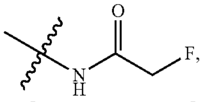, 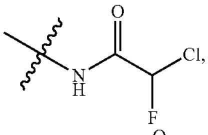, 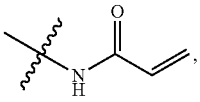, 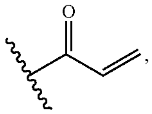, 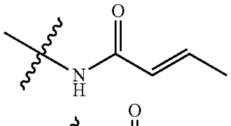, 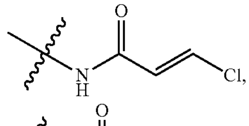, 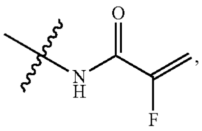, 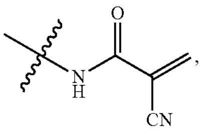, and 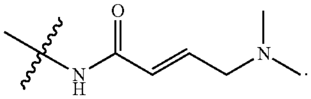.

n can be an integer selected from 1 to 5. In some aspects, n can be 2, 3, or 4.

m can be an integer selected from 0 to 4. In some aspects, m can be 1, 2, or 3.

$R_2$ can be H, $C_{1-8}$alkyl, $CH_2CH_2(OCH_2CH_2)_{1-5}$, $CO(CH_2)_{0-5}CH_3$, $(CH_2)_{0-5}CH{=}CH_2$, $(CH_2)_{0-5}C{\equiv}CH$, $CONH(CH_2)_{0-5}CH{=}CH_2$, $CO(CH_2)_{0-5}CH{=}CH_2$, $SO_2(CH_2)_{0-5}CH{=}CH_2$, $CONH(CH_2)_{0-5}C{\equiv}CH$, $CO(CH_2)_{0-5}C{\equiv}CH$, or $SO_2(CH_2)_{0-5}C{\equiv}CH$, each of which can be optionally substituted by one, two, three, or four $R_5$.

Each $R_3$ and $R_4$ can be independently H, methyl, ethyl, F, Br, Cl, $CF_3$, or CN.

Each $R_5$ can be independently selected from the group consisting of H, methyl, ethyl, propyl, isopropyl, cyclopropyl, cyclobutyl, F, Br, Cl, $CF_3$, $NO_2$, OH, $OCH_3$, CN, and amino group unsubstituted or substituted with methyl, ethyl, or propyl.

In some embodiments, the invention provides a compound according to Formula (V) or an optically pure stereoisomer, solvate, or pharmaceutically acceptable salt thereof.

Formula (V)

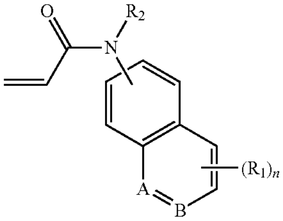

In some embodiments, each A and B can be independently carbon or nitrogen. n can be an integer selected from 0 to 4.

In some embodiments, each $R_1$ can be independently F, Br, Cl, $CF_3$, CN, $N_3$, $NH_2$, $NO_2$, OH, $OCH_3$, $CO(CH_2)_{0-5}CH_3$, $O(CH_2)_{0-5}CH_3$, $(CH_2)_{0-9}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH{=}CH_2$, $(CH_2)_{0-5}CH{=}CHCH_3$, $(CH_2)_{0-5}C{\equiv}CH$, $(CH_2)_{0-5}C{\equiv}CCH_3$, $NHCO(CH_2)_{0-5}CH{=}CH_2$, $NHCO(CH_2)_{0-5}CH{=}CHCH_3$, $NHCONH(CH_2)_{0-5}CH{=}CH_2$, $NHCONH(CH_2)_{0-5}CH{=}CHCH_3$, $O(CH_2)_{0-5}CH{=}CH_2$, $O(CH_2)_{0-5}CH{=}CHCH_3$, $CO(CH_2)_{0-5}CH{=}CH_2$, $CO(CH_2)_{0-5}CH{=}CHCH_3$, $OCO(CH_2)_{0-5}CH{=}CH_2$, $OCO(CH_2)_{0-5}CH{=}CHCH_3$, $SO_2(CH_2)_{0-5}CH{=}CH_2$, $SO_2(CH_2)_{0-5}CH{=}CHCH_3$, $NHCO(CH_2)_{0-5}C{\equiv}CH$, $NHCO(CH_2)_{0-5}C{\equiv}CCH_3$, $NHCONH(CH_2)_{0-5}C{\equiv}CH$, $NHCONH(CH_2)_{0-5}C{\equiv}CCH_3$, $O(CH_2)_{0-5}C{\equiv}CH$, $O(CH_2)_{0-5}C{\equiv}CCH_3$, $SO_2(CH_2)_{0-5}C{\equiv}CH$, $SO_2(CH_2)_{0-5}C{\equiv}CCH_3$, $CO(CH_2)_{0-5}C{\equiv}CH$, $CO(CH_2)_{0-5}C{\equiv}CCH_3$, $OCO(CH_2)_{0-5}C{\equiv}CH$, or $OCO(CH_2)_{0-5}C{\equiv}CCH_3$, each of these groups can be optionally substituted by one, two, three, or four $R_3$.

In some embodiments, $R_2$ is H or $C_{1-3}$alkyl optionally substituted by one, two, three, or four $R_3$.

In some embodiments, each $R_3$ can be independently selected from the group consisting of H, methyl, ethyl, propyl, isopropyl, cyclopropyl, cyclobutyl, F, Br, Cl, $CF_3$, $NO_2$, OH, $OCH_3$, CN, and amino group unsubstituted or substituted with methyl, ethyl, or propyl.

In some embodiments, the invention provides a compound according to Formula (VI) or an optically pure stereoisomer, solvate, or pharmaceutically acceptable salt thereof.

$$(R_1)_n\text{-Ring}_1\text{-Ring}_2\text{-}(R_2)_m \qquad \text{Formula (VI)}$$

Wherein each $Ring_1$ and $Ring_2$ can be independently selected from the group consisting of phenyl, naphthyl, anthracene,

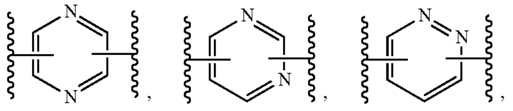,
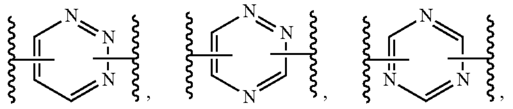,
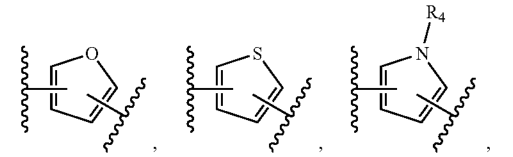,
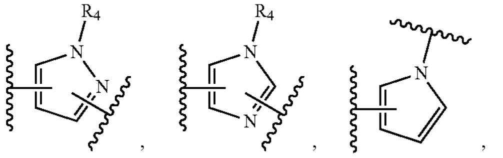,
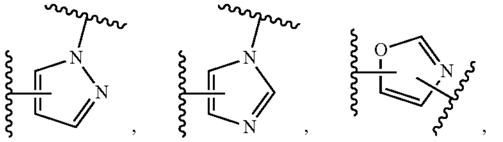,
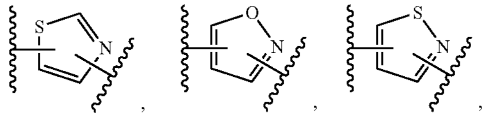,
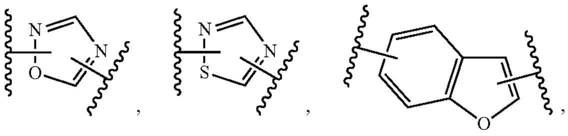,
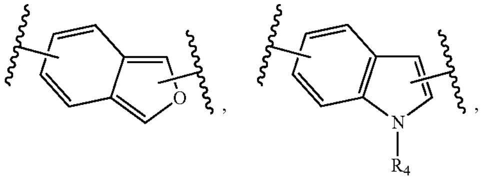,
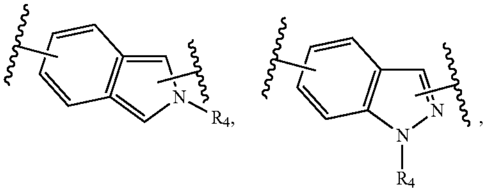,
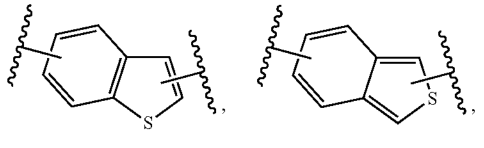,
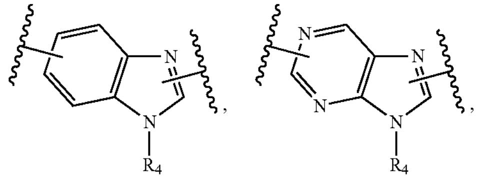, -continued

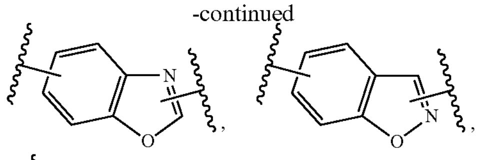,
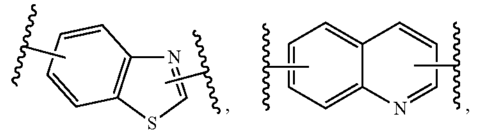,
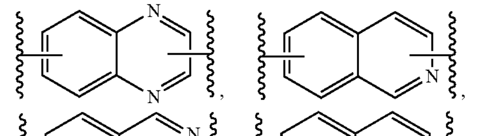,
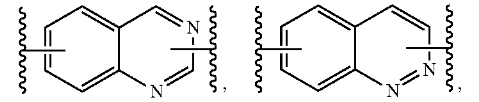,
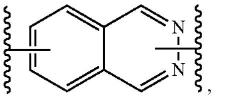, and 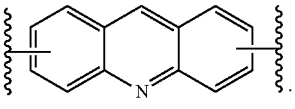.

Each $R_1$ can be independently $CO(CH_2)_{0-5}CH_3$, $O(CH_2)_{0-5}CH_3$, $OCO(CH_2)_{0-5}CH_3$, NHC $CH_2)_{0-5}CH_3$, $NHCONH(CH_2)_{0-5}CH_3$, $NH(CH_2)—CH_3$, $(CH_2)_{0-5}CH=CH_2$, $(CH_2)_{0-5}CH=CHCH_3$, $(CH_2)_{0-5}C\equiv CH$, $(CH_2)_{0-5}C\equiv CCH_3$, $NHCO(CH_2)_{0-5}CH=CH_2$, NH $CO(CH_2)_{0-5}CH=CH$ $CH_3$, $NHCONH(CH_2)_{0-5}=CH_2$, $NHCONH(CH_2)_{0-5}CH=CHCH_3$, $O(CH_2)_{0-5}CH=CH_2$, $O(CH_2)_{0-5}CH=CHCH_3$, $CO(CH_2)_{0-5}CH=CH_2$, CO $(CH_2)_{0-5}CH=CHCH_3$, $OCO(CH_2)_{0-5}CH=CH_2$, OCO $(CH_2)_{0-5}CH=CHCH_3$, $SO_2(CH_2)_{0-5}CH=CH_2$, $SO_2(CH_2)_{0-5}CH=CHCH_3$, $NHCO(CH_2)_{0-5}C\equiv H$, NHCO $(CH_2)_{0-5}C\equiv CCH_3$, $NHCONH(CH_2)_{0-5}C\equiv CH$, $NHCONH(CH_2)_{0-5}C\equiv CCH_3$, $O(CH_2)_{0-5}C\equiv CH$, $O(CH_2)_{0-5}C\equiv CCH_3$, $SO_2(CH_2)_{0-5}C\equiv CH$, $SO_2$ $(CH_2)_{0-5}C\equiv CCH_3$, $CO(CH_2)_{0-5}C\equiv CH$, CO $(CH_2)_{0-5}C\equiv CCH_3$, $OCO(CH_2)_{0-5}C\equiv CH$, or OCO $(CH_2)_{0-5}C\equiv CCH_3$, each of which can be optionally substituted by one, two, three, or four $R_3$.

Each $R_2$ can be independently F, Br, Cl, $CF_3$, CN, $N_3$, $NH_2$, $NO_2$, OH, $OCH_3$, $CO(CH_2)_{0-5}CH_3$, $O(CH_2)_{0-5}CH_3$, $(CH_2)_{0-9}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH=CH_2$, $(CH_2)_{0-5}CH=CHCH_3$, $(CH_2)_{0-5}C\equiv CH$, $(CH_2)_{0-5}C\equiv CCH_3$, $NHCO(CH_2)_{0-5}CH=CH_2$, $NHCO(CH_2)_{0-5}CH=CHCH_3$, NHCONH $(CH_2)_{0-5}CH=CH_2$, $NHCONH(CH_2)_{0-5}CH=CHCH_3$, $O(CH_2)_{0-5}CH=CH_2$, $O(CH_2)_{0-5}CH=CHCH_3$, CO $(CH_2)_{0-5}CH=CH_2$, $CO(CH_2)_{0-5}CH=CHCH_3$, OCO $(CH_2)_{0-5}CH=CH_2$, $OCO(CH_2)_{0-5}CH=CHCH_3$, $SO_2$ $(CH_2)_{0-5}CH=CH_2$, $SO_2(CH_2)_{0-5}CH=CHCH_3$, NHCO $(CH_2)_{0-5}C\equiv CH$, $NHCO(CH_2)_{0-5}C\equiv CCH_3$, NHCONH $(CH_2)_{0-5}C\equiv CH$, $NHCONH(CH_2)_{0-5}C\equiv CCH_3$, $O(CH_2)_{0-5}C\equiv CH$, $O(CH_2)_{0-5}C\equiv CCH_3$, $SO_2(CH_2)_{0-5}C\equiv CH$, $SO_2(CH_2)_{0-5}C\equiv CCH_3$, $CO(CH_2)_{0-5}C\equiv CH$, $CO(CH_2)_{0-5}C\equiv CCH_3$, $OCO(CH_2)_{0-5}C\equiv CH$, or OCO $(CH_2)_{0-5}C\equiv CCH_3$, each of these groups can be optionally substituted by one, two, three, or four $R_3$.

In certain aspects, each $R_1$ or $R_2$ can be independently selected from the group consisting of

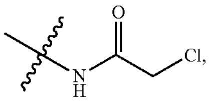, 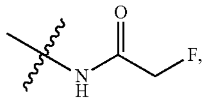,

-continued

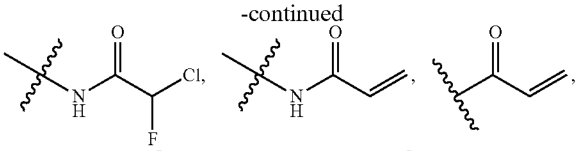

, , ,

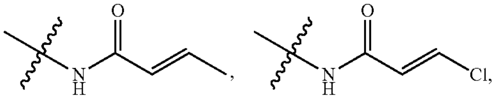

, ,

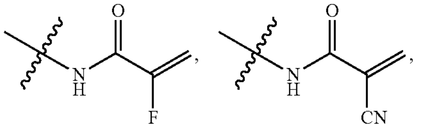

, , and

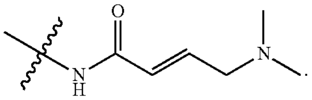

.

Each $R_3$ can be independently selected from the group consisting of H, methyl, ethyl, propyl, isopropyl, cyclopropyl, cyclobutyl, F, Br, Cl, $CF_3$, $NO_2$, OH, $OCH_3$, CN, and amino group unsubstituted or substituted with methyl, ethyl, or propyl.

Each $R_4$ can be independently H or $C_{1-3}$alkyl optionally substituted by one, two, three, or four $R_3$.

n can be an integer selected from 0 to 5. In some aspects, n can be 1, 2, 3, or 4. In some aspects, n can be 1.

m can be an integer selected from 0 to 5. In some aspects, m can be 1, 2, 3, or 4. In some aspects, m can be 1.

In some embodiments, the invention provides a compound according to Formula (VII) or an optically pure stereoisomer, solvate, or pharmaceutically acceptable salt thereof.

Formula (VII)

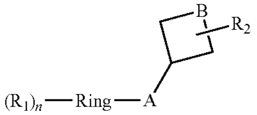

n can be an integer selected from 0 to 5. In some aspects, n can be 1, 2, 3, or 4. In some aspects, n can be 1.

A can be $—O—(CH_2)_m—$, $—CO—(CH_2)_m—$, $—CO—O—(CH_2)_m—$, $—S—(CH_2)_m—$, $—SO—(CH_2)_m—$, $—SO_2—(CH_2)_m—$, $—NR_4—(CH_2)_m—$, $—CO—NR_4—(CH_2)_m—$, $—NR_4—CO—NR_4—(CH_2)_m$, $—OPO—(CH_2)_m—$, $—OPO_2—(CH_2)_m—$, or $—(CR_5R_6)_m—$.

Each m can be independently an integer selected from 0 to 5.

Wherein Ring can be independently selected from the group consisting of phenyl, naphthyl, anthracene,

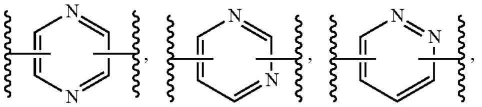

, , ,

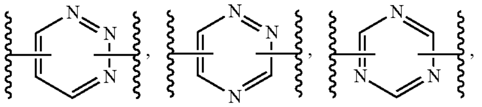

, , ,

-continued

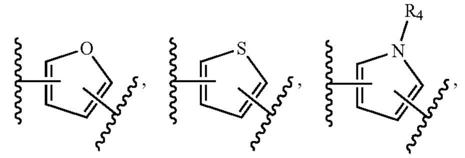

, , ,

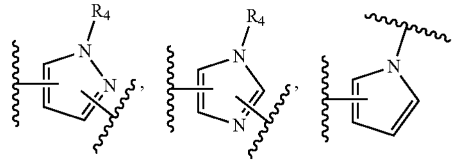

, , ,

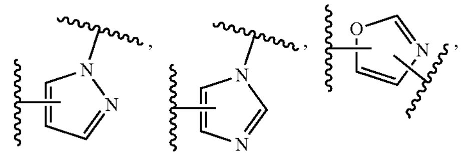

, , ,

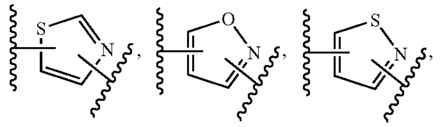

, , ,

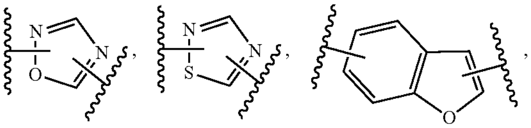

, , ,

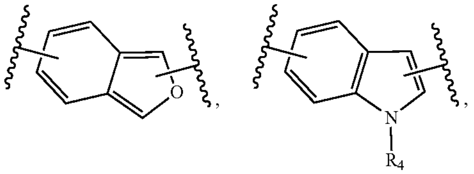

, ,

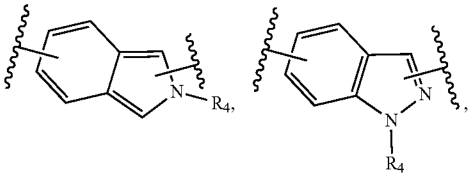

, ,

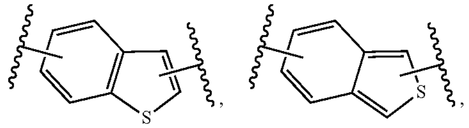

, ,

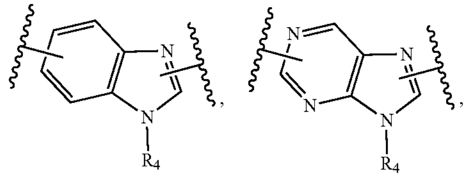

, ,

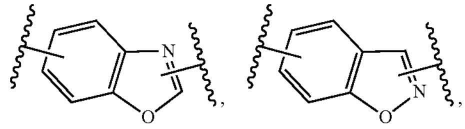

, ,

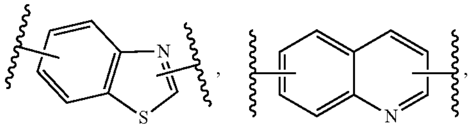

, ,

-continued

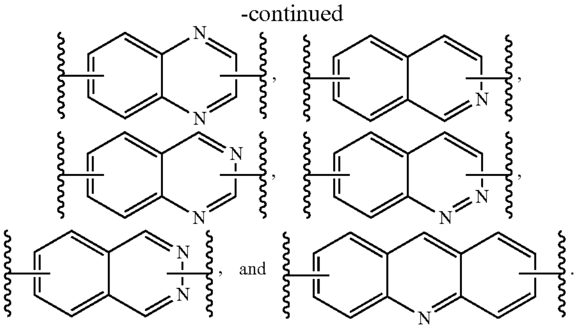

, , , , and .

Each $R_1$ can be independently $CO(CH_2)_{0-5}CH_3$, $O(CH_2)_{0-5}CH_3$, $OCO(CH_2)_{0-5}CH_3$, $NHCO(CH_2)_{0-5}CH_3$, $NHCONH(CH_2)_{0-5}CH_3$, $NH(CH_2)_{0-5}CH_3$, $(CH_2)_{0-5}CH{=}CH_2$, $(CH_2)_{0-5}CH{=}CHCH_3$, $(CH_2)_{0-5}C{\equiv}CH$, $(CH_2)_{0-5}C{\equiv}CCH_3$, $NHCO(CH_2)_{0-5}CH{=}CH_2$, $NHCO(CH_2)_{0-5}CH{=}CHCH_3$, $NHCONH(CH_2)_{0-5}CH{=}CH_2$, $NHCONH(CH_2)_{0-5}CH{=}CHCH_3$, $O(CH_2)_{0-5}CH{=}CH_2$, $O(CH_2)_{0-5}CH{=}CHCH_3$, $CO(CH_2)_{0-5}CH{=}CH_2$, $CO(CH_2)_{0-5}CH{=}CHCH_3$, $OCO(CH_2)_{0-5}CH{=}CH_2$, $OCO(CH_2)_{0-5}CH{=}CHCH_3$, $SO_2(CH_2)_{0-5}CH{=}CH_2$, $SO_2(CH_2)_{0-5}CH{=}CHCH_3$, $NHCO(CH_2)_{0-5}C{\equiv}CH$, $NHCO(CH_2)_{0-5}C{\equiv}CCH_3$, $NHCONH(CH_2)_{0-5}C{\equiv}CH$, $NHCONH(CH_2)_{0-5}C{\equiv}CCH_3$, $O(CH_2)_{0-5}C{\equiv}CH$, $O(CH_2)_{0-5}C{\equiv}CCH_3$, $SO_2(CH_2)_{0-5}C{\equiv}CH$, $SO_2(CH_2)_{0-5}C{\equiv}CCH_3$, $CO(CH_2)_{0-5}C{\equiv}CH$, $CO(CH_2)_{0-5}C{\equiv}CCH_3$, $OCO(CH_2)_{0-5}C{\equiv}CH$, or $OCO(CH_2)_{0-5}C{\equiv}CCH_3$, each of which can be optionally substituted by one, two, three, or four $R_3$.

In some embodiments, B is carbon, oxygen, sulfur, or nitrogen.

When B is carbon, oxygen, or sulfur, $R_2$ can be selected from the group consisting of

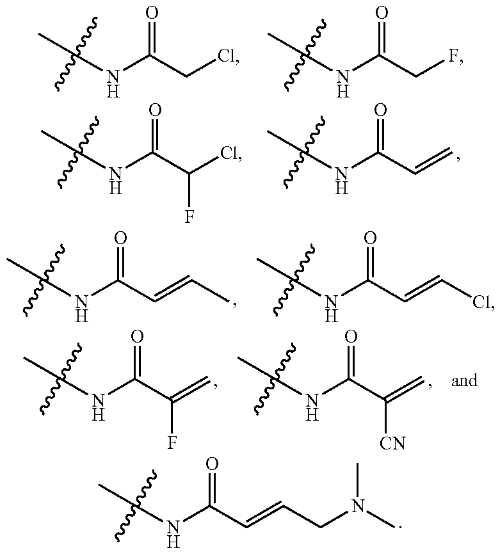

, , , , , , , and .

When B is nitrogen, $R_2$ can be connected to B to form

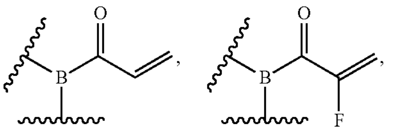

, ,

-continued

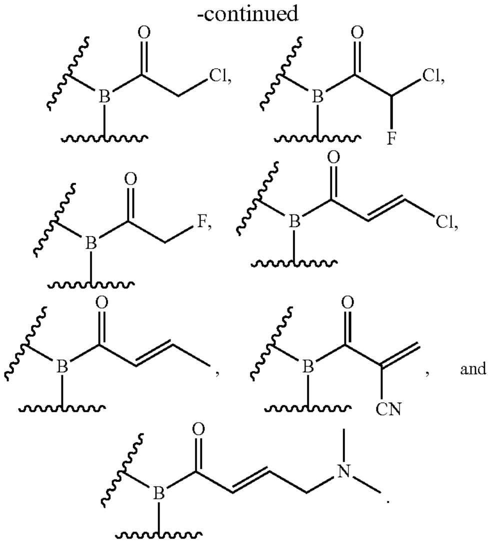

, , , , , , and .

Each $R_3$ can be independently selected from the group consisting of H, methyl, ethyl, propyl, isopropyl, cyclopropyl, cyclobutyl, F, Br, Cl, $CF_3$, $NO_2$, OH, $OCH_3$, CN, and amino group unsubstituted or substituted with methyl, ethyl, or propyl.

Each $R_4$ can be independently H or $C_{1-3}$alkyl optionally substituted by one, two, three, or four $R_3$.

Each $R_5$ and $R_6$ can be independently H, methyl, ethyl, F, Br, Cl, $CF_3$, $NO_2$, OH, $OCH_3$, or CN.

Scheme 1. Synthesis of Formula (I) assuming n = m = 1 and $R_2$ is $NHCOCH{=}CH_2$.

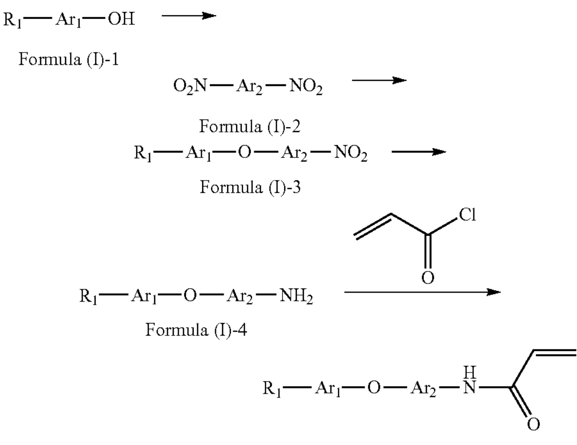

Formula (I)-1

Formula (I)-2

Formula (I)-3

Formula (I)-4

Formula (I)-5

Scheme 1 illustrates synthesis of Formula (I) according to some aspects of the present disclosure. For purposes of this illustration, n and m in Formula (I) is 1, and $R_2$ is $NHCOCH{=}CH_2$. Hydroxyl derivative of $Ar_1$ carrying $R_1$ substituent (Formula (I)-1) and dinitro $Ar_2$ (Formula (I)-2) can react using salt such as cesium carbonate in a polar solvent at high temperature to form the diaromatic ether derivative with a nitro group on $Ar_2$ (Formula (I)-3), which can be reduced into an amine substituent (Formula (I)-4), enabling reaction with acryloyl chloride to obtain the inhibitor compound (Formula (I)-5). In some aspects, Formula (I)-2 can be a fluoro nitro $Ar_2$, the fluoro substituent can react with the OH group on Formula (I)-1 to obtain the ether intermediate Formula (I)-3.

Scheme 2. Synthesis of Formula (III) assuming m = 1 and $R_1$ is $NHCOCH{=}CH_2$.

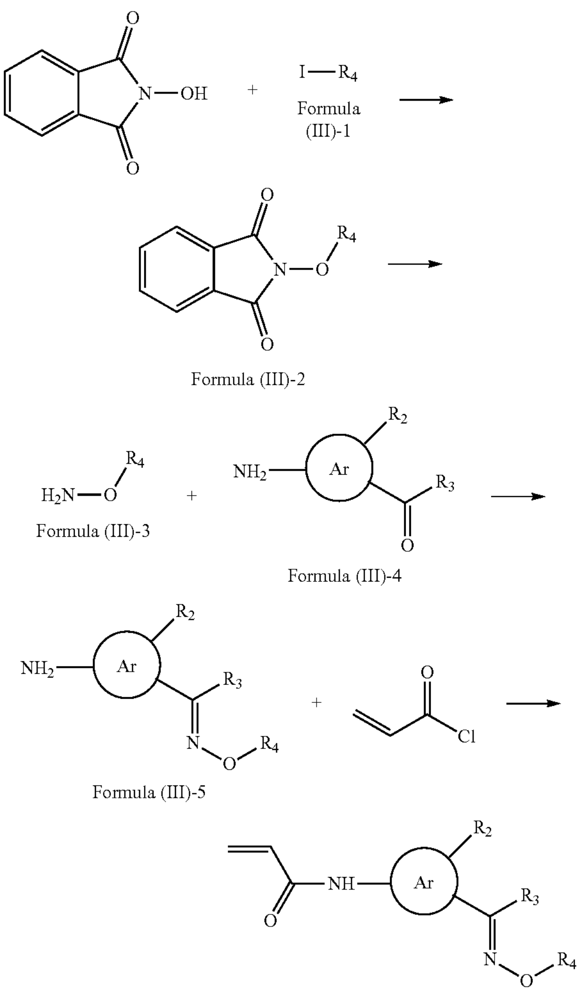

Formula (III)-1

Formula (III)-2

Formula (III)-3

Formula (III)-4

Formula (III)-5

Formula (III)-6

Scheme 2 illustrates synthesis of Formula (III) according to some aspects of the present disclosure. For purposes of this illustration, m in Formula (III) is 1, and $R_1$ is $NHCOCH{=}CH_2$. In the first step, iodide derivative carrying an $R_4$ substituent (Formula (III)-1) reacts with N-hydroxyphthalimide to form an intermediate Formula (III)-2, which is reduced to form hydroxylamine derivative Formula (III)-3. An amine-carrying aromatic carbonyl compound Formula (III)-4 can be added to react with Formula (III)-3 to form the oxime intermediate Formula (III)-5, whose amine group can then react with acryloyl chloride to obtain the inhibitor compound Formula (III)-6.

Using the synthetic methods set forth in schemes 1 and 2 above, a variety of different TEAD1 inhibitor compounds were obtained and tested. Table 1 below shows the inhibitor compounds synthesized in the present disclosure.

TABLE 1

The TEAD inhibitor compounds in the present disclosure.

| Compound No. | Molecular Structure |
|---|---|
| Compound 1 | 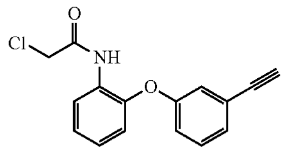 [SMILES: C#Cc1cccc(Oc2ccccc2NC(=O)CCl)c1] |
| Compound 2 | 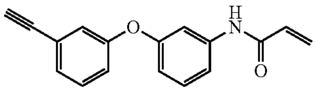 [SMILES: C#Cc1cccc(Oc2cccc(NC(=O)C=C)c2)c1] |
| Compound 3 | 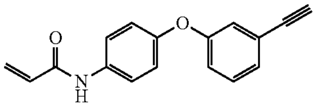 [SMILES: C#Cc1cccc(Oc2ccc(NC(=O)C=C)cc2)c1] |
| Compound 4 | 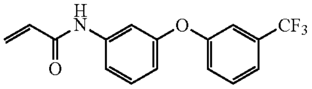 [SMILES: C=CC(=O)Nc1cccc(Oc2cccc(C(F)(F)F)c2)c1] |
| Compound 5 | 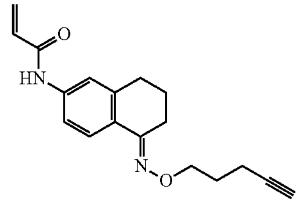 [SMILES: C#CCCCO/N=C1\CCCc2cc(NC(=O)C=C)ccc21] |
| Compound 6 | 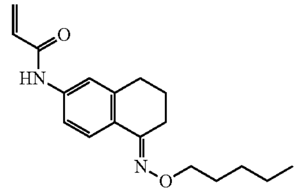 [SMILES: C=CC(=O)Nc1ccc2c(c1)CCC/C2=N\OCCCCC] |
| Compound 7 | 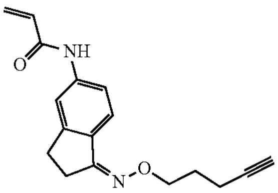 [SMILES: C#CCCCO/N=C1/CCc2cc(NC(=O)C=C)ccc21] |
| Compound 8 | 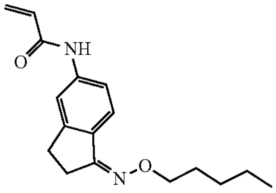 [SMILES: C=CC(=O)Nc1ccc2c(c1)CC/C2=N/OCCCCC] |
| Compound 9 | 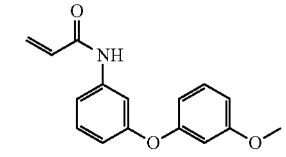 [SMILES: C=CC(=O)Nc1cccc(Oc2cccc(OC)c2)c1] |

TABLE 1-continued
The TEAD inhibitor compounds in the present disclosure.
| Compound No. | Molecular Structure |
| --- | --- |
| Compound 10 | 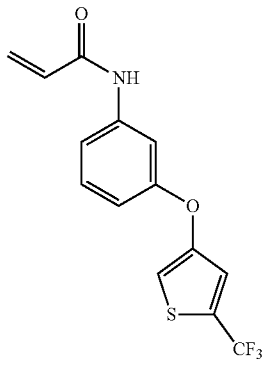 [SMILES: C=CC(=O)Nc1cccc(Oc2csc(C(F)(F)F)c2)c1] |
| Compound 11 | 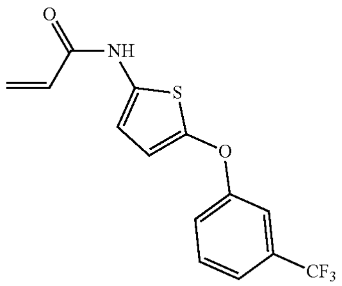 [SMILES: C=CC(=O)Nc1ccc(Oc2cccc(C(F)(F)F)c2)s1] |
| Compound 12 | 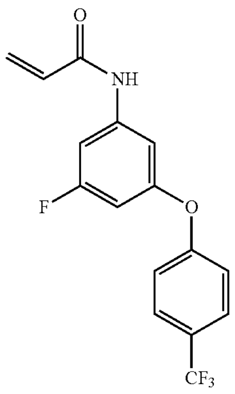 [SMILES: C=CC(=O)Nc1cc(F)cc(Oc2ccc(C(F)(F)F)cc2)c1] |
| Compound 13 | 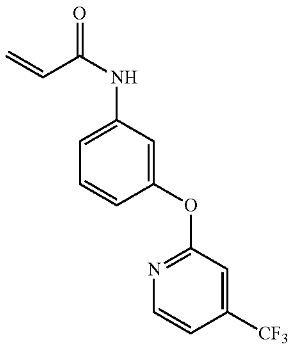 [SMILES: C=CC(=O)Nc1cccc(Oc2cc(C(F)(F)F)ccn2)c1] |
| Compound 14 | 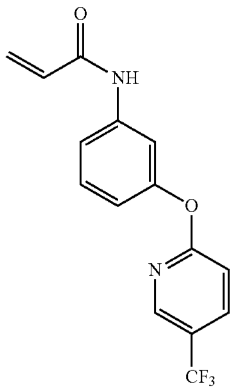 [SMILES: C=CC(=O)Nc1cccc(Oc2ccc(C(F)(F)F)cn2)c1] |
| Compound 15 | 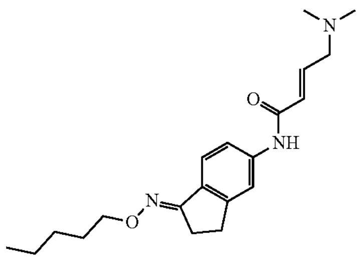 [SMILES: CCCCCO/N=C1\CCc2cc(NC(=O)/C=C/CN(C)C)ccc21] |
| Compound 16 | 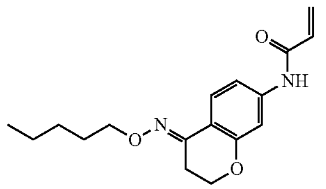 [SMILES: C=CC(=O)Nc1ccc2c(c1)OCC/C2=N\OCCCCC] |
| Compound 17 | 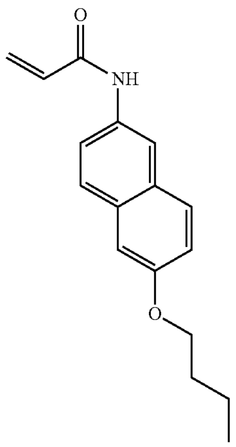 [SMILES: C=CC(=O)Nc1ccc2cc(OCCCC)ccc2c1] |

TABLE 1-continued
| The TEAD inhibitor compounds in the present disclosure. | |
|---|---|
| Compound No. | Molecular Structure |
| Compound 18 | 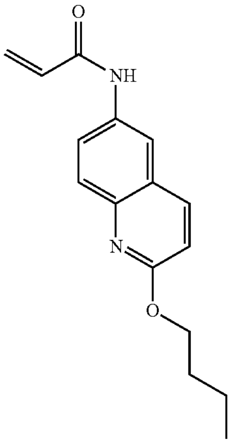 [SMILES: C=CC(=O)Nc1ccc2nc(OCCCC)ccc2c1] |
| Compound 19 | 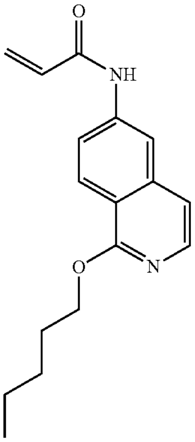 [SMILES: C=CC(=O)Nc1ccc2c(OCCCCC)nccc2c1] |
| Compound 20 | 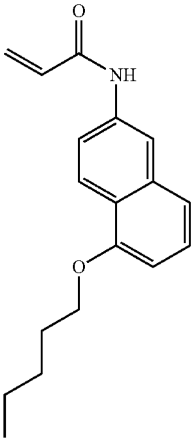 [SMILES: C=CC(=O)Nc1ccc2c(OCCCCC)cccc2c1] |
TABLE 1-continued
| The TEAD inhibitor compounds in the present disclosure. | |
|---|---|
| Compound No. | Molecular Structure |
| Compound 21 | 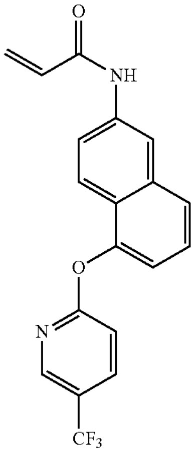 [SMILES: C=CC(=O)Nc1ccc2c(Oc3ccc(C(F)(F)F)cn3)cccc2c1] |
| Compound 22 | 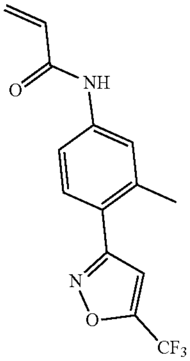 [SMILES: C=CC(=O)Nc1ccc(-c2cc(C(F)(F)F)on2)c(C)c1] |
| Compound 23 | 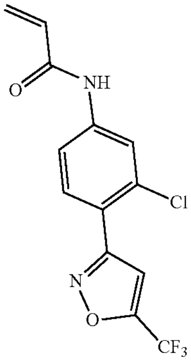 [SMILES: C=CC(=O)Nc1ccc(-c2cc(C(F)(F)F)on2)c(Cl)c1] |
| Compound 24 | 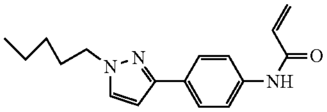 [SMILES: C=CC(=O)Nc1ccc(-c2ccn(CCCCC)n2)cc1] |
| Compound 25 | 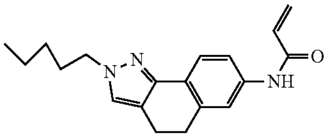 [SMILES: C=CC(=O)Nc1ccc2c(c1)CCc1cn(CCCCC)nc1-2] |

TABLE 1-continued
| The TEAD inhibitor compounds in the present disclosure. | |
|---|---|
| Compound No. | Molecular Structure |
| Compound 26 | 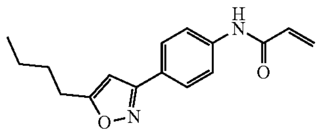 [SMILES: C=CC(=O)Nc1ccc(-c2cc(CCCC)on2)cc1] |
| Compound 27 | 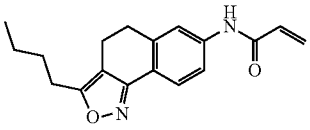 [SMILES: C=CC(=O)Nc1ccc2c(c1)CCc1c-2noc1CCCC] |
| Compound 28 | 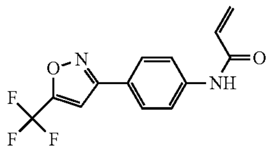 [SMILES: C=CC(=O)Nc1ccc(-c2cc(C(F)(F)F)on2)cc1] |
| Compound 29 | 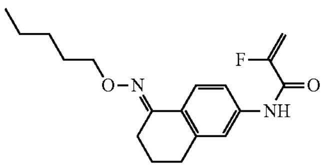 [SMILES: C=C(F)C(=O)Nc1ccc2c(c1)CCC/C2=N\OCCCCC] |
| Compound 30 | 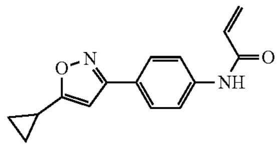 [SMILES: C=CC(=O)Nc1ccc(-c2cc(C3CC3)on2)cc1] |
| Compound 31 | 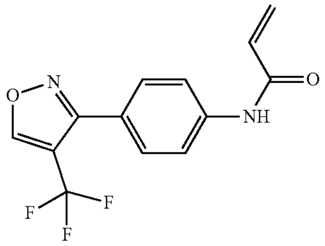 [SMILES: C=CC(=O)Nc1ccc(-c2nocc2C(F)(F)F)cc1] |
| Compound 32 | 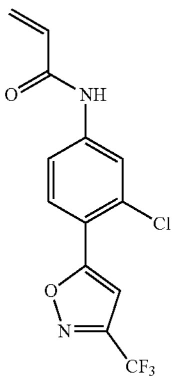 [SMILES: C=CC(=O)Nc1ccc(-c2cc(C(F)(F)F)no2)c(Cl)c1] |
TABLE 1-continued
| The TEAD inhibitor compounds in the present disclosure. | |
|---|---|
| Compound No. | Molecular Structure |
| Compound 33 | 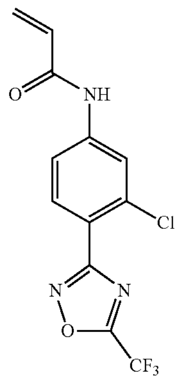 |
| Compound 34 | 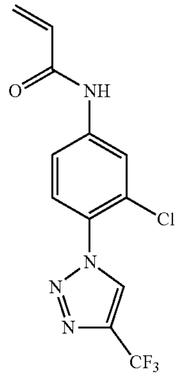 [SMILES: C=CC(=O)Nc1ccc(-n2cc(C(F)(F)F)nn2)c(Cl)c1] |
| Compound 35 | 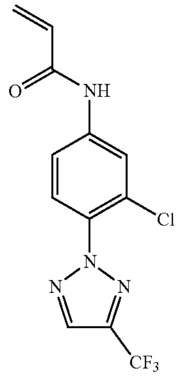 [SMILES: C=CC(=O)Nc1ccc(-n2ncc(C(F)(F)F)n2)c(Cl)c1] |
| Compound 36 | 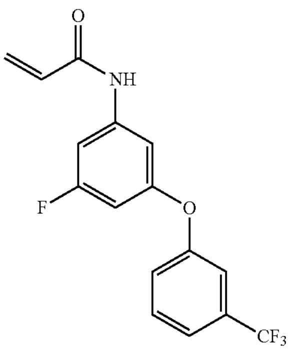 [SMILES: C=CC(=O)Nc1cc(F)cc(Oc2cccc(C(F)(F)F)c2)c1] |

TABLE 1-continued
| The TEAD inhibitor compounds in the present disclosure. | |
|---|---|
| Compound No. | Molecular Structure |
| Compound 37 | 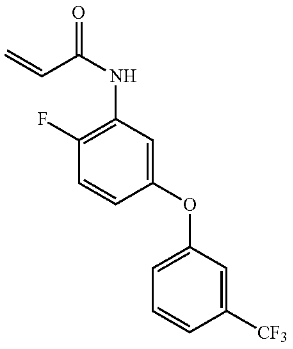 [SMILES: C=CC(=O)Nc1cc(Oc2cccc(C(F)(F)F)c2)ccc1F] |
| Compound 38 | 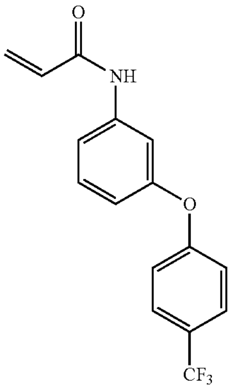 [SMILES: C=CC(=O)Nc1cccc(Oc2ccc(C(F)(F)F)cc2)c1] |
| Compound 39 | 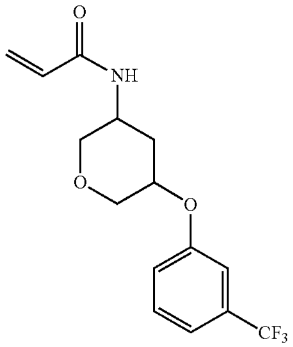 [SMILES: C=CC(=O)NC1COCC(Oc2cccc(C(F)(F)F)c2)C1] |
| Compound 40 | 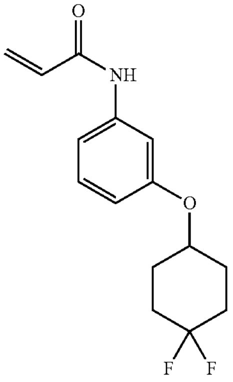 [SMILES: C=CC(=O)Nc1cccc(OC2CCC(F)(F)CC2)c1] |
TABLE 1-continued
| The TEAD inhibitor compounds in the present disclosure. | |
|---|---|
| Compound No. | Molecular Structure |
| Compound 41 | 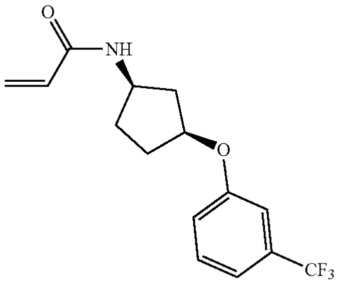 [SMILES: C=CC(=O)N[C@@H]1CC[C@H](Oc2cccc(C(F)(F)F)c2)C1] |
| Compound 42 | 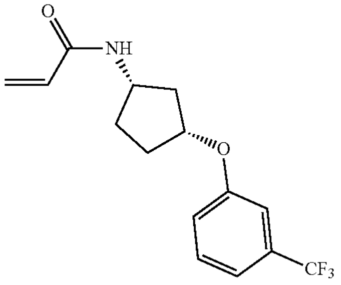 [SMILES: C=CC(=O)N[C@H]1CC[C@@H](Oc2cccc(C(F)(F)F)c2)C1] |
| Compound 43 | 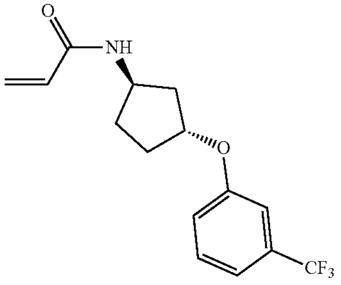 [SMILES: C=CC(=O)N[C@@H]1CC[C@@H](Oc2cccc(C(F)(F)F)c2)C1] |
| Compound 44 | 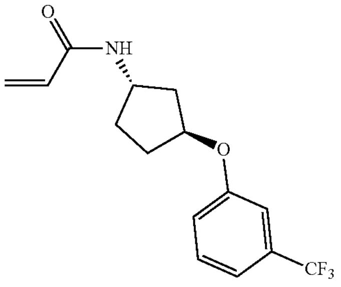 [SMILES: C=CC(=O)N[C@H]1CC[C@H](Oc2cccc(C(F)(F)F)c2)C1] |
| Compound 45 | 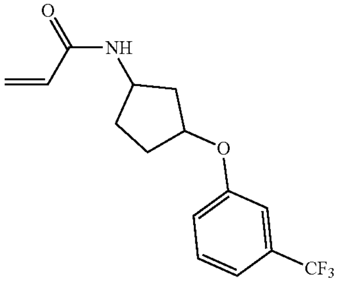 [SMILES: C=CC(=O)NC1CCC(Oc2cccc(C(F)(F)F)c2)C1] |

TABLE 1-continued
| The TEAD inhibitor compounds in the present disclosure. | |
|---|---|
| Compound No. | Molecular Structure |
| Compound 46 | 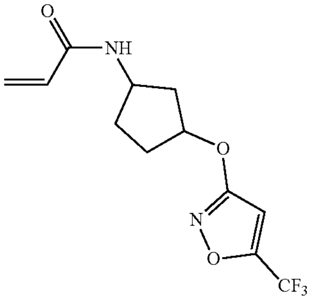 [SMILES: C=CC(=O)NC1CCC(Oc2cc(C(F)(F)F)on2)C1] |
| Compound 47 | 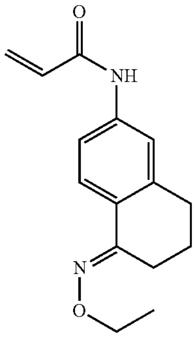 [SMILES: C=CC(=O)Nc1ccc2c(c1)CCC/C2=N\OCC] |
| Compound 48 | 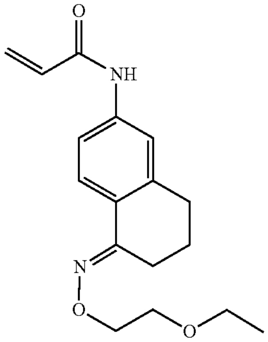 [SMILES: C=CC(=O)Nc1ccc2c(c1)CCC/C2=N\OCCOCC] |
| Compound 49 | 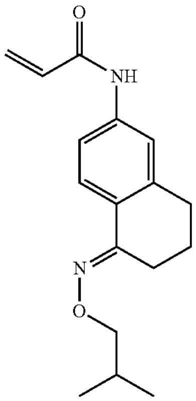 [SMILES: C=CC(=O)Nc1ccc2c(c1)CCC/C2=N\OCC(C)C] |
TABLE 1-continued
| The TEAD inhibitor compounds in the present disclosure. | |
|---|---|
| Compound No. | Molecular Structure |
| Compound 50 | 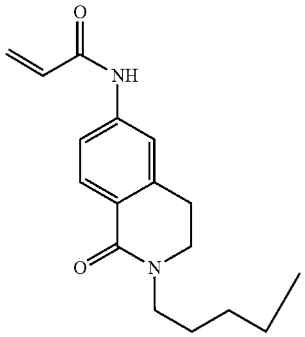 [SMILES: C=CC(=O)Nc1ccc2c(c1)CCN(CCCCC)C2=O] |
| Compound 51 | 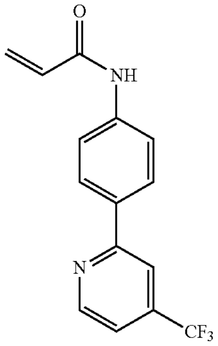 [SMILES: C=CC(=O)Nc1ccc(-c2cc(C(F)(F)F)ccn2)cc1] |
| Compound 52 | 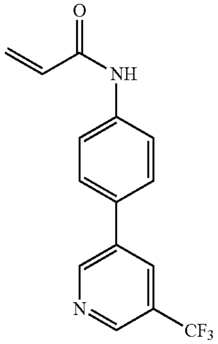 [SMILES: C=CC(=O)Nc1ccc(-c2cncc(C(F)(F)F)c2)cc1] |
| Compound 53 | 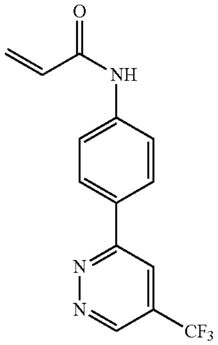 [SMILES: C=CC(=O)Nc1ccc(-c2cc(C(F)(F)F)cnn2)cc1] |

TABLE 1-continued

| The TEAD inhibitor compounds in the present disclosure. | |
|---|---|
| Compound No. | Molecular Structure |
| Compound 54 | 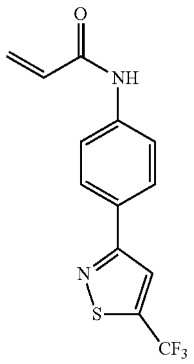 [SMILES: C=CC(=O)Nc1ccc(-c2cc(C(F)(F)F)sn2)cc1] |
| Compound 55 | 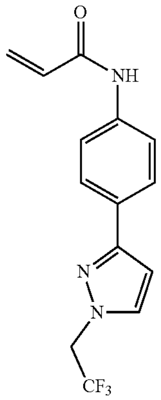 [SMILES: C=CC(=O)Nc1ccc(-c2ccn(CC(F)(F)F)n2)cc1] |
| Compound 56 | 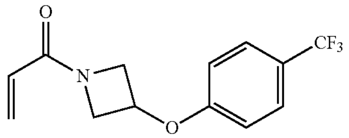 [SMILES: C=CC(=O)N1CC(Oc2ccc(C(F)(F)F)cc2)C1] |
| Compound 57 | 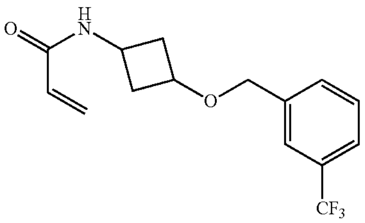 [SMILES: C=CC(=O)NC1CC(OCc2cccc(C(F)(F)F)c2)C1] |
| Compound 58 | 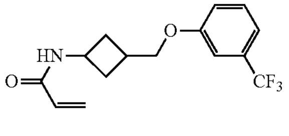 [SMILES: C=CC(=O)NC1CC(COc2cccc(C(F)(F)F)c2)C1] |
| Compound 59 | 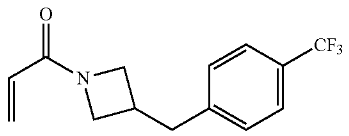 [SMILES: C=CC(=O)N1CC(Cc2ccc(C(F)(F)F)cc2)C1] |

TABLE 1-continued

| The TEAD inhibitor compounds in the present disclosure. | |
|---|---|
| Compound No. | Molecular Structure |
| Compound 60 | 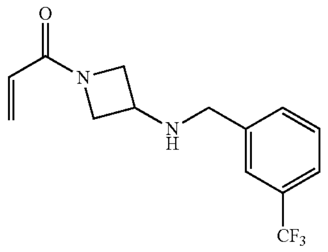 [SMILES: C=CC(=O)N1CC(NCc2cccc(C(F)(F)F)c2)C1] |
| Compound 61 | 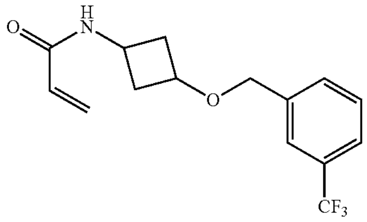 [SMILES: C=CC(=O)NC1CC(OCc2cccc(C(F)(F)F)c2)C1] |
| Compound 62 | 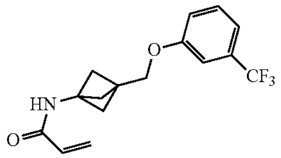 [SMILES: C=CC(=O)NC12CC(COc3cccc(C(F)(F)F)c3)(C1)C2] |
| Compound 63 | 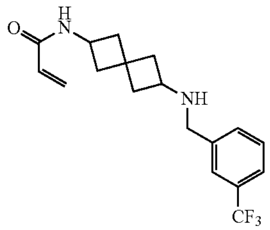 [SMILES: C=CC(=O)NC1CC2(CC(NCc3cccc(C(F)(F)F)c3)C2)C1] |
| Compound 64 | 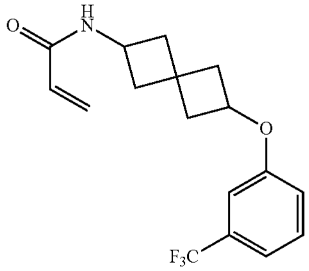 [SMILES: C=CC(=O)NC1CC2(C1)CC(Oc1cccc(C(F)(F)F)c1)C2] |
| Compound 65 | 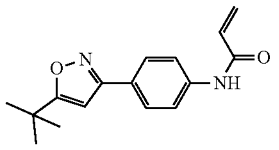 [SMILES: C=CC(=O)Nc1ccc(-c2cc(C(C)(C)C)on2)cc1] |

The term "treatment" is used interchangeably herein with the term "therapeutic method" and refers to both 1) therapeutic treatments or measures that cure, slow down, lessen symptoms of, and/or halt progression of a diagnosed pathologic conditions, disease or disorder, and 2) and prophylactic/preventative measures. Those in need of treatment may include individuals already having a particular medical disease or disorder as well as those who may ultimately acquire the disorder (i.e., those needing preventive measures).

The term "subject" as used herein refers to any individual or patient to which the subject methods are performed. Generally, the subject is human, although as will be appreciated by those in the art, the subject may be an animal.

The terms "therapeutically effective amount", "effective dose", "therapeutically effective dose", "effective amount," or the like refer to the amount of a subject compound that will elicit the biological or medical response in a tissue, system, animal or human that is being sought by administering said compound. Generally, the response is either amelioration of symptoms in a patient or a desired biological outcome. Such amount should be sufficient to inhibit TEAD1 activity.

Also disclosed herein are pharmaceutical compositions including compounds with the structures of Formula (I), Formula (II), Formula (III), Formula (IV), Formula (V), Formula (VI), or Formula (VII). The term "pharmaceutically acceptable carrier" refers to a non-toxic carrier that may be administered to a patient, together with a compound of this disclosure, and which does not destroy the pharmacological activity thereof. Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable carriers that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as α-tocopherol, polyethyleneglycol 1000 succinate, or other similar polymeric delivery matrices.

In pharmaceutical composition comprising only the compounds described herein as the active component, methods for administering these compositions may additionally comprise the step of administering to the subject an additional agent or therapy. Such therapies include, but are not limited to, an anemia therapy, a diabetes therapy, a hypertension therapy, a cholesterol therapy, neuropharmacologic drugs, drugs modulating cardiovascular function, drugs modulating inflammation, immune function, production of blood cells; hormones and antagonists, drugs affecting gastrointestinal function, chemotherapeutics of microbial diseases, and/or chemotherapeutics of neoplastic disease. Other pharmacological therapies can include any other drug or biologic found in any drug class. For example, other drug classes can comprise allergy/cold/ENT therapies, analgesics, anesthetics, anti-inflammatories, antimicrobials, antivirals, asthma/pulmonary therapies, cardiovascular therapies, dermatology therapies, endocrine/metabolic therapies, gastrointestinal therapies, cancer therapies, immunology therapies, neurologic therapies, ophthalmic therapies, psychiatric therapies or rheumatologic therapies. Other examples of agents or therapies that can be administered with the compounds described herein include a matrix metalloprotease inhibitor, a lipoxygenase inhibitor, a cytokine antagonist, an immunosuppressant, a cytokine, a growth factor, an immunomodulator, a prostaglandin or an anti-vascular hyperproliferation compound.

The term "therapeutically effective amount" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following: (1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

The compounds of this disclosure may be employed in a conventional manner for controlling the disease described herein, including, but not limited to, cancer. Such methods of treatment, their dosage levels and requirements may be selected by those of ordinary skill in the art from available methods and techniques. For example, the compounds of this disclosure may be combined with a pharmaceutically acceptable adjuvant for administration to a patient suffering from cancer in a pharmaceutically acceptable manner and in an amount effective to treat cancer.

Alternatively, the compounds of this disclosure may be used in compositions and methods for treating or protecting individuals against the diseases described herein, including but not limited to a cancer, over extended periods of time. The compounds may be employed in such compositions either alone or together with other compounds of this disclosure in a manner consistent with the conventional utilization of such compounds in pharmaceutical compositions. For example, a compound of this disclosure may be combined with pharmaceutically acceptable adjuvants conventionally employed in vaccines and administered in prophylactically effective amounts to protect individuals over an extended period of time against the diseases described herein, including, but not limited to, cancer.

As used herein, the terms "combination," "combined," and related terms refer to the simultaneous or sequential administration of therapeutic agents in accordance with this disclosure. For example, a described compound may be administered with another therapeutic agent simultaneously or sequentially in separate unit dosage forms or together in a single unit dosage form. Accordingly, the present disclosure provides a single unit dosage form comprising a described compound, an additional therapeutic agent, and a pharmaceutically acceptable carrier, adjuvant, or vehicle. Two or more agents are typically considered to be administered "in combination" when a patient or individual is simultaneously exposed to both agents. In many embodiments, two or more agents are considered to be administered "in combination" when a patient or individual simultaneously shows therapeutically relevant levels of the agents in a particular target tissue or sample (e.g., in brain, in serum, etc.).

When the compounds of this disclosure are administered in combination therapies with other agents, they may be administered sequentially or concurrently to the patient. Alternatively, pharmaceutical or prophylactic compositions according to this disclosure comprise a combination of ivermectin, or any other compound described herein, and another therapeutic or prophylactic agent. Additional therapeutic agents that are normally administered to treat a particular disease or condition may be referred to as "agents appropriate for the disease, or condition, being treated."

The compounds utilized in the compositions and methods of this disclosure may also be modified by appending appropriate functionalities to enhance selective biological properties. Such modifications are known in the art and include those, which increase biological penetration into a given biological system (e.g., blood, lymphatic system, or central nervous system), increase oral availability, increase solubility to allow administration by injection, alter metabolism and/or alter rate of excretion.

According to a preferred embodiment, the compositions of this disclosure are formulated for pharmaceutical administration to a subject or patient, e.g., a mammal, preferably a human being. Such pharmaceutical compositions are used to ameliorate, treat or prevent any of the diseases described herein including but not limited to cancer in a subject.

Agents of the disclosure are often administered as pharmaceutical compositions comprising an active therapeutic agent, i.e., and a variety of other pharmaceutically acceptable components. See Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In some embodiments, the present disclosure provides pharmaceutically acceptable compositions comprising a therapeutically effective amount of one or more of a described compound, formulated together with one or more pharmaceutically acceptable carriers (additives) and/or diluents for use in treating the diseases described herein, including, but not limited to cancer. While it is possible for a described compound to be administered alone, it is preferable to administer a described compound as a pharmaceutical formulation (composition) as described herein. Described compounds may be formulated for administration in any convenient way for use in human or veterinary medicine, by analogy with other pharmaceuticals.

As described in detail, pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations for use in accordance with the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient, which can be combined with a carrier material, to produce a single dosage form will vary depending upon the host being treated, and the particular mode of administration. The amount of active ingredient that can be combined with a carrier material to produce a single dosage form will generally be that amount of the compound, which produces a therapeutic effect. Generally, this amount will range from about 1% to about 99% of active ingredient. In some embodiments, this amount will range from about 5% to about 70%, from about 10% to about 50%, or from about 20% to about 40%.

In certain embodiments, a formulation as described herein comprises an excipient selected from the group consisting of cyclodextrins, liposomes, micelle forming agents, e.g., bile acids, and polymeric carriers, e.g., polyesters and polyanhydrides; and a compound of the present disclosure. In certain embodiments, an aforementioned formulation renders orally bioavailable a described compound of the present disclosure.

Methods of preparing formulations or compositions comprising described compounds include a step of bringing into association a compound of the present disclosure with the carrier and, optionally, one or more accessory ingredients. In general, formulations may be prepared by uniformly and intimately bringing into association a compound of the present disclosure with liquid carriers, or finely divided solid carriers, or both, and then, if necessary, shaping the product.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In some cases, in order to prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the described compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

The pharmaceutical compositions of this disclosure may be orally administered in any orally acceptable dosage form including, but not limited to, capsules, tablets, and aqueous suspensions and solutions. In the case of tablets for oral use, carriers, which are commonly used include lactose and corn starch. Lubricating agents, such as magnesium stearate, are also typically added. For oral administration in a capsule form, useful diluents include lactose and dried cornstarch. When aqueous suspensions and solutions and propylene glycol are administered orally, the active ingredient is combined with emulsifying and suspending agents. If desired, certain sweetening and/or flavoring and/or coloring agents may be added.

Formulations described herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compounds described herein may also be administered as a bolus, electuary or paste.

In solid dosage forms for oral administration (capsules, tablets, pills, dragees, powders, granules and the like), an active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Tablets may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent. If a solid carrier is used, the preparation can be in tablet form, placed in a hard gelatin capsule in powder or pellet form, or in the form of a troche or lozenge. The amount of solid carrier will vary, e.g., from about 25 to 800 mg, preferably about 25 mg to 400 mg. When a liquid carrier is used, the preparation can be, e.g., in the form of a syrup, emulsion, soft gelatin capsule, sterile injectable liquid such as an ampule or nonaqueous liquid suspension. Where the composition is in the form of a capsule, any routine encapsulation is suitable, for example, using the aforementioned carriers in a hard gelatin capsule shell.

Tablets and other solid dosage forms, such as dragees, capsules, pills and granules, may optionally be scored or prepared with coatings and shells, such as enteric coatings and other coatings well known in the pharmaceutical-formulating art. They may alternatively or additionally be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral compositions can also include adjuvants such as wetting agents, emulsifying and suspending agents, sweetening, flavoring, coloring, perfuming and preservative agents.

Suspensions, in addition to active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The pharmaceutical compositions of this disclosure may also be administered in the form of suppositories for rectal administration. These compositions can be prepared by mixing a compound of this disclosure with a suitable non-irritating excipient, which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this disclosure is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate-60, cetyl esters wax, cetearyl alcohol, 2-octyldodecanol, benzyl alcohol and water. The pharmaceutical compositions of this disclosure may also be topically applied to the lower intestinal tract by rectal suppository formulation or in a suitable enema formulation. Topically-administered transdermal patches are also included in this disclosure.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

Transdermal patches have the added advantage of providing controlled delivery of a compound of the present disclosure to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Examples of suitable aqueous and nonaqueous carriers, which may be employed in the pharmaceutical compositions of the disclosure, include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Such compositions may also contain adjuvants such as preservatives, wetting agents, emulsifying agents and dispersing agents. Inclusion of one or more antibacterial and/or antifungal agents, for example, paraben, chlorobutanol, phenol sorbic acid, and the like, may be desirable in certain embodiments. It may alternatively or additionally be desirable to include isotonic agents, such as sugars, sodium chloride, and the like into the compositions. In addition, prolonged absorption of the injectable pharmaceutical form may be brought about by the inclusion of agents, which delay absorption such as aluminum monostearate and gelatin.

In certain embodiments, a described compound or pharmaceutical preparation is administered orally. In other embodiments, a described compound or pharmaceutical preparation is administered intravenously. Alternative routes of administration include sublingual, intramuscular, and transdermal administrations.

When compounds described herein are administered as pharmaceuticals, to humans and animals, they can be given per se or as a pharmaceutical composition containing, for example, 0.10% to 99.5% of active ingredient in combination with a pharmaceutically acceptable carrier. In some embodiments, 0.5% to 90% of active ingredient can be used.

Preparations described herein may be given orally, parenterally, topically, or rectally. They are of course given in forms suitable for the relevant administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

Such compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, compounds described herein which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of the disclosure may be varied so as to obtain an amount of the active ingredient that is effective to achieve the desired therapeutic response for a particular patient, composition, and mode of administration, without being toxic to the patient.

The terms “administration of” and or “administering” should be understood to mean providing a pharmaceutical composition in a therapeutically effective amount to the subject in need of treatment. Administration routes can be enteral, topical or parenteral. As such, administration routes include but are not limited to intracutaneous, subcutaneous, intravenous, intraperitoneal, intraarterial, intrathecal, intracapsular, intraorbital, intracardiac, intradermal, transdermal, transtracheal, subcuticular, intraarticulare, subcapsular, subarachnoid, intraspinal and intrasternal, oral, sublingual buccal, rectal, vaginal, nasal ocular administrations, as well infusion, inhalation, and nebulization.

The term “cancer” refers to a group diseases characterized by abnormal and uncontrolled cell proliferation starting at one site (primary site) with the potential to invade and to spread to others sites (secondary sites, metastases) which differentiate cancer (malignant tumor) from benign tumor. Virtually all the organs can be affected, leading to more than 100 types of cancer that can affect humans. Cancers can result from many causes including genetic predisposition, viral infection, exposure to ionizing radiation, exposure environmental pollutant, tobacco and or alcohol use, obesity, poor diet, lack of physical activity or any combination thereof.

Exemplary cancers described by the national cancer institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing’s Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin’s Lymphoma, Adult; Hodgkin’s Lymphoma, Childhood; Hodgkin’s Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi’s Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS—Related; Lymphoma, Central Nervous System (Primary); Lymphoma, Cutaneous T-Cell; Lymphoma, Hodgkin’s, Adult; Lymphoma, Hodgkin’s; Childhood; Lymphoma, Hodgkin’s During Pregnancy; Lymphoma, Non-Hodgkin’s, Adult; Lymphoma, Non-Hodgkin’s, Childhood; Lymphoma, Non-Hodgkin’s During Pregnancy; Lymphoma, Primary Central Nervous System; Macroglobulinemia, Waldenstrom’s; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplasia Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin’s Lymphoma, Adult; Non-Hodgkin’s Lymphoma, Childhood; Non-Hodgkin’s Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood’, Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin’s Lymphoma; Pregnancy and Non-Hodgkin’s Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland’Cancer, Childhood; Sarcoma, Ewing’s Family of Tumors; Sarcoma, Kaposi’s; Sarcoma (OsteosarcomaVMalignant Fibrous Histiocytoma of Bone; Sarcoma, Rhabdomyosarcoma, Childhood; Sarcoma, Soft Tissue, Adult; Sarcoma, Soft Tissue, Childhood;

Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

In certain aspects, cancer include Lung cancer, Breast cancer, Colorectal cancer, Prostate cancer, Stomach cancer, Liver cancer, cervical cancer, Esophageal cancer, Bladder cancer, Non-Hodgkin lymphoma, Leukemia, Pancreatic cancer, Kidney cancer, endometrial cancer, Head and neck cancer, Lip cancer, oral cancer, Thyroid cancer, Brain cancer, Ovary cancer, Melanoma, Gallbladder cancer, Laryngeal cancer, Multiple myeloma, Nasopharyngeal cancer, Hodgkin lymphoma, Testis cancer and Kaposi sarcoma.

The compounds of the disclosure can be administered in combination with one or more additional therapeutic agents. The phrases "combination therapy", "combined with" and the like refer to the use of more than one medication or treatment simultaneously to increase the response. The TEAD1 inhibitor of the present disclosure might for example be used in combination with other drugs or treatment in use to treat cancer. In various aspect, the compound is administered prior to, simultaneously with or following the administration of the chemotherapeutic agent. In some embodiments where the subject has a tumor, a compound of the invention and/or chemotherapeutic agent is administered following resection of the tumor.

The term "anti-cancer therapy" refers to any therapy or treatment that can be used for the treatment of a cancer. Anti-cancer therapies include, but are not limited to, small molecule or big molecule therapies, surgery, radiotherapy, chemotherapy, immune therapy and targeted therapies.

Examples of chemotherapeutic agents or anti-cancer agents include, but are not limited to, Actinomycin, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fiuorouracil, Gemcitabine, Hydroxyurea, Idarubicin, Imatinib, lrinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, Vinorelbine, panitumamab, Erbitux (cetuximab), matuzumab, IMC-IIF 8, TheraCIM hR3, denosumab, Avastin (bevacizumab), Humira (adalimumab), Herceptin (trastuzumab), Remicade (infliximab), rituximab, Synagis (palivizumab), Mylotarg (gemtuzumab oxogamicin), Raptiva (efalizumab), Tysabri (natalizumab), Zenapax (dacliximab), NeutroSpec (Technetium (99mTc) fanolesomab), tocilizumab, ProstaScint (Indium-Ill labeled Capromab Pendetide), Bexxar (tositumomab), Zevalin (ibritumomab tiuxetan (IDEC-Y2B8) conjugated to yttrium 90), Xolair (omalizumab), MabThera (Rituximab), ReoPro (abciximab), MabCampath (alemtuzumab), Simulect (basiliximab), LeukoScan (sulesomab), CEA-Scan (arcitumomab), Verluma (nofetumomab), Panorex (Edrecolomab), alemtuzumab, CDP 870, natalizumab Gilotrif (afatinib), Lynparza (olaparib), Perjeta (pertuzumab), Otdivo (nivolumab), Bosulif (bosutinib), Cabometyx (cabozantinib), Ogivri (trastuzumab-dkst), Sutent (sunitinib malate), Adcetris (brentuximab vedotin), Alecensa (alectinib), Calquence (acalabrutinib), Yescarta (ciloleucel), Verzenio (abemaciclib), Keytruda (pembrolizumab), Aliqopa (copanlisib), Nerlynx (neratinib), Imfinzi (durvalumab), Darzalex (daratumumab), Tecentriq (atezolizumab), and Tarceva (erlotinib). Examples of immunotherapeutic agent include, but are not limited to, interleukins (Il-2, Il-7, Il-12), cytokines (Interferons, G-CSF, imiquimod), chemokines (CCL3, CCl26, CXCL7), immunomodulatory imide drugs (thalidomide and its analogues).

In one aspect, the disclosure provides a method of inhibiting TEAD1 in a subject comprising administering a compound of Formula (I), Formula (II), Formula (III), Formula (IV), or Formula (V), or an optically pure stereoisomer, pharmaceutically acceptable salt, or solvate thereof. In certain aspects, the compound is at least one of the compounds as shown in Table 1 or an optically pure stereoisomer, pharmaceutically acceptable salt, or solvate thereof.

In another aspect, the present disclosure is directed to the use of compounds of Formula (I), Formula (II), Formula (III), Formula (IV), or Formula (V), or an optically pure stereoisomer, pharmaceutically acceptable salt, or solvate thereof in the treatment of any cancer indication where YAP is localized in the nucleus of the tumor cells, including, but is not limited to, lung, thyroid, ovarian, colorectal, prostate, pancreas, esophagus, liver, breast, and skin cancer.

In still another aspect, the disclosed compounds or pharmaceutical composition thereof can disrupt YAP interactions with TEAD. In certain aspects, the disclosed compounds or pharmaceutical composition thereof can prevent YAP from binding to TEAD. In some aspects, the disclosed compounds or pharmaceutical composition thereof can compete with YAP for binding to TEAD. In some aspects, the disclosed compounds or pharmaceutical composition thereof can bind to TEAD. In some aspects, the disclosed compounds or pharmaceutical composition thereof can bind to TEAD1.

By "pharmaceutically acceptable" it is meant the carrier, diluent or excipient must be compatible with the other ingredients of the formulation and not deleterious to the recipient thereof. For example, the carrier, diluent, or excipient or composition thereof may be administered to a subject along with a TEAD inhibitor of the disclosure without causing any undesirable biological effects or interacting in an undesirable manner with the TEAD inhibitor of the pharmaceutical composition in which it is contained.

In treatment, the dose of agent optionally ranges from about 0.0001 mg/kg to 100 mg/kg, about 0.01 mg/kg to 5 mg/kg, about 0.15 mg/kg to 3 mg/kg, 0.5 mg/kg to 2 mg/kg and about 1 mg/kg to 2 mg/kg of the subject's body weight. In other embodiments the dose ranges from about 100 mg/kg to 5 g/kg, about 500 mg/kg to 2 mg/kg and about 750 mg/kg to 1.5 g/kg of the subject's body weight. For example, depending on the type and severity of the disease, about 1 μg/kg to 15 mg/kg (e.g., 0.1-20 mg/kg) of agent is a candidate dosage for administration to the patient, whether, for example, by one or more separate administrations, or by continuous infusion. A typical daily dosage is in the range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. Unit doses can be in the range, for instance of about 5 mg to 500 mg, such as 50 mg, 100 mg, 150 mg, 200 mg, 250 mg and 300 mg. The progress of therapy is monitored by conventional techniques and assays.

In some embodiments, an agent is administered to a human patient at an effective amount (or dose) of less than about 1 μg/kg, for instance, about 0.35 to 0.75 μg/kg or about 0.40 to 0.60 μg/kg. In some embodiments, the dose of an agent is about 0.35 μg/kg, or about 0.40 μg/kg, or about 0.45 μg/kg, or about 0.50 μg/kg, or about 0.55 μg/kg, or about 0.60 μg/kg, or about 0.65 μg/kg, or about 0.70 μg/kg, or about 0.75 μg/kg, or about 0.80 μg/kg, or about 0.85 μg/kg, or about 0.90 μg/kg, or about 0.95 μg/kg or about 1 μg/kg. In various embodiments, the absolute dose of an agent is about 2 μg/subject to 45 μg/subject, or about 5 to 40, or about 10 to 30, or about 15 to 25 μg/subject. In some embodiments, the absolute dose of an agent is about 20 μg, or about 30 μg, or about 40 μg.

In various embodiments, the dose of an agent may be determined by the human patient's body weight. For example, an absolute dose of an agent of about 2 μg for a pediatric human patient of about 0 to 5 kg (e.g. about 0, or about 1, or about 2, or about 3, or about 4, or about 5 kg); or about 3 μg for a pediatric human patient of about 6 to 8 kg (e.g. about 6, or about 7, or about 8 kg), or about 5 μg for a pediatric human patient of about 9 to 13 kg (e.g. 9, or about 10, or about 11, or about 12, or about 13 kg); or about 8 μg for a pediatric human patient of about 14 to about 20 kg (e.g. about 14, or about 16, or about 18, or about 20 kg), or about 12 μg for a pediatric human patient of about 21 to about 30 kg (e.g. about 21, or about 23, or about 25, or about 27, or about 30 kg), or about 13 μg for a pediatric human patient of about 31 to about 33 kg (e.g. about 31, or about 32, or about 33 kg), or about 20 μg for an adult human patient of about 34 to about 50 kg (e.g. about 34, or about 36, or about 38, or about 40, or about 42, or about 44, or about 46, or about 48, or about 50 kg), or about 30 μg for an adult human patient of about 51 to about 75 kg (e.g. about 51, or about 55, or about 60, or about 65, or about 70, or about 75 kg), or about 45 μg for an adult human patient of greater than about 114 kg (e.g. about 114, or about 120, or about 130, or about 140, or about 150 kg).

In certain embodiments, an agent in accordance with the methods provided herein is administered subcutaneously (s.c.), intravenously (i.v.), intramuscularly (i.m.), intranasally or topically. Administration of an agent described herein can, independently, be one to four times daily or one to four times per month or one to six times per year or once every two, three, four or five years. Administration can be for the duration of one day or one month, two months, three months, six months, one year, two years, three years, and may even be for the life of the human patient. The dosage may be administered as a single dose or divided into multiple doses. In some embodiments, an agent is administered about 1 to 3 times (e.g. 1, or 2 or 3 times).

Presented below are examples discussing synthesis and characterization of TEAD1 inhibitors contemplated for the discussed applications. The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

Example 1

Synthesis of Compound 1

Scheme 3. Synthesis of compound 1

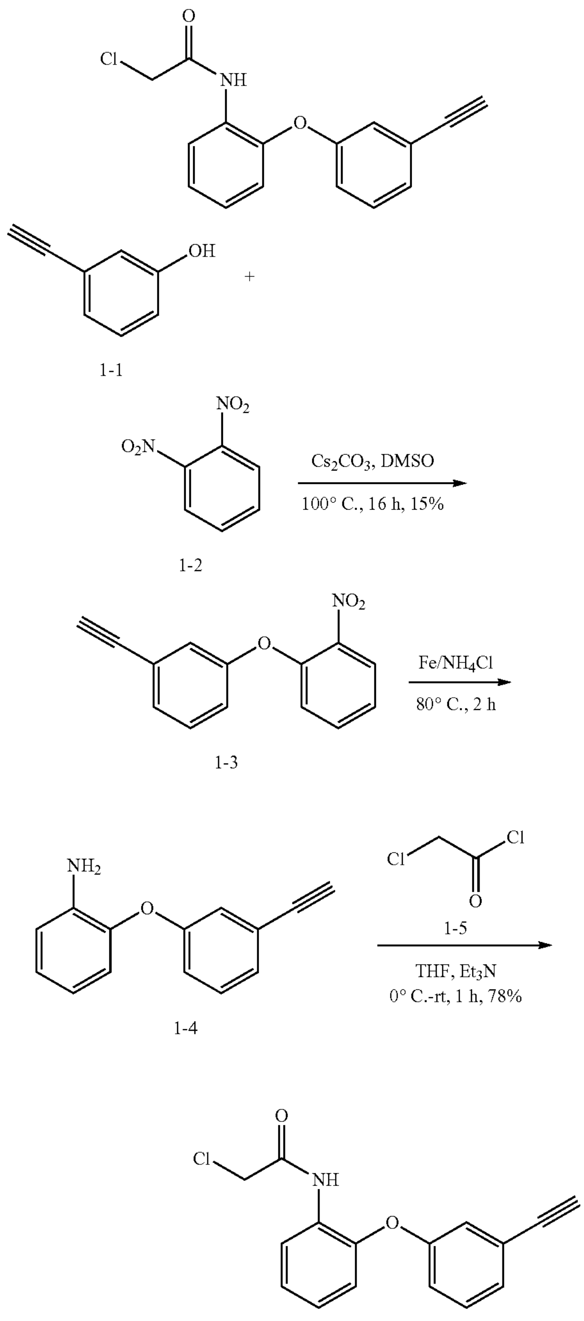

compound 1

Compound 1 was synthesized based on synthetic scheme 3. The synthetic process for each of the step is described as below.

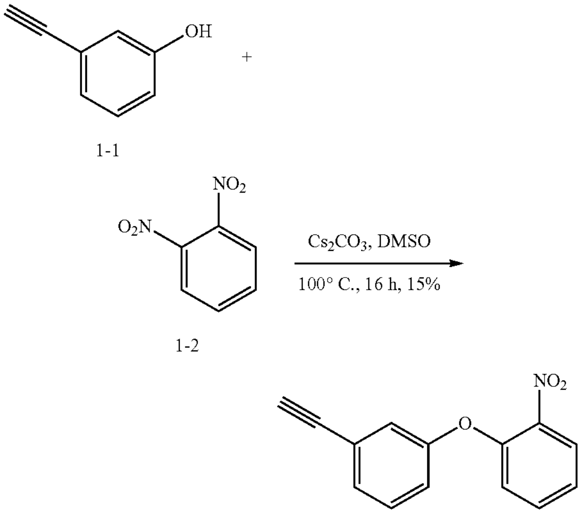

1-1

1-2

1-3

The mixture of compound 1-1 (1.5 g, 12.7 mmol, 1.42 eq), compound 1-2 (1.5 g, 8.9 mmol, 1.0 eq) and cesium carbonate (5.8 g, 17.8 mmol, 2.0 eq) in dimethyl sulfoxide (15 mL) was stirred at 100° C. for 16 h in sealed tube. The reaction was monitored by thin layer chromatography (TLC). The result mixture was added water and extracted with ethyl acetate (15 mL×3). The combined organics were washed with brine, dried over anhydrous sodium sulfate and concentrated under reduced pressure. The residue was purified by prep-TLC (petroleum ether:ethyl acetate, 3:1) to give the compound 1-3 (310 mg, 15%). TLC: petroleum ether: ethyl acetate=3:1, UV 254 nm; $R_f$: (1-2)=0.6; $R_f$: (1-3)=0.8.

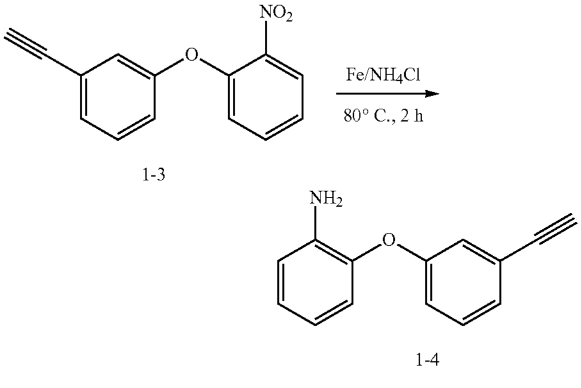

1-3

1-4

The mixture of compound 1-3 (310 mg, 1.30 mmol, 1.0 eq), Iron (363.0 mg, 6.5 mmol, 5.0 eq) and ammonium chloride (695.37 mg, 13.0 mmol, 10.0 eq) in etanol/water (8 mL/2 mL) was stirred at 80° C. for 2 h. TLC analysis of the reaction mixture showed partial conversion to the desired product. The result mixture was added water and extracted with ethyl acetate (10 mL×3). The combined organics were washed with brine, dried over anhydrous sodium sulfate and concentrated under reduced pressure. The residue was purified by prep-TLC (dichloromethane: methanol, 10:1) to give the compound 1-4 (310 mg, crude). TLC: petroleum ether: ethyl acetate=1:1, UV 254 nm; $R_f$: (1-3)=0.6; $R_f$: (1-4)=0.4.

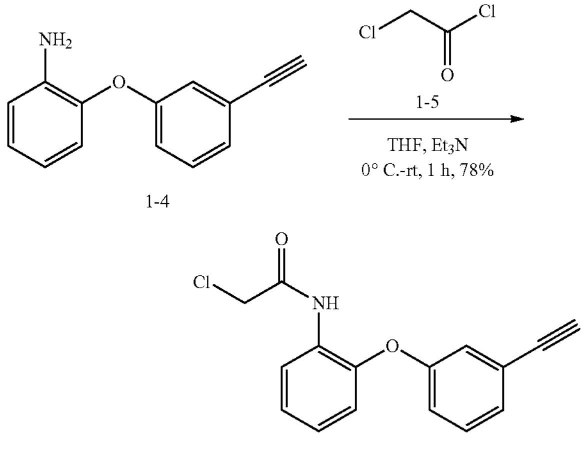

1-4

1-5 compound 1

Compound 1-4 (310 mg, 1.5 mmol, 1.0 eq) was dissolved in tetrahydrofuran (10 mL) and triethylamine (305 mg, 3 mmol, 2.0 eq) was added. The mixture stirred at 0° C. and compound 1-5 (272 mg, 3 mmol, 2.0 eq) was added drop wise. The mixture stirred at room temperature for 1 h. TLC analysis of the reaction mixture showed partial conversion to the desired product. The mixture was added ethyl acetate (20 mL) and water (40 mL), extracted and organic phase was washed by brine, dry by sodium sulfate, concentrated to give compound 1 (crude) and was added petroleum ether (10 mL), ethyl acetate (1 mL), stirred 10 min, filtered and the filter cake was dried to give compound 1 (333 mg, 78%) as off-white solid. LCMS: [M+1]=264; $^1H$ NMR (400 MHz, $CDCl_3$): δ 8.55-8.53 (m, 1H), 7.77 (s, 1H), 7.24 (m, 2H), 7.15 (m, 2H), 7.04-6.99 (m, 2H), 6.83 (m, 1H), 6.36 (m, 1H), 6.26-6.19 (m, 1H), 5.75-5.73 (d, J=10.0 Hz, 1H) and 3.08 (s, 1H).

Example 2

Synthesis of Compound 2

Scheme 4. Synthesis of compound 2

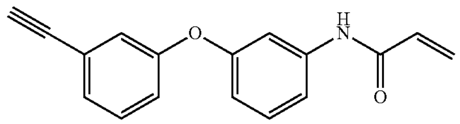

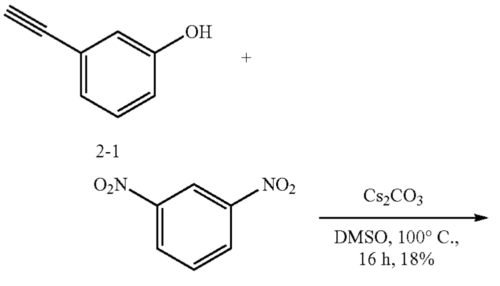

2-1

2-2

-continued

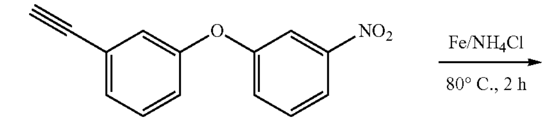

2-3

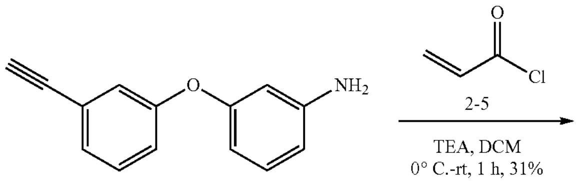

2-4

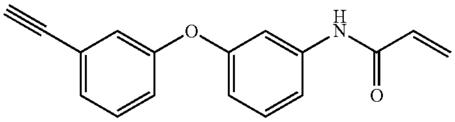

compound 2

Compound 2 was synthesized based on synthetic scheme 4. The synthetic process for each of the step is described as below.

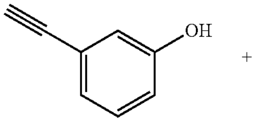

2-1

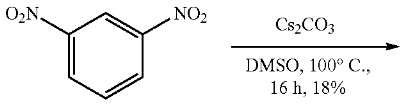

2-2

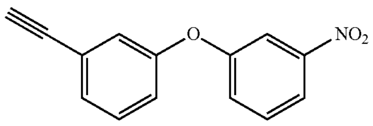

2-3

The mixture of compound 2-1 (500 mg, 4.24 mmol, 1.42 eq), compound 2-2 (500 mg, 2.98 mmol, 1.0 eq) and cesium carbonate (1.956 g, 6.0 mmol, 2.0 eq) in dimethyl sulfoxide (5 mL) was stirred at 100° C. for 16 h in sealed tube. The reaction was monitored by TLC. The result mixture was added water and extracted with ethyl acetate (5 mL×3). The combined organics were washed with brine, dried over anhydrous sodium sulfate and concentrated under reduced pressure. The residue was purified by prep-TLC (petroleum ether:ethyl acetate, 3:1) to give the compound 2-3 (130 mg, 18%). TLC: petroleum ether:ethyl acetate=3:1, UV 254 nm; $R_f$: (2-2)=0.6; $R_f$: (2-3)=0.8.

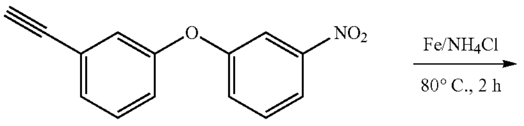

2-3

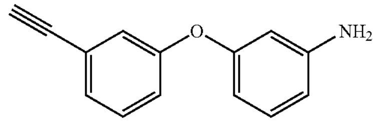

2-4

The mixture of compound 2-3 (130 mg, 0.54 mmol, 1.0 eq), Iron (151.89 mg, 2.72 mmol, 5.0 eq) and ammonium chloride (288.85 mg, 5.4 mmol, 10.0 eq) in etanol/water (4 mL/1 mL) was stirred at 80° C. for 2 h. TLC analysis of the reaction mixture showed partial conversion to the desired product. The result mixture was added water and extracted with ethyl acetate (5 mL×3). The combined organics were washed with brine, dried over anhydrous sodium sulfate and concentrated under reduced pressure. The residue was purified by prep-TLC (dichloromethane: methanol, 10:1) to give the compound 2-4 (130 mg, crude). TLC: petroleum ether: ethyl acetate=1:1, UV 254 nm; $R_f$: (2-3)=0.6; $R_f$: (2-4)=0.4.

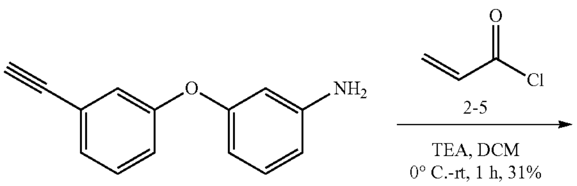

2-4

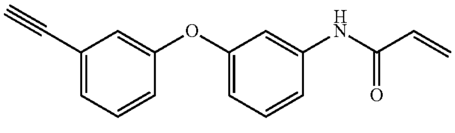

compound 2

Compound 2-4 (130 mg, 0.62 mmol, 1.0 eq) was dissolved in tetrahydrofuran (5 mL) and triethylamine (125.6 mg, 1.24 mmol, 2.0 eq) was added. The mixture stirred at 0° C. and compound 2-5 (111.6 mg, 1.24 mmol, 2.0 eq) was added drop wise. The mixture stirred at room temperature for 1 h. TLC analysis of the reaction mixture showed partial conversion to the desired product. The mixture was added ethyl acetate (5 mL) and water (10 mL), extracted and organic phase was washed by brine, dry by sodium sulfate, concentrated to give compound 2 (crude) and was added petroleum ether (10 mL), ethyl acetate (1 mL), stirred 10 min, filtered and the filter cake was dried to give compound 2 (51 mg, 31%) as colorless oil. LCMS: [M+1]=264; $^1$H NMR (400 MHz, DMSO): δ 10.22 (s, 1H), 7.40-7.30 (m, 4H), 7.24-7.22 (m, 1H), 7.05 (m, 2H), 6.74-6.72 (m, 1H), 6.32 (m, 1H), 6.22-6.18 (m, 1H), 5.74-5.71 (dd, J=10.0 Hz, 2.2 Hz, 1H) and 4.24 (s, 1H).

Example 3

Synthesis of Compound 3

Scheme 5. Sythesis of compound 3

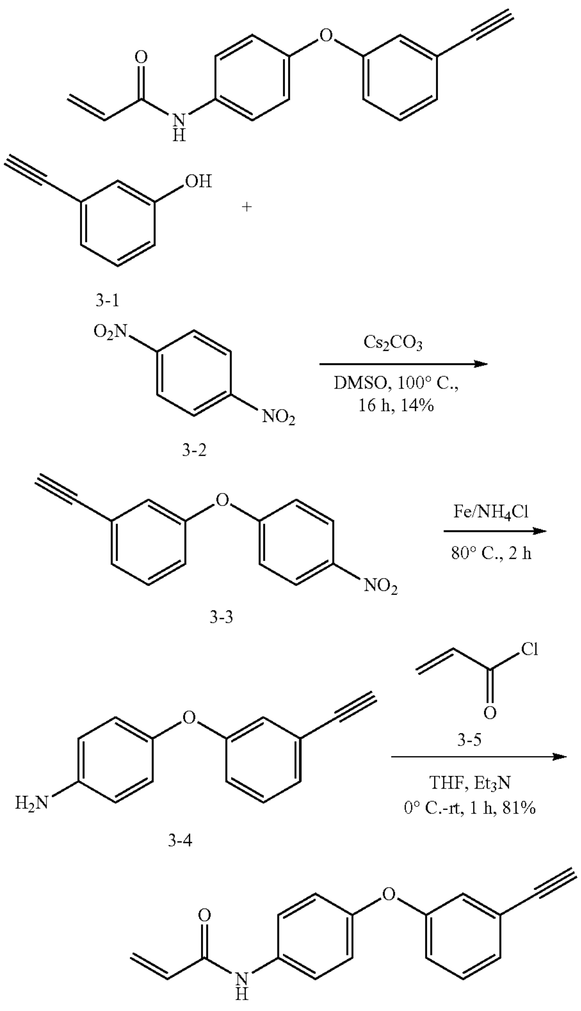

3-1, 3-2, 3-3, 3-4, compound 3

Compound 3 was synthesized based on synthetic scheme 5. The synthetic process for each of the step is described as below.

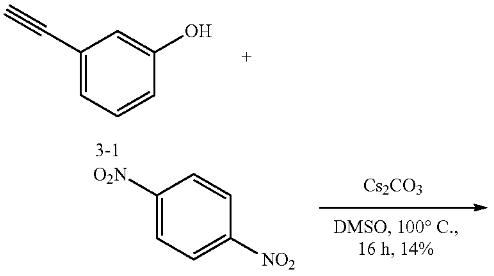

3-1, 3-2

-continued

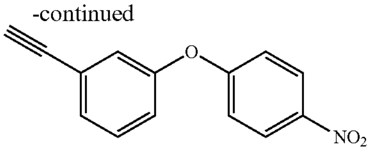

3-3

The mixture of compound 3-1 (421 mg, 3.57 mmol, 1.2 eq), compound 3-2 (500 mg, 2.98 mmol, 1.0 eq) and cesium carbonate (1.956 g, 6.0 mmol, 2.0 eq) in dimethyl sulfoxide (5 mL) was stirred at 100° C. for 16 h in sealed tube. The reaction was monitored by TLC. The result mixture was added water and extracted with ethyl acetate (5 mL×3). The combined organics were washed with brine, dried over anhydrous sodium sulfate and concentrated under reduced pressure. The residue was purified by prep-TLC (petroleum ether:ethyl acetate, 3:1) to give the compound 3-3 (100 mg, 14%). TLC: petroleum ether:ethyl acetate=3:1, UV 254 nm; $R_f$: (3-2)=0.6; $R_f$: (3-3)=0.8.

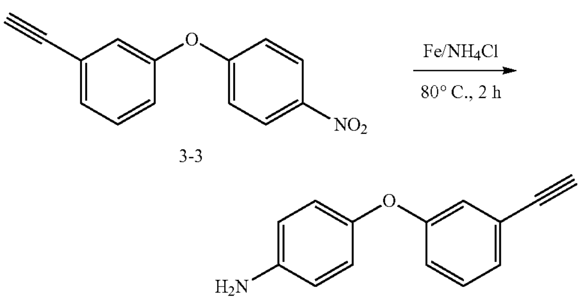

3-3, 3-4

The mixture of compound 3-3 (310 mg, 1.30 mmol 1.0 eq), Iron (363.0 mg, 6.5 mmol, 5.0 eq) and ammonium chloride (695.37 mg, 13.0 mmol, 10.0 eq) in etanol/water (8 mL/2 mL) was stirred at 80° C. for 2 h. TLC analysis of the reaction mixture showed partial conversion to the desired product. The result mixture was added water and extracted with ethyl acetate (10 mL×3). The combined organics were washed with brine, dried over anhydrous sodium sulfate and concentrated under reduced pressure. The residue was purified by prep-TLC (dichloromethane: methanol, 10:1) to give the compound 3-4 (313 mg, crude). TLC: petroleum ether: ethyl acetate=1:1, UV 254 nm; $R_f$: (3-3)=0.6; $R_f$: (3-4)=0.4.

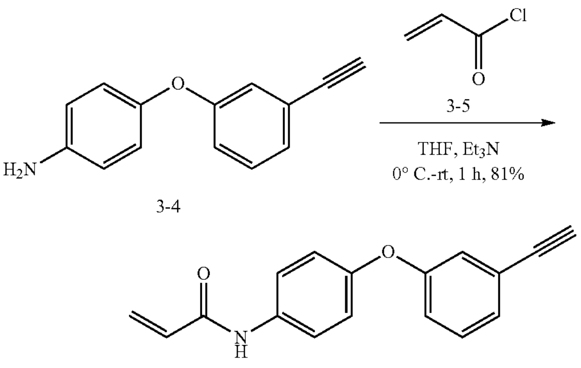

3-4, compound 3

Compound 3-4 (313 mg, 1.5 mmol, 1.0 eq) was dissolved in tetrahydrofuran (10 mL) and triethylamine (305 mg, 3 mmol, 2.0 eq) was added. The mixture stirred at 0° C. and compound 3-5 (272 mg, 3 mmol, 2.0 eq) was added drop wise. The mixture stirred at room temperature for 1 h. TLC analysis of the reaction mixture showed partial conversion to the desired product. The mixture was added ethyl acetate (20 mL) and water (40 mL), extracted and organic phase was washed by brine, dry by sodium sulfate, concentrated to give compound 3 (460 mg, crude) and was added petroleum ether (10 mL), ethyl acetate (1 mL), stirred 10 min, filtered and the filter cake was dried to give compound 3 (320 mg, 81%) as off-white solid. LCMS: [M+1]=264; $^{1}H$ NMR (400 MHz, DMSO): δ 10.16 (s, 1H), 7.69-7.66 (d, J=9.2 Hz, 2H), 7.34 (m, 1H), 7.20 (m, 1H), 7.02-6.95 (m, 4H), 6.40-6.36 (m, 1H), 6.24-6.20 (m, 1H), 5.74-5.71 (dd, J=10.4 Hz, 2.2 Hz, 1H) and 4.19 (s, 1H).

Example 4

Synthesis of Compound 4

Scheme 6. Synthesis of compound 4

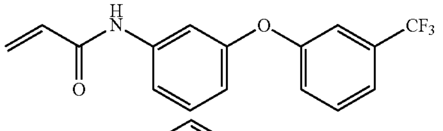

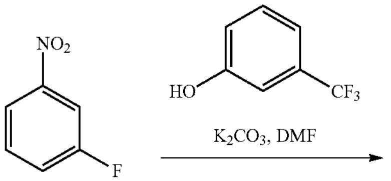

4-1

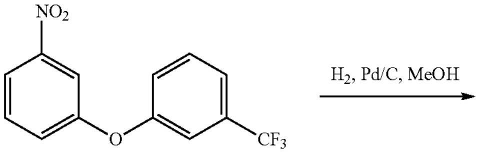

4-2

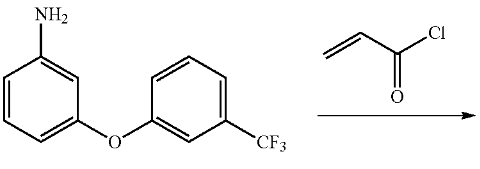

4-3

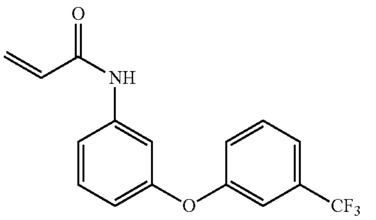

compound 4

Compound 4 was synthesized based on synthetic scheme 6. The synthetic process for each of the step is described as below.

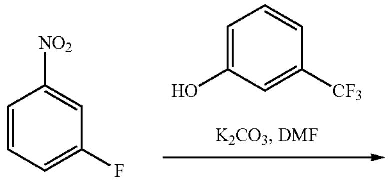

4-1

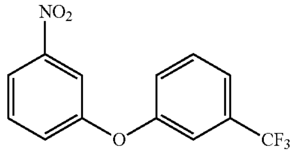

4-2

To a solution of 1-fluoro-3-nitrobenzene (compound 4-1, 500 mg, 3.54 mmol) in DMF (15 mL) was added 3-(trifluoromethyl)phenol (746.78 mg, 4.60 mmol) and $K_2CO_3$ (980.20 mg, 7.09 mmol), the reaction was stirred at 160° C. for 16 h under $N_2$ atmosphere. The reaction was diluted with water (35 mL) and extracted with EA (3*15 mL). The combined organic layers were washed with brine (15 mL) twice, dried over sodium sulfate, filtered and concentrated. The residue was purified by silica gel chromatography (petroleum ether/ethyl acetate=1%) to afford 1-nitro-3-(3-(trifluoromethyl)phenoxy)benzene (compound 4-2, 500 mg, 50% yield) as a yellow oil. $^{1}H$ NMR (400 MHz, CDCl3) δ 8.02 (ddd, J=8.2, 2.1, 0.9 Hz, 1H), 7.85 (t, J=2.3 Hz, 1H), 7.56 (td, J=8.1, 4.6 Hz, 2H), 7.48 (d, J=7.8 Hz, 1H), 7.37 (ddd, J=8.2, 2.4, 0.9 Hz, 1H), 7.33 (s, 1H), 7.28-7.23 (m, 1H).

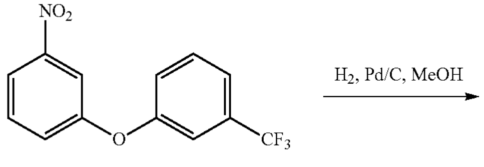

4-2

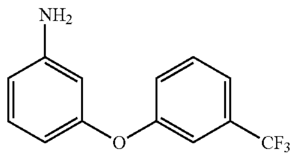

4-3

The suspension of 1-nitro-3-[3-(trifluoromethyl)phenoxy]benzene (compound 4-2, 500 mg, 1.76 mmol) and pd/C (100 mg, 50% water of wet) in MeOH (15 mL) was degassed and purge with H2 several times, the reaction was stirred at r.t for 4 h. The reaction was filtered, the filtrate was concentrated to obtained 3-(3-(trifluoromethyl)phenoxy)aniline (compound 4-3, 380 mg, 85% yield) as a white oil. Mass Spectrum (ESI) m/z=253.8 (M+1).

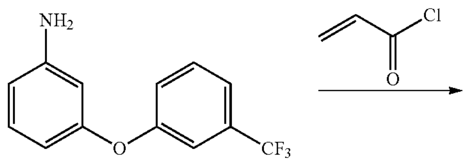

4-3

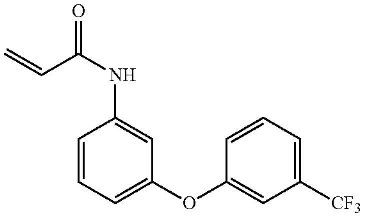

compound 4

At 0° C., to a solution of 3-[3-(trifluoromethyl)phenoxy] aniline (compound 4-3, 380 mg, 1.50 mmol) in NMP (10 mL) was added prop-2-enoyl chloride (135.8 mg, 1.50 mmol), the reaction was stirred at r.t for 12 hours. The reaction was diluted with water and extracted with ethyl acetate (EA). The combined organic layers were washed with brine, dried over sodium sulfate, filtered and concentrated. The residue was purified by silica gel chromatography (ethyl acetate/petroleum ether=10%) to afford compound 4 (59 mg, 13% yield) as a white solid. Mass Spectrum (ESI) m/z=307.8 (M+1). $^{1}$H NMR (400 MHz, $CDCl_3$) δ ppm 7.48-7.29 (m, 6H), 7.25 (s, 1H), 7.17 (dd, J=8.1, 2.0 Hz, 1H), 6.82-6.74 (m, 1H), 6.43 (dd, J=16.8, 1.1 Hz, 1H), 6.23 (dd, J=16.8, 10.2 Hz, 1H), 5.78 (dd, J=10.2, 1.1 Hz, 1H).

Example 5

Synthesis of Compound 5

Scheme 7. Synthesis of compound 5.

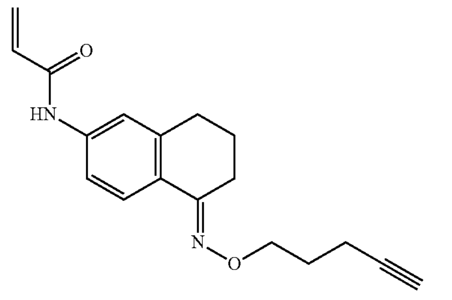

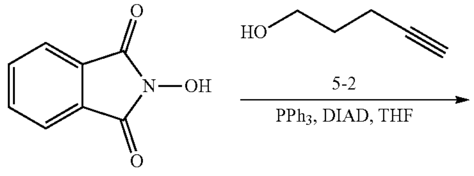

5-1

-continued

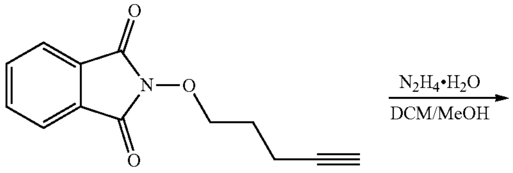

5-3

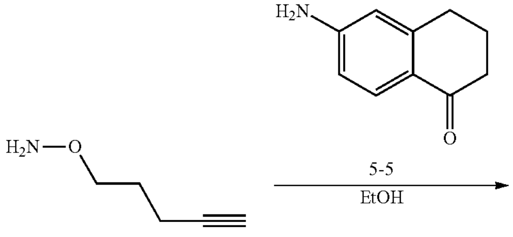

5-4

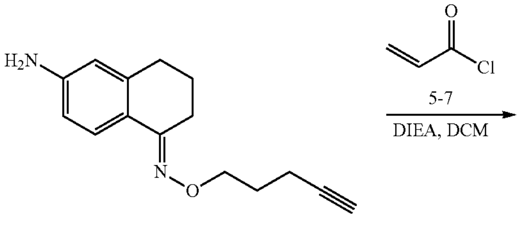

5-6

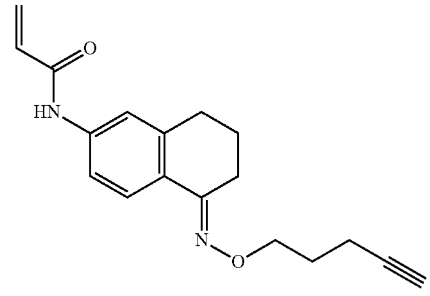

compound 5

Compound 5 was synthesized based on synthetic scheme 7. LCMS: MS (ESI) m/z=297.2 [M+H]+. $^{1}$H NMR (400 MHz, $CDCl_3$): δ=7.93 (d, J=8.6 Hz, 1H), 7.60 (brs, 1H), 7.41 (brs, 1H), 7.25-7.19 (m, 1H), 6.44 (d, J=4.0 Hz, 1H), 6.31-6.18 (m, 1H), 5.78 (dd, J=1.0, 10.0 Hz, 1H), 4.26 (t, J=12.0 Hz, 2H), 2.72 (t, J=12.0 Hz, 4H), 2.34 (d, J=4.0 Hz, 2H), 1.99-1.96 (m, 1H), 1.99-1.95 (m, 1H), 2.00-1.92 (m, 1H), 1.87-1.87 (m, 1H), 1.83 (d, J=6.4 Hz, 2H), 1.63 (s, 1H).

Example 6
Synthesis of Compound 6
Scheme 8. Synthesis of compound 6.
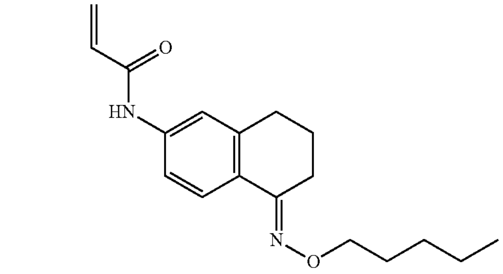
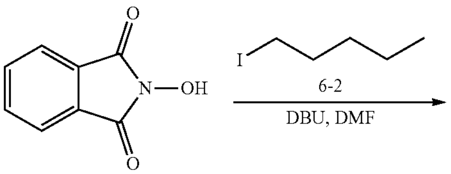
6-1
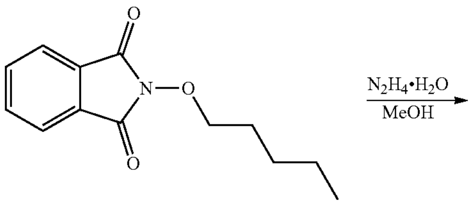
6-3
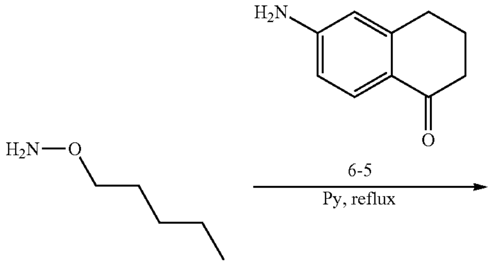
6-4
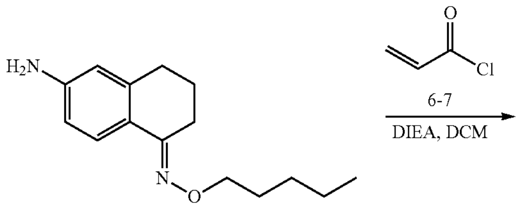
6-6
-continued
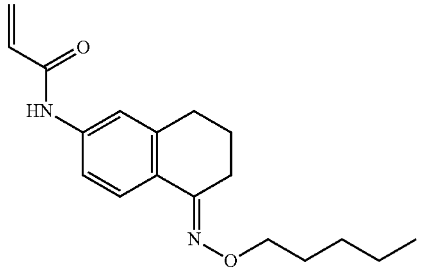
compound 6
Compound 6 was synthesized based on synthetic scheme 8. LCMS: MS (ESI) m/z=301.2 $[M+H]^+$. $^1$H NMR (400 MHz, $CDCl_3$): δ=7.95 (d, J=12.0 Hz, 1H), 7.61 (brs, 1H), 7.24-7.15 (m, 2H), 6.45 (d, J=16.0 Hz, 1H), 6.28-6.19 (m, 1H), 5.79 (d, J=12.0 Hz, 1H), 4.17 (t, J=12.0 Hz, 2H), 2.78-2.71 (m, 4H), 1.85 (d, J=6.4 Hz, 2H), 1.76-1.66 (m, 2H), 1.43-1.32 (m, 4H), 0.97-0.86 (m, 3H).
Example 7
Synthesis of Compound 7
Scheme 9. Synthesis of compound 7.
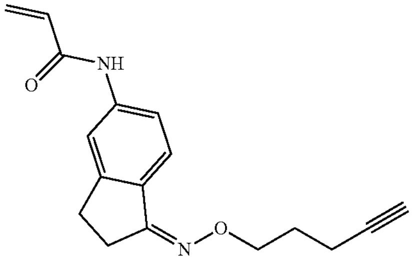
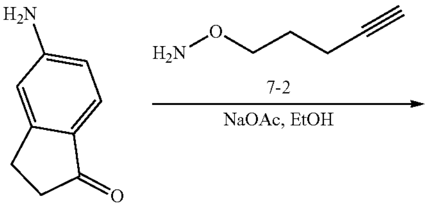
7-1
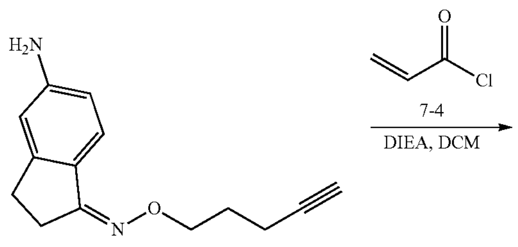
7-3

-continued

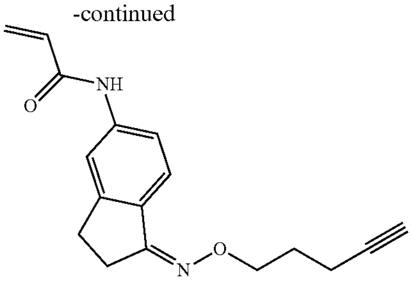

compound 7

Compound 7 was synthesized based on synthetic scheme 9. LCMS: MS (ESI) m/z=283.1 $[M+H]^+$. $^1H$ NMR (400 MHz, $CDCl_3$): δ=6.5-6.4 (m, 1H), 6.3-6.15 (m, 1H), 5.81 (d, J=10 Hz, 1H), 4.3-4.2 (m, 2H), 3.1-3.0 (m, 2H), 2.9-2.8 (m, 2H), 2.4-2.3 (m, 2H), 2.0-1.9 (m, 3H).

Example 8

Synthesis of Compound 8

Scheme 10. Synthesis of compound 8.

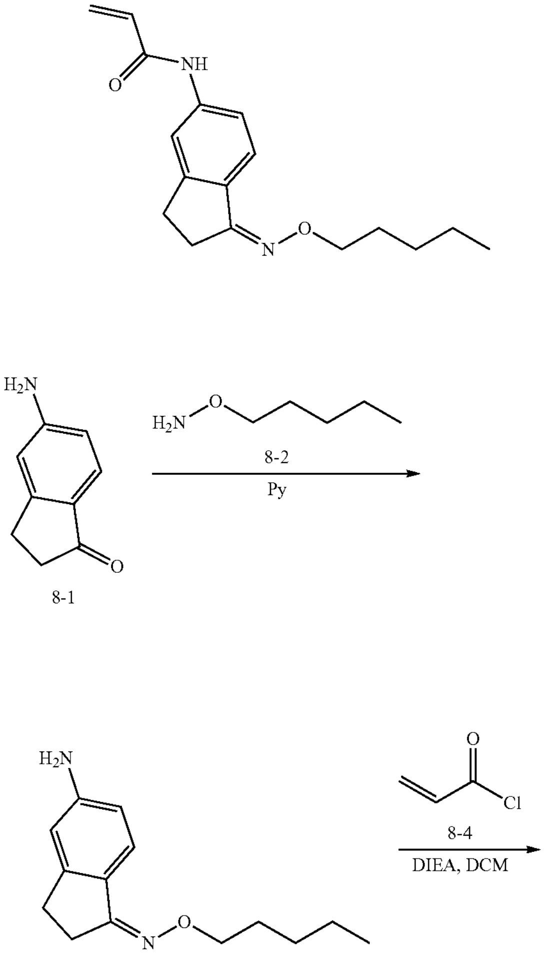

-continued

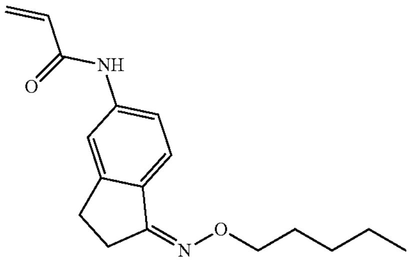

compound 8

Compound 8 was synthesized based on synthetic scheme 10. LCMS: MS (ESI) m/z=287.2 $[M+H]^+$. $^1H$ NMR (400 MHz, $CDCl_3$): δ=7.82 (s, 1H), 7.64 (d, J=8.4 Hz, 1H), 7.42 (s, 1H), 7.3-7.2 (m, 1H), 6.5-6.4 (m, 1H), 6.3-6.2 (m, 1H), 5.8 (d, J=10.4 Hz, 1H), 4.2-4.1 (m, 2H), 3.1-3.0 (m, 2H), 3.0-2.9 (m, 2H), 1.8-1.7 (m, 2H), 1.4-1.3 (m, 4H), 1.0-0.9 (m, 3H).

Example 9

Synthesis of Compound 9 (N-(3-(3-methoxyphenoxy)phenyl)acrylamide)

Scheme 11. Synthesis of compound 9.

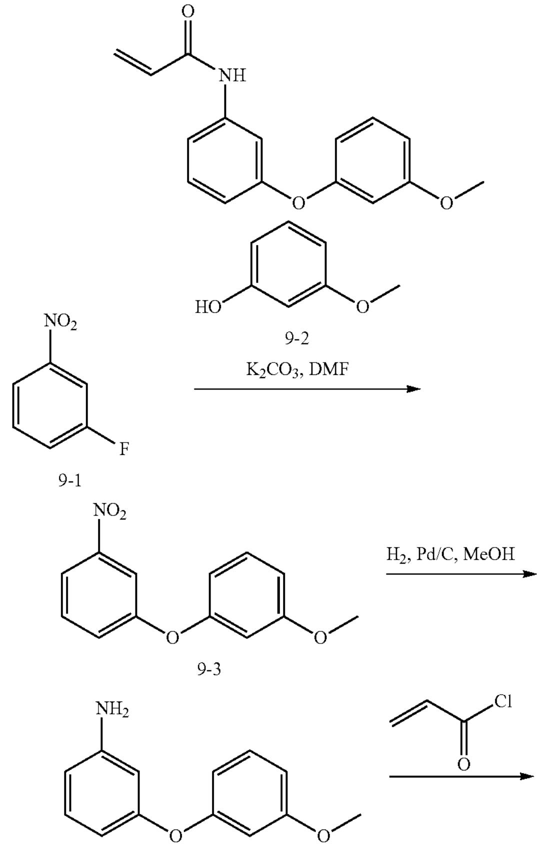

-continued

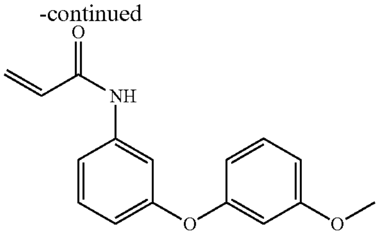

compound 9

Synthesis of 1-methoxy-3-(3-nitrophenoxy)benzene (9-3). To a solution of 1-fluoro-3-nitrobenzene (1 g, 0.0071 mol) in DMF (15 mL) was added 3-methoxyphenol (1.1458 g, 0.0092 mol) and $K_2CO_3$ (1.96 g, 0.014 mol), the reaction was stirred at 150° C. for 16 hours under $N_2$ atmosphere. The reaction was diluted with water (35 mL) and extracted with EA (3×15 mL). The combined organic layers were washed with brine (15 mL×2), dried over sodium sulfate, filtered, and concentrated. The residue was purified by silica gel chromatography (PE/EA=1%) to afford 1-methoxy-3-(3-nitrophenoxy)benzene (1.02 g, 59.1% yield) as a yellow oil. LCMS has no response.

Synthesis of 3-(3-methoxyphenoxy)aniline (9-4). The suspension of 1-(3-methoxyphenoxy)-3-nitrobenzene (1.07 g, 0.0044 mol) and Pd/C (1.0 g, 50% water of wet) in MeOH (15 mL) was degassed and purge with $H_2$ three times, the reaction was stirred at room temperature for 4 hours. The reaction was filtered, the filtrate was concentrated to give 3-(3-methoxyphenoxy)aniline (840 mg, 84.1% yield) as a white oil. Mass Spectrum (ESI) m/z=251.9 $[M+1]^+$.

Synthesis of N-(3-(3-methoxyphenoxy)phenyl)acrylamide (compound 9). At 0° C., to a solution of 3-(3-methoxyphenoxy)aniline (108 mg, 0.5 mmol) in NMP (10 mL) was added prop-2-enoyl chloride (45.25 mg, 0.5 mmol), the reaction was stirred at room temperature for 12 hours. The reaction was diluted with water and extracted with EA. The combined organic layers were washed with brine, dried over sodium sulfate, filtered, and concentrated. The residue was purified by silica gel chromatography (EA/PE=10%) to afford N-(3-(3-methoxyphenoxy)phenyl)acrylamide (78 mg, 57.9% yield) as a white oil. Mass Spectrum (ESI) m/z=269.8 $[M+1]^+$. $^1H$ NMR (400 MHz, $CDCl_3$) δ ppm 7.54 (s, 1H), 7.41-7.17 (m, 4H), 6.80 (dd, J=8.1, 1.5 Hz, 1H), 6.71-6.63 (m, 1H), 6.63-6.57 (m, 2H), 6.43 (dd, J=16.8, 1.2 Hz, 1H), 6.24 (dd, J=16.9, 10.2 Hz, 1H), 5.76 (dd, J=10.2, 1.2 Hz, 1H), 3.79 (s, 3H).

Example 10

Synthesis of Compound 10 (N-(3-((5-(trifluoromethyl)thiophen-3-yl)oxy)phenyl)acrylamide)

Scheme 12. Synthesis of compound 10.

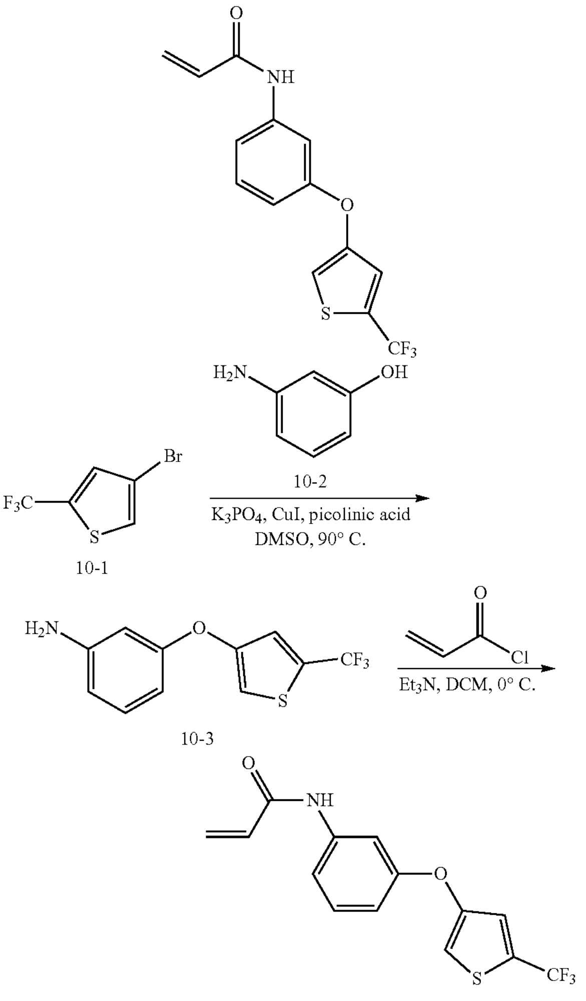

10-1

10-3 compound 10

Synthesis of 3-((5-(trifluoromethyl)thiophen-3-yl)oxy)aniline (10-3). Added copper(I) iodide (17 mg, 0.086 mmol, 5 mol %), 2-picolinic acid (21 mg, 0.17 mmol, 10 mol %), 4-bromo-2-(trifluoromethyl)thiophene (230 mg, 1.0 mmol), 3-aminophenol (130 mg, 1.2 mmol) and $K_3PO_4$ (731 mg, 3.45 mmol) in an oven-dried screw cap test tube with magnetic stirbar. Evacuated the tube. Refilled the reaction mixture tube with argon. Repeated the evacuation/backfill sequence two times. Added remaining liquid reagent to the mixture under a counterflow of argon, followed by dimethyl sulfoxide (2.0 mL) by syringe. Placed the reaction mixture tube in a preheated oil bath at 80° C. Stirred the reaction mixture vigorously for 24 hours. cooled to room temperature, then poured into water (10 mL). The mixture was extracted with EtOAc (3×15 mL). and dried over anhydrous sodium sulfate and concentrated in vacuo. The residue was purified by Prep-TLC (eluent: PE/EtOAc=4/1) to afford 3-((5-(trifluoromethyl)thiophen-3-yl)oxy)aniline (15 mg, 90% purity, 3.01% yield) as a yellow solid. $[M+H]^+$ m/z 259.246, found 260. $^1H$ NMR (400 MHz, DMSO-$d_6$, ppm) δ 7.56 (s, 1H), 7.26 (d, J=1.7 Hz, 1H), 7.00 (t, J=8.0 Hz, 1H), 6.34 (dd, J=8.0, 1.0 Hz, 1H), 6.24 (d, J=2.0 Hz, 1H), 6.18 (dd, J=8.0, 2.3 Hz, 1H), 5.28 (s, 2H).

Synthesis of N-(3-((5-(trifluoromethyl)thiophen-3-yl)oxy)phenyl)acrylamide (compound 10). A round-bottom flask containing a mixture of 3-((5-(trifluoromethyl)thiophen-3-yl)oxy)aniline [15 mg, 0.06 mmol], prop-2-enoyl chloride [5.21 mg, 0.06 mmol] and $Et_3N$ [12 mg, 0.12 mmol] in DCM (2 mL) was stirred at room temperature for 1 h. $H_2O$ (10 mL) was added and extracted with DCM (10 mL×3) and the combined organic phases were washed with brine (10 mL×3), dried over anhydrous sodium sulfate and concentrated in vacuo. The residue was purified by Prep-TLC (eluent: PE/EtOAc=2/1) to afford N-(3-((5-(trifluoromethyl)thiophen-3-yl)oxy)phenyl)acrylamide (18 mg, 97.72% purity, 97.22% yield) as a yellow solid. $[M+H]^+$ m/z 313.294, found 314. $^1H$ NMR (400 MHz, DMSO-$d_6$, ppm) δ 10.25 (s, 1H), 7.66 (s, 1H), 7.50 (s, 1H), 7.43 (d, J=7.9 Hz, 1H), 7.36 (dd, J=15.1, 6.9 Hz, 2H), 6.80 (d, J=7.9 Hz, 1H), 6.40 (dd, J=16.9, 10.1 Hz, 1H), 6.25 (d, J=16.9 Hz, 1H), 5.76 (d, J=10.1 Hz, 1H).

Example 11

Synthesis of Compound 11 (N-(5-(3-(trifluoromethyl)phenoxy)thiophen-2-yl)acrylamide)

Scheme 13. Synthesis of compound 11.

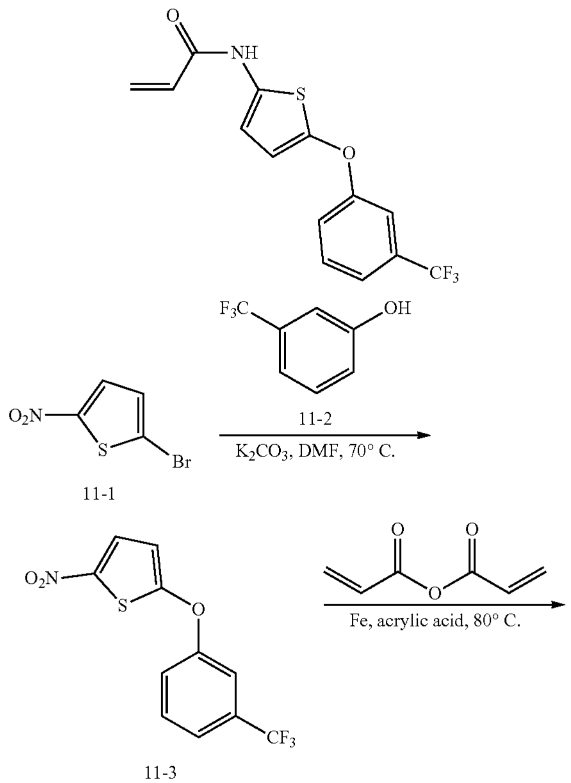

11-1

11-3

-continued

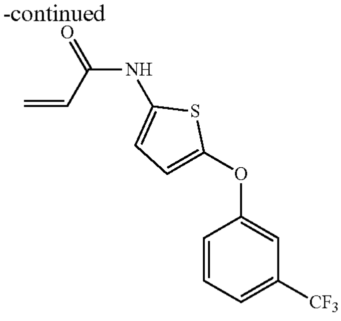

compound 11

Synthesis of 2-nitro-5-(3-(trifluoromethyl)phenoxy)thiophene (11-3). A round-bottom flask containing a mixture of 2-bromo-5-nitrothiophene [1 g, 4.83 mmol], 3-(trifluoromethyl)phenol [783 mg, 4.83 mmol] and $K_2CO_3$ [1.3 g, 9.66 mmol] was placed in DMF (10 mL) heated to 70° C. and refluxed for 5 h. cooled to room temperature, then poured into water (10 mL). The mixture was extracted with EtOAc (3×15 mL). and dried over anhydrous sodium sulfate and concentrated in vacuo. The residue was purified by flash chromatography (eluent: PE/EtOAc=4/1) to afford 2-nitro-5-(3-(trifluoromethyl)phenoxy)thiophene (3) (1.35 g, 95% purity, 91.67% yield) as a yellow oil. $[M+H]^+$ m/z 289.228, found 290. $^1H$ NMR (400 MHz, DMSO-$d_6$, ppm) δ 8.08 (d, J=4.7 Hz, 1H), 7.81-7.66 (m, 4H), 6.82 (d, J=4.7 Hz, 1H).

Synthesis of N-(5-(3-(trifluoromethyl)phenoxy)thiophen-2-yl)acrylamide (compound 11). A round-bottom flask containing a mixture of 2-nitro-5-(3-(trifluoromethyl)phenoxy)thiophene [424 mg, 1.46 mmol], prop-2-enoyl prop-2-enoate [276 mg, 2.19 mmol] and Fe [420 mg, 7.30 mmol] in Acrylic acid (5 mL) was stirred at 80° C. and refluxed for 16 h. $H_2O$ (10 mL) was added and extracted with EtOAc (15 mL×3) and the combined organic phases were washed with brine (10 mL×3), dried over anhydrous sodium sulfate and concentrated in vacuo. The residue was purified by Prep-TLC (eluent: PE/EtOAc=2/1) to afford N-(5-(3-(trifluoromethyl)phenoxy)thiophen-2-yl)acrylamide (72 mg, 95.17% purity, 14.92% yield) as a brown solid. $[M+H]^+$ m/z 313.294, found 314. $^1H$ NMR (400 MHz, DMSO-$d_6$, ppm) δ 11.47 (s, 1H), 7.63 (t, J=7.5 Hz, 1H), 7.50 (d, J=7.6 Hz, 1H), 7.43-7.33 (m, 2H), 6.65-6.59 (m, 1H), 6.51-6.47 (m, 1H), 6.38 (ddd, J=17.0, 9.9, 2.4 Hz, 1H), 6.27 (d, J=17.1 Hz, 1H), 5.81 (d, J=9.9 Hz, 1H).

Example 12

Synthesis of Compound 12 (N-(3-fluoro-5-(4-(trifluoromethyl)phenoxy)phenyl)acrylamide)

Scheme 14. Synthesis of compound 12.

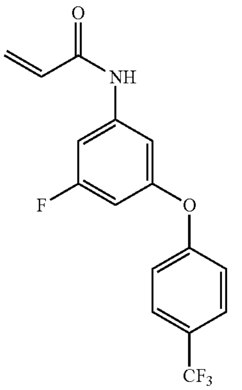

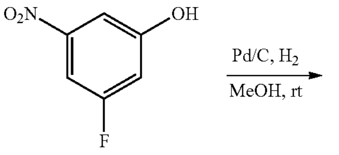

12-1

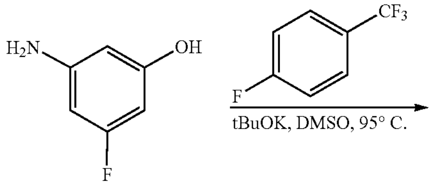

12-2

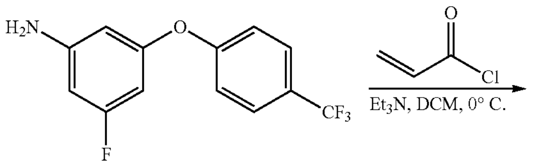

12-3

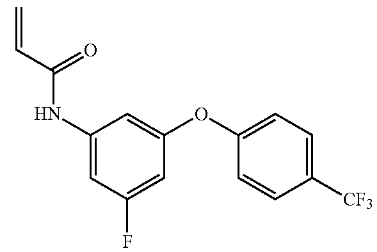

compound 12

Preparation of 3-amino-5-fluorophenol (12-2). Added Pd/C (100 mg, 0.1 eq) to a solution of 3-fluoro-5-nitrophenol (1.0 g, 6.4 mmol) in methanol (10 mL). the mixture was stirred at room temperature under hydrogen for 1 hour. Filtered the mixture through Celite and concentrated the filtrate under reduced pressure to afford 3-amino-5-fluorophenol (710 mg, 95% purity, 82.81% yield) as a brown solid. $[M+H]^+$ m/z 127.118, found 128. $^1H$ NMR (400 MHz, MeOD-$d_4$, ppm) δ 5.97 (t, J=2.0 Hz, 2H), 5.94 (t, J=2.1 Hz, 1H), 5.92 (t, J=2.1 Hz, 1H), 5.85 (t, J=2.2 Hz, 1H), 5.82 (t, J=2.2 Hz, 1H).

Preparation of 3-fluoro-5-(4-(trifluoromethyl)phenoxy) aniline (12-3). To a stirred solution of 3-amino-5-fluorophenol (700 mg, 5.51 mmol) and 1-fluoro-4-(trifluoromethyl) benzene (909 mg, 5.51 mmol) in DMSO (10 mL) was added in one portion potassium tert-butoxide (739 mg, 6.61 mmol). The resulting dark solution was heated for 4 hours at 95° C., cooled to room temperature, then poured into water (60 mL). The mixture was extracted with ether (3×15 mL). The organic phase was washed with 2N sodium hydroxide (2×10 mL) and water (10 mL), dried ($Na_2SO_4$) and the solvent evaporated to give a dark oil. This oil was distilled to give the title compound 3-fluoro-5-(4-(trifluoromethyl)phenoxy) aniline (520 mg, 95% purity, 32.95% yield) as a yellow oil. $[M+H]^+$ m/z 271.215, found 272. $^1H$ NMR (400 MHz, DMSO-$d_6$, ppm) δ 7.75 (d, J=8.6 Hz, 2H), 7.19 (d, J=8.4 Hz, 2H), 6.17 (d, J=11.7 Hz, 1H), 6.06 (d, J=9.3 Hz, 2H), 5.67 (s, 2H).

Preparation of N-(3-fluoro-5-(4-(trifluoromethyl)phenoxy)phenyl)acrylamide (compound 12). To a mixture of 3-fluoro-5-(4-(trifluoromethyl)phenoxy)aniline (520 mg, 1.91 mmol), prop-2-enoyl chloride (173 mg, 1.91 mmol) in DCM (10 mL) was added $Et_3N$ (386 mg, 3.82 mmol) at 0° C., And the mixture was warmed to room temperature for 1 h. $H_2O$ (15 mL) was added and extracted with DCM (40 mL×3) and the combined organic phases were washed with brine (10 mL×3), dried over anhydrous sodium sulfate and concentrated in vacuo. The residue was purified by Flash chromatography (eluent: PE/EtOAc=2/1) to afford N-(3-fluoro-5-(4-(trifluoromethyl)phenoxy)phenyl)acrylamide (330 mg, 97.24% purity, 51.49% yield) as a yellow solid. $[M+H]^+$ m/z 325.263, found 326. $^1H$ NMR (400 MHz, DMSO-$d_6$, ppm) δ 10.41 (s, 1H), 7.79 (d, J=8.6 Hz, 2H), 7.48 (d, J=11.2 Hz, 1H), 7.27 (d, J=8.6 Hz, 2H), 7.14 (s, 1H), 6.78 (dd, J=9.8, 2.1 Hz, 1H), 6.31 (qd, J=16.9, 5.9 Hz, 2H), 5.80 (dd, J=9.8, 2.0 Hz, 1H).

Example 13

Synthesis of Compound 13 (N-(3-((4-(Trifluoromethyl)Pyridin-2-yl)oxy)phenyl)acrylamide)

Scheme 15. Synthesis of compound 13.

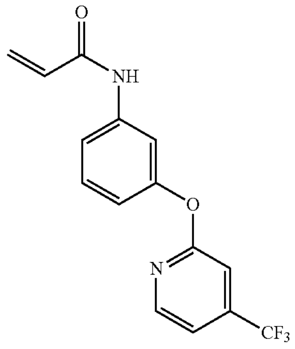

-continued

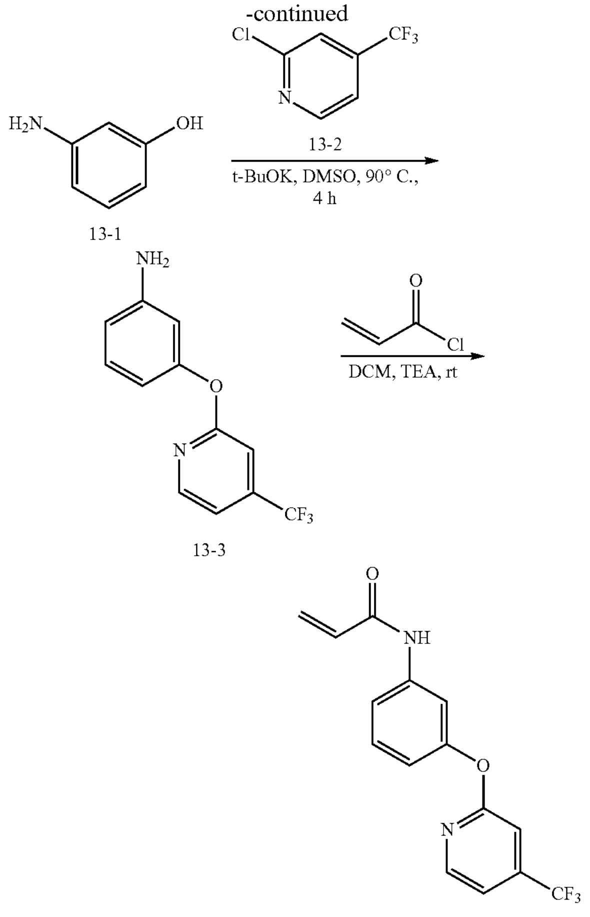

13-1
13-2
13-3
compound 13

Preparation of 3-((4-(trifluoromethyl)pyridin-2-yl)oxy)aniline (13-3). A mixture of 3-aminophenol (500 mg, 4.58 mmol), 2-chloro-4-(trifluoromethyl)pyridine (836 mg, 4.58 mmol) and t-BuOK (771 mg, 6.87 mmol) in DMSO (15 mL) was stirred at 90° C. for 4 h. The reaction mixture was cooled to rt and $H_2O$ (100 mL) was added. The mixture was extracted with EtOAc (40 mL×3) and the combined organic phases were washed with brine (20 mL×3), dried over anhydrous sodium sulfate, and concentrated in vacuo. The residue was purified by Flash chromatography (eluent: PE/EtOAc=2/1) to afford 3-((4-(trifluoromethyl)pyridin-2-yl)oxy)aniline (300 mg, 85% purity, 21.8% yield) as a yellow solid. $[M+H]^+$ m/z 255.07, found 255. $^1$H NMR (400 MHz, DMSO-$d_6$, ppm) δ 8.43 (d, J=5.2 Hz, 1H), 7.46 (d, J=5.1 Hz, 1H), 7.32 (s, 1H), 7.05 (t, J=8.0 Hz, 1H), 6.44 (dd, J=7.8, 1.7 Hz, 1H), 6.37-6.17 (m, 2H), 5.28 (s, 2H).

Preparation of N-(3-((4-(trifluoromethyl)pyridin-2-yl)oxy)phenyl)acrylamide (compound 13). Under $N_2$, to a solution of 3-({4-[(difluoromethyl)-$1^{2}-fluoranyl]pyridin-2-yl}oxy)aniline (300 mg, 1.18 mmol), prop-2-enoyl chloride (201 mg, 2.22 mmol) in DCM (4 mL) was added triethylamine (225 mg, 2.22 mmol) dropwise at rt and the reaction mixture was kept stirring at rt for additional 4 h. Evaporated and the residue was purified by Flash chromatography (eluent: PE/EtOAc=5/1) to afford N-(3-((4-(trifluoromethyl)pyridin-2-yl)oxy)phenyl)acrylamide (100 mg, 98.51% purity, 27.1% yield) as a withe solid. [M+H]+m/z 309.08, found 309. $^1$H NMR (400 MHz, DMSO-$d_6$, ppm) δ 10.28 (s, 1H), 8.43 (d, J=5.2 Hz, 1H), 7.63 (s, 1H), 7.51 (d, J=5.3 Hz, 1H), 7.47 (d, J=9.8 Hz, 2H), 7.39 (t, J=8.1 Hz, 1H), 6.96-6.85 (m, 1H), 6.43 (dd, J=17.0, 10.1 Hz, 1H), 6.26 (dd, J=17.0, 1.7 Hz, 1H), 5.77 (dd, J=10.1, 1.7 Hz, 1H).

Example 14

Synthesis of Compound 14 (N-(3-((5-(trifluoromethyl)pyridin-2-yl)oxy)phenyl)acrylamide)

Scheme 16. Synthesis of compound 14.

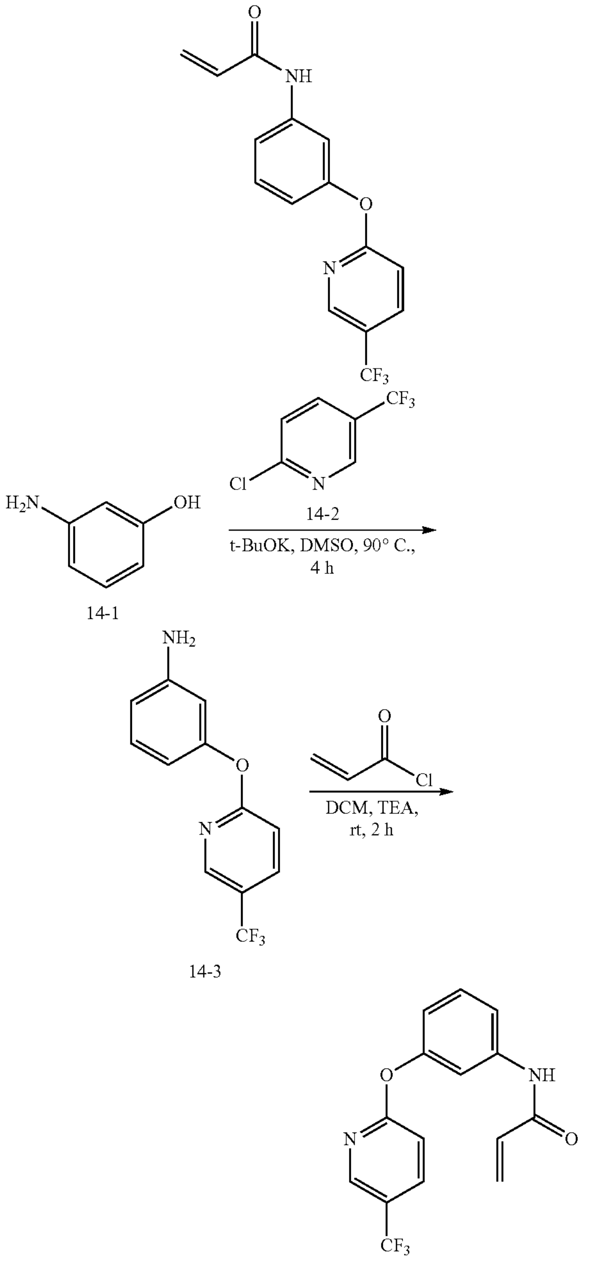

14-1
14-2
14-3
compound 14

Preparation of 3-((5-(trifluoromethyl)pyridin-2-yl)oxy)aniline (14-3). A mixture of 3-aminophenol (500 mg, 4.58 mmol), 2-chloro-5-(trifluoromethyl)pyridine (836 mg, 4.58 mmol) and t-BuOK (771 mg, 6.87 mmol) in DMSO (15 mL)

was stirred at 90° C. for 4 h. The reaction mixture was cooled to rt and $H_2O$ (100 mL) was added. The mixture was extracted with EtOAc (40 mL×3) and the combined organic phases were washed with brine (20 mL×3), dried over anhydrous sodium sulfate and concentrated in vacuo. The residue was purified by Flash chromatography (eluent: PE/EtOAc=2/1) to afford 3-((5-(trifluoromethyl)pyridin-2-yl)oxy)aniline (300 mg, 95.0% purity, 24.3% yield) as a yellow solid. $[M+H]^+$ m/z 255.07, found 255. $^1H$ NMR (400 MHz, DMSO-$d_6$, ppm) δ 8.59 (s, 1H), 8.19 (d, J=8.7 Hz, 1H), 7.18-7.01 (m, 2H), 6.45 (dd, J=8.1, 0.8 Hz, 1H), 6.34-6.23 (m, 2H), 5.29 (s, 2H).

Preparation of N-(3-((5-(trifluoromethyl)pyridin-2-yl)oxy)phenyl)acrylamide (compound 14). Under $N_2$, to a solution of 3-((5-(trifluoromethyl)pyridin-2-yl)oxy)aniline (200 mg, 0.79 mmol), prop-2-enoyl chloride (134 mg, 1.48 mmol) in DCM (4 mL) was added triethylamine (150 mg, 1.48 mmol) dropwise at rt and the reaction mixture was kept stirring at rt for additional 4 h. Evaporated and the residue was purified by Flash chromatography (eluent: PE/EtOAc=5/1) to afford N-(3-((5-(trifluoromethyl)pyridin-2-yl)oxy)phenyl)acrylamide (100 mg, 99.2% purity, 43.3% yield) as a withe solid. [M+H]+m/z 309.08, found 309. $^1H$ NMR (400 MHz, DMSO-$d_6$, ppm) δ 10.29 (s, 1H), 8.64-8.51 (m, 1H), 8.25 (dd, J=8.7, 2.5 Hz, 1H), 7.64 (s, 1H), 7.52-7.35 (m, 2H), 7.26 (d, J=8.7 Hz, 1H), 6.98-6.88 (m, 1H), 6.42 (dd, J=17.0, 10.1 Hz, 1H), 6.25 (dd, J=17.0, 1.8 Hz, 1H), 5.77 (dd, J=10.0, 1.8 Hz, 1H).

Example 15

Synthesis of Compound 15 ((E)-4-(dimethylamino)-N—((E)-1-((pentyloxy)imino)-2,3-dihydro-1H-inden-5-yl)but-2-enamide)

Scheme 17. Synthesis of compound 15.

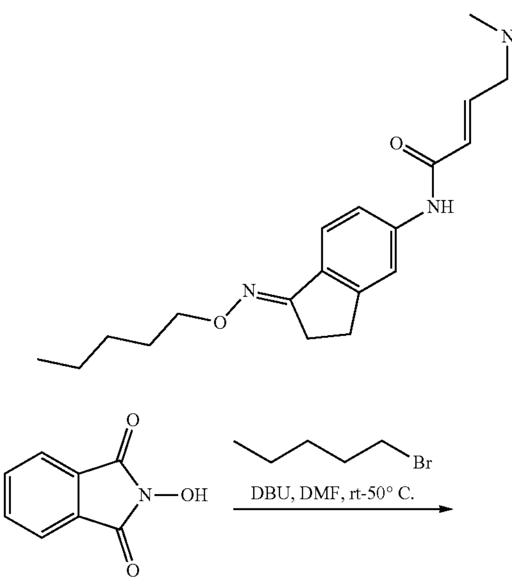

15-1

-continued

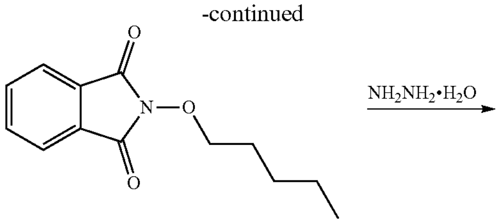

15-2

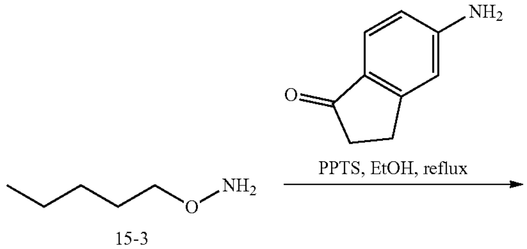

15-3

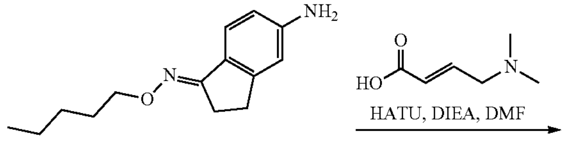

15-4

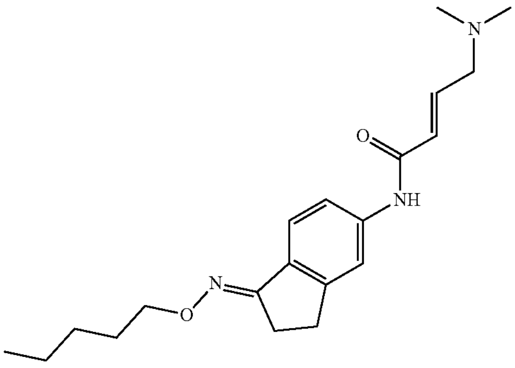

compound 6

Preparation of 2-(pentyloxy)isoindoline-1,3-dione (15-2). To a solution of N-hydroxyphthalimide (1631 mg, 10 mmol) in DMF (10 mL) was added pentylbromide (1510 mg, 10 mol) dropwise at −10° C., followed by DBU (1674 mg, 11 mol) dropwise at this temperature, then the mixture was stirred at 50° C. for 2 h. After cooling to 25° C., it was quenched with $H_2O$ (20 mL) and extracted with EtOAc (20 mL×3). The organic phases were combined, washed with brine, dried over $Na_2SO_4$, filtered, and concentrated in vacuo. The residue was purified by silica gel chromatography (PE/EtOAc=50:1 to 3:1) to afford 2-(pentyloxy)isoindoline-1,3-dione (1300 mg, purity: ~90%, 50.17% yield) as a white solid. $[M+H]^+$ m/z=234.7, found 234.7.

Preparation of O-pentylhydroxylamine (15-3). To a solution of 2-(pentyloxy)isoindoline-1,3-dione (1300 mg, 5.57 mmol) in DCM (10 mL) was added $NH_2NH_2 \cdot H_2O$ (214 mg. 6.68 mmol), the resulting mixture stirred at 25° C. for 18 h. The solid was removed off by filtration. The filtrate was diluted with DCM (30 mL), extracted with NaOH (2M, 10 mL×2). The organic layer was concentrated in vacuo to afford 0-pentylhydroxylamine (600 g, crude) as a colorless oil. $[M+H]^+$ m/z=104.7, found 104.7.

Preparation of (E)-5-amino-2,3-dihydro-1H-inden-1-one O-pentyl oxime (15-4). To a solution of O-pentylhydroxylamine (280 mg, 2.71 mmol) and 5-amino-2,3-dihydro-1H-inden-1-one (200 mg, 1.35 mmol) in EtOH (5 mL) was added PPTS (34 mg, 0.13 mmol), which was refluxed for 2 h, then cooled to room temperature, the pH of the reaction mixture was adjusted to 8 with sat. $NaHCO_3$. The solvent was removed off under vacuum. The mixture was diluted with $H_2O$ (15 mL) and extracted with EtOAc (20 mL×3). The organic phases were combined, washed with brine, dried over $Na_2SO_4$, filtered, and concentrated in vacuo. The residue was purified by silica gel chromatography (PE/EtOAc=10:1 to 3:1) to afford (E)-5-amino-2,3-dihydro-1H-inden-1-one O-pentyl oxime (200 mg, purity: ~85%, 53.85% yield) as a white solid. $[M+H]^+$ m/z=234.7, found 234.7.

Preparation of (E)-4-(dimethylamino)-N—((E)-1-((pentyloxy)imino)-2,3-dihydro-1H-inden-5-yl)but-2-enamide (compound 15). To a solution of (E)-5-amino-2,3-dihydro-1H-inden-1-one O-pentyl oxime (200 mg, 0.86 mmol), (E)-4-(dimethylamino)but-2-enoic acid (111 mg, 0.86 mmol) and HATU (392 mg, 1.03 mmol) in DMF (5 mL) was added DIEA (222 mg, 1.72 mmol), which was stirred at 25° C. for 4 h. It was diluted with $H_2O$ (20 mL) and extracted with EtOAc (10 mL×3). The combined organic phase was washed with brine, dried over $Na_2SO_4$, filtered, and concentrated in vacuo. The residue was purified by prep-HPLC to afford (E)-4-(dimethylamino)-N—((E)-1-((pentyloxy)imino)-2,3-dihydro-1H-inden-5-yl)but-2-enamide (16 mg, purity: ~98%, 5.31% yield) as a white solid. $[M+H]^+$ m/z=344.2, found 344.2. $^1H$ NMR (400 MHz, CDCl3) δ 7.79 (s, 1H), 7.62 (d, J=8.3 Hz, 1H), 7.47 (s, 1H), 7.24 (d, J=8.3 Hz, 1H), 6.97 (m, 1H), 6.18-6.09 (m, 1H), 4.15 (m, 2H), 3.18-3.10 (m, 2H), 3.06-2.95 (m, 2H), 2.93-2.82 (m, 2H), 2.30 (s, 6H), 1.79-1.67 (m, 2H), 1.41-1.33 (m, 4H), 0.94-0.88 (m, 3H).

Example 16

Synthesis of Compound 16

((E)-N-(4-((pentyloxy)imino)chroman-7-yl)acrylamide)

Scheme 18. Synthesis of compound 16.

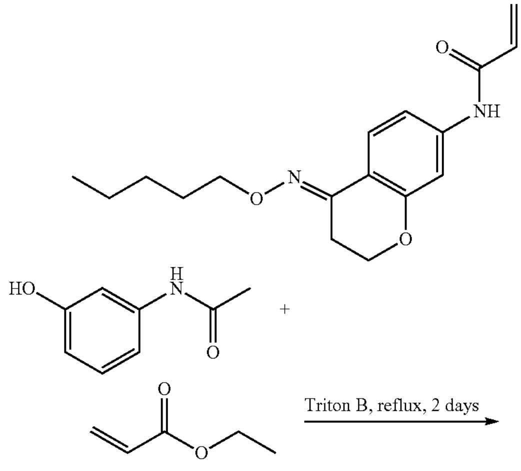

-continued

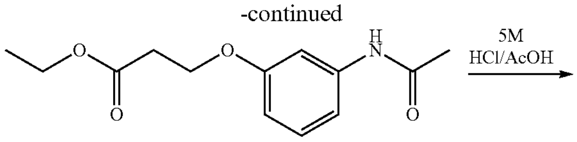

16-1

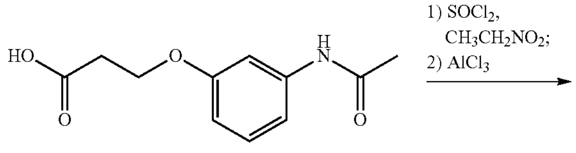

16-2

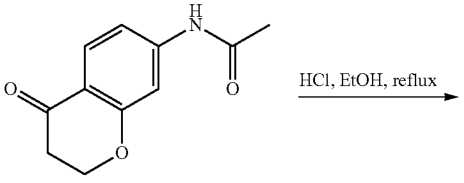

16-3

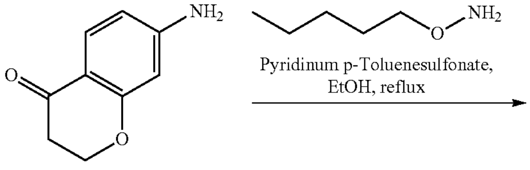

16-4

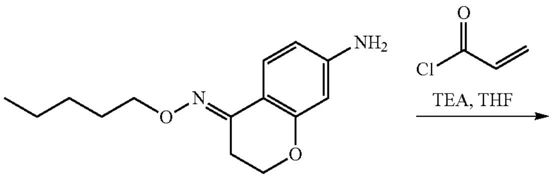

16-5

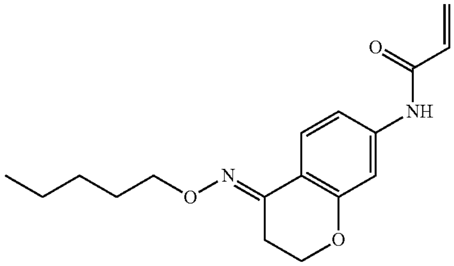

compound 16

Preparation of ethyl 3-(3-acetamidophenoxy)propanoate (16-1). To a mixture of N-(3-hydroxyphenyl)acetamide (10.0 g, 65 mmol) and ethyl acrylate (20 mL) was added Triton B (40% methanol solution, 3.46 mL, 8.37 mmol), which was refluxed for 2 days. The reaction mixture was concentrated in vacuo. The residue was purified by flash column chromatography eluting with ethyl acetate/hexane (1:1) to give ethyl 3-(3-acetamidophenoxy)propanoate (3.6 g, 22%) as a white powder. $[M+H]^+$ m/z 252.12, found 252.1.

Preparation of 3-(3-acetamidophenoxy)propanoic acid (16-2). A mixture of ethyl 3-(3-acetamidophenoxy)propanoate (3.6 g, 14.3 mmol) and 5 M HCl (15 mL) in acetic acid (15 mL) was stirred at 60 degrees for 2 h. The solvent was removed off in vacuo and the residue was diluted with water (30 mL), extracted with ethyl acetate (30 mL×3). The organic layers were combined, washed with brine, dried over $Na_2SO_4$, and concentrated in vacuo. The residue was solidified from ethyl acetate and hexane to give 3-(3-acetamidophenoxy)propanoic acid (2.0 g, 2.9 mmol, 62%) as a white powder. $[M+H]^+$ m/z=224.08, found 224.1.

Preparation of N-(4-oxochroman-7-yl)acetamide (16-3). To a solution of 3-(3-acetamidophenoxy)propanoic acid (2.0 g, 8.87 mmol) in nitroethane (15 mL) was added thionyl chloride (1.28 g, 10.75 mmol) in one portion, which was stirred at room temperature for 2 h. The resulting mixture was cooled to 5 degrees with an ice bath, then anhydrous aluminum chloride (3.59 g, 26.88 mmol) was added, which was warmed to room temperature and stirred for 30 min. It was quenched with ice/water (30 mL), extracted with ethyl acetate (30 mL×3). The combined extraction was washed with brine, dried over $Na_2SO_4$, and concentrated in vacuo. The residue was solidified from ethyl acetate and hexane to give N-(4-oxochroman-7-yl)acetamide (580 mg, 2.82 mmol, 32%) as a white powder. $[M+H]^+$ m/z=206.07, found 206.0.

Preparation of 7-aminochroman-4-one (16-4). A solution of N-(4-oxochroman-7-yl)acetamide (580 mg, 2.83 mmol) and 12 M HCl (1 mL) in EtOH/water (10 mL/1 mL) was refluxed for 2 h. The solvent was removed off to give the residue. The residue was suspended in saturated aq. $NaHCO_3$ (30 mL), which was extracted with ethyl acetate (10 mL×3). The organic layers were combined, washed with brine, dried over Na2SO4, filtered, and concentrated in vacuum to afford 7-aminochroman-4-one (400 mg, 2.44 mmol, 86%) as a white solid. $[M+H]^+$ m/z=164.06, found 164.1.

Preparation of (E)-7-aminochroman-4-one O-pentyl oxime (16-5). A mixture of 7-aminochroman-4-one (400 mg, 2.45 mmol), O-pentylhydroxylamine (400 mg, 3.9 mmol) and Pyridinium p-toluenesulfonate (100 mg, 0.4 mmol) was stirred at 90 degrees for 16 h. The solvent was removed off under reduced pressure. The residue was diluted with water (10 mL) and extracted with ethyl acetate (10 mL×3). The organic layers were combined, concentrated in vacuum to give the crude product, which was purified by flash column chromatography eluting with hexane/ethyl acetate/$NH_3H_2O$ (100/20/0.3) to afford (E)-7-aminochroman-4-one O-pentyl oxime (200 mg, 0.81 mmol, 25%) as a yellow oil. LCMS (ESI) calcd for $C_{14}H_{21}N_2O_2$ $[M+H]^+$ m/z=248.15, found 249.2.

Preparation of (E)-N-(4-((pentyloxy)imino)chroman-7-yl)acrylamide (compound 16). To a stirred solution of (E)-7-aminochroman-4-one O-pentyl oxime (200 mg, 0.806 mmol) and TEA (166 mg, 1.612 mmol) in dichloromethane (20 mL) was added a solution of acryloyl chloride (73 mg, 0.806 mmol) in dichloromethane (5 mL) dropwise at −20 degrees, and further stirred for 1 h at this temperature. The water (10 mL) was slowly added to the above reaction mixture at 0 degrees and extracted with dichloromethane (10 mL×3). The combined organic layers were dried over Na2SO4, filtrated, and concentrated in vacuum to give the residue, which was purified by flash column chromatography eluting with hexane/ethyl acetate (2/1) to afford (E)-N-(4-((pentyloxy)imino)chroman-7-yl)acrylamide (60.0 mg, 0.2 mmol, 25%) as a white solid. $[M+H]^+$ m/z=303.16, found 301.3. $^1H$ NMR (400 MHz, MeOD): δ 7.78 (d, J=8.8 Hz, 1H), 7.37 (d, J=2.4 Hz, 1H), 7.09 (dd, J=8.8, 2.4 Hz, 1H), 6.45-6.32 (m, 2H), 5.77 (dd, J=8.8, 2.4 Hz, 1H), 4.18 (t, J=6.0 Hz, 2H), 4.14 (t, J=6.4 Hz, 2H), 2.87 (t, J=6.0 Hz, 2H), 1.73-1.67 (m, 2H), 1.41-1.36 (m, 4H), 0.95-0.91 (m, 3H).

Example 17

Synthesis of Compound 17

(N-(6-butoxynaphthalen-2-yl)prop-2-enamide)

Scheme 19. Synthesis of compound 17.

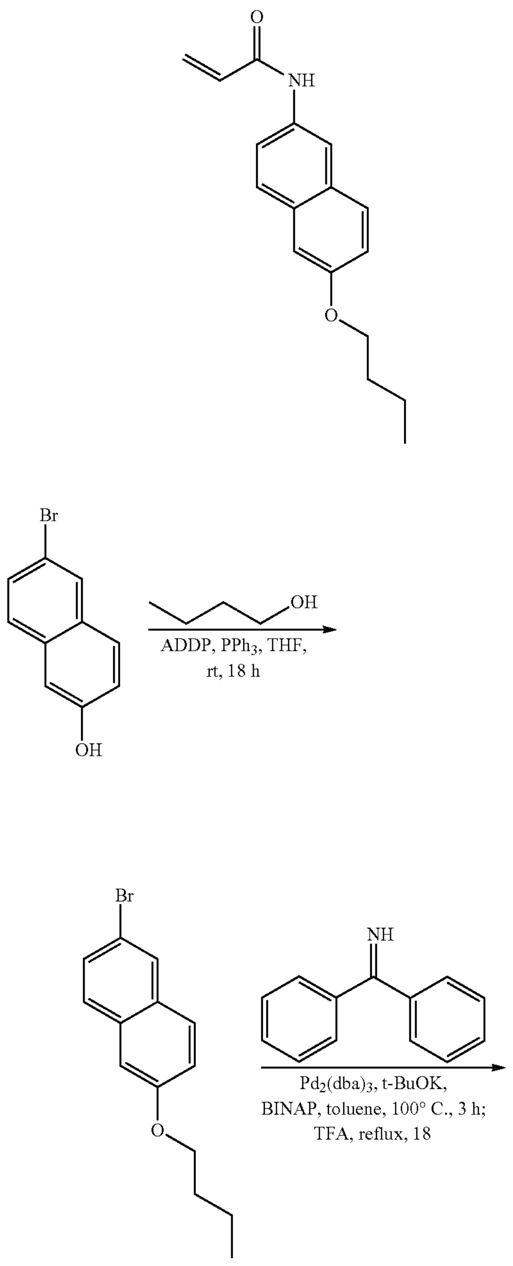

17-1

-continued

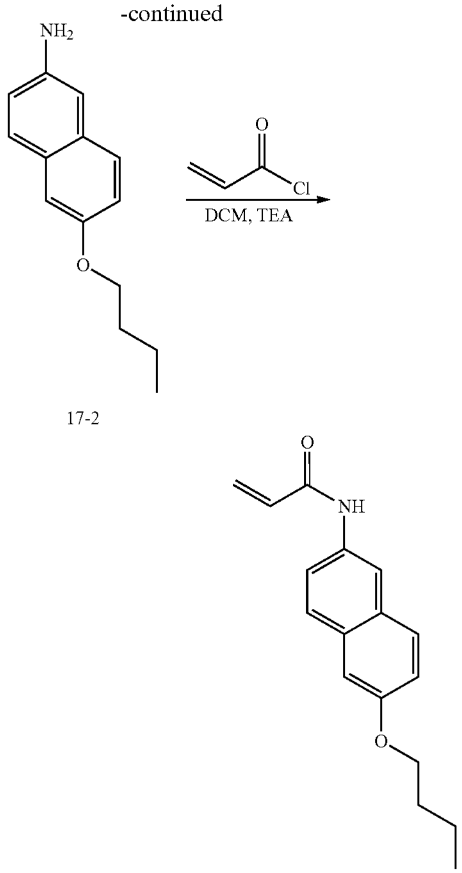

17-2 compound 17

Preparation of 2-bromo-6-butoxynaphthalene (17-1). Under $N_2$, to a solution of ADDP (2.27 g, 9.00 mmol) in THF (15 mL) at 0° C. was added triphenylphosphine (2.36 g, 9.00 mmol) dropwise and the mixture was kept stirring for additional 25 mins. Then, 6-bromonaphthalen-2-ol (1) (1 g, 4.5 mmol) and butan-1-ol (0.4 g, 5.3 mol) in THF (2 mL) was added slowly. The reaction mixture was stirred at room temperature for 18 h. $H_2O$ (100 mL) was added, extracted with EtOAc (50 mL×3) and the combined organic phases were washed with brine (60 mL), dried over anhydrous sodium sulfate, and concentrated in vacuo. The residue was purified by flash column chromatography (eluent: 10% EtOAc in PE) to afford 2-bromo-6-butoxynaphthalene (1.2 g, 95% purity, 91.1% yield) as a yellow solid. 1H NMR (400 MHz, DMSO-$d_6$, ppm) δ 8.10 (d, J=1.6 Hz, 1H), 7.79 (dd, J=17.1, 8.9 Hz, 2H), 7.55 (dd, J=8.7, 1.9 Hz, 1H), 7.35 (d, J=2.3 Hz, 1H), 7.20 (dd, J=9.0, 2.4 Hz, 1H), 4.08 (t, J=6.5 Hz, 2H), 1.83-1.71 (m, 2H), 1.54-1.41 (m, 2H), 0.95 (t, J=7.4 Hz, 3H).

Preparation of 6-butoxynaphthalen-2-amine (17-2). Under $N_2$, to a solution of 2-bromo-6-butoxynaphthalene (1.2 g, 4.30 mmol) in toluene (20 mL) was added diphenylmethanimine (0.94 g, 5.10 mmol), t-BuOK (1.45 g, 12.90 mmol), BINAP (1.07 g, 1.70 mmol) and $Pd_2(dba)_3$ (0.79 g, 0.80 mmol). The reaction mixture was stirred at 100° C. for 3 h. The reaction mixture was cooled to rt and $H_2O$ (100 mL) was added, extracted with EtOAc (40 mL×3) and the combined organic phases were washed with brine (20 mL×3), dried over anhydrous sodium sulfate, and concentrated in vacuo. The residue in TFA (30 mL) was refluxed for 18 h. The solvent was removed under reduced pressure. $NaHCO_3$ (aq.) (100 mL) was added and extracted with EtOAc (50 mL×3). The combined organic phases were washed with brine (10 mL×3), dried over anhydrous sodium sulfate, and concentrated in vacuo. The residue was purified by Flash chromatography (eluent: 50% EtOAc in PE) to afford 6-butoxynaphthalen-2-amine (0.845 g, 94% purity, 86% yield) as a yellow oil. $[M+H]^+$ m/z 216.13, found 216.05.

Preparation of N-(6-butoxynaphthalen-2-yl)prop-2-enamide (compound 17). To a solution of 6-butoxynaphthalen-2-amine (300 mg, 1.39 mmol), prop-2-enoyl chloride (151 mg, 1.67 mmol) in DCM (4 mL) was added triethylamine (423 mg, 4.18 mmol) dropwise at room temperature and the reaction mixture was kept stirring at room temperature for additional 2 h. Evaporated and the residue was purified by Flash chromatography (eluent: PE/EtOAc=1/1) to afford N-(6-butoxynaphthalen-2-yl)prop-2-enamide (112 mg, 98% purity, 27.9% yield) as a yellow solid. $[M+H]^+$ m/z 269.14, found 270. 1H NMR (400 MHz, $CDCl_3$) δ 8.18 (s, 1H), 7.65 (dd, J=8.8, 4.4 Hz, 2H), 7.59 (s, 1H), 7.48 (d, J=8.2 Hz, 1H), 7.13 (dd, J=8.9, 2.4 Hz, 1H), 7.07 (d, J=2.1 Hz, 1H), 6.46 (d, J=16.7 Hz, 1H), 6.30 (dd, J=16.8, 10.2 Hz, 1H), 5.76 (dd, J=10.2, 1.0 Hz, 1H), 4.06 (t, J=6.5 Hz, 2H), 1.90-1.76 (m, 2H), 1.60-1.48 (m, 2H), 1.00 (t, J=7.4 Hz, 3H).

Example 18

Synthesis of Compound 18

(N-(2-butoxyquinolin-6-yl)acrylamide)

Scheme 20. Synthesis of compound 18.

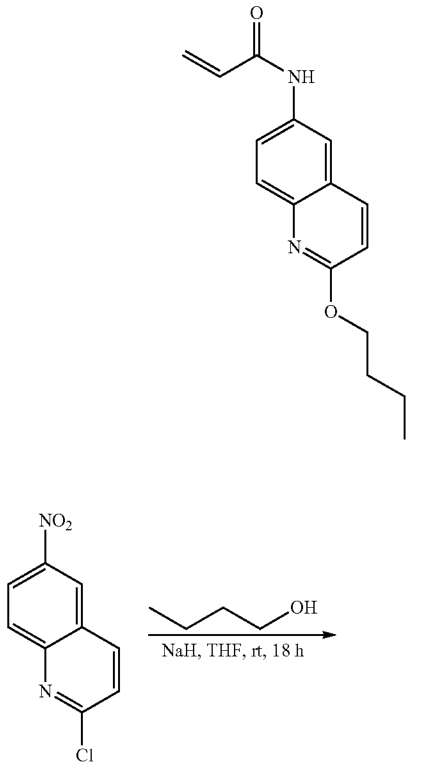

-continued

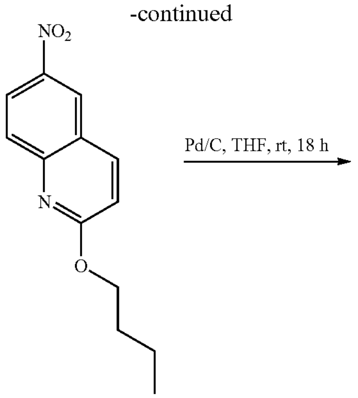

18-1

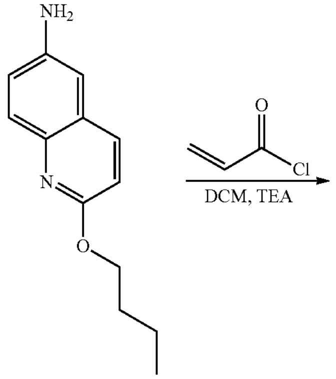

18-2

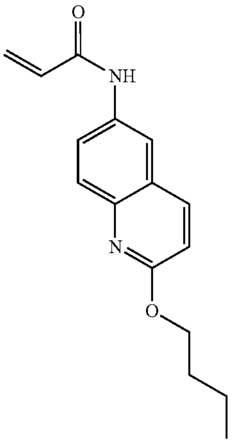

compound 18

Preparation of 2-butoxy-6-nitroquinoline (18-1). Under $N_2$, to a solution of butan-1-ol (384 mg, 5.19 mmol) in dry THF (18 mL) was added NaH (60%) (260 mg, 6.5 mmol) at 0° C. and the mixture was kept stirring at 0° C. for additional 0.5 h. Then, 2-chloro-6-nitroquinoline (900 mg, 4.33 mmol) was added dropwise. The resulting reaction mixture was then warmed to room temperature slowly and stirred for additional 18 h. The reaction mixture was diluted with $NH_4Cl$ (aq.) (50 mL) and extracted with EtOAc (20 mL×3). The combined organic phases were washed with brine (20 mL), dried over anhydrous sodium sulfate, and concentrated in vacuo to afford 2-butoxy-6-nitroquinoline (400 mg, crude, 37.5% yield) as a yellow oil, which was used directly in the next step without further purification. [M+H]+m/z 247.10, found 247.

Preparation of 2-butoxyquinolin-6-amine (18-2). Under $H_2$, a mixture of 2-butoxy-6-nitroquinoline (400 mg, 1.63 mmol) and Pd/C (10%, 40 mg) in MeOH (10 mL) was stirred at rt for 18 h. Filtered, the filtrate was concentrated in vacuo to afford 2-butoxyquinolin-6-amine (260 mg, crude, 73.8% yield) as a yellow solid, which was used directly in the next step without further purification. $[M+H]^+$ m/z 217.13, found 217.

Preparation of N-(2-butoxyquinolin-6-yl)acrylamide (compound 18). Under $N_2$, to a solution of 2-butoxyquinolin-6-amine (260 mg, 1.20 mmol), prop-2-enoyl chloride (130 mg, 1.44 mmol) in DCM (5 mL) was added triethylamine (242 mg, 2.40 mmol) dropwise at rt and the reaction mixture was kept stirring at rt for additional 2 h. Evaporated and the residue was purified by Flash chromatography (eluent: DCM/MeOH=20/1) to afford N-(2-butoxyquinolin-6-yl)acrylamide (70 mg, 99.1% purity, 21.6% yield) as a withe solid. $[M+H]^+$ nm/z 271.14, found 271. $^1$H NMR (400 MHz, $CDCl_3$) δ 8.30 (s, 1H), 7.95 (d, J=8.9 Hz, 1H), 7.83 (d, J=8.8 Hz, 1H), 7.66-7.40 (m, 2H), 6.89 (d, J=8.9 Hz, 1H), 6.48 (dd, J=16.8, 1.2 Hz, 1H), 6.31 (dd, J=16.8, 10.2 Hz, 1H), 5.80 (dd, J=10.2, 1.1 Hz, 1H), 4.47 (t, J=6.6 Hz, 2H), 1.88-1.74 (m, 2H), 1.61-1.46 (m, 2H), 1.00 (t, J=7.4 Hz, 3H).

Example 19

Synthesis of Compound 19

(N-(1-(pentyloxy)isoquinolin-6-yl)acrylamide)

Scheme 21. Synthesis of compound 19.

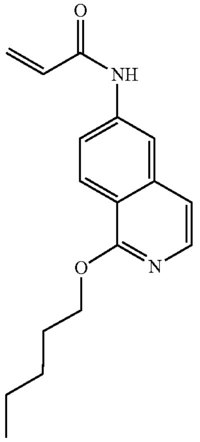

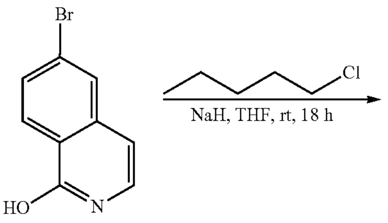

-continued

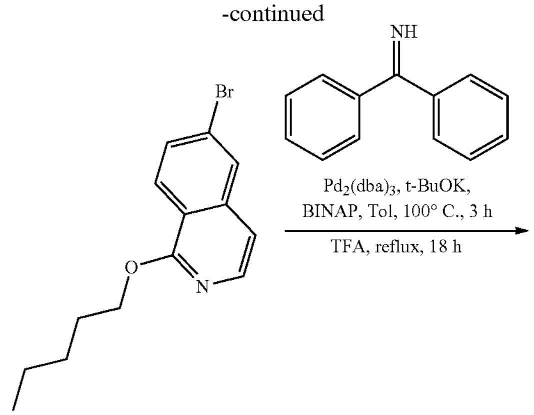

19-1

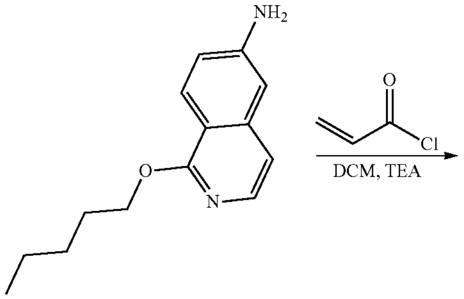

19-2

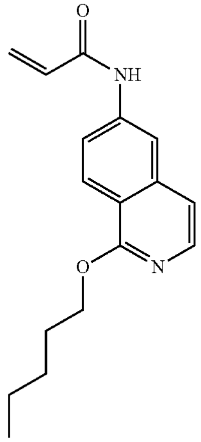

compound 19

Preparation of 5-((5-(trifluoromethyl)pyridin-2-yl)oxy)naphthalen-2-amine (19-1). Under $N_2$, to a solution of 6-bromoisoquinolin-1-ol (500 mg, 2.62 mmol) in THF (5 mL) was added NaH (60%) (247 mg, 6.18 mmol) and the mixture was stirred at rt for 0.5 h. Then, 1-chloropentane (218 mg, 2.47 mmol) was added dropwise. The reaction mixture was stirred at rt for 18 h. $NH_4Cl$ (aq.) (30 mL) was added, extracted with EtOAc (20 mL×3) and the combined organic phases were washed with brine (10 mL×3), dried over anhydrous sodium sulfate, and concentrated in vacuo. The residue was purified by Flash chromatography (eluent: PE/EtOAc=1/1) to afford 6-bromo-1-(pentyloxy)isoquinoline (550 mg, 91% purity, 82.5% yield) as a yellow solid. $[M+H]^+$ m/z 294.04, found 293.90.

Preparation of 1-(pentyloxy)isoquinolin-6-amine (19-2). Under $N_2$, a mixture of 6-bromo-1-(pentyloxy)isoquinoline (450 mg, 1.53 mmol), diphenylmethanimine (332 mg, 1.84 mmol), t-BuOK (515 mg, 4.59 mmol), BINAP (381 mg, 0.61 mmol) and $Pd_2(dba)_3$ (560 mg, 0.31 mmol) in Toluene (10 mL) was stirred at 100° C. for 3 h. The reaction mixture was cooled to rt and $H_2O$ (50 mL) was added, extracted with EtOAc (20 mL×3) and the combined organic phases were washed with brine (10 mL×3), dried over anhydrous sodium sulfate, and concentrated in vacuo. The residue in TFA (20 mL) was refluxed for 18 h. The solvent was removed under reduced pressure. $NaHCO_3$ (aq.) (50 mL) was added and extracted with EtOAc (20 mL×3). The combined organic phases were washed with brine (10 mL×3), dried over anhydrous sodium sulfate, and concentrated in vacuo. The residue was purified by Flash chromatography (eluent: PE/EtOAc=1/2) to afford 1-(pentyloxy)isoquinolin-6-amine (274 mg, 95% purity, 74.8% yield) as a yellow oil. $[M+H]^+$ m/z 331.14, found 331.05.

Preparation of N-(1-(pentyloxy)isoquinolin-6-yl)acrylamide (compound 19). Under $N_2$, to a solution of 1-(pentyloxy)isoquinolin-6-amine (274 mg, 1.19 mmol), prop-2-enoyl chloride (129 mg, 1.43 mmol) in DCM (4 mL) was added triethylamine (361 mg, 3.57 mmol) dropwise at rt and the reaction mixture was kept stirring at rt for additional 2 h. Evaporated and the residue was purified by Flash chromatography (eluent: PE/EtOAc=1/1) to afford N-(1-(pentyloxy)isoquinolin-6-yl)acrylamide (65 mg, 99% purity, 19.0% yield) as a pale yellow solid. $[M+H]^+$ m/z 285.15, found 285. $^1H$ NMR (400 MHz, $CDCl_3$) δ 8.24 (s, 1H), 8.22-8.14 (m, 1H), 8.07-7.65 (m, 2H), 7.51 (dd, J=8.4, 2.8 Hz, 1H), 7.18-7.03 (m, 1H), 6.50 (dd, J=16.9, 1.3 Hz, 1H), 6.41-6.24 (m, 1H), 5.87-5.73 (m, 1H), 4.52-4.37 (m, 2H), 1.95-1.82 (m, 2H), 1.57-1.34 (m, 4H), 1.01-0.87 (m, 3H).

Example 20

Synthesis of Compound 20

(N-(5-(pentyloxy)naphthalen-2-yl)acrylamide)

Scheme 22. Synthesis of compound 20.

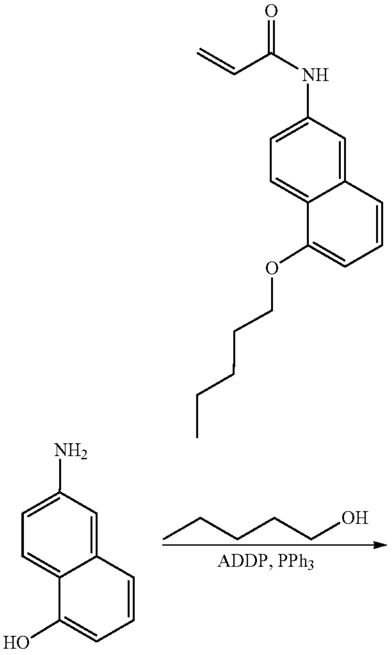

-continued

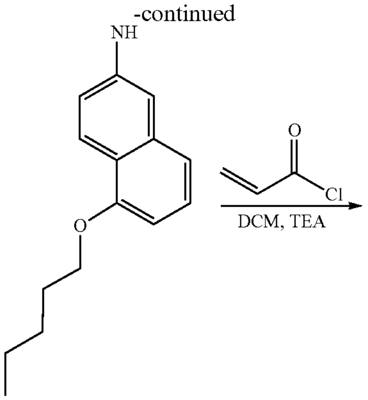

20-1

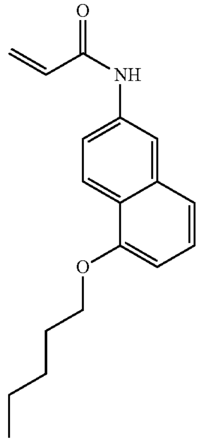

compound 20

Preparation of 5-(pentyloxy)naphthalen-2-amine (20-1). Under $N_2$, to a solution of ADDP (1.58 g, 6.28 mmol) in dry $CDCl_3$ (15 mL) added $PPh_3$ (1.65 g, 6.28 mmol) at 0° C. and the mixture was kept stirring at 0° C. for additional 20 mins. Then, 6-aminonaphthalen-1-ol (500 mg, 3.14 mmol) and pentan-1-ol (276 mg, 3.14 mmol) in dry $CDCl_3$ (2 mL) were added dropwise. The resulting reaction mixture was then warmed to room temperature slowly and stirred for additional 18 h. The solvent was removed under reduced pressure. Water (50 mL) was added and the mixture was extracted with EtOAc (30 mL×3). The combined organic phases were washed with brine (20 mL), dried over anhydrous sodium sulfate, and concentrated in vacuo. The residue was purified by Flash chromatography (eluent: DCM/MeOH=50/1) to afford 5-(pentyloxy)naphthalen-2-amine (600 mg, 85% purity, 70.8% yield) as a white solid. $[M+H]^+$ m/z 230.15, found 230.

Preparation of N-(5-(pentyloxy)naphthalen-2-yl)acrylamide (compound 20). Under $N_2$, to a solution of 5-(pentyloxy)naphthalen-2-amine (2) (200 mg, 0.87 mmol), prop-2-enoyl chloride (118 mg, 1.31 mmol) in DCM (4 mL) was added triethylamine (264 mg, 2.62 mmol) dropwise at rt and the reaction mixture was kept stirring at rt for additional 2 h. Evaporated and the residue was purified by Flash chromatography and Prep-HPLC to afford N-(5-(pentyloxy)naphthalen-2-yl)acrylamide (60 mg, 97% purity, 23.6% yield) as a withe solid. $[M+H]^+$ m/z 284.16, found 284. $^1H$ NMR (400 MHz, $CDCl_3$) δ 8.37-8.11 (m, 2H), 7.55-7.28 (m, 4H), 6.73 (dd, J=6.0, 2.4 Hz, 1H), 6.48 (dd, J=16.8, 1.0 Hz, 1H), 6.30

(dd, J=16.8, 10.2 Hz, 1H), 5.80 (dd, J=10.2, 1.1 Hz, 1H), 4.12 (t, J=6.4 Hz, 2H), 2.02-1.82 (m, 2H), 1.67-1.36 (m, 4H), 0.96 (t, J=7.2 Hz, 3H).

Example 21

Synthesis of Compound 21

(N-(5-((5-(trifluoromethyl)pyridin-2-yl)oxy)naphthalen-2-yl)acrylamide)

Scheme 23. Synthesis of compound 21.

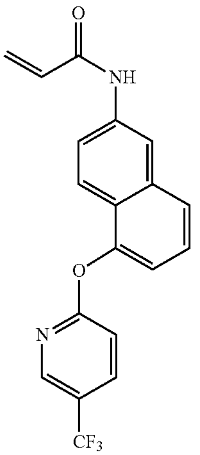

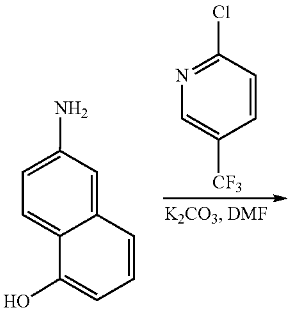

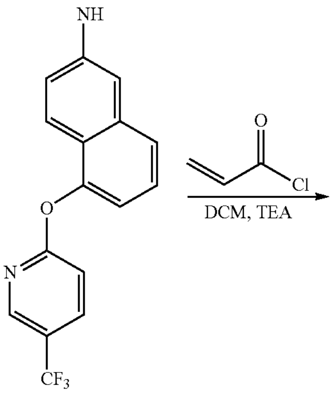

21-1

-continued

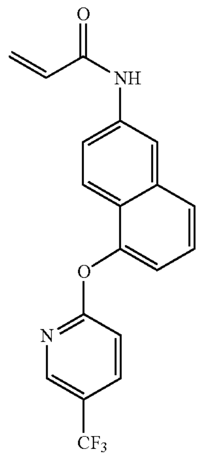

compound 21

Preparation of 5-((5-(trifluoromethyl)pyridin-2-yl)oxy)naphthalen-2-amine (21-1). A mixture of 2-chloro-5-(trifluoromethyl)pyridine (344 mg, 1.88 mmol), 6-aminonaphthalen-1-ol (300 mg, 1.88 mmol) and $K_2CO_3$ (520 mg, 3.76 mmol) in DMF (5 mL) was stirred at 80° C. for 4 h. The reaction mixture was cooled to rt and $H_2O$ (50 mL) was added. The mixture was extracted with EtOAc (20 mL×3) and the combined organic phases were washed with brine (10 mL×3), dried over anhydrous sodium sulfate, and concentrated in vacuo. The residue was purified by Flash chromatography (eluent: PE/EtOAc=5/1) to afford 5-((5-(trifluoromethyl)pyridin-2-yl)oxy)naphthalen-2-amine (290 mg, 85% purity, 42.8% yield) as a yellow solid. $^1H$ NMR (400 MHz, DMSO-$d_6$, ppm) δ 8.52 (d, J=0.6 Hz, 1H), 8.27-8.18 (m, 1H), 7.46 (dd, J=13.0, 8.6 Hz, 2H), 7.36-7.19 (m, 2H), 6.96-6.81 (m, 3H), 5.52 (s, 2H).

Preparation of N-(5-((5-(trifluoromethyl)pyridin-2-yl)oxy)naphthalen-2-yl)acrylamide (compound 21). Under $N_2$, to a solution of 5-((5-(trifluoromethyl)pyridin-2-yl)oxy)naphthalen-2-amine (290 mg, 0.95 mmol), prop-2-enoyl chloride (123 mg, 1.37 mmol) in DCM (4 mL) was added triethylamine (138 mg, 1.37 mmol) dropwise at rt and the reaction mixture was kept stirring at rt for additional 2 h. Evaporated and the residue was purified by Flash chromatography (eluent: PE/EtOAc=5/1) to afford N-(5-((5-(trifluoromethyl)pyridin-2-yl)oxy)naphthalen-2-yl)acrylamide (101 mg, 97.1% purity, 24.0% yield) as a withe solid. $[M+H]^+$ m/z 359.09, found 359. $^1H$ NMR (400 MHz, DMSO-$d_6$, ppm) δ 10.41 (s, 1H), 8.51 (s, 2H), 8.28 (dd, J=8.7, 2.6 Hz, 1H), 7.78 (t, J=8.1 Hz, 2H), 7.62 (dd, J=9.1, 1.9 Hz, 1H), 7.53 (t, J=7.9 Hz, 1H), 7.37 (d, J=8.7 Hz, 1H), 7.26 (d, J=7.5 Hz, 1H), 6.50 (dd, J=17.0, 10.1 Hz, 1H), 6.31 (dd, J=17.0, 1.9 Hz, 1H), 5.80 (dd, J=10.1, 1.9 Hz, 1H).

Example 22

Synthesis of Compound 22

(N-(3-methyl-4-(5-(trifluoromethyl)isoxazol-3-yl)phenyl)acrylamide)

Scheme 24. Synthesis of compound 22.

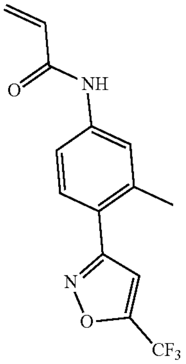

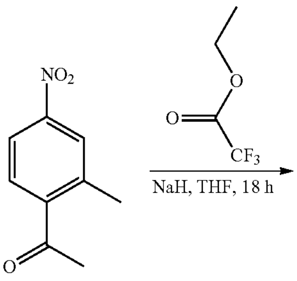

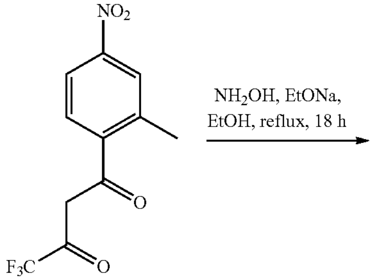

22-1

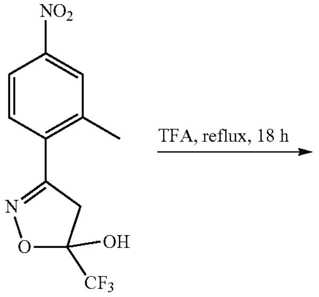

22-2

-continued

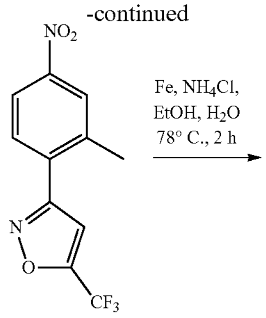

22-3

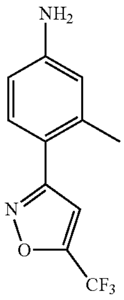

22-4

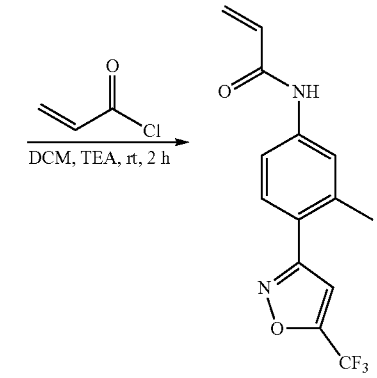

compound 22

Preparation of 4,4,4-trifluoro-1-(2-methyl-4-nitrophenyl) butane-1,3-dione (22-1). Under $N_2$, to a solution of 1-(2-methyl-4-nitrophenyl)ethan-1-one (900 mg, 5.02 mmol) in dry THF (20 mL) was added NaH (60%) (301 mg, 7.53 mmol) at 0° C. and the mixture was kept stirring at 0° C. for additional 0.5 h. Then, ethyl 2,2,2-trifluoroacetate (934 mg, 6.53 mmol) was added dropwise. The resulting reaction mixture was then warmed to room temperature slowly and stirred for additional 18 h. The reaction mixture was diluted with $NH_4Cl$ (aq.) (50 mL) and extracted with EtOAc (20 mL×3) and the combined organic phases were washed with brine (20 mL), dried over anhydrous sodium sulfate, and concentrated in vacuo to afford 4,4,4-trifluoro-1-(2-methyl-4-nitrophenyl)butane-1,3-dione (1 g, crude, 72.5% yield) as a yellow oil, which was used directly in the next step without further purification. $^1$H NMR (400 MHz, $CDCl_3$) δ 8.08 (s, 1H), 8.02 (d, J=8.5 Hz, 1H), 7.42 (d, J=8.5 Hz, 1H), 3.72 (d, J=17.9 Hz, 1H), 3.50 (d, J=17.9 Hz, 1H), 2.58 (s, 3H).

Preparation of 3-(2-methyl-4-nitrophenyl)-5-(trifluoromethyl)-4,5-dihydroisoxazol-5-ol (22-2). A mixture of AcONa (440 mg, 5.4 mmol) and $NH_2OH·HCl$ (380 mg, 5.4 mmol) in EtOH (15 mL) was stirred at 80° C. for 20 mins, then 4,4,4-trifluoro-1-(2-methyl-4-nitrophenyl)butane-1,3-dione (1 g, 3.6 mmol) was added. The reaction mixture was stirred at 80° C. for 18 h. EtOH was removed under reduced pressure. The residue was diluted with $H_2O$ (100 mL) and extracted with EtOAc (30 mL×4) and the combined organic phases were washed with brine (20 mL), dried over anhydrous sodium sulfate, and concentrated in vacuo to afford 3-(2-methyl-4-nitrophenyl)-5-(trifluoromethyl)-4,5-dihydroisoxazol-5-ol (1.2 g, 75% purity, 86.1% yield) as a yellow solid, which was used directly in the next step without further purification. $^1$H NMR (400 MHz, DMSO-$d_6$, ppm) δ 8.78 (s, 1H), 8.24 (d, J=1.4 Hz, 1H), 8.14 (dd, J=8.6, 2.2 Hz, 1H), 7.81 (d, J=8.6 Hz, 1H), 4.08 (d, J=17.9 Hz, 1H), 3.63 (d, J=18.6 Hz, 1H), 2.61 (s, 3H).

Preparation of 3-(2-methyl-4-nitrophenyl)-5-(trifluoromethyl)isoxazole (22-3). 3-(2-methyl-4-nitrophenyl)-5-(trifluoromethyl)isoxazole (1.2 g, 4.14 mmol) in TFA (35 mL) was stirred at 70° C. for 18 h. TFA was removed under reduced pressure and the residue was diluted with $NaHCO_3$ (aq.) (40 mL) and extracted with EtOAc (30 mL×4) and the combined organic phases were washed with brine (20 mL), dried over anhydrous sodium sulfate and concentrated in vacuo to afford 3-(2-methyl-4-nitrophenyl)-5-(trifluoromethyl)isoxazole (1.5 g, 60% purity, 57.0% yield) as a yellow solid, which was used directly in the next step without further purification. $^1$H NMR (400 MHz, $CDCl_3$) δ 8.22 (d, J=2.2 Hz, 1H), 8.16 (dd, J=8.5, 2.3 Hz, 1H), 7.69 (d, J=8.5 Hz, 1H), 6.96 (s, 1H), 2.62 (s, 3H).

Preparation of 3-(2-methyl-4-nitrophenyl)-5-(trifluoromethyl)isoxazole (22-4). A mixture of 3-(2-methyl-4-nitrophenyl)-5-(trifluoromethyl)isoxazole (1.1 g, 4.0 mmol), Fe (780 mg, 14.0 mmol) and $NH_4Cl$ (870 mg, 16.0 mmol) in EtOH (15 mL) and $H_2O$ (3 mL) was stirred at 78° C. for 2 h. Evaporated and the residue was purified by Flash chromatography (eluent: PE/EtOAc=10/1) to afford 3-(2-methyl-4-nitrophenyl)-5-(trifluoromethyl)isoxazole (600 mg, 85% purity, 52.4% yield) as a yellow solid. [M+H]+m/z 243.07, found 243.

Preparation of N-(3-methyl-4-(5-(trifluoromethyl)isoxazol-3-yl)phenyl)acrylamide (compound 22). Under $N_2$, to a solution of 3-(2-methyl-4-nitrophenyl)-5-(trifluoromethyl) isoxazole (180 mg, 0.74 mmol), prop-2-enoyl chloride (80 mg, 0.88 mmol) in DCM (4 mL) was added triethylamine (90 mg, 0.88 mmol) dropwise at rt and the reaction mixture was kept stirring at rt for additional 2 h. Evaporated and the residue was purified by Flash chromatography (eluent: PE/EtOAc=5/1) to afford N-(3-methyl-4-(5-(trifluoromethyl)isoxazol-3-yl)phenyl)acrylamide (50 mg, 98% purity, 22.2% yield) as a white solid. $[M+H]^+$ m/z 297.25, found 297. $^1$H NMR (400 MHz, $CDCl_3$) δ 7.63-7.53 (m, 2H), 7.49 (d, J=8.3 Hz, 1H), 7.31 (s, 1H), 6.88 (s, 1H), 6.48 (d, J=16.8 Hz, 1H), 6.26 (dd, J=16.8, 10.2 Hz, 1H), 5.83 (d, J=10.2 Hz, 1H), 2.51 (s, 3H).

Example 23

Synthesis of Compound 23

(N-(3-chloro-4-(5-(trifluoromethyl)isoxazol-3-yl) phenyl)acrylamide)

Scheme 25. Synthesis of compound 23.

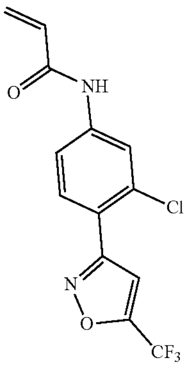

-continued

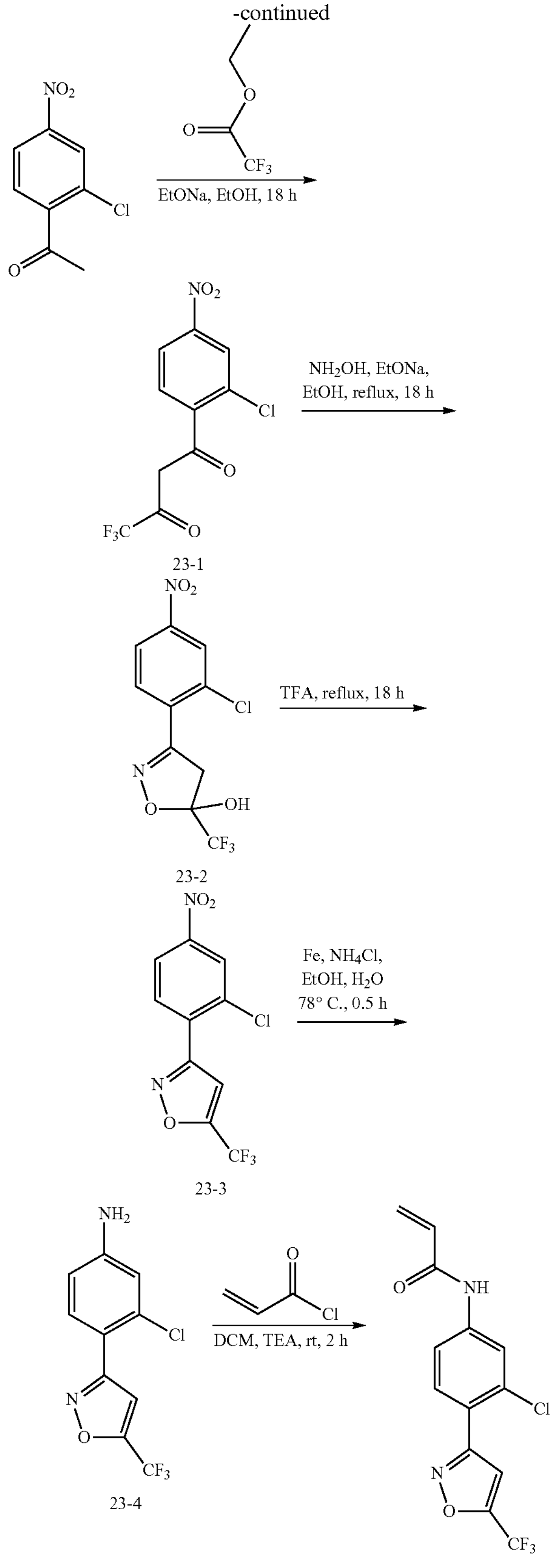

23-1

23-2

23-3

23-4 compound 23

Preparation of 1-(2-chloro-4-nitrophenyl)-4,4,4-trifluorobutane-1,3-dione (23-1). Under $N_2$, to a solution of 1-(2-methyl-4-nitrophenyl)ethan-1-one (1.8 g, 9.00 mmol) and ethyl 2,2,2-trifluoroacetate (1.4 g, 9.90 mmol) in dry EtOH (36 mL) was added EtONa (530 mg, 12.60 mmol) at 0° C. The reaction mixture heated to 80° C. for 18 h. The solvent was removed under reduced pressure and $NH_4Cl$ (aq.) (50 mL) was added. The mixture was extracted with EtOAc (20 mL×3) and the combined organic phases were washed with brine (20 mL), dried over anhydrous sodium sulfate, and concentrated in vacuo to afford 1-(2-chloro-4-nitrophenyl)-4,4,4-trifluorobutane-1,3-dione (1.5 g, crude, 56% yield) as a yellow oil, which was used directly in the next step without further purification. $^1H$ NMR (400 MHz, $CDCl_3$) δ 8.21 (d, J=1.5 Hz, 1H), 8.15-8.01 (m, 1H), 7.60 (d, J=8.5 Hz, 1H), 2.60 (s, 2H).

Preparation of 3-(2-chloro-4-nitrophenyl)-5-(trifluoromethyl)-4,5-dihydroisoxazol-5-ol (23-2). A mixture of AcONa (627 mg, 7.60 mmol) and $NH_2OH{\cdot}HCl$ (535 mg, 7.60 mmol) in EtOH (30 mL) was stirred at 80° C. for 20 mins, then 1-(2-chloro-4-nitrophenyl)-4,4,4-trifluorobutane-1,3-dione (2) (1.5 g, 5.1 mmol) was added. The reaction mixture was stirred at 80° C. for 18 h. EtOH was removed under reduced pressure. The residue was diluted with $H_2O$ (100 mL) and extracted with EtOAc (30 mL×4) and the combined organic phases were washed with brine (20 mL), dried over anhydrous sodium sulfate, and concentrated in vacuo. The residue was purified by silica gel chromatography (PE/EtOAc=10/1) to afford 3-(2-chloro-4-nitrophenyl)-5-(trifluoromethyl)-4,5-dihydroisoxazol-5-ol (800 mg, crude, 50% yield) as a yellow solid. $^1H$ NMR (400 MHz, $CDCl_3$) δ 8.34 (d, J=2.2 Hz, 1H), 8.19 (dd, J=8.6, 2.2 Hz, 1H), 7.97 (d, J=8.6 Hz, 1H), 3.95 (d, J=18.4 Hz, 1H), 3.70 (d, J=18.4, 0.9 Hz, 1H).

Preparation of 3-(2-chloro-4-nitrophenyl)-5-(trifluoromethyl)isoxazole (23-3). 3-(2-chloro-4-nitrophenyl)-5-(trifluoromethyl)-4,5-dihydroisoxazol-5-ol (800 mg, 2.58 mmol) in TFA (30 mL) was stirred at 70° C. for 18 h. TFA was removed under reduced pressure and the residue was diluted with $NaHCO_3$ (aq.) (100 mL) and extracted with EtOAc (30 mL×4) and the combined organic phases were washed with brine (20 mL), dried over anhydrous sodium sulfate and concentrated in vacuo to afford 3-(2-chloro-4-nitrophenyl)-5-(trifluoromethyl)isoxazole (400 mg, 60% purity, 53.0% yield) as a yellow solid, which was used directly in the next step without further purification. 1H NMR (400 MHz, DMSO-$d_6$, ppm) δ 8.26 (s, 1H), 8.17 (d, J=8.4 Hz, 1H), 7.56 (d, J=8.1 Hz, 1H), 5.48 (s, 1H).

Preparation of 3-chloro-4-(5-(trifluoromethyl)isoxazol-3-yl)aniline (23-4). A mixture of 3-(2-chloro-4-nitrophenyl)-5-(trifluoromethyl) (400 mg, 1.37 mmol), Fe (269 mg, 4.8 mmol) and $NH_4Cl$ (254 mg, 4.8 mmol) in EtOH (9 mL) and $H_2O$ (3 mL) was stirred at 78° C. for 0.5 h. Evaporated and the residue was purified by Flash chromatography (eluent: PE/EtOAc=10/1) to afford 3-chloro-4-(5-(trifluoromethyl) isoxazol-3-yl)aniline (100 mg, 85% purity, 27.8% yield) as a yellow solid. $[M+H]^+$ m/z 263.01, found 263.

Preparation of N-(3-chloro-4-(5-(trifluoromethyl)isoxazol-3-yl)phenyl)acrylamide (compound 23). Under $N_2$, to a solution of 3-chloro-4-(5-(trifluoromethyl)isoxazol-3-yl) aniline (300 mg, 1.14 mmol), prop-2-enoyl chloride (124 mg, 1.364 mmol) in DCM (5 mL) was added triethylamine (140 mg, 1.364 mmol) dropwise at rt and the reaction mixture was kept stirring at rt for additional 2 h. Evaporated and the residue was purified by Flash chromatography (eluent: PE/EtOAc=5/1) to afford N-(3-chloro-4-(5-(trifluoromethyl)isoxazol-3-yl)phenyl)acrylamide (70 mg, 99.3% purity, 34.4% yield) as a withe solid. $[M+H]^+$ m/z 317.02, found 317. $^1H$ NMR (400 MHz, DMSO-$d_6$, ppm) δ 10.61 (s, 1H), 8.12 (s, 1H), 7.90 (s, 1H), 7.73 (dd, J=24.9, 8.5 Hz, 2H), 6.53-6.22 (m, 2H), 5.93-5.73 (m, 1H).

Example 24

Synthesis of Compound 24

(N-(4-(1-pentyl-1H-pyrazol-3-yl)phenyl)acrylamide)

Scheme 26. Synthesis of compound 24.

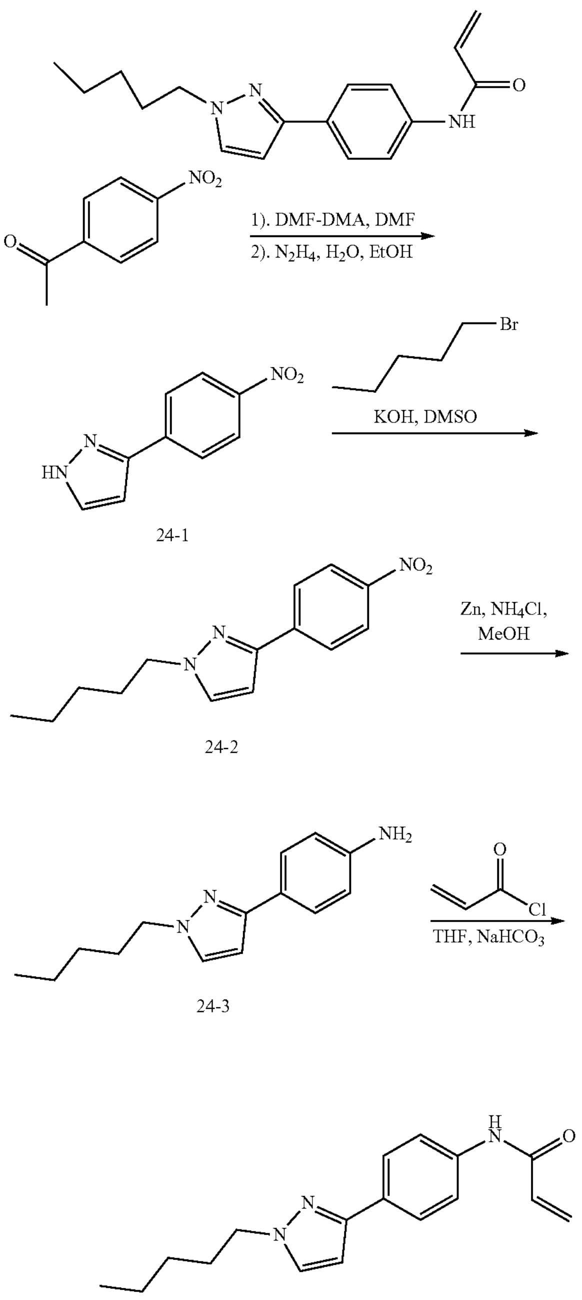

24-1

24-2

24-3 compound 24

Preparation of 3-(4-nitrophenyl)-1H-pyrazole (24-1). A solution of 1-(4-nitrophenyl) ethanone (1 g, 6.05 mmol) and N,N-dimethylformamide dimethyl acetal (0.87 g, 7.26 mmol) in N,N-dimethylformamide (10 mL) was stirred for 1 h at 80° C. The reaction was concentrated, the residue was dissolved in ethanol (10 mL) and treated with hydrazine monohydrate (1 mL, 18.16 mmol). After the reaction was stirred at 70° C. for 2 h, it was cooled to room temperature and poured into ice-water (20 mL). The solid was collected by filtration, washed with water (4×5 mL), and dried to provide the 3-(4-nitrophenyl)-1H-pyrazole as a yellow powder. 1 g, 90% purity, 78.69% yield. $[M+H]^+$ m/z 189.17, found 190. $^1H$ NMR (301 MHz, d6-DMSO) δ 13.25 (s, 1H), 8.43-8.16 (m, 2H), 8.06 (dd, J=20.8, 8.6 Hz, 2H), 7.89 (d, J=1.5 Hz, 1H), 6.95 (d, J=1.9 Hz, 1H).

Preparation of 3-(4-nitrophenyl)-1-pentyl-1H-pyrazole (24-2). To a mixture of 3-(4-nitrophenyl)-1H-pyrazole (500 mg, 2.64 mmol) and KOH (163 mg, 2.91 mmol) in DMSO (5 mL) was added 1-bromopentane (439 mg, 2.91 mmol), the resulting mixture was stirred at 25° C. for 1 hr. The reaction was quenched with ice water (25 mL) and extracted with EtOAc (10 mL×3). The combined organic phase was washed with brine, dried over $Na_2SO_4$, and concentrated in vacuo. The residue was purified by silica gel chromatography (PE/EtOAc=10:1 to 2:1) to afford 3-(4-nitrophenyl)-1-pentyl-1H-pyrazole (560 mg, 90% purity, 73.54% yield) as a yellow solid. $[M+H]^+$ m/z=259.31, found 260. $^1H$ NMR (400 MHz, $CDCl_3$) δ 8.25 (d, J=8.8 Hz, 2H), 7.95 (d, J=8.8 Hz, 2H), 7.45 (d, J=2.2 Hz, 1H), 6.64 (d, J=2.2 Hz, 1H), 4.20-4.11 (m, 2H), 1.92 (dd, J=14.4, 7.2 Hz, 2H), 1.43-1.28 (m, 4H), 0.98-0.83 (m, 3H).

Preparation of 4-(1-pentyl-1H-pyrazol-3-yl)aniline (24-3). To a solution of 3-(4-nitrophenyl)-1-pentylpyrazole (560 mg, 2.16 mmol) in MeOH (5 mL) was added Zinc powder (1.41 g, 21.6 mmol), then saturated $NH_4Cl$ (5 mL) was added dropwise, TLC showed the reaction was completed. The mixture was filtered and diluted with ice/water (25 mL). It was extracted with EtOAc (10 mL×3). The combined organic phase was washed with brine, dried over $Na_2SO_4$, filtered, and concentrated in vacuo to give crude 4-(1-pentyl-1H-pyrazol-3-yl)aniline as a yellow solid. 510 mg, 90%, yield 92.67%. The crude product was used directly in next step without further purification. $[M+H]^+$ m/z=229.33, found 230.

Preparation of N-(4-(1-pentyl-1H-pyrazol-3-yl)phenyl) acrylamide (compound 24). To a solution of 4-(1-pentylpyrazol-3-yl)aniline (250 mg, 1.09 mmol) in THF/aq. $NaHCO_3$(V:V=1:1, 10 mL) was added prop-2-enoyl chloride (148 mg, 1.64 mmol) dropwise. The reaction was stirred for 10 min at 25° C. TLC showed the reaction was completed, it was quenched with MeOH (1 mL) and water (10 mL). The resulting mixture was extracted with EtOAc (10 mL×2). The organic layers were combined, washed with brine, dried over $Na_2SO_4$, filtered, and concentrated in vacuo. The residue was purified by silica gel chromatography (PE/EtOAc=10:1-2:1) and Prep-HPLC to afford N-(4-(1-pentyl-1H-pyrazol-3-yl)phenyl)acrylamide (180 mg, 99.83% purity, 57.7% yield) as a white solid. $[M+H]^+$ m/z=283.38, found 284. $^1H$ NMR (400 MHz, $CDCl_3$) δ 7.79 (d, J=8.6 Hz, 2H), 7.63 (d, J=8.6 Hz, 2H), 7.39 (d, J=2.2 Hz, 1H), 7.33 (s, 1H), 6.51 (d, J=2.2 Hz, 1H), 6.45 (dd, J=16.8, 1.1 Hz, 1H), 6.26 (dd, J=16.8, 10.2 Hz, 1H), 5.78 (dd, J=10.2, 1.1 Hz, 1H), 4.15 (t, J=7.3 Hz, 2H), 1.92 (dd, J=14.6, 7.5 Hz, 2H), 1.46-1.26 (m, 4H), 0.90 (t, J=7.0 Hz, 3H).

Example 25

Synthesis of Compound 25

(N-(2-pentyl-4,5-dihydro-2H-benzo[e]isoindol-7-yl) acrylamide)

Scheme 27. Synthesis of compound 25.

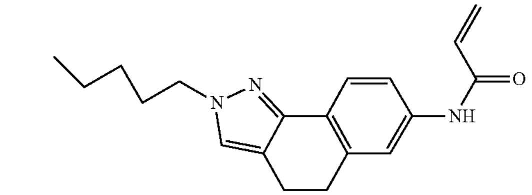

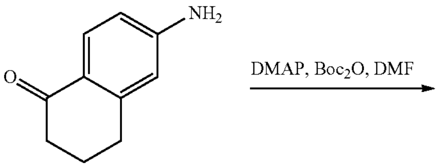

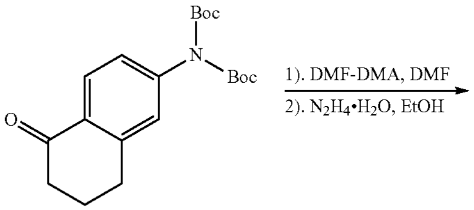

25-1

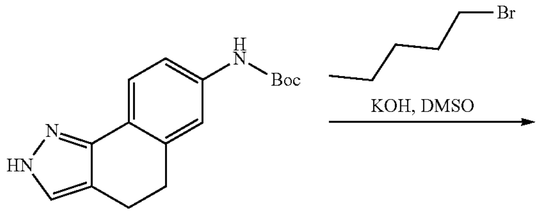

25-2

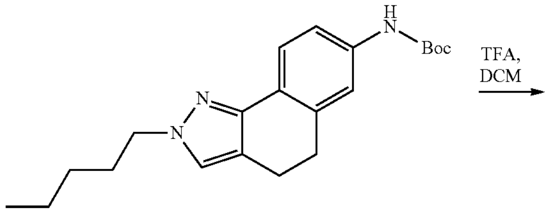

25-3

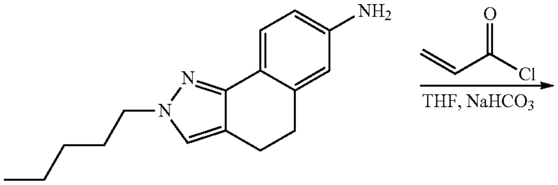

25-4

-continued

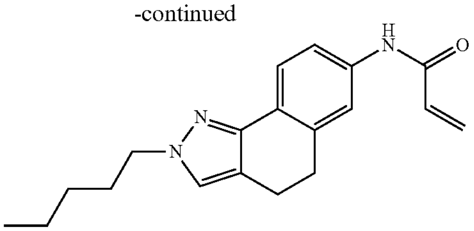

compound 25

Preparation of tert-butyl (tert-butoxycarbonyl)(5-oxo-5,6,7,8-tetrahydronaphthalen-2-yl)carbamate (25-1). A mixture of 6-amino-3,4-dihydro-2H-naphthalen-1-one (4.00 g, 24.81 mmol), $Boc_2O$ (13.54 g, 62.02 mmol) and DMAP (3.03 g, 24.81 mmol) in DMF (50 mL) was stirred at 25° C. for 16 hrs. The reaction was quenched with ice water (250 mL) and extracted with EtOAc (200 mL×3). The combined organic phase was washed with brine, dried over $Na_2SO_4$, filtered, and concentrated in vacuo. The residue was purified by silica gel chromatography (PE/EtOAc=10:1 to 3:1) to afford tert-butyl (tert-butoxycarbonyl)(5-oxo-5,6,7,8-tetrahydronaphthalen-2-yl)carbamate as a white solid. 4.64 g, 90% purity, 46.61% yield. $[M+H]^+$ m/z 361.44, found 362. $^1H$ NMR (301 MHz, $CDCl_3$) δ 8.04 (d, J=8.2 Hz, 1H), 7.06 (d, J=2.4 Hz, 2H), 2.97 (t, J=5.9 Hz, 2H), 2.72-2.60 (m, 2H), 2.16 (d, J=6.1 Hz, 2H), 1.45 (s, 18H).

Preparation of 3-(4-nitrophenyl)-1-pentyl-1H-pyrazole (25-2). A solution of tert-butyl (tert-butoxycarbonyl)(5-oxo-5,6,7,8-tetrahydronaphthalen-2-yl)carbamate (2.70 g, 7.48 mmol) in DMF (25 mL) was added DMF-DMA (1.84 g, 15.44 mmol) and was stirred at 90° C. for 1 h. The reaction was concentrated, the residue was dissolved in ethanol (50 mL) and treated with hydrazine monohydrate (2.6 mL, 49.4 mmol), which was stirred at 70° C. for 2 h. It was cooled to room temperature and poured into ice-water (100 mL), which was extracted with EtOAc (50 mL×3). The combined organic phase was washed with brine, dried over $Na_2SO_4$, filtered, and concentrated in vacuo. The residue was purified by silica gel chromatography (PE/EtOAc=10:1 to 3:1) to afford 3-(4-nitrophenyl)-1-pentyl-1H-pyrazole (450 mg, 90% purity, 13.79% yield) as a yellow solid. $[M+H]^+$ m/z=285.35, found 286.

Preparation of tert-butyl (2-pentyl-4,5-dihydro-2H-benzo[g] indazol-7-yl)carbamate (25-3). To a solution of tert-butyl (4,5-dihydro-2H-benzo[g] indazol-7-yl)carbamate (375 mg, 1.31 mmol) in DMSO (5 mL) was added 1-bromopentane (218 mg, 1.44 mmol) and KOH (147 mg, 2.62 mmol). The resulting mixture was stirred at 25° C. for 1 hr. The reaction was quenched with ice water (25 mL) and extracted with EtOAc (10 mL×3). The combined organic phase was washed with brine, dried over $Na_2SO_4$, filtered, and concentrated in vacuo. The residue was purified by silica gel chromatography (PE/EtOAc=10:1 to 2:1) to afford tert-butyl (2-pentyl-4,5-dihydro-2H-benzo[g] indazol-7-yl)carbamate (320 mg, 75%, yield 51.39%) as yellow solid. $[M+H]^+$ m/z=355.48, found 356. $^1H$ NMR (301 MHz, DMSO) δ 9.33 (s, 1H), 7.49 (d, J=7.9 Hz, 2H), 7.38 (s, 1H), 7.27 (d, J=7.9 Hz, 1H), 4.04 (t, J=6.9 Hz, 2H), 2.76 (q, J=7.3 Hz, 2H), 2.65 (q, J=7.4 Hz, 2H), 1.83-1.71 (m, 2H), 1.47 (s, 9H), 1.32-1.15 (m, 4H), 0.85 (t, J=7.1 Hz, 3H).

Preparation of 2-pentyl-4,5-dihydro-2H-benzo[g] indazol-7-amine (25-4). To a solution of tert-butyl (2-pentyl-4,5-dihydro-2H-benzo[g] indazol-7-yl)carbamate (400 mg, 1.12 mmol) in DCM (10 mL) was added TFA (5 mL) in one charge at 25° C., the resulting mixture was stirred for 2 h.

The solvent was removed off under reduced pressure. The residue was diluted with EtOAc (10 mL) and adjusted to pH ~8 with aq. $NaHCO_3$, which was extracted with EtOAc (20 mL×2). The organic layers were combined, washed with brine, dried over $Na_2SO_4$, filtered, and concentrated in vacuo. The residue was purified by silica gel chromatography (PE/EtOAc=10:1 to 3:1) to afford 2-pentyl-4,5-dihydro-2H-benzo[g] indazol-7-amine. (130 mg, 90% purity, 40.91% yield) as a yellow solid. [M+H]+m/z=255.37, found 256.

Preparation of N-(2-pentyl-4,5-dihydro-2H-benzo[e] isoindol-7-yl)acrylamide (compound 25). To a solution of 2-pentyl-4,5-dihydro-2H-benzo[g] indazol-7-amine (130 mg, 0.51 mmol) in THF/sat. $NaHCO_3$ (V:V=1:1, 10 mL) was added prop-2-enoyl chloride (92 mg, 1.02 mmol) dropwise. The reaction was stirred for 10 min at 25° C. TLC showed the reaction was completed, it was quenched with MeOH (1 mL) and water (10 mL). The resulting mixture was extracted with EtOAc (10 mL×2). The organic layers were combined and washed with brine, dried over $Na_2SO_4$, filtered, and concentrated in vacuo. The residue was purified by silica gel chromatography (PE/EtOAc=10:1 to 2:1) and prep-HPLC to afford N-(2-pentyl-4,5-dihydro-2H-benzo[e]isoindol-7-yl) acrylamide (100 mg, 96.75% purity, 62.1% yield) as a white solid. $[M+H]^+$ m/z=309.41, found 310. $^1H$ NMR (400 MHz, $CDCl_3$) δ 7.80 (d, J=8.2 Hz, 1H), 7.69 (s, 1H), 7.35-7.27 (m, 2H), 7.16 (s, 1H), 6.44 (dd, J=16.8, 1.2 Hz, 1H), 6.25 (dd, J=16.8, 10.2 Hz, 1H), 5.77 (dd, J=10.2, 1.3 Hz, 1H), 4.12 (t, J=7.3 Hz, 2H), 2.93 (t, J=7.3 Hz, 2H), 2.75 (t, J=7.3 Hz, 2H), 1.89 (dt, J=14.7, 7.4 Hz, 2H), 1.42-1.25 (m, 4H), 0.90 (t, J=7.0 Hz, 3H).

Example 26

Synthesis of Compound 26

(N-(4-(5-butylisoxazol-3-yl)phenyl)acrylamide)

Scheme 28. Synthesis of compound 26.

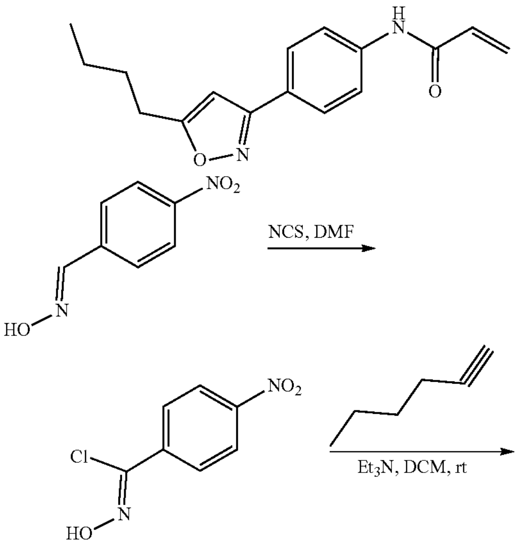

26-1

-continued

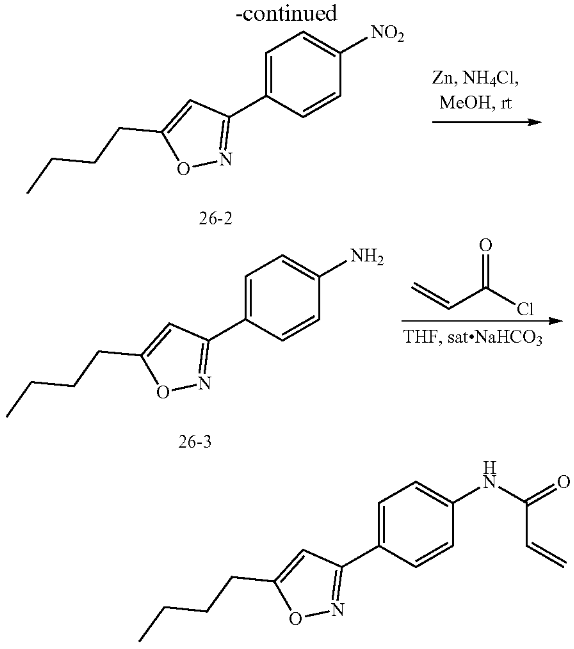

26-2

26-3 compound 26

Preparation of N-hydroxy-4-nitrobenzimidoyl chloride (26-1). N-Chlorosuccinimide (3.00 g, 18.06 mmol) was added portion wise to a solution of aldoxime 1-chloropyrrolidine-2,5-dione (2.41 mg, 18.06 mmol) in DMF (30 mL) at 0° C. The reaction mixture was recovered to room temperature naturally and stirred at this temperature for 2 h. The resulting mixture was quenched with water (100 mL) and extracted with EA (3×80 mL). The combined organic layer was washed with brine, dried over $Na_2SO_4$, filtered, and concentrated under reduced pressure. The crude N-hydroxy-4-nitrobenzimidoyl chloride was obtained as a yellow oil (5.2 g, 50% purity, 71.77% yield), and was used in the next step without further purification. LC-MS: (ESI) m/z (M+1), 201.0.

Preparation of 5-butyl-3-(4-nitrophenyl)isoxazole (26-2). To a solution of N-hydroxy-4-nitrobenzenecarbonimidoyl chloride (5.20 g, 50% purity, 12.96 mmol) in DCM (40 mL) was added hex-1-yne (1.27 g, 15.55 mmol) and triethylamine (2.62 g, 25.92 mmol) at 0° C. The reaction mixture was warmed up to room temperature naturally and stirred at this temperature for 18 h. The reaction was concentrated under reduced pressure. The residue was purified by silica gel chromatography (PE/EtOAc=2/1) to afford the product as a colorless oil (0.66 g, 90%, 20.70% yield). LC-MS: (ESI) m/z (M+1), 247.0.

Preparation of 4-(5-butylisoxazol-3-yl)aniline (26-3). To a mixture of 5-butyl-3-(4-nitrophenyl)-1,2-oxazole (227 mg, 0.92 mmol) and Zn dust (1.20 g, 18.40 mmol) in MeOH (5 mL) was added saturated $NH_4Cl$ (5 mL) dropwise, until TLC showed the reaction was completed, the solid was filtered off and the filtrate was concentrated in vacuo. The residue was purified by silica gel chromatography (PE/EtOAc=1/1) to afford 4-(5-butylisoxazol-3-yl)aniline as a white solid (270 mg, 70%, 94.99% yield). LC-MS: (ESI) m/z (M+1), 217.0.

Preparation of N-(4-(5-butylisoxazol-3-yl)phenyl)acrylamide (26-4). To a solution of 4-(5-butyl-1,2-oxazol-3-yl) aniline (270 mg, 70%, 0.87 mmol) in in THF/sat. $NaHCO_3$ (V:V=1:1, 10 mL) was added prop-2-enoyl chloride (158 mg, 1.74 mmol) at 0° C., the reaction mixture was stirred for 10 min at 25° C. TLC showed the reaction was completed, it was quenched with MeOH (1 mL) and water (10 mL). The resulting mixture was extracted with EtOAc (10 mL×2). The organic phase was combined and washed with brine, dried over $Na_2SO_4$, filtered, and concentrated in vacuo. The residue was purified by silica gel chromatography (DCM/MeOH=10/1) to afford N-(4-(5-butylisoxazol-3-yl)phenyl)acrylamide as a white solid (100 mg, 97%, 47.24% yield). LC-MS: (ESI) m/z (M+1), 271.0, $^1$H NMR (301 MHz, $CDCl_3$) δ 7.76 (d, J=8.6 Hz, 2H), 7.68 (d, J=9.0 Hz, 3H), 6.47 (d, J=16.8 Hz, 1H), 6.29 (q, J=10.0 Hz, 2H), 5.79 (d, J=10.1 Hz, 1H), 2.79 (t, J=7.6 Hz, 2H), 1.73 (dt, J=15.2, 7.5 Hz, 2H), 1.43 (dq, J=14.5, 7.3 Hz, 2H), 1.06-0.80 (m, 3H).

Example 27

Synthesis of Compound 27

(N-(3-butyl-4,5-dihydronaphtho[1,2-c]isoxazol-7-yl)acrylamide)

Scheme 29. Synthesis of compound 27.

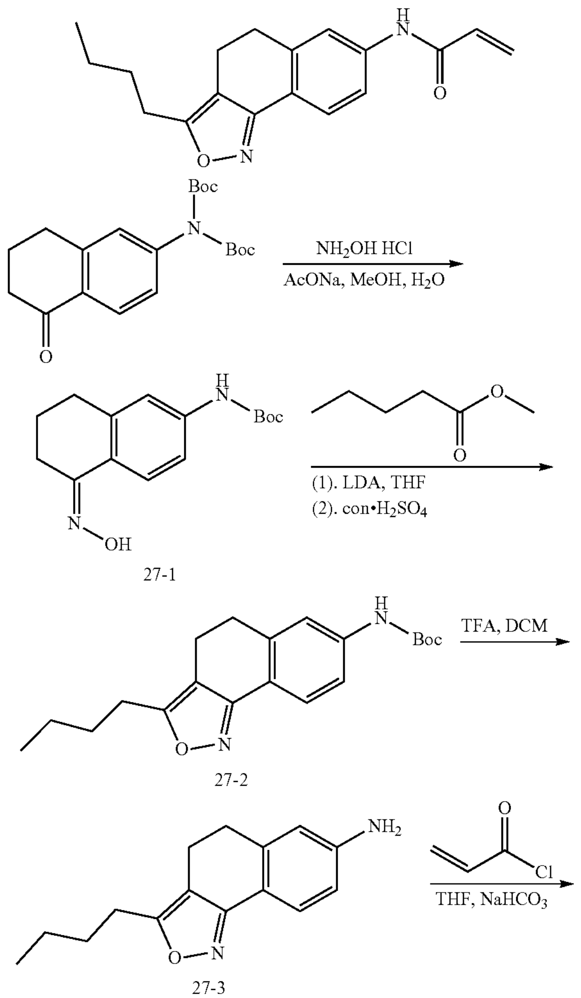

27-1

27-2

27-3

-continued

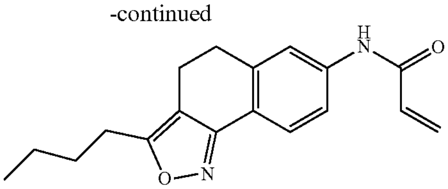

compound 27

Preparation of tert-butyl (Z)-(5-(hydroxyimino)-5,6,7,8-tetrahydronaphthalen-2-yl)carbamate (27-1). Hydroxylamine hydrochloride (252 mg, 3.63 mmol) and NaOAc (406 mg, 4.95 mmol) was added to a solution of tert-butyl (tert-butoxycarbonyl)(5-oxo-5,6,7,8-tetrahydronaphthalen-2-yl)carbamate (1.20 g, 3.30 mmol) in EtOH/$H_2O$ (V:V=1:1, 20 mL). The resulting mixture was stirred at 90° C. for 8 h. Diluted the reaction mixture with water (20 mL) and extract the mixture with EtOAc (20 mL×3). The combined organic phase was washed with brine, dried over $Na_2SO_4$, and concentrated in vacuo. The residue was purified by silica gel chromatography (PE/EtOAc=10:1 to 3:1) to afford tert-butyl (Z)-(5-(hydroxyimino)-5,6,7,8-tetrahydronaphthalen-2-yl) carbamate (950 mg, 90% purity, 90.53% yield) as a white solid. $[M+H]^+$ m/z=276.34, found 277.

Preparation of tert-butyl (3-butyl-4,5-dihydronaphtho[1,2-c]isoxazol-7-yl)carbamate (27-2). LDA solution (5.08 mL, 10.15 mmol) was added slowly to a stirring solution of tert-butyl (5-(hydroxyimino)-5,6,7,8-tetrahydronaphthalen-2-yl)carbamate (800 mg, 2.9 mmol) in THF (10 mL) at 0° C. and the reaction mixture was stirred at 0° C. for 15 min. then a solution of ethyl pentanoate (302 mg, 2.32 mmol) in THF (2 ml) was added dropwise, after the addition, it was warmed to room temperature naturally and stirred at this temperature for 4 hrs. It was quenched with 0.5 mL con. $H_2SO_4$ at 0° C. and stirred at 25° C. for 0.5 h, then brine was added. The organic layer was collected, which was added 0.5 mL con. $H_2SO_4$ and stirred at 25° C. for 1 h, until LCMS showed the reaction was finished. The reaction was quenched with ice water (25 mL) and extracted with EtOAc (10 mL×3). The combined organic phase was washed with brine, dried over $Na_2SO_4$, filtered, and concentrated in vacuo. The residue was purified by silica gel chromatography (DCM/MeOH=50:1 to 1:1) to afford tert-butyl (3-butyl-4,5-dihydronaphtho[1,2-c]isoxazol-7-yl)carbamate (240 mg, 90%, yield 21.69%) as white solid. $[M+H]^+$ m/z=342.44, found 343.

Preparation of 3-butyl-4,5-dihydronaphtho[1,2-c]isoxazol-7-amine (27-3). To a solution of tert-butyl (3-butyl-4,5-dihydronaphtho[1,2-c]isoxazol-7-yl)carbamate (300 mg, 0.87 mmol) in DCM (5 mL) was added TFA (2 mL) in one charge at 25° C. The reaction mixture was stirred at this temperature for 0.5 hour. The solvent was concentrated in vacuo. The residue was diluted with EtOAc (10 mL) and adjusted to pH 9-10 with aq. $NaHCO_3$. The organic phase was combined and washed with brine, dried over $Na_2SO_4$, filtered, and concentrated in vacuo to give crude 3-butyl-4,5-dihydronaphtho[1,2-c]isoxazol-7-amine. The crude product was used directly in next step without purification. 200 mg, 90% purity, 85.38% yield, yellow oil. $[M+H]^+$ m/z=242.32, found 243.

Preparation of N-(3-butyl-4,5-dihydronaphtho[1,2-c]isoxazol-7-yl)acrylamide (compound 27). To a solution of 3-butyl-4,5-dihydronaphtho[1,2-c]isoxazol-7-amine (200 mg, 0.83 mmol) in THF/sat. $NaHCO_3$(V:V=1:1, 10 mL) was added prop-2-enoyl chloride (150 mg, 1.66 mmol) dropwise.

The reaction was stirred for 10 min at 25° C. TLC showed the reaction was completed, it was quenched with MeOH (1 mL) and water (10 mL). The resulting mixture was extracted with EtOAc (10 mL×2). The organic phase was combined and washed with brine, dried over $Na_2SO_4$, filtered, and concentrated in vacuo. The residue was purified by silica gel chromatography (PE/EtOAc=10:1-2:1) and prep-HPLC to afford N-(2-pentyl-4,5-dihydro-2H-benzo[e]isoindol-7-yl) acrylamide (95 mg, 96.03% purity, 37.07% yield) as a white solid. $[M+H]^+$ m/z=296.37, found 297. $^1H$ NMR (400 MHz, $CDCl_3$) δ 7.89 (d, J=8.3 Hz, 1H), 7.82 (s, 1H), 7.40-7.27 (m, 2H), 6.46 (dd, J=16.8, 1.2 Hz, 1H), 6.26 (dd, J=16.8, 10.2 Hz, 1H), 5.81 (dd, J=10.2, 1.2 Hz, 1H), 2.94 (t, J=7.1 Hz, 2H), 2.71 (dt, J=23.9, 7.1 Hz, 4H), 1.77-1.65 (m, 2H), 1.39 (dq, J=14.7, 7.4 Hz, 2H), 0.94 (t, J=7.4 Hz, 3H).

Example 28

Synthesis of Compound 28

(N-(4-(5-(trifluoromethyl)isoxazol-3-yl)phenyl)acrylamide)

Scheme 30. Synthesis of compound 28.

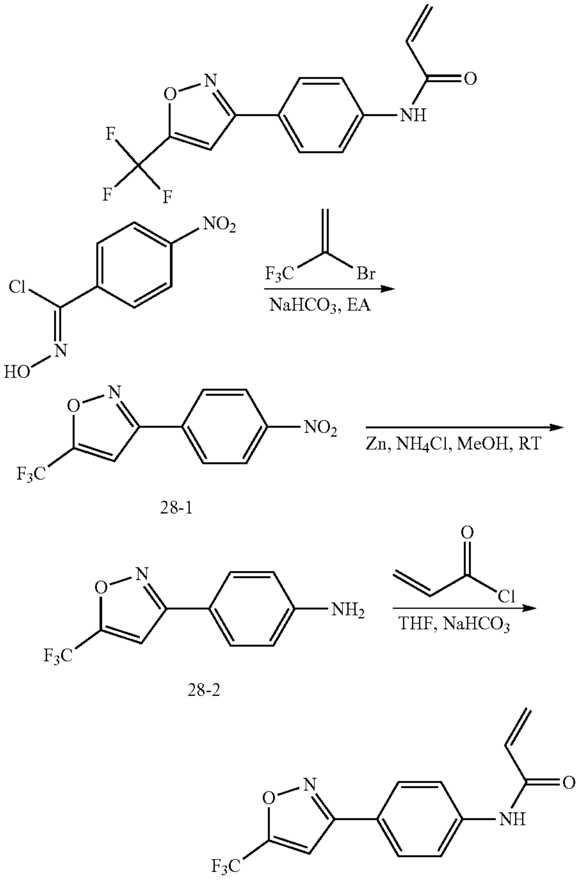

28-1

28-2 compound 28

Preparation of 3-(4-nitrophenyl)-5-(trifluoromethyl) isoxazole (28-1). To a solution of (Z)—N-hydroxy-4-nitrobenzimidoyl chloride (500 mg, 2.49 mmol) in EA (10 mL) was added 2-bromo-3,3,3-trifluoroprop-1-ene (1315 mg, 7.48 mmol) and $NaHCO_3$ (628 mg, 7.48 mmol). The reaction mixture was stirred at rt for 12 h. The resulting mixture was concentrated under reduced pressure. The crude was subjected to column chromatography purification on silica gel, eluting with PE/EA 1/1 to afford 3-(4-nitrophenyl)-5-(trifluoromethyl)isoxazole as a white solid (400 mg, 80%, 49.84% yield (ESI) m/z (M+1), 258.8.

Preparation of 4-(5-(trifluoromethyl)isoxazol-3-yl)aniline (28-2). To a solution of 3-(4-nitrophenyl)-5-(trifluoromethyl)isoxazole (400 mg, 1.54 mmol) in $MeOH/H_2O$ (1/1=10 mL) was added Zn (302 mg, 4.63 mmol) and $NH_4Cl$ (247 mg, 4.63 mmol). The reaction mixture was stirred at 50° C. for 1 h. The solid was filtrated off and the filtrate under reduced pressure. 4-(5-(trifluoromethyl)isoxazol-3-yl) aniline was obtained as a yellow solid (300 mg, 80%, 68.38% yield), confirmed by LCMS and used in the next step without further purification. LC-MS: (ESI) m/z (M+1), 228.8.

Preparation of N-(4-(5-(trifluoromethyl)isoxazol-3-yl) phenyl)acrylamide (compound 28). To a solution of (4-(5-(trifluoromethyl)isoxazol-3-yl)aniline (200 mg, 0.87 mmol) in $THF/NaHCO_3(aq)$ (1/1=10 mL) at 0° C. was added acryloyl chloride (87 mg, 0.96 mmol). The reaction mixture was stirred at this temperature for 1 h. It was diluted with water (10 mL), extracted with EA (10 mL*3), washed with brine (20 mL), dried over sodium sulfate, and concentrated under vacuum. The residue was purified by silica gel chromatography (PE/EtOAc=3/1) to afford N-(4-(5-(trifluoromethyl)isoxazol-3-yl)phenyl)acrylamide as a white solid (100 mg, 99%, 40.82% yield). (ESI) m/z (M+1), 282.8. $^1H$ NMR (400 MHz, MeOD) δ 11.25 (s, 1H), 8.85 (d, J=0.9 Hz, 1H), 8.78-8.73 (m, 2H), 8.69-8.64 (m, 2H), 7.28 (dd, J=17.0, 10.1 Hz, 1H), 7.12 (dd, J=17.0, 2.0 Hz, 1H), 6.63 (dd, J=10.0, 2.0 Hz, 1H).

Example 29

Synthesis of Compound 29

((E)-2-fluoro-N-(5-((pentyloxy)imino)-5,6,7,8-tetrahydronaphthalen-2-yl)acrylamide)

Scheme 31. Synthesis of compound 29.

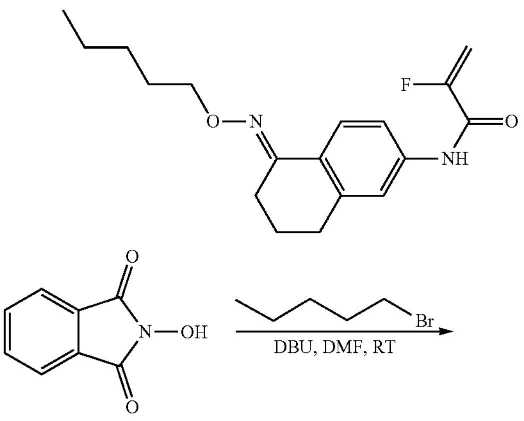

-continued

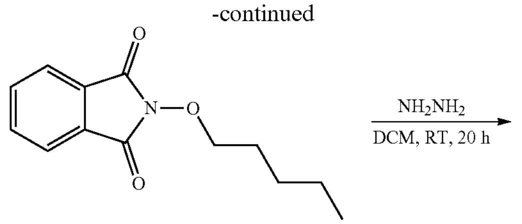

29-1

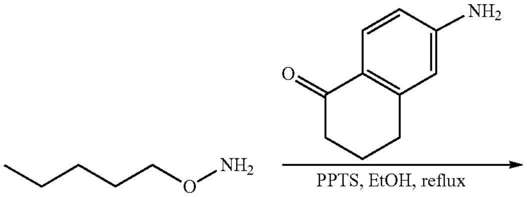

29-2

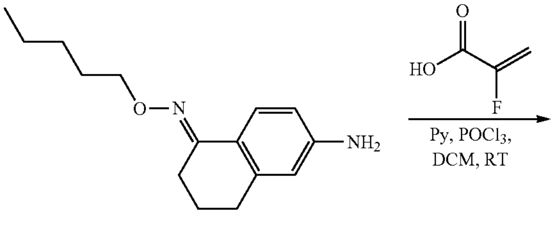

29-3

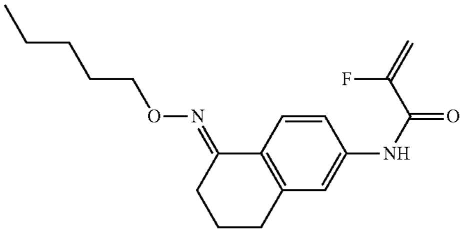

compound 29

Preparation of 2-(pentyloxy)isoindoline-1,3-dione (29-1). To a solution of 2-hydroxyisoindole-1,3-dione (5.76 g, 35.31 mmol) and 1-bromopentane (5.87 g, 38.87 mmol) in DMF (50 mL) was added 1,8-Diazabicyclo[5.4.0]undec-7-ene (5.91 g, 38.87 mmol) dropwise. The reaction mixture was stirred at rt for 3 h. The resulting mixture was diluted with water and extracted with EA (3×100 mL). The combined organic layer was washed with brine, dried over $Na_2SO_4$, and concentrated under reduced pressure. The crude was subjected to column chromatography purification on silica gel, eluting with PE/EA 2/1 to afford 2-(pentyloxy)isoindoline-1,3-dione as a colorless oil (8.6 g, 80%, 83.57% yield). LC-MS: (ESI) m/z (M+1), 234.0.

Preparation of O-pentylhydroxylamine (29-2). To a solution of 2-(pentyloxy)isoindoline-1,3-dione (8.60 g, 36.86 mmol) in DCM (80 mL) was added hydrazine hydrate (1.60 g, 49.92 mmol). The reaction mixture was stirred at rt for 18 h. The solid was filtrated off and the filtrate was washed with NaOH (2M, 3×50 mL), brine, dried over $Na_2SO_4$, filtered, and concentrated under reduced pressure. O-pentylhydroxylamine was obtained as a colorless oil (3.7 g, 60%, 58.27% yield), confirmed by LCMS and used in the next step without further purification. LC-MS: (ESI) m/z (M+1), 103.7.

Preparation of (E)-6-amino-3,4-dihydronaphthalen-1(2H)-one O-pentyl oxime (29-3). To a solution of 6-amino-3,4-dihydro-2H-naphthalen-1-one (2.70 g, 16.74 mmol) and O-pentylhydroxylamine (3.45 g, 33.49 mmol) in EtOH (35 mL) was added PPTS (0.42 g, 1.67 mmol). The reaction mixture was stirred at 80° C. for 6 h. The solvent was removed off in vacuo. The residue was purified by silica gel chromatography (PE/EtOAc=5/1) to afford (E)-6-amino-3,4-dihydronaphthalen-1(2H)-one O-pentyl oxime as a colorless oil (1.0 g, 90%, 21.81% yield). LC-MS: (ESI) m/z (M+1), 246.9.

Preparation of (E)-2-fluoro-N-(5-((pentyloxy)imino)-5,6,7,8-tetrahydronaphthalen-2-yl)acrylamide (compound 29). To a solution of (5E)-5-[(pentyloxy)imino]-7,8-dihydro-6H-naphthalen-2-amine (300 mg, 1.21 mmol), 2-fluoroprop-2-enoic acid (110 mg, 1.21 mmol) and pyridine (289 mg, 3.65 mmol) in DCM (10 mL) at 0° C. was added phosphoryl trichloride (187 mg, 1.21 mmol). The reaction mixture was warmed up to rt and stirred at this temperature for 2 h. It was diluted with water (2 mL), concentrated under 30° C. to remove off DCM. The residue was purified by Genal-Prep-HPLC (ACN-H20, 0.1% FA, 80/20-95/5) to afford (E)-2-fluoro-N-(5-((pentyloxy)imino)-5,6,7,8-tetrahydronaphthalen-2-yl)acrylamide as a white solid (25 mg, 99%, 13.28% yield). LC-MS: (ESI) m/z (M+1), 319.2. $^1H$ NMR (400 MHz, $CDCl_3$) δ 7.97 (d, J=8.6 Hz, 1H), 7.90 (d, J=3.9 Hz, 1H), 7.57 (d, J=2.1 Hz, 1H), 7.29 (d, J=2.3 Hz, 1H), 5.83 (dd, J=47.9, 3.4 Hz, 1H), 5.26 (dd, J=15.3, 3.4 Hz, 1H), 4.17 (t, J=6.7 Hz, 2H), 2.74 (td, J=6.4, 3.5 Hz, 4H), 1.88-1.80 (m, 2H), 1.72 (dq, J=9.6, 7.1 Hz, 2H), 1.42-1.32 (m, 4H), 0.97-0.87 (m, 3H).

Example 30

Synthesis of Compound 30

(N-(4-(5-cyclopropylisoxazol-3-yl)phenyl)acrylamide)

Scheme 32. Synthesis of compound 30.

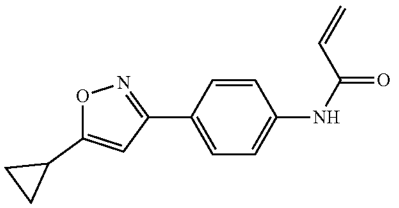

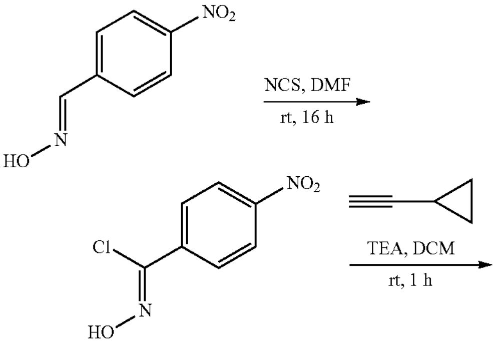

30-1

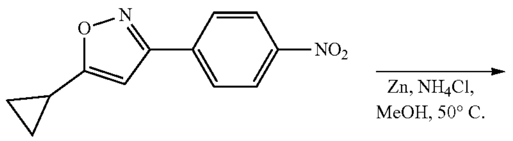

30-2

-continued

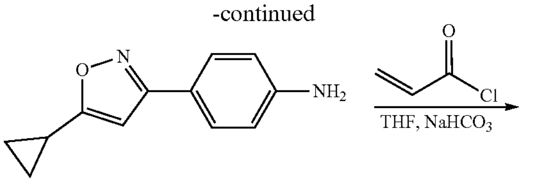

30-3

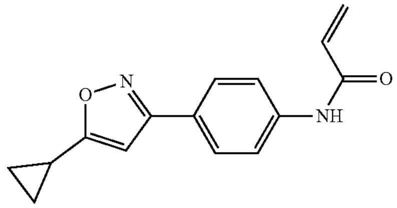

compound 30

Preparation of (Z)—N-hydroxy-4-nitrobenzimidoyl chloride (30-1). To a solution of (E)-4-nitrobenzaldehyde oxime (8.00 g, 48.19 mmol) in DMF (80 mL) was added NCS (7.08 g, 53.00 mmol)portion wise at 0° C. The resulting mixture was warmed to room temperature naturally and stirred at this temperature for 16 h. It was quenched with sat. $Na_2S_2O_3$ (20 mL) and water (80 mL), then extracted with EA (3x50 mL). The organic layers were combined, washed with brine, dried over $Na_2SO_4$, and concentrated under reduced pressure. Afford (Z)—N-hydroxy-4-nitrobenzimidoyl chloride as a yellow solid (8.00 g, crude), which was used directly for the next step. LC-MS: (ESI) m/z (M+1), 201.

Preparation of 5-cyclopropyl-3-(4-nitrophenyl)isoxazole (30-2). To a solution of 2-(pentyloxy)isoindoline-1,3-dione (1.00 g, 50.00 mmol) in DCM (25 mL) was added ethynylcyclopropane (0.50 g, 75.00 mmol) and triethylamine (0.61 g, 60.00 mmol). The resulting mixture was stirred at rt for 1 h. It was quenched with $H_2O$ (30 mL) and extracted with EA (3x30 mL). The organic layers were combined, washed with brine, dried over $Na_2SO_4$, and concentrated under reduced pressure. The residue was purified by silica gel chromatography (PE/EtOAc=5/1) to afford 5-cyclopropyl-3-(4-nitrophenyl)isoxazole as a yellow solid (0.60 g, 90%, 46.00% yield). LC-MS: (ESI) m/z (M+1), 230.9.

Preparation of 4-(5-cyclopropylisoxazol-3-yl)aniline (30-3). To a mixture of 5-cyclopropyl-3-(4-nitrophenyl)isoxazole (600 mg, 2.60 mmol) in MeOH (5 mL) and $NH_4Cl$ sat (5 mL) was added Zn dust (850 mg, 13.03 mmol) in one charge. The resulting mixture was stirred for 1 h at 50° C. The solid was filtrated off and washed with DCM (10 mL) and $H_2O$ (10 mL). The filtrate was extracted with DCM (3x20 mL). The organic layers were combined, washed with brine, dried over $Na_2SO_4$, and concentrated under reduced pressure. The crude 4-(5-cyclopropylisoxazol-3-yl)aniline was obtained as a yellow oil (500 mg, 90%, 86.23% yield) and used in the next step without further purification. LC-MS: (ESI) m/z (M+1), 200.9.

Preparation of N-(4-(5-cyclopropylisoxazol-3-yl)phenyl) acrylamide (compound 30). To a solution of 4-(5-cyclopropylisoxazol-3-yl)aniline (400 mg, 1.99 mmol) in THF (8 mL) and sat. $NaHCO_3$ (3 mL) was added acryloyl chloride (217 mg, 2.39 mmol) at 0° C. The resulting mixture was stirred at this temperature for 0.5 h. It was quenched with $H_2O$ (15 mL) and extracted with EA (3x30 mL). The organic layers were combined, washed with brine, dried over $Na_2SO_4$, and concentrated under reduced pressure. The residue was purified by silica gel chromatography (PE/EtOAc=1/1) to afford N-(4-(5-cyclopropylisoxazol-3-yl)phenyl)acrylamide as a white solid (123 mg, 100%, 24.21% yield). LC-MS: (ESI) m/z (M+1), 254.9. $^1$H NMR (400 MHz, DMSO) δ 10.35 (s, 1H), 7.78 (s, 4H), 6.69 (s, 1H), 6.46 (dd, J=17.0, 10.1 Hz, 1H), 6.29 (dd, J=17.0, 2.0 Hz, 1H), 5.79 (dd, J=10.1, 2.0 Hz, 1H), 2.20-2.13 (m, 1H), 1.21-1.02 (m, 2H), 1.00-0.77 (m, 2H).

Example 31

Synthesis of Compound 31

(N-(4-(4-(trifluoromethyl)isoxazol-3-yl)phenyl)acrylamide)

Scheme 33. Synthesis of compound 31.

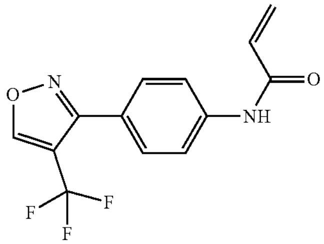

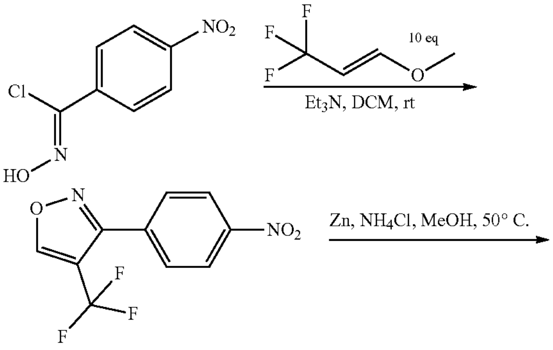

31-1

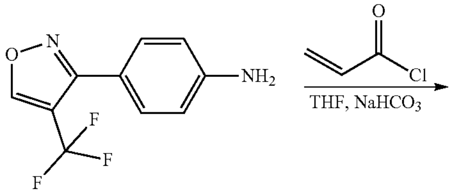

31-2

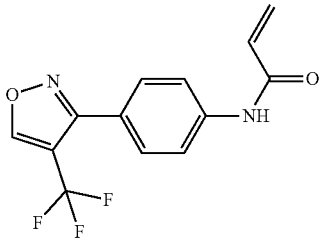

compound 31

Preparation of 3-(4-nitrophenyl)-4-(trifluoromethyl) isoxazole (31-1). To a solution of N,4-dihydroxybenzenecarbonimidoyl chloride (700 mg, 3.49 mmol) in DCM at 0° C. was added (1E)-3,3,3-trifluoro-1-methoxyprop-1-ene (4.40 g, 34.89 mmol) followed by TEA (353 mg, 3.49 mmol). The solution was stirred at rt for 16 h. The resulting mixture was diluted with water and extracted with EA (3x50 mL). The organic layers were combined, washed with brine, dried over $Na_2SO_4$, filtered, and concentrated under reduced pressure. The crude was subjected to column chromatography purification on silica gel, eluting with PE/EA (5:1) to afford 3-(4-nitrophenyl)-4-(trifluoromethyl)isoxazole as a white solid (170 mg, 90%, 17.93% yield). LC-MS: (ESI) m/z (M+1), 258.8.

Preparation of 4-(4-(trifluoromethyl)isoxazol-3-yl)aniline (31-2). To a solution of 3-(4-nitrophenyl)-4-(trifluoromethyl)-1,2-oxazole (170 mg, 0.66 mmol) in MeOH (2 mL) was added Zn powder (431 mg, 6.59 mmol) and sat. $NH_4Cl$ (0.5 mL). The mixture was stirred at room temperature for 2 h, The solid was filtrated off and the filtrate was diluted with water (20 mL), which was extracted with EA (3*20 mL). The organic layers were combined, washed with brine, dried over $Na_2SO_4$, and concentrated under reduced pressure. 4-(4-(Trifluoromethyl)isoxazol-3-yl)aniline was obtained as a white solid (120 mg, 90%, 71.88% yield), confirmed by LCMS and used in the next batch without further purification. LC-MS: (ESI) m/z (M+1), 229.0.

Preparation of N-(4-(4-(trifluoromethyl)isoxazol-3-yl)phenyl)acrylamide (compound 31). To a mixture of 4-[4-(trifluoromethyl)-1,2-oxazol-3-yl]aniline (100 mg, 0.43 mmol) in THF/sat. aq. $NaHCO_3$ (8 mL, 1:1) was added prop-2-enoyl chloride (80 mg, 0.86 mmol) at 0° C., after the addition, it was stirred at room temperature for 10 min. It was diluted with water (10 mL), which was extracted with EA (3*10 mL). The organic layers were combined, washed with brine, dried over $Na_2SO_4$, filtered, and concentrated under reduced pressure. The residue was purified by silica gel chromatography (PE/EtOAc=1/1) to afford N-(4-(4-(trifluoromethyl)isoxazol-3-yl)phenyl)acrylamide as a white solid. (25.6 mg, 95.27%, 20.49% yield). LC-MS: (ESI) m/z (M+1), 282.9. $^1H$ NMR (400 MHz, CDCl3) δ 8.84-8.79 (m, 1H), 7.78-7.69 (m, 4H), 7.35 (s, 1H), 6.49 (dd, J=16.8, 1.1 Hz, 1H), 6.27 (dd, J=16.8, 10.2 Hz, 1H), 5.84 (dd, J=10.2, 1.1 Hz, 1H).

Example 32

Synthesis of Compound 32

(N-(3-chloro-4-(3-(trifluoromethyl)isoxazol-5-yl)phenyl)acrylamide)

Scheme 34. Synthesis of compound 32.

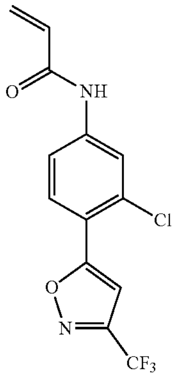

-continued

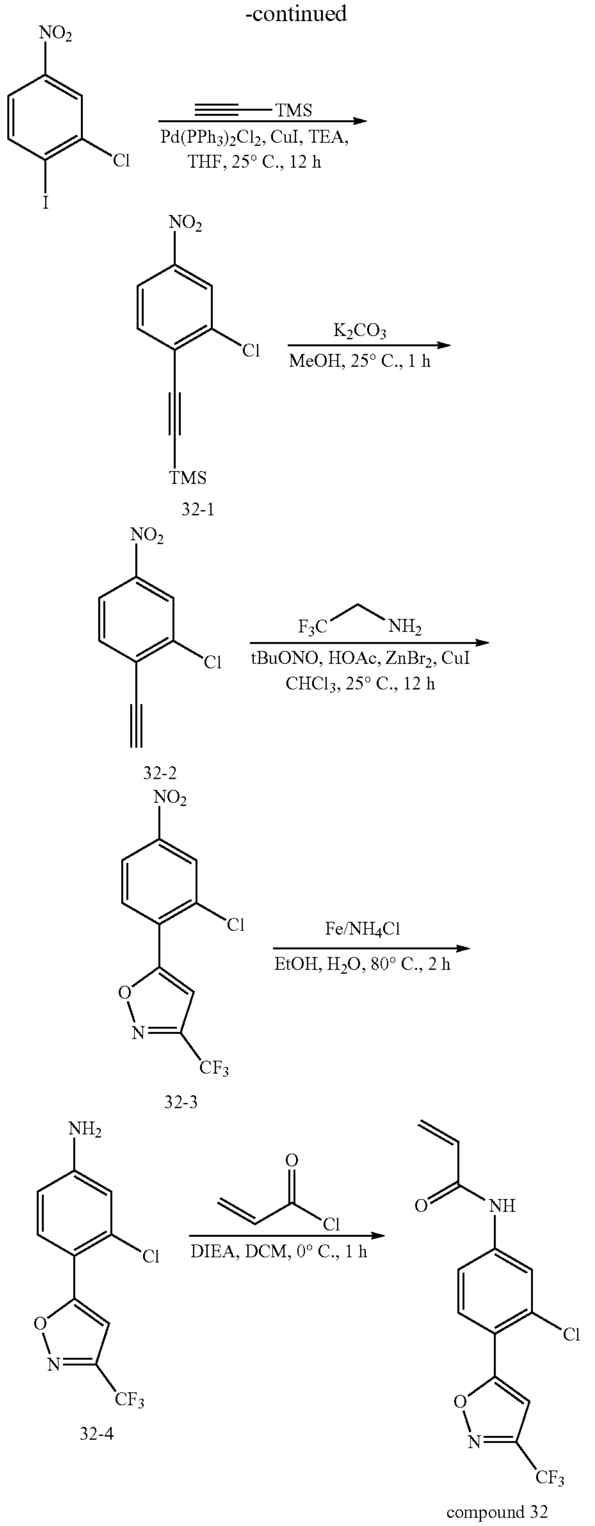

32-1

32-2

32-3

32-4 compound 32

Preparation of ((2-chloro-4-nitrophenyl)ethynyl)trimethylsilane (32-1). A mixture of compound 2-chloro-1-iodo-4-nitrobenzene (500 mg, 1.76 mmol, 1.0 eq) in THF (10 mL) was added triethylamine (357 mg, 3.53 mmol, 2.0 eq), copper(I) iodide (50 mg, 0.26 mmol, 0.15 eq) and $Pd(PPh_3)_2Cl_2$ (62 mg, 0.08 mmol, 0.15 eq) at 25° C. The mixture was stirred at 25° C. for 10 minutes under $N_2$, then compound 2 (312 mg, 3.18 mmol, 1.8 eq) was added. The resulting mixture was stirred at 25° C. for 12 hours. After completion, the mixture was quenched with $H_2O$ (30 mL), extracted with EtOAc (30 mL×3). The organic layer was washed with $H_2O$ (20 mL), brine (20 mL), dried over anhydrous $Na_2SO_4$, filtrated and concentrated in vacuo to give a residue. The residue was purified by column chromatography ($SiO_2$, Petroleum ether:EtOAc=10:1) to afford ((2-chloro-4-nitrophenyl)ethynyl)trimethylsilane (250 mg, 53.1% yield) as a yellow solid. $^1H$ NMR: 400 MHz, $CDCl_3$ δ 8.28 (d, J=2.4 Hz, 1H), 8.07 (dd, J=8.8, 2.2 Hz, 1H), 7.64 (d, J=8.4 Hz, 1H), 0.30 (s, 9H).

Preparation of 2-chloro-1-ethynyl-4-nitrobenzene (32-2). A mixture of ((2-chloro-4-nitrophenyl)ethynyl)trimethylsilane (200 mg, 0.79 mmol, 1.0 eq) in MeOH (5 mL) was added potassium carbonate (272 mg, 1.97 mmol, 2.5 eq) at 25° C. The mixture was stirred at 25° C. for 1 hour under $N_2$. After completion, the mixture was quenched with $H_2O$ (50 mL), extracted with DCM (50 mL×2). The organic layer was washed with brine (50 mL), dried over anhydrous $Na_2SO_4$, filtrated and concentrated in vacuo to give a residue. The residue was purified by column chromatography ($SiO_2$, Petroleum ether:EtOAc=10:1) to afford 2-chloro-1-ethynyl-4-nitrobenzene (120 mg, 80.0% yield) as a yellow solid. $^1H$ NMR: 400 MHz, $CDCl_3$ δ 8.30 (d, J=2.4 Hz, 1H), 8.10 (dd, J=8.8, 2.2 Hz, 1H), 7.70 (d, J=8.4 Hz, 1H), 3.66 (s, 1H).

Preparation of 5-(2-chloro-4-nitrophenyl)-3-(trifluoromethyl)isoxazole (32-3). A mixture of 2-chloro-1-ethynyl-4-nitrobenzene (300 mg, 1.65 mmol, 1.0 eq) in $CHCl_3$ (10 mL) was added 2,2,2-trifluoroethylamine (496 mg, 4.96 mmol, 3.0 eq), tert-butyl nitrite (511 mg, 4.96 mmol, 3.0 eq) and AcOH (40 mg, 0.66 mmol, 0.4 eq) at 25° C. The mixture was stirred at 25° C. for 5 minutes under $N_2$. Then copper(I) iodide (31 mg, 0.17 mmol, 0.1 eq) and $ZnBr_2$ (743 mg, 3.30 mmol, 2.0 eq) was added. The resulting mixture was stirred at 25° C. for 12 hours. After completion, the mixture was quenched with $H_2O$ (50 mL), extracted with DCM (50 mL×3). The organic layer was washed with $H_2O$ (20 mL), brine (20 mL), dried over anhydrous $Na_2SO_4$, filtrated and concentrated in vacuo to give a residue. The residue was purified by column chromatography ($SiO_2$, Petroleum ether: EtOAc=10:1) to afford 5-(2-chloro-4-nitrophenyl)-3-(trifluoromethyl)isoxazole (250 mg, 49.0% yield) as a yellow solid. $^1H$ NMR: 400 MHz, $CDCl_3$ δ 8.45 (d, J=2.4 Hz, 1H), 8.30 (dd, J=3.6, 2.4 Hz, 1H), 8.22 (d, J=8.8 Hz, 1H), 7.37 (s, 1H).

Preparation of 3-chloro-4-(3-(trifluoromethyl)isoxazol-5-yl)aniline (32-4). A mixture of 5-(2-chloro-4-nitrophenyl)-3-(trifluoromethyl)isoxazole (250 mg, 0.85 mmol, 1.0 eq) in EtOH (10 mL) and $H_2O$ (2 mL) was added iron (476 mg, 8.5 mmol, 10 eq) and ammonium chloride (228 mg, 4.3 mmol, 5.0 eq) at 20° C. The mixture was stirred at 80° C. for 2 hours under $N_2$. The reaction mixture was filtered, extracted with EtOAc (50 mL×3). The organic layer was washed with $H_2O$ (50 mL), brine (50 mL), dried over anhydrous $Na_2SO_4$, filtrated and concentrated in vacuo to give a residue. The residue was purified by column chromatography ($SiO_2$, Petroleum ether:EtOAc=10:1) to afford 3-chloro-4-(3-(trifluoromethyl)isoxazol-5-yl)aniline (150 mg, 60.1% yield) as a yellow solid. $^1H$ NMR: 400 MHz, DMSO-$d_6$ δ 7.63 (d, J=8.8 Hz, 1H), 7.29 (s, 1H), 6.76 (d, J=2.4 Hz, 1H), 6.66 (dd, J=8.8, 2.4 Hz, 1H), 6.22 (s, 2H).

Preparation of N-(3-chloro-4-(3-(trifluoromethyl)isoxazol-5-yl)phenyl)acrylamide (compound 32). A mixture of 3-chloro-4-(3-(trifluoromethyl)isoxazol-5-yl)aniline (150 mg, 0.57 mmol, 1.0 eq) and DIEA (220 mg, 1.7 mmol, 3.0 eq) in DCM (5 mL) was added acryloyl chloride (57 mg, 0.63 mmol, 1.1 eq) in DCM (2 mL) at 0° C. The mixture was stirred at 0° C. for 1 hour under $N_2$. The reaction was quenched with $H_2O$ (20 mL), extracted with DCM (20 mL×2). The organic layer was dried over anhydrous $Na_2SO_4$, filtrated and concentrated in vacuo to give a residue. The residue was purified by prep-HPLC to afford N-(3-chloro-4-(3-(trifluoromethyl)isoxazol-5-yl)phenyl) acrylamide (60.7 mg, 33.2% yield) as a white solid. $^1H$ NMR: 400 MHz, $CDCl_3$ δ 8.05 (d, J=2.0 Hz, 1H), 7.96 (d, J=8.8 Hz, 1H), 7.54 (dd, J=8.8, 2.2 Hz, 1H), 7.35 (s, 1H), 7.14 (s, 1H), 6.51 (dd, J=16.8, 0.8 Hz, 1H), 6.26 (dd, J=16.8, 10.4 Hz, 1H), 5.88 (dd, J=10.4, 0.8 Hz, 1H). MS (ESI) m/z=317.1 $[M+H]^+$.

Example 33

Synthesis of Compound 33

(N-(3-chloro-4-(5-(trifluoromethyl)-1,2,4-oxadiazol-3-yl)phenyl)acrylamide)

Scheme 35. Synthesis of compound 33.

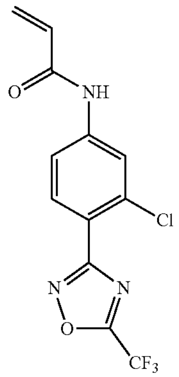

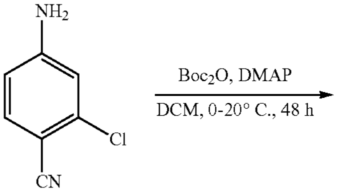

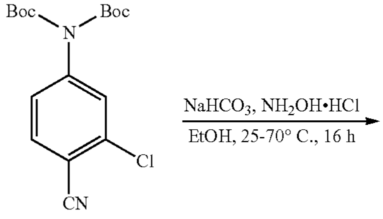

33-1

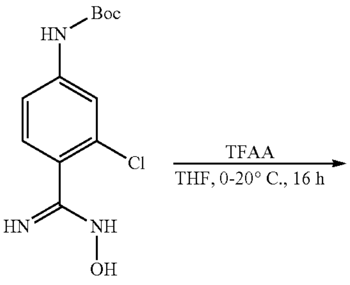

33-2

-continued

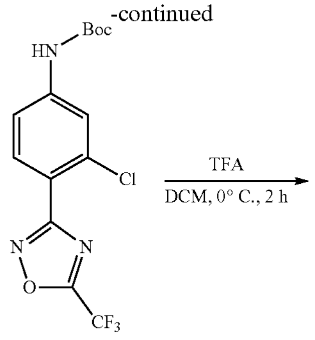

33-3

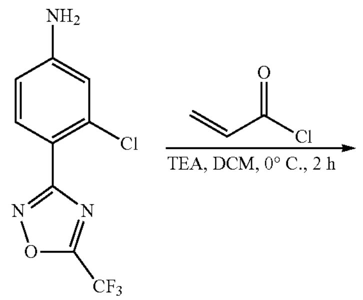

33-4

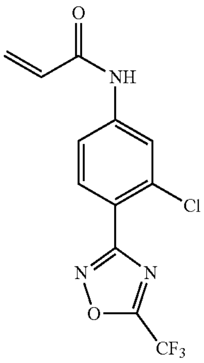

compound 33

Preparation of tert-butyl (tert-butoxycarbonyl)(3-chloro-4-cyanophenyl)carbamate (33-1). To a solution of 4-amino-2-chlorobenzonitrile (24.0 g, 157 mmol, 1.0 eq) in dichloromethane (240 mL), DMAP (1.92 g, 15.7 mmol, 0.1 eq) and $Boc_2O$ (137 g, 629 mmol, 4.0 eq) was added at 0° C. The resulting reaction mixture was stirred at 25° C. for 48 hours. TLC (Petroleum ether/Ethyl acetate=5:1, $R_f$(P)=0.5, $R_f$(R)=0.2) showed that the starting material was consumed completely. The mixture was quenched by water (100 mL) and extracted with ethyl acetate (500 mL). The organic layer was dried over $Na_2SO_4$ and concentrated in vacuo to afford a residue. The crude product was purified by column chromatography ($SiO_2$, Ethyl acetate/Petroleum ether=0% to 12%) to afford tert-butyl (tert-butoxycarbonyl)(3-chloro-4-cyanophenyl)carbamate (22.1 g, 39.2% yield) as a white solid. $^1$H NMR: 400 MHz, $CDCl_3$ δ 7.67 (d, J=8.4 Hz, 1H), 7.35 (d, J=1.6 Hz, 1H), 7.18 (dd, J=8.4, 2.0 Hz, 1H), 1.45 (s, 18H).

Preparation of tert-butyl (3-chloro-4-(N-hydroxycarbamimidoyl)phenyl)carbamate (33-2). To a solution of tert-butyl (tert-butoxycarbonyl)(3-chloro-4-cyanophenyl)carbamate (2.00 g, 6.2 mmol, 1.0 eq) in EtOH (20 mL) was added $NH_2OH{\cdot}HCl$ (650 mg, 9.3 mmol, 1.5 eq) and $NaHCO_3$ (1.04 g, 12.4 mmol, 2.0 eq) slowly, the mixture was then stirred at 70° C. for 16 hours. LCMS showed that tert-butyl (tert-butoxycarbonyl)(3-chloro-4-cyanophenyl)carbamate was consumed completely. The reaction mixture was concentrated in vacuo to afford tert-butyl (3-chloro-4-(N-hydroxycarbamimidoyl)phenyl)carbamate (2.12 g, crude). The crude product was used for the next step without any purification. MS (ESI) m/z=286.1 $[M+H]^+$.

Preparation of tert-butyl (3-chloro-4-(5-(trifluoromethyl)-1,2,4-oxadiazol-3-yl)phenyl)carbamate (33-3). To a solution of tert-butyl (3-chloro-4-(N-hydroxycarbamimidoyl)phenyl)carbamate (1.00 g, 3.5 mmol, 1.0 eq) in THF (10 mL) was added TFAA (2.21 g, 10.5 mmol, 3.0 eq) at 0° C. dropwise, the mixture was then stirred at 20° C. for 16 hours. LCMS showed that the starting material was consumed completely. The mixture was quenched by aq. $NaHCO_3$ (50 mL, 5%) and extracted with ethyl acetate (50 mL×3), the organic layer was then dried over $Na_2SO_4$ and concentrated in vacuo to afford a residue, purified the residue by column chromatography ($SiO_2$, Ethyl acetate/Petroleum ether=0% to 12%) to afford tert-butyl (3-chloro-4-(5-(trifluoromethyl)-1,2,4-oxadiazol-3-yl)phenyl)carbamate (405 mg, 31.4%, yield) as a pale-yellow solid. $^1$H NMR: 400 MHz, DMSO-$d_6$ δ 10.01 (s, 1H), 7.94 (d, J=8.8 Hz, 1H), 7.85 (d, J=2.0 Hz, 1H), 7.62 (dd, J=8.8, 2.0 Hz, 1H), 1.50 (s, 9H).

Preparation of 3-chloro-4-(5-(trifluoromethyl)-1,2,4-oxadiazol-3-yl)aniline (33-4). To a solution of tert-butyl (3-chloro-4-(5-(trifluoromethyl)-1,2,4-oxadiazol-3-yl)phenyl)carbamate (300 mg, 0.8 mmol, 1.0 eq) in DCM (8 mL) was added TFA (2 mL) dropwise at 0° C., the mixture was then stirred at 0° C. for 2 hours. LCMS showed that tert-butyl (3-chloro-4-(5-(trifluoromethyl)-1,2,4-oxadiazol-3-yl)phenyl)carbamate was consumed completely. The mixture was quenched by 5% aq. $NaHCO_3$ (50 mL) and extracted with ethyl acetate (50 mL×3), the organic layer was then dried over $Na_2SO_4$ and concentrated in vacuo to afford 3-chloro-4-(5-(trifluoromethyl)-1,2,4-oxadiazol-3-yl)aniline (200 mg, 91.3% yield) as a white solid. MS (ESI) m/z=263.90 $[M+H]^+$ $^1$H NMR: 400 MHz, $CDCl_3$ δ 7.83 (d, J=8.4 Hz, 1H), 6.82 (d, J=2.4 Hz, 1H), 6.65 (dd, J=8.4, 2.4 Hz, 1H), 3.26 (s, 2H).

Preparation of N-(3-chloro-4-(5-(trifluoromethyl)-1,2,4-oxadiazol-3-yl)phenyl)acrylamide (compound 33). To a solution of 3-chloro-4-(5-(trifluoromethyl)-1,2,4-oxadiazol-3-yl)aniline (200 mg, 0.75 mmol, 1.0 eq) and DIEA (294 mg, 2.2 mmol, 3.0 eq) in DCM (2 mL) was added acryloyl chloride (61 mg, 0.68 mmol, 0.9 eq) dropwise at 0° C. The mixture was then stirred at 0° C. for 2 hours. LCMS showed that starting material was consumed completely. The reaction mixture was quenched by water (20 mL) and extracted with ethyl acetate (30 mL×3). The organic layer was then dried over $Na_2SO_4$ and concentrated in vacuo to afford a residue, purify the residue by prep-HPLC (column: Gemini, phase: ACN-$H_2O$ (0.1% FA), gradient: 55-80) to afford N-(3-chloro-4-(5-(trifluoromethyl)-1,2,4-oxadiazol-3-yl)phenyl)acrylamide (65.2 mg, 26.7% yield) as a white solid. MS (ESI) m/z=318.05 $[M+H]^+$. $^1$H NMR: 400 MHz, DMSO-$d_6$ δ 10.67 (s, 1H), 8.15 (d, J=2.0 Hz, 1H), 8.02 (d, J=8.8 Hz, 1H), 7.77 (dd, J=8.8, 2.0 Hz, 1H), 6.45 (dd, J=16.8, 10.0 Hz, 1H), 6.34 (dd, J=17.2, 2.0 Hz, 1H), 5.87 (dd, J=10.0, 2.0 Hz, 1H).

Example 34

Synthesis of Compounds 34 and 35

(N-(3-chloro-4-(4-(trifluoromethyl)-1H-1,2,3-triazol-1-yl)phenyl)acrylamide and N-(3-chloro-4-(4-(trifluoromethyl)-2H-1,2,3-triazol-2-yl)phenyl)acrylamide)

Scheme 36. Synthesis of compounds 34 and 35.

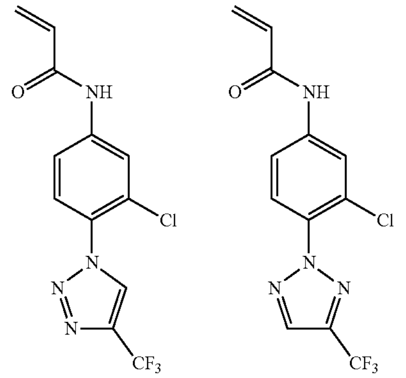

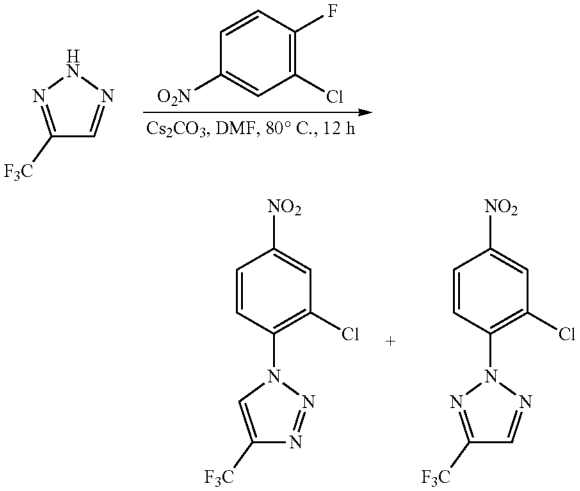

34-1 + 34-2

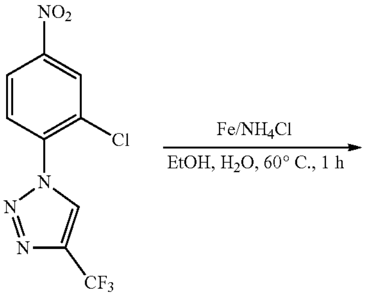

34-1

-continued

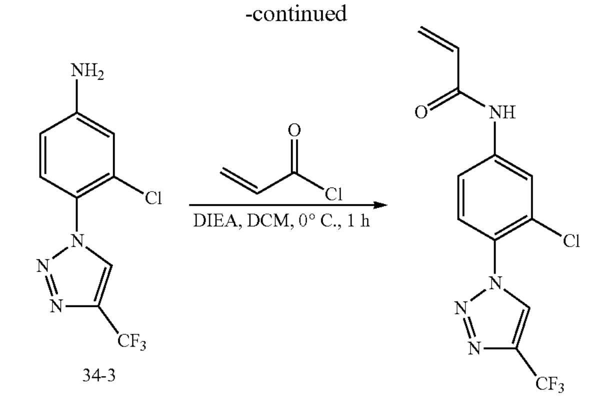

34-3 compound 34

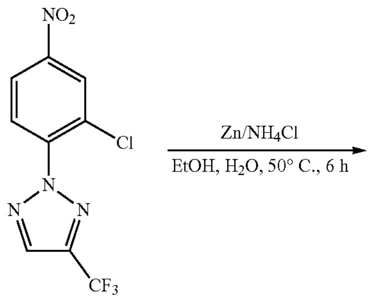

34-2

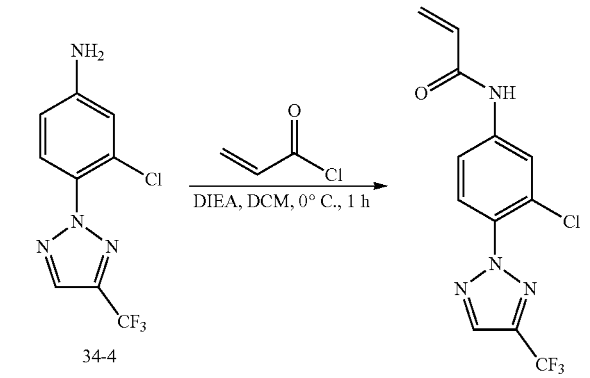

34-4 compound 35

Preparation of 1-(2-Chloro-4-nitrophenyl)-4-(trifluoromethyl)-1H-1,2,3-triazole (34-1) and 2-(2-chloro-4-nitrophenyl)-4-(trifluoromethyl)-2H-1,2,3-triazole (34-2). To a mixture of 4-(trifluoromethyl)-2H-1,2,3-triazole (3.0 g, 21.7 mmol, 1.0 eq), 2-chloro-1-fluoro-4-nitrobenzene (4.57 g, 26.0 mmol, 1.2 eq) and $Cs_2CO_3$ (10.6 g, 32.5 mmol, 1.5 eq) in DMF (60 mL) was stirred at 80° C. for 12 hours. TLC (Petroleum ether/Ethyl acetate=3:1, $R_f$ (R1)=0.50, $R_f$ (P2)=0.70) showed that the starting material was consumed completely. The mixture was cooled to room temperature, diluted with water (300 mL), and extracted with ethyl acetate (100 mL×3). The organic phase was dried over anhydrous sodium sulfate and concentrated under reduced pressure to remove the solvent. The crude product was purified by column chromatography (SiO2, Ethyl acetate/Petroleum ether=0% to 2%), separating two regioisomeric products.

1-(2-Chloro-4-nitrophenyl)-4-(trifluoromethyl)-1H-1,2,3-triazole (180 mg, 2.82% yield) was obtained as yellow solid, which was detected by $^{1}H$ NMR 400 MHz, $CDCl_3$ δ 8.53 (d, J=2.4 Hz, 1H), 8.46 (d, J=0.8 Hz, 1H), 8.38 (dd, J=8.8, 2.4 Hz, 1H), 7.97 (d, J=8.8 Hz, 1H).

2-(2-chloro-4-nitrophenyl)-4-(trifluoromethyl)-2H-1,2,3-triazole (1.21 g, 18.8% yield) was obtained as yellow oil, which was detected by 1H NMR (δ 8.50 (d, J=2.4 Hz, 1H), 8.31 (dd, J=8.8, 2.4 Hz, 1H), 8.18 (s, 1H), 7.93 (d, J=8.8 Hz, 1H).

Preparation of 3-chloro-4-(4-(trifluoromethyl)-1H-1,2,3-triazol-1-yl)aniline (compound 34). To a solution of 1-(2-chloro-4-nitrophenyl)-4-(trifluoromethyl)-1H-1,2,3-triazole (180 mg, 0.61 mmol, 1.0 eq) in MeOH/$H_2O$=(4 mL/1 mL) was added Fe (342 mg, 6.13 mmol, 10.0 eq) and ammonium chloride (328 mg, 6.13 mmol, 10.0 eq) at 20° C., the mixture was then stirred at 60° C. for 2 hours. LCMS (ENB214100-016-M1) showed that compound 8A was consumed completely. After completion, filtrate the reaction mixture and wash the filter cake by MeOH (30 mL), collect the filtrate and concentrate in vacuo to afford a residue, dissolve the residue in tetrahydrofuran (30 mL) and concentrate in vacuo for twice to ensure that no MeOH residual. 3-chloro-4-(4-(trifluoromethyl)-1H-1,2,3-triazol-1-yl)aniline (170 mg, purity: 90%, yield: 94.7%), was then used in the next step without any purification. MS (ESI) m/z=262.8 $[M+H]^+$.

Preparation of 3-chloro-4-(4-(trifluoromethyl)-1H-1,2,3-triazol-1-yl)aniline (compound 34-3). To a solution of 1-(2-chloro-4-nitrophenyl)-4-(trifluoromethyl)-1H-1,2,3-triazole (180 mg, 0.61 mmol, 1.0 eq) in MeOH/$H_2O$=(4 mL/1 mL) was added Fe (342 mg, 6.13 mmol, 10.0 eq) and ammonium chloride (328 mg, 6.13 mmol, 10.0 eq) at 20° C., the mixture was then stirred at 60° C. for 2 hours. LCMS (ENB214100-016-M1) showed that compound 8A was consumed completely. After completion, filtrate the reaction mixture and wash the filter cake by MeOH (30 mL), collect the filtrate and concentrate in vacuo to afford a residue, dissolve the residue in tetrahydrofuran (30 mL) and concentrate in vacuo for twice to ensure that no MeOH residual. 3-chloro-4-(4-(trifluoromethyl)-1H-1,2,3-triazol-1-yl)aniline (170 mg, purity: 90%, yield: 94.7%), was then used in the next step without any purification. MS (ESI) m/z=262.8 $[M+H]^+$.

Preparation of N-(3-chloro-4-(4-(trifluoromethyl)-1H-1,2,3-triazol-1-yl)phenyl)acrylamide (compound 34). To a solution of 3-chloro-4-(4-(trifluoromethyl)-1H-1,2,3-triazol-1-yl)aniline (170 mg, 0.64 mmol, 1.0 eq) and DIEA (250 mg, 1.93 mmol, 3.0 eq) in dichloromethane (2 mL) was added prop-2-enoyl chloride (58 mg, 0.64 mmol, 1.0 eq) dropwise at 0° C., the mixture was then stirred at 0° C. for 3 hours. After completion, the reaction mixture was quenched by water and extracted with EA (10 mL×3), the organic layer was then dried over $Na_2SO_4$ and concentrated in vacuo to afford a residue, purify the residue by prep-HPLC (column: Gemini, phase: ACN-H2O (0.1% FA), gradient: 52-65FA (35)) to afford N-(3-chloro-4-(4-(trifluoromethyl)-1H-1,2,3-triazol-1-yl)phenyl)acrylamide as a white solid (47 mg, 23.68%). MS (ESI) m/z=317.1 $[M+H]^+$. $^1$H NMR 400 MHz, $CDCl_3$ δ 8.27 (s, 1H), 8.11 (s, 1H), 7.60 (s, 2H), 7.42 (s, 1H), 6.52 (d, J=16.8 Hz, 1H), 6.27 (dd, J=16.8, 10.3 Hz, 1H), 5.90 (d, J=10.2 Hz, 1H).

Preparation of 3-chloro-4-(4-(trifluoromethyl)-2H-1,2,3-triazol-2-yl)aniline (compound 34-4). To a solution of 2-(2-chloro-4-nitrophenyl)-4-(trifluoromethyl)-2H-1,2,3-triazole (500 mg, 1.70 mmol, 1.0 eq) in EtOH (10 mL) and $H_2O$ (1 mL) was added Ammonium chloride (455 mg, 8.53 mmol, 5.0 eq), followed by Zn (1.11 g, 17.0 mmol, 10.0 eq) was stirred at 50° C. for 6 hours. LCMS (ENB214106-19-P1M) showed that the starting material was consumed completely. The mixture was diluted with EtOH (20 mL), filtered, and concentrated under reduced pressure to remove the solvent. The residue was diluted with water (30 mL) and extracted with Ethyl acetate (30 mL×3), the organic phase was dried over anhydrous sodium sulfate and concentrated under reduced pressure to remove the solvent. 3-chloro-4-(4-(trifluoromethyl)-2H-1,2,3-triazol-2-yl)aniline was obtained as yellow gum and was used for the next step without any purification (610 mg, crude). $^1$H NMR: 400 MHz, $CDCl_3$ δ 8.09-8.06 (m, 1H), 8.05 (s, 1H), 7.43 (d, J=8.8 Hz, 1H), 7.31 (d, J=8.8 Hz, 1H), 6.99 (d, J=2.4 Hz, 1H), 6.81 (dd, J=8.8, 2.4 Hz, 1H), 6.78 (d, J=2.4 Hz, 1H), 6.61 (dd, J=8.8, 2.4 Hz, 1H), 6.18 (s, 1H).

Preparation of N-(3-chloro-4-(4-(trifluoromethyl)-2H-1,2,3-triazol-2-yl)phenyl)acrylamide (compound 35). To a solution of -chloro-4-(4-(trifluoromethyl)-2H-1,2,3-triazol-2-yl)aniline (500 mg, 1.90 mmol, 1.0 eq) and DIEA (738 mg, 5.71 mmol, 3.0 eq) in dichloromethane (10 mL) at 0° C. was added prop-2-enoyl chloride dropwise, the mixture was then stirred at 0° C. for 30 min. After completion, quench the mixture by water (30 mL) and extracted with EA (30 mL×3), the mixture was then dried over $Na_2SO_4$ and concentrated in vacuo to afford a residue, purified the residue by prep-HPLC (column: Gemini, phase: ACN-$H_2O$ (0.1% FA), gradient: 55-85) to afford N-(3-chloro-4-(4-(trifluoromethyl)-2H-1,2,3-triazol-2-yl)phenyl)acrylamide as a white solid. (65 mg, 10.6%), MS (ESI) m/z=317.1 $[M+H]^+$. $^1$H NMR: 400 MHz, $CDCl_3$ δ 8.09 (s, 1H), 7.98 (d, J=2.0 Hz, 1H), 7.61 (7.65-7.55, 2H), 7.51 (s, 1H), 6.50 (dd, J=16.8, 0.8 Hz, 1H), 6.27 (dd, J=16.8, 10.0 Hz, 1H), 5.87 (dd, J=10.0, 0.8 Hz, 1H).

Example 35

Synthesis of Compound 36

(N-(3-fluoro-5-(3-(trifluoromethyl)phenoxy)phenyl) acrylamide)

Scheme 37. Synthesis of compounds 36.

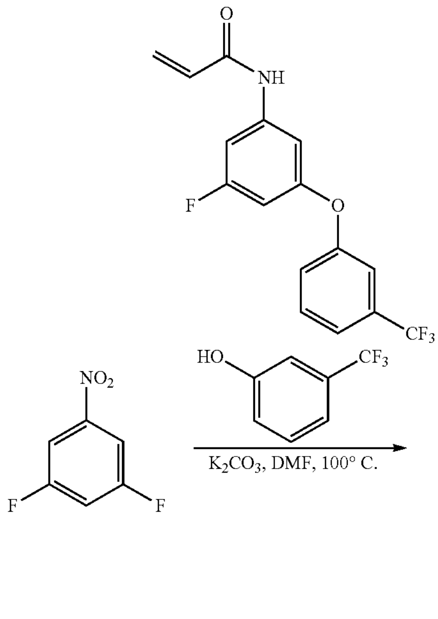

-continued

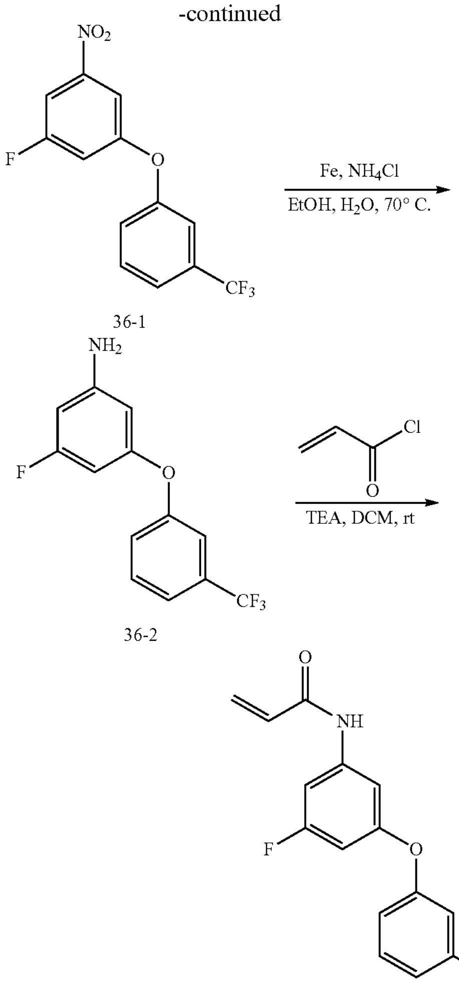

36-1

36-2 compound 36

Preparation of 1-fluoro-3-nitro-5-(3-(trifluoromethyl)phenoxy)benzene (36-1). To a solution of 3,5-difluoronitrobenzene (500 mg, 3.14 mmol) in DMF (20 mL) was added 3-trifluoromethylphenol (611 mg, 3.77 mmol) and $K_2CO_3$ (881 mg, 6.29 mmol). The mixture was stirred at 100° C. for 16 hours. The mixture was diluted with EA (50 mL) was washed with $H_2O$ (20 mL×2), brine (20 mL), dried over $Na_2SO_4$, filtered, and concentrated in vacuo to afford crude product. The crude product was purified by flash chromatography (silica, solvent gradient: 0-30% EA in PE) to give 1-fluoro-3-nitro-5-(3-(trifluoromethyl)phenoxy)benzene (300 mg) as a yellow solid, yield: 31.7%. $^1H$ NMR (400 MHz, $CDCL_3$): δ ppm 7.71-7.68 (m, 1H), 7.63-7.62 (m, 1H), 7.59-7.51 (m, 2H), 7.34-7.33 (m, 1H), 7.27-7.26 (m, 1H), 7.05-7.02 (m, 1H).

Preparation of 3-fluoro-5-(3-(trifluoromethyl)phenoxy)aniline (36-2). To a solution of 1-fluoro-3-nitro-5-(3-(trifluoromethyl)phenoxy)benzene (300 mg, 1.00 mmol) in EtOH (10 mL) and $H_2O$ (2 mL) was added iron powder (556 mg, 9.96 mmol) and ammonium chloride (533 mg, 9.96 mmol). The mixture was stirred at 70° C. for 2 hours. The mixture was filtered and the filtrate was concentrated in vacuo to give residue. The residue was diluted with $H_2O$ (20 mL), extracted with EA (30 mL×2). The organic layers were combined, dried over $Na_2SO_4$, filtered, and concentrated in vacuo to afford crude product. The crude product was purified by flash chromatography (silica, solvent gradient: PE/EtOAc 5:1) to give 3-fluoro-5-(3-(trifluoromethyl)phenoxy)aniline (210 mg) as a yellow solid, yield: 77.8%. $^1H$ NMR (400 MHz, $CDCL_3$) δ ppm 7.47-7.43 (m, 1H), 7.38-7.36 (m, 1H), 7.27 (s, 1H), 7.21-7.19 (m, 1H), 6.20-6.16 (m, 1H), 6.12-6.09 (m, 2H), 3.94 (m, 2H). MS Calcd.: 271.1, MS Found: 271.8 $[M+H]^+$.

N-(3-fluoro-5-(3-(trifluoromethyl)phenoxy)phenyl)acrylamide (compound 36). To a solution of 3-fluoro-5-(3-(trifluoromethyl)phenoxy)aniline (210 mg, 0.77 mmol) in DCM (10 mL) was added prop-2-enoyl chloride (105 mg, 1.16 mmol) followed by TEA (157 mg, 1.55 mmol). The mixture was stirred at room temperature for 2 hours. The reaction mixture diluted with water (50 mL), extracted with DCM (3×30 mL). The organic layers were washed with brine (2×30 mL), dried over anhydrous $Na_2SO_4$ and concentrated under vacuum to afford crude product, which was purified by silica gel chromatography (elution gradient: ethyl acetate/petroleum ether, 4/1, v/v) to afford N-(3-fluoro-5-(3-(trifluoromethyl)phenoxy)phenyl)acrylamide (72 mg) as a yellow solid, yield: 28.6%. $^1H$ NMR (400 MHz, DMSO-$d_6$) δ ppm 10.41 (s, 1H), 7.68 (t, J=8.0 Hz, 1H), 7.58 (d, J=7.6 Hz, 2H), 7.47-7.41 (m, 2H), 7.08 (s, 1H), 6.75-6.72 (m, 1H), 6.39-6.21 (m, 2H), 5.79 (dd, J=9.6, 2.4 Hz, 1H). MS Calcd.: 325.1, MS Found: 325.8 $[M+H]^+$.

Example 36

Synthesis of Compound 37

(N-(2-fluoro-5-(3-(trifluoromethyl)phenoxy)phenyl)acrylamide)

Scheme 38. Synthesis of compounds 37.

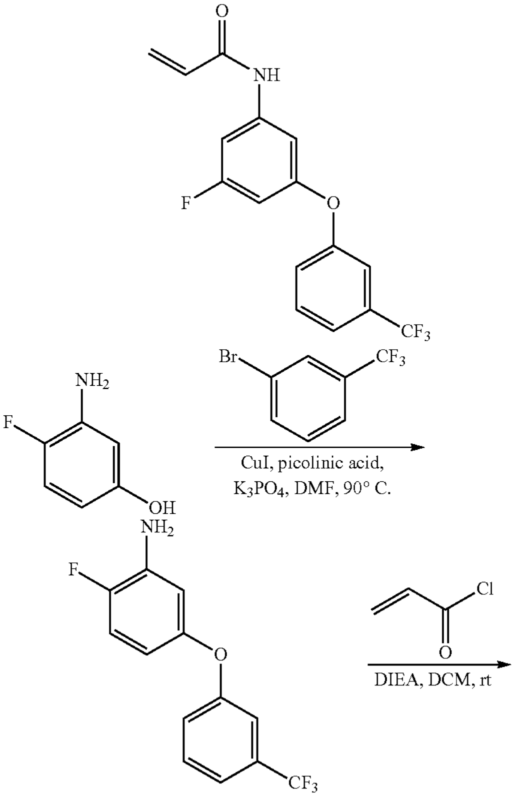

37-1

-continued

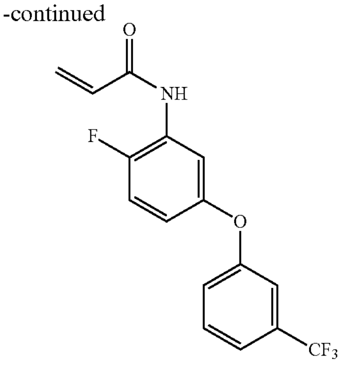

compound 37

Preparation of 2-fluoro-5-(3-(trifluoromethyl)phenoxy) aniline (37-1). To a solution of 3-amino-4-fluorophenol (500 mg, 3.93 mmol) in DMSO (10 mL) was added 1-bromo-3-(trifluoromethyl)benzene (1.3 g, 5.90 mmol), picolinic acid (145 mg, 1.18 mmol), CuI (75 mg, 0.39 mmol) and $K_3PO_4$ (2.5 g, 11.80 mmol). The mixture was stirred at 90° C. under $N_2$ for 16 hours. The mixture was diluted with EA (50 mL), washed with $H_2O$ (20 mL×2) and brine (20 mL), dried over $Na_2SO_4$, filtered, and concentrated in vacuo to afford crude product. The crude product was purified by flash chromatography (silica, solvent gradient: 0-30% EA in PE) to give 2-fluoro-5-(3-(trifluoromethyl)phenoxy)aniline (180 mg) as a yellow solid, yield: 16.9%. $^1H$ NMR (400 MHz, DMSO-$d_6$): δ ppm 7.60 (t, J=7.8 Hz, 1H), 7.45 (d, J=8.0 Hz, 1H), 7.26-7.24 (m, 2H), 7.05-7.00 (m, 1H), 6.46 (dd, J=7.6, 2.8 Hz, 1H), 6.23-6.20 (m, 1H), 5.38 (m, 2H). MS Calcd.: 271.1, MS Found: 271.8 $[M+H]^+$.

Preparation of N-(2-fluoro-5-(3-(trifluoromethyl)phenoxy)phenyl)acrylamide (compound 37). To a solution of 2-fluoro-5-(3-(trifluoromethyl)phenoxy)aniline (180 mg, 0.66 mmol) in DCM (10 mL) was added prop-2-enoyl chloride (90 mg, 1.00 mmol) followed by TEA (134 mg, 1.33 mmol). The mixture was stirred at room temperature for 2 hours. The reaction mixture diluted with water (50 mL), extracted with DCM (3×30 mL). The organic layers were washed with brine (2×30 mL), dried over anhydrous $Na_2SO_4$ and concentrated under vacuum to afford crude product, which was purified by silica gel chromatography (elution gradient: ethyl acetate/petroleum ether, 5/1, v/v) to afford N-(2-fluoro-5-(3-(trifluoromethyl)phenoxy)phenyl)acrylamide (66 mg) as a white solid, yield: 30.6%. $^1H$ NMR (400 MHz, DMSO-$d_6$) δ ppm 10.07 (s, 1H), 7.89-7.87 (m, 1H), 7.58 (d, J=8.0 Hz, 1H), 7.46 (d, J=7.6 Hz, 1H), 7.35-7.25 (m, 3H), 6.89-6.85 (m, 1H), 6.65-6.58 (m, 1H), 6.22 (dd, J=17.2, 2.0 Hz, 1H), 5.74 (dd, J=10.0, 2.0 Hz, 1H). MS Calcd.: 325.1, MS Found: 325.7 $[M+H]^+$.

Example 37

Synthesis of Compound 38

(N-(3-(4-(trifluoromethyl)phenoxy)phenyl)acrylamide)

Scheme 39. Synthesis of compound 38.

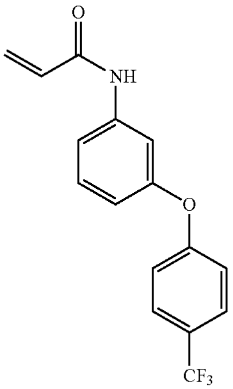

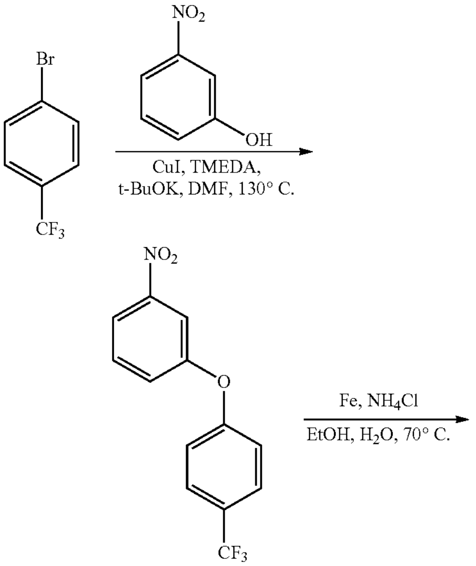

38-1

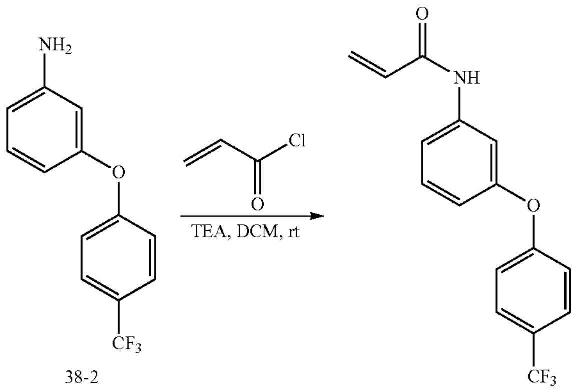

38-2 compound 38

Preparation of 1-nitro-3-(4-(trifluoromethyl)phenoxy) benzene (38-1). To a solution of 1-bromo-4-(trifluoromethyl)benzene (500 mg, 2.22 mmol) in DMF (10 mL) was added 3-nitrophenol (371 mg, 2.67 mmol), TMEDA (78 mg, 0.67 mmol), CuI (42 mg, 0.22 mmol) and t-BuOK (499 mg, 4.44 mmol). The mixture was stirred at 130° C. under $N_2$ for 16 hours. The mixture was filtered and the filtrate was concentrated in vacuo to give crude product. The crude product was diluted with $H_2O$ (20 mL), extracted with EA (30 mL×2). The organic layers were combined, dried over $Na_2SO_4$, filtered, and concentrated in vacuo to afford crude product. The crude product was purified by flash chromatography (silica, solvent gradient: 0-30% EA in PE) to give 1-nitro-3-(4-(trifluoromethyl)phenoxy)benzene (310 mg) as a yellow oil, yield: 49.3%. $^1$H NMR (400 MHz, $CDCl_3$): δ ppm 8.05-8.02 (m, 1H), 7.87 (t, J=2.4 Hz, 1H), 7.66 (d, J=8.4 Hz, 2H), 7.56 (t, J=8.2 Hz, 1H), 7.39-7.37 (m, 1H), 7.13 (d, J=8.4 Hz, 2H).

Preparation of 3-(4-(trifluoromethyl)phenoxy)aniline (38-2). To a solution of 1-nitro-3-(4-(trifluoromethyl)phenoxy) benzene (310 mg, 1.10 mmol) in EtOH (10 mL) and $H_2O$ (2 mL) was added iron powder (611 mg, 10.95 mmol) and ammonium chloride (586 mg, 10.95 mmol). The mixture was stirred at 70° C. for 2 hours. The mixture was filtered and the filtrate was concentrated in vacuo to give residue. The residue was diluted with $H_2O$ (20 mL), extracted with EA (30 mL×2). The organic layers were combined, dried over $Na_2SO_4$, filtered, and concentrated in vacuo to afford crude product. The crude product was purified by column chromatography (silica, solvent gradient: 1:3 EA in PE) to give 3-(4-(trifluoromethyl)phenoxy)aniline (270 mg) as a yellow solid, yield: 97.5%. $^1$H NMR (400 MHz, $CDCl_3$) δ ppm 7.56-7.54 (m, 2H), 7.14 (t, J=8.0 Hz, 1H), 7.05-7.03 (m, 2H), 6.54-6.51 (m, 1H), 6.45-6.43 (m, 1H), 6.39 (t, J=2.2 Hz, 1H). MS Calcd.: 253.1, MS Found: 253.8 $[M+H]^+$.

Preparation of N-(3-(4-(trifluoromethyl)phenoxy)phenyl) acrylamide (compound 38). To a solution of 3-(4-(trifluoromethyl)phenoxy)aniline (270 mg, 1.07 mmol) in DCM (10 mL) was added prop-2-enoyl chloride (150 mg, 1.66 mmol) followed by TEA (224 mg, 2.21 mmol). The mixture was stirred at room temperature for 2 hours. The reaction mixture diluted with water (50 mL), extracted with DCM (3×30 mL). The organic layers were washed with brine (2×30 mL), dried over anhydrous $Na_2SO_4$ and concentrated under vacuum to afford crude product, which was purified by prep-HPLC to afford N-(3-(4-(trifluoromethyl)phenoxy) phenyl)acrylamide (83 mg) as a yellow solid, yield: 25.4%. $^1$H NMR (400 MHz, DMSO-$d_6$) δ ppm 10.29 (s, 1H), 7.76 (d, J=8.8 Hz, 2H), 7.54 (t, J=2.0 Hz, 1H), 7.47-7.38 (m, 2H), 7.19 (d, J=8.4 Hz, 2H), 6.86-6.84 (m, 1H), 6.44-6.37 (m, 1H), 6.27-6.22 (m, 1H), 5.77 (dd, J=10.0, 2.0 Hz, 1H). MS Calcd.: 307.1, MS Found: 307.7 $[M+H]^+$.

Example 38

Synthesis of Compound 39

(N-(5-(3-(trifluoromethyl)phenoxy)tetrahydro-2H-pyran-3-yl)acrylamide)

Scheme 40. Synthesis of compounds 39.

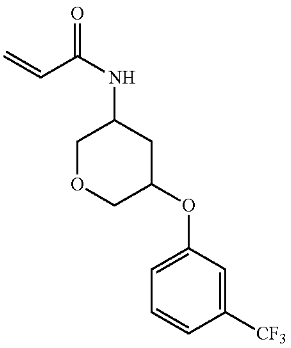

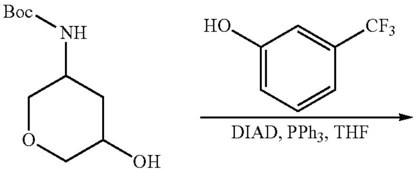

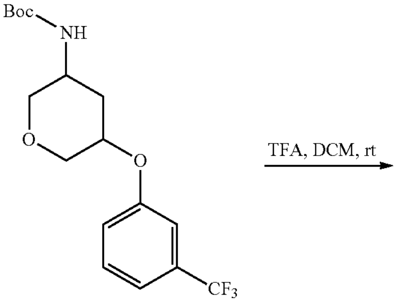

39-1

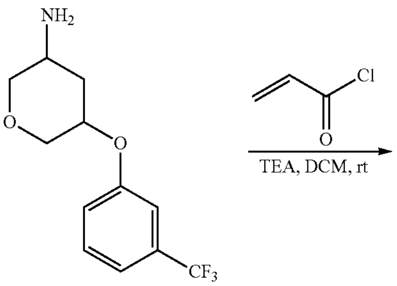

39-2

-continued

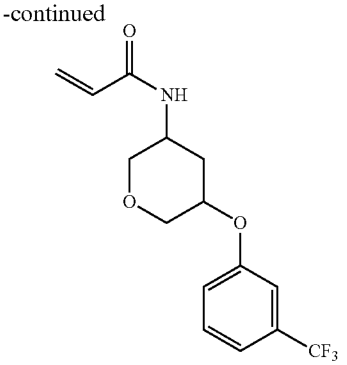

compound 39

Preparation of tert-butyl(5-(3-(trifluoromethyl)phenoxy) tetrahydro-2H-pyran-3-yl)carbamate (39-1). To a solution of tert-butyl (5-hydroxytetrahydro-2H-pyran-3-yl)carbamate (500 mg, 2.3 mmol), 3-(trifluoromethyl)phenol (408 mg, 2.52 mmol), and $PPh_3$ (660 mg, 2.52 mmol) in THF (30 mL) was added DIAD (509 mg, 2.52 mmol) dropwise at 0° C. The mixture was stirred at room temperature under N2 for 4 hours. The mixture was quenched with $H_2O$ (30 mL), extracted with EA (30 mL×3). The organic layers were combined, dried over $Na_2SO_4$, filtered, and concentrated in vacuo to afford crude product. The crude product was purified by flash chromatography (silica, solvent gradient: PE/EtOAc 3:1) to give tert-butyl (5-(3-(trifluoromethyl) phenoxy)tetrahydro-2H-pyran-3-yl)carbamate (470 mg) as a yellow gum, yield: 56.1%. MS Calcd.: 361.2, MS Found: 305.8 $[M-56]^+$.

Preparation of 5-(3-(trifluoromethyl)phenoxy)tetrahydro-2H-pyran-3-amine (39-2). To a solution of tert-butyl (5-(3-(trifluoromethyl)phenoxy)tetrahydro-2H-pyran-3-yl)carbamate (470 mg, 1.3 mmol) in DCM (8 mL) was added trifluoroacetic acid (740 mg, 6.48 mmol) dropwise at 0° C. The mixture was stirred at room temperature under $N_2$ for 2 hours. The mixture was concentrated in vacuo to afford crude product. The crude product was purified by flash chromatography (DCM/MeOH, 10/1, v/v) to afford 5-(3-(trifluoromethyl)phenoxy)tetrahydro-2H-pyran-3-amine (200 mg) as a yellow gum, yield: 64.8%. MS Calcd.: 261.1, MS Found: 261.9 $[M+H]^+$.

Preparation of N-(5-(3-(trifluoromethyl)phenoxy)tetrahydro-2H-pyran-3-yl) acrylamide (compound 39). To a solution of 5-(3-(trifluoromethyl)phenoxy)tetrahydro-2H-pyran-3-amine (220 mg, 0.84 mmol) in DCM (10 mL) was added prop-2-enoyl chloride (99 mg, 1.09 mmol) followed by TEA (170 mg, 1.68 mmol). The mixture was stirred at room temperature for 15 hours. The reaction mixture diluted with water (20 mL), extracted with DCM (3×30 mL). The organic layers were washed with brine (2×30 mL), dried over anhydrous $Na_2SO_4$ and concentrated under vacuum to afford crude product, which was purified by silica gel chromatography (elution gradient: ethyl acetate/petroleum ether, 1/1, v/v) to afford N-(5-(3-(trifluoromethyl)phenoxy) tetrahydro-2H-pyran-3-yl)acrylamide (90 mg) as a white solid, yield: 34.0%. $^1H$ NMR (400 MHz, CDC13) δ ppm 7.45-7.41 (m, 1H). 7.27-7.25 (m, 1H). 7.12-7.06 (m, 2H). 6.74-6.72 (m, 1H). 6.24-6.22 (m, 1H). 6.11-6.07 (m, 1H). 5.68-5.65 (m, 1H). 4.52 (S, 1H). 4.31 (S, 1H). 4.05-4.04 (m, 1H). 3.86-3.85 (m, 1H). 3.74-3.72 (m, 1H). 3.71-3.69 (m, 2H). 2.22-2.12 (m, 2H). MS Calcd.: 315.3, MS Found: 316.1 $[M+H]^+$.

Example 39

Synthesis of Compound 40

(N-(3-((4,4-difluorocyclohexyl)oxy)phenyl)acrylamide)

Scheme 41. Synthesis of compound 40.

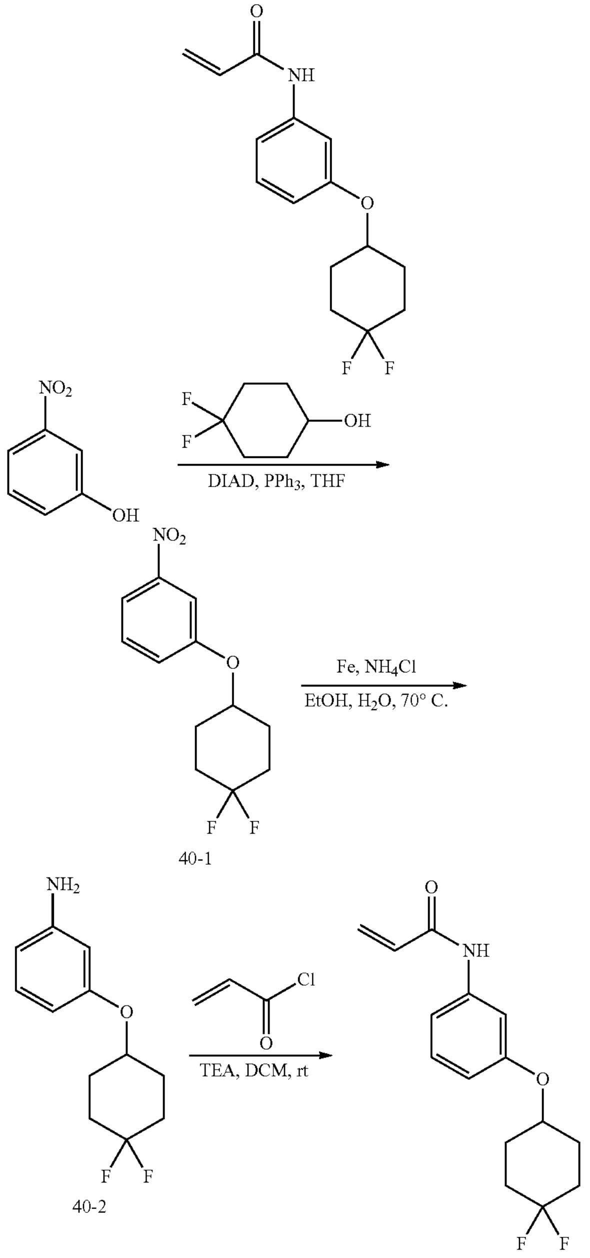

40-1

40-2 compound 40

Preparation of 1-((4,4-difluorocyclohexyl)oxy)-3-nitrobenzene (40-1). To a solution of 3-nitrophenol (1 g, 7.19 mmol), 4,4-difluorocyclohexanol (0.98 g, 7.19 mmol), and $PPh_3$ (2.27 g, 8.62 mmol) in THF (30 mL) was added DIAD (1.83 g, 8.62 mmol) dropwise at 0° C. The mixture was stirred at room temperature under $N_2$ for 6 hours. The mixture was quenched with $H_2O$ (30 mL), extracted with EA (30 mL×3). The organic layers were combined, dried over $Na_2SO_4$, filtered, and concentrated in vacuo to afford crude product. The crude product was purified by flash chromatography (silica, solvent gradient: PE/EtOAc 5:1) to give 1-((4,4-difluorocyclohexyl)oxy)-3-nitrobenzene (600 mg) as a yellow oil, yield: 32.4%. MS Calcd.: 257.1, MS Found: 280.0 [M+Na]*.

Preparation of 3-((4,4-difluorocyclohexyl)oxy)aniline (40-2). To a solution of 1-((4,4-difluorocyclohexyl)oxy)-3-nitrobenzene (500 mg, 1.94 mmol) in EtOH (12 mL) and $H_2O$ (4 mL) was added iron powder (545 mg, 9.73 mmol) and ammonium chloride (525 mg, 9.73 mmol). The mixture was stirred at 70° C. for 2 hours. The solution was evaporated and diluted with $H_2O$ (10 mL), extracted with EA (30×3). The organic layers were combined, dried over $Na_2SO_4$, filtered, and concentrated in vacuo to afford crude product. The crude product was purified by flash chromatography (silica, solvent gradient: PE/EtOAc 2:1) to give 3-((4,4-difluorocyclohexyl)oxy)aniline (300 mg) as a yellow solid, yield: 68.04%. MS Calcd.: 227.1, MS Found: 227.9 $[M+H]^+$.

Preparation of N-(3-((4,4-difluorocyclohexyl)oxy)phenyl)acrylamide (compound 40). To a solution of 3-((4,4-difluorocyclohexyl)oxy)aniline (300 mg, 1.32 mmol) in DCM (10 mL) was added prop-2-enoyl chloride (119 mg, 1.32 mmol) followed by TEA (400 mg, 3.96 mmol). The mixture was stirred at room temperature for 2 hours. The reaction mixture diluted with water (50 mL), extracted with DCM (3×30 mL). The organic layers were washed with brine (2×30 mL), dried over anhydrous $Na_2SO_4$ and concentrated under vacuum to afford crude product, which was purified by silica gel chromatography (elution gradient: ethyl acetate/petroleum ether, 1/1, v/v) to afford N-(3-((4,4-difluorocyclohexyl)oxy)phenyl)acrylamide (70 mg) as an off-white solid, yield: 18.9%. $^1H$ NMR (400 MHz, $CDCl_3$) δ ppm 7.51 (s, 1H), 7.32 (s, 1H), 7.21 (t, J=8.1 Hz, 1H), 6.93 (d, J=7.9 Hz, 1H), 6.67 (dd, J=8.2, 2.0 Hz, 1H), 6.43 (dd, J=16.8, 1.1 Hz, 1H), 6.23 (dd, J=16.8, 10.2 Hz, 1H), 5.77 (dd, J=10.2, 1.2 Hz, 1H), 4.50 (d, J=2.5 Hz, 1H), 2.20-1.83 (m, 8H). MS Calcd.: 281.1, MS Found: 281.8 $[M+H]^+$.

Example 40

Synthesis of Compounds 41 and 42

(N-((1R*,3S*)-3-(3-(trifluoromethyl)phenoxy)cyclopentyl)acrylamide and N-((1S*,3R*)-3-(3-(trifluoromethyl)phenoxy)cyclopentyl)acrylamide)

Scheme 42. Synthesis of compound 41 and 42.

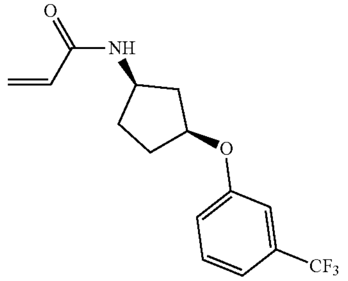

-continued

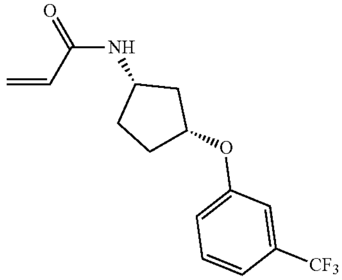

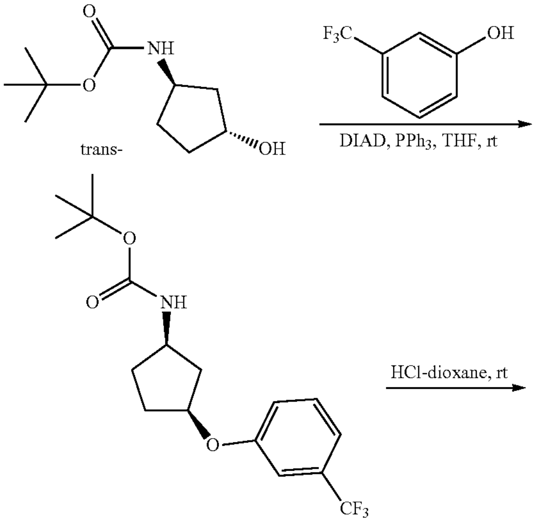

41-1

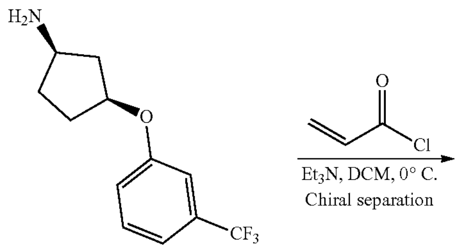

41-2

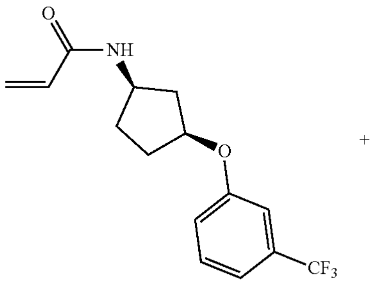

compound 41

-continued

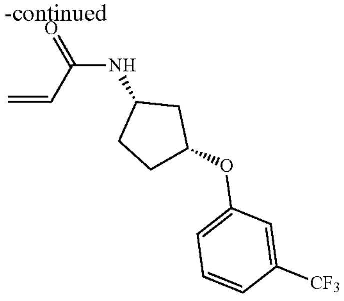

compound 42

Synthesis of tert-butyl ((trans)-3-(3-(trifluoromethyl)phenoxy)cyclopentyl)carbamate (41-1). A round-bottom flask containing a mixture of tert-butyl ((trans)-3-hydroxycyclopentyl)carbamate [1.2 g, 5.96 mmol], 3-(trifluoromethyl) phenol [1.16 g, 7.15 mmol] and $PPh_3$ [2.36 g, 8.94 mmol] were dissolved in THF (10 mL) at cooled under $N_2$, and then DIAD [2.4 g, 11.92 mmol] was added dropwise, the mixture was warmed to room temperature for 16 h. $H_2O$ (15 mL) was added and extracted with EtOAc (30 mL×3) and the combined organic phases were washed with brine (10 mL×3), dried over anhydrous sodium sulfate and concentrated in vacuo. The residue was purified by Flash chromatography (eluent: PE/EtOAc=2/1) to afford tert-butyl ((trans)-3-(3-(trifluoromethyl)phenoxy)cyclopentyl)carbamate (1.2 g, 85% purity, 69.76% yield) as a yellow oil. $[M+H]^+$ m/z 345.362, found 246, 290.

Synthesis of (trans)-3-(3-(trifluoromethyl)phenoxy)cyclopentan-1-amine (41-2). A round-bottom flask containing a mixture of tert-butyl ((trans)-3-(3-(trifluoromethyl)phenoxy)cyclopentyl)carbamate [2 g, 5.8 mmol] in HCl/1,4-dioxane [10 mL] was stirred at room temperature for 1 h. The mixture was under reduced pressure and concentrated to give the title compound (trans)-3-(3-(trifluoromethyl)phenoxy)cyclopentan-1-amine (1.4 g, 95% purity, 93.10% yield) as a yellow solid. $[M+H]^+$ m/z 245.245, found 246.

Preparation of N-((1R*,3S*)-3-(3-(trifluoromethyl)phenoxy)cyclopentyl)acrylamide (compound 41) and N-((1S*,3R*)-3-(3-(trifluoromethyl)phenoxy)cyclopentyl)acrylamide (compound 42). To a mixture of (trans)-3-(3-(trifluoromethyl)phenoxy)cyclopentan-1-amine (500 mg, 2.04 mmol), prop-2-enoyl chloride (184 mg, 2.04 mmol) in DCM (8 mL) was added $Et_3N$ (410 mg, 4.08 mmol) at 0° C., and the mixture was warmed to room temperature for 2 h. $H_2O$ (15 mL) was added and extracted with DCM (40 mL×3) and the combined organic phases were washed with brine (10 mL×3), dried over anhydrous sodium sulfate and concentrated in vacuo. The residue was purified by flash chromatography (eluent: PE/EtOAc=1/1) and SFC (DAICEL AD-H 4.6 mm I.D.*250 mm L 5 μm, 85% $CO_2$-15% MeOH [0.2% ($NH_3$+FA)]) to afford two stereoisomers, and stereochemistry was arbitrarily assigned to each stereoisomer: N-((1R*,3S*)-3-(3-(trifluoromethyl)phenoxy)cyclopentyl)acrylamide (Retention time: 3.59 min.) (106 mg, 97.43% purity, 16.92% yield) as a white solid and N-((1S*,3R*)-3-(3-(trifluoromethyl)phenoxy)cyclopentyl)acrylamide (Retention time: 4.25 min.) (110 mg, 97.29% purity, 17.53% yield).

N-((1R*,3S*)-3-(3-(trifluoromethyl)phenoxy)cyclopentyl)acrylamide: $^1H$ NMR (400 MHz, DMSO-$d_6$, ppm) δ 8.17 (d, J=7.1 Hz, 1H), 7.52 (t, J=8.0 Hz, 1H), 7.32-7.08 (m, 3H), 6.22 (dd, J=17.1, 10.1 Hz, 1H), 6.06 (dd, J=17.1, 2.2 Hz, 1H), 5.56 (dd, J=10.1, 2.2 Hz, 1H), 4.97-4.85 (m, 1H), 4.17 (dd, J=14.9, 7.6 Hz, 1H), 2.50-2.42 (m, 1H), 2.03-1.80 (m, 3H), 1.72-1.50 (m, 2H).

N-((1S*,3R*)-3-(3-(trifluoromethyl)phenoxy)cyclopentyl)acrylamide: $^1H$ NMR (400 MHz, DMSO-$d_6$, ppm) δ 8.18 (d, J=7.0 Hz, 1H), 7.52 (t, J=8.0 Hz, 1H), 7.30-7.20 (m, 2H), 7.18 (s, 1H), 6.22 (dd, J=17.1, 10.1 Hz, 1H), 6.06 (dd, J=17.1, 2.2 Hz, 1H), 5.56 (dd, J=10.1, 2.2 Hz, 1H), 4.96-4.85 (m, 1H), 4.16 (dd, J=14.8, 7.5 Hz, 1H), 2.50-2.43 (m, 1H), 2.02-1.82 (m, 3H), 1.69-1.52 (m, 2H). $[M+H]^+$ m/z 299.293, found 300.

Example 41

Synthesis of Compound 43

(N-((1R,3R)-3-(3-(trifluoromethyl)phenoxy)cyclopentyl)acrylamide)

Scheme 43. Synthesis of compound 43.

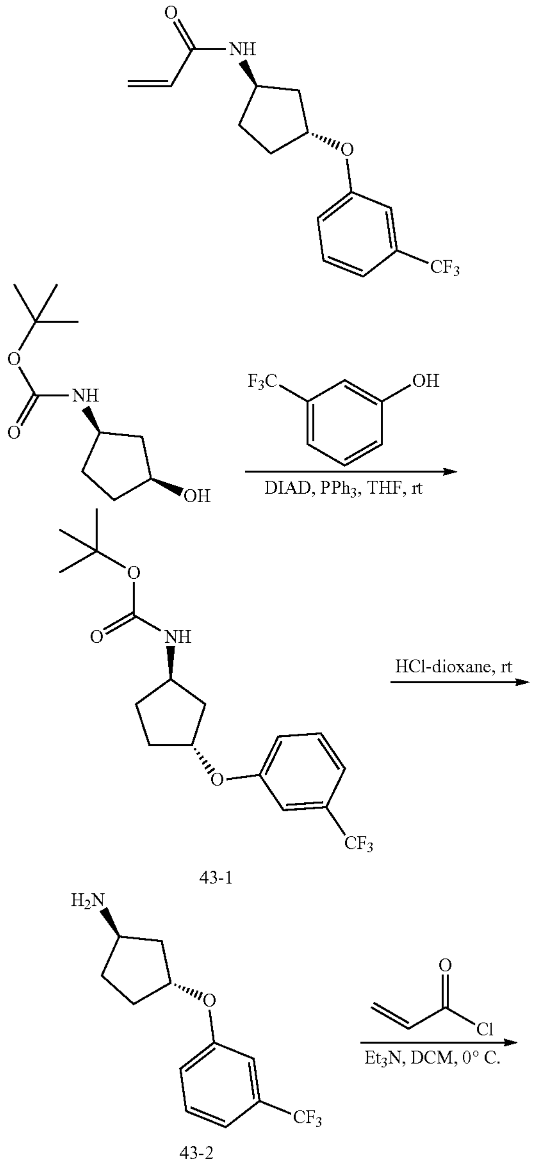

43-1

43-2

-continued

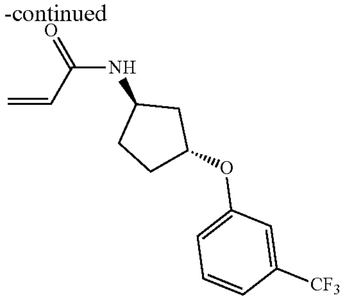

compound 43

Preparation of tert-butyl ((1R,3R)-3-(3-(trifluoromethyl) phenoxy)cyclopentyl)carbamate (43-1). To a solution of tert-butyl ((1R,3S)-3-hydroxycyclopentyl)carbamate [505 mg, 2.5 mmol],3-(trifluoromethyl)phenol [440 mg, 2.7 mmol] and $PPh_3$ [983 mg, 3.75 mmol] in THF [10 mL] stirred under nitrogen at 0° C. was added DIAD [1.01 g, 5 mmol] dropwise. The reaction mixture was stirred at room temperature for 12 h. $H_2O$ (15 mL) was added and extracted with EtOAc (30 mL×3) and the combined organic phases were washed with brine (10 mL×3), dried over anhydrous sodium sulfate, and concentrated in vacuo. The residue was purified by Flash chromatography (eluent: PE/EtOAc=3/1) to afford tert-butyl ((1R,3R)-3-(3-(trifluoromethyl)phenoxy) cyclopentyl)carbamate (427 mg, 90% purity, 44% yield) as a white solid. $[M+H]^+$ m/z 345.362, found 246, 290. $^1H$ NMR (400 MHz, $CDCl_3$, ppm) δ 7.35 (t, J=8.0 Hz, 1H), 7.16 (d, J=7.7 Hz, 1H), 7.05 (s, 1H), 7.01-6.95 (m, 1H), 4.83 (td, J=5.8, 2.8 Hz, 1H), 4.68 (s, 1H), 4.20 (s, 1H), 2.33-2.12 (m, 3H), 1.90-1.76 (m, 2H), 1.45 (s, 9H), 1.24 (d, J=13.7 Hz, 1H).

Preparation of (1R,3R)-3-(3-(trifluoromethyl)phenoxy) cyclopentan-1-amine (43-2). HCl (4N in dioxane) (6 mL) was added to a solution of tert-butyl ((1R,3R)-3-(3-(trifluoromethyl)phenoxy)cyclopentyl)carbamate (510 mg, 1.4 mmol) in dioxane (10 mL). The mixture was stirred at room temperature for 10 hours. the mixture was under reduced pressure and concentrated to give the title compound (1R, 3R)-3-(3-(trifluoromethyl)phenoxy)cyclopentan-1-amine (370 mg, 95% purity, 97% yield) as a white solid. $[M+H]^+$ m/z 245.245, found 246.

Preparation of N-((1R,3R)-3-(3-(trifluoromethyl)phenoxy)cyclopentyl)acrylamide (compound 43). To a mixture of (1R,3R)-3-(3-(trifluoromethyl)phenoxy)cyclopentan-1-amine (429 mg, 1.74 mmol), prop-2-enoyl chloride (219 mg, 2.4 mmol) in DCM (12 mL) was added $Et_3N$ (360 mg, 3.4 mmol) at 0° C., And the mixture was warmed to room temperature for 16 h. $H_2O$ (15 mL) was added and extracted with DCM (40 mL×3) and the combined organic phases were washed with brine (10 mL×3), dried over anhydrous sodium sulfate and concentrated in vacuo. The residue was purified by Flash chromatography (eluent: PE/EtOAc=8/1) to afford N-((1R,3R)-3-(3-(trifluoromethyl)phenoxy)cyclopentyl)acrylamide (347 mg, 96% purity, 65% yield) as a white solid. $[M+H]^+$ m/z 299.293, found 300. $^1H$ NMR (400 MHz, $CDCl_3$, ppm) δ 7.36 (t, J=8.0 Hz, 1H), 7.18 (d, J=7.7 Hz, 1H), 7.06 (s, 1H), 7.01 (dd, J=8.3, 2.0 Hz, 1H), 6.29 (dd, J=16.9, 1.1 Hz, 1H), 6.08 (dd, J=16.9, 10.3 Hz, 1H), 5.85-5.52 (m, 2H), 4.87 (dt, J=8.8, 2.8 Hz, 1H), 4.56 (dd, J=14.9, 7.4 Hz, 1H), 2.44-2.15 (m, 3H), 1.99-1.79 (m, 2H), 1.62-1.50 (m, 1H).

Example 42

Synthesis of Compound 44

(N-((1S,3S)-3-(3-(trifluoromethyl)phenoxy)cyclopentyl)acrylamide)

Scheme 44. Synthesis of compound 44.

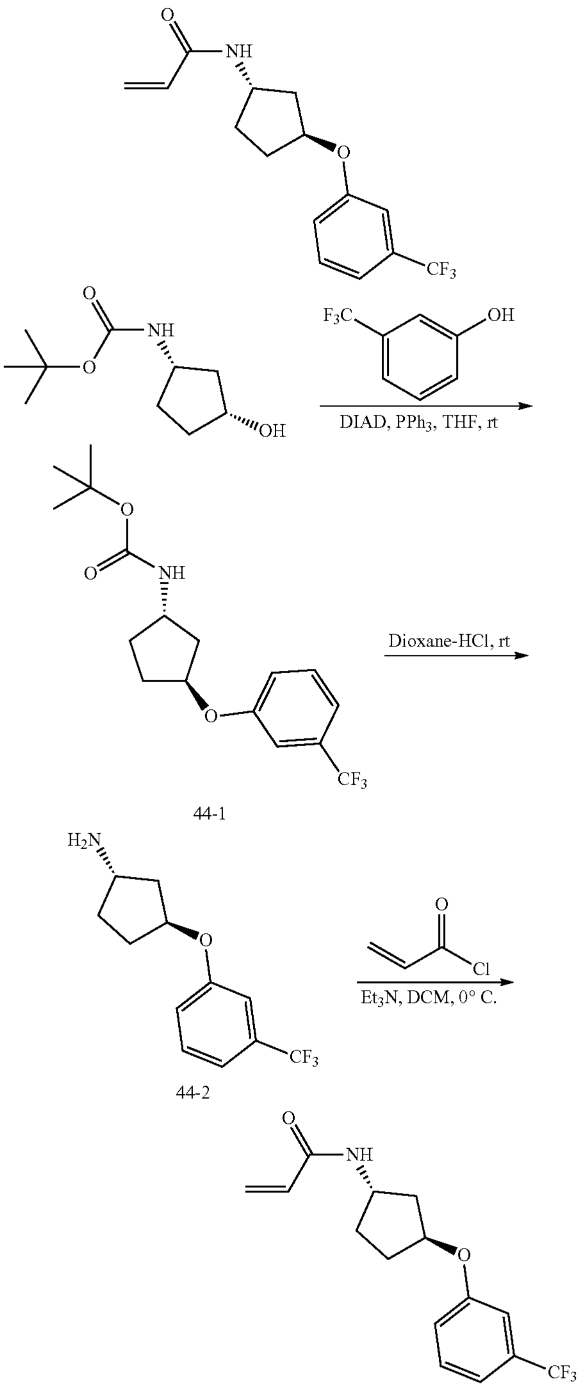

compound 44

Preparation of tert-butyl ((1S,3S)-3-(3-(trifluoromethyl) phenoxy)cyclopentyl)carbamate (44-1). To a solution of tert-butyl ((1S,3R)-3-hydroxycyclopentyl)carbamate [505 mg, 2.5 mmol], 3-(trifluoromethyl)phenol [440 mg, 2.7 mmol] and $PPh_3$ [983 mg, 3.75 mmol] in THF [10 mL] stirred under nitrogen at 0° C. was added DIAD [1.01 g, 5 mmol] dropwise. The reaction mixture was stirred at room temperature for 12 h. $H_2O$ (15 mL) was added and extracted with EtOAc (30 mL×3) and the combined organic phases were washed with brine (10 mL×3), dried over anhydrous sodium sulfate, and concentrated in vacuo. The residue was purified by Flash chromatography (eluent: PE/EtOAc=10/1) to afford tert-butyl ((1S,3S)-3-(3-(trifluoromethyl)phenoxy)cyclopentyl)carbamate (600 mg, 92% purity, 63% yield) as a white solid. $[M+H]^+$ m/z 345.362, found 246, 290.

Preparation of (1S,3S)-3-(3-(trifluoromethyl)phenoxy)cyclopentan-1-amine (44-2). HCl (4N in dioxane) (6 mL) was added to a solution of tert-butyl ((1S,3S)-3-(3-(trifluoromethyl)phenoxy)cyclopentyl)carbamate (540 mg, 1.55 mmol) in dioxane (10 mL). The mixture was stirred at room temperature for 10 hours. the mixture was under reduced pressure and concentrated to give the title compound (1S, 3S)-3-(3-(trifluoromethyl)phenoxy)cyclopentan-1-amine (405 mg, 93% purity, 98% yield) as a white solid. $[M+H]^+$ m/z 245.245, found 246.

Preparation of N-((1S,3S)-3-(3-(trifluoromethyl)phenoxy)cyclopentyl)acrylamide (compound 44). To a mixture of (1S,3S)-3-(3-(trifluoromethyl)phenoxy)cyclopentan-1-amine (500 mg, 2.0 mmol), prop-2-enoyl chloride (284 mg, 2.8 mmol) in DCM (12 mL) was added $Et_3N$ (404 mg, 4 mmol) at 0° C., And the mixture was warmed to room temperature for 16 h. $H_2O$ (15 mL) was added and extracted with DCM (40 mL×3) and the combined organic phases were washed with brine (10 mL×3), dried over anhydrous sodium sulfate and concentrated in vacuo. The residue was purified by Flash chromatography (eluent: PE/EtOAc=8/1) to afford N-((1S,3S)-3-(3-(trifluoromethyl)phenoxy)cyclopentyl)acrylamide (341 mg, 97% purity, 55% yield) as a white solid. $[M+H]^+$ m/z 299.293, found 300. $^1H$ NMR (400 MHz, $CDCl_3$, ppm) δ 7.36 (t, J=8.0 Hz, 1H), 7.18 (d, J=7.7 Hz, 1H), 7.06 (s, 1H), 7.01 (dd, J=8.3, 2.1 Hz, 1H), 6.29 (dd, J=16.9, 1.3 Hz, 1H), 6.07 (dd, J=16.9, 10.3 Hz, 1H), 5.64 (dt, J=10.4, 5.2 Hz, 2H), 4.87 (ddd, J=8.4, 5.7, 2.4 Hz, 1H), 4.56 (dd, J=14.9, 7.4 Hz, 1H), 2.43-2.17 (m, 3H), 1.97-1.81 (m, 2H), 1.62-1.50 (m, 1H).

Example 43

Synthesis of Compound 45

(N-(3-(3-(trifluoromethyl)phenoxy)cyclopentyl)acrylamide)

Scheme 45. Synthesis of compound 45.

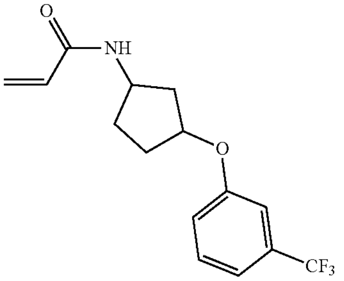

-continued

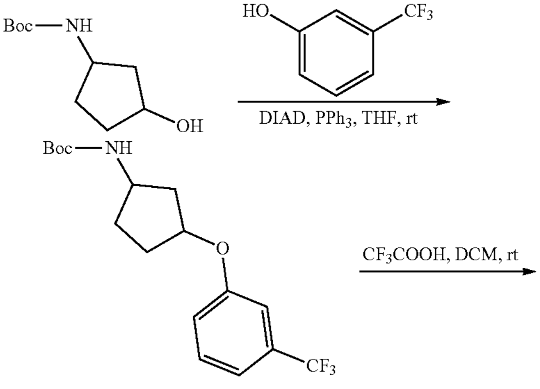

45-1

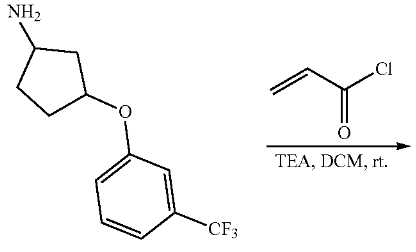

45-2

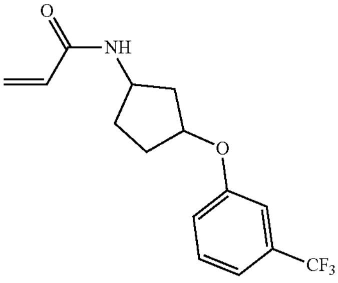

compound 45

Preparation of tert-butyl (3-(3-(trifluoromethyl)phenoxy)cyclopentyl)carbamate (45-1). To a solution of tert-butyl (3-hydroxycyclopentyl)carbamate (500 mg, 2.47 mmol), 3-(trifluoromethyl)phenol (440 mg, 2.72 mmol) and $PPh_3$ (713 mg, 2.72 mmol) in THF (30 mL) was added DIAD (550 mg, 2.72 mmol) dropwise at 0° C. The mixture was stirred at room temperature under N2 for 2 hours. The mixture was quenched with $H_2O$ (30 mL), extracted with EA (30 mL×3). The organic layers were combined, dried over $Na_2SO_4$, filtered, and concentrated in vacuo to afford crude product. The crude product was purified by flash chromatography (silica, solvent gradient: PE/EtOAc 3:1) to give tert-butyl (3-(3-(trifluoromethyl)phenoxy)cyclopentyl)carbamate (830 mg) as a yellow oil, yield: 97.1%. MS Calcd.: 345.4, MS Found: 367.7 $[M+Na]^+$.

Preparation of 3-(3-(trifluoromethyl)phenoxy)cyclopentan-1-amine (45-2). To a solution of tert-butyl (3-(3-(trifluoromethyl)phenoxy)cyclopentyl)carbamate (830 mg, 2.4 mmol) in DCM (12 mL) was added trifluoroacetic acid (1.37 g, 12 mmol). The mixture was stirred at 25° C. for 2 hours. The solution was evaporated. The crude product was purified by silica gel chromatography (DCM/MeOH, 10/1, v/v) to afford 3-(3-(trifluoromethyl)phenoxy)cyclopentan-1-amine (540 mg) as a yellow gum, yield: 91.6%. MS Calcd.: 245.2, MS Found: 245.8 $[M+H]^+$.

Preparation of N-(3-(3-(trifluoromethyl)phenoxy)cyclopentyl)acrylamide (compound 45). To a solution of 3-(3-

(trifluoromethyl)phenoxy)cyclopentan-1-amine (500 mg, 2 mmol) in DCM (10 mL) was added prop-2-enoyl chloride (221 mg, 2.4 mmol) followed by TEA (412 mg, 4 mmol). The mixture was stirred at room temperature for 3 hours. The reaction mixture diluted with water (50 mL), extracted with DCM (3x30 mL). The organic layers were washed with brine (2x30 mL), dried over anhydrous $Na_2SO_4$ and concentrated under vacuum to afford crude product, which was purified by silica gel chromatography (elution gradient: ethyl acetate/petroleum ether, 1/1, v/v) to afford N-(3-(3-(trifluoromethyl)phenoxy)cyclopentyl)acrylamide (90 mg) as a colorless gum, yield: 14.8%. $^1H$ NMR (400 MHz, DMSO-$d_6$) δ ppm 8.18-8.17 (m, 1H). 7.54-7.50 (m, 1H). 7.29-7.19 (m, 3H). 6.19-6.18 (m, 1H). 6.10-6.03 (m, 1H). 5.59-5.54 (m, 1H). 4.92-4.90 (m, 1H). 4.18-4.13 (m, 1H). 2.44-2.43 (m, 1H). 1.94-1.85 (m, 3H). 1.67-1.53 (m, 2H). MS Calcd.: 299.3, MS Found: 299.8 $[M+H]^+$.

Example 44

Synthesis of Compound 46

(N-(3-((5-(trifluoromethyl)isoxazol-3-yl)oxy)cyclopentyl)acrylamide)

Scheme 46. Synthesis of compound 46.

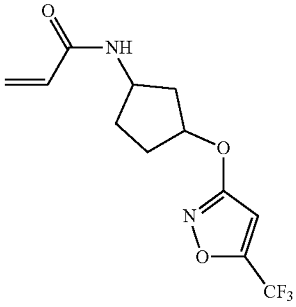

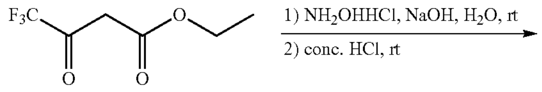

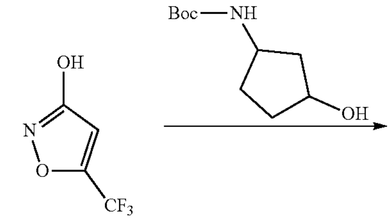

46-1

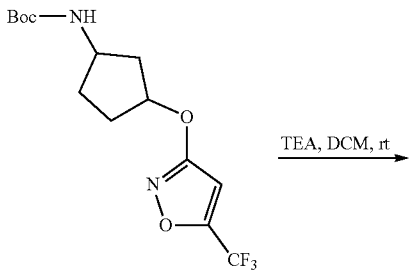

46-2

-continued

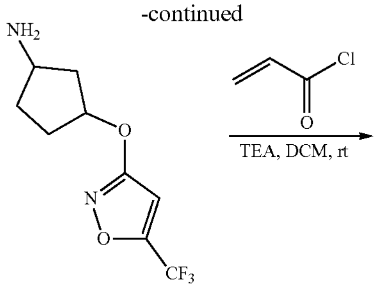

46-3

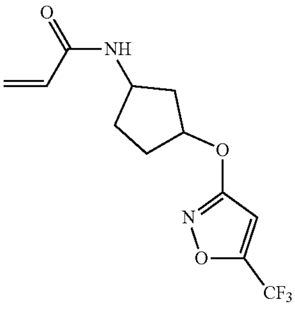

compound 46

Preparation of 5-(trifluoromethyl)isoxazol-3-ol (46-1). To a solution of sodium hydroxide (2.18 g, 54 mmol) in water (30 mL) was added hydroxylamine hydrochloride (1.89 g, 27 mmol), followed by ethyl 4,4,4-trifluoro-3-oxobutanoate (5 g, 27 mmol) at 0° C. The mixture was stirred at room temperature under N2 for 16 hours. Conc. hydrochloride (5.4 mL) was added into the reaction mixture and stirred at rt for 1 hour. The mixture was diluted with $H_2O$ (30 mL), extracted with EA (30 mLx3). The organic layers were combined, dried over $Na_2SO_4$, filtered, and concentrated in vacuo to afford crude product. The crude product was purified by flash chromatography (DCM/MeOH, 10/1, v/v) to give 5-(trifluoromethyl)isoxazol-3-ol (1.1 g) as a yellow gum, yield: 26.6%. MS Calcd.: 153.1, MS Found: 153.9 $[M+H]^+$.

Preparation of tert-butyl (3-((5-(trifluoromethyl)isoxazol-3-yl)oxy) cyclopentyl)carbamate (46-2). To a solution of 5-(trifluoromethyl)isoxazol-3-ol (600 mg, 3.9 mmol), tert-butyl (3-hydroxycyclopentyl)carbamate (872 mg, 4.3 mmol), and $PPh_3$ (1.13 g, 4.3 mmol) in THF (30 mL) was added DIAD (872 mg, 4.3 mmol) dropwise at 0° C. The mixture was stirred at room temperature under N2 for 2 hours. The mixture was quenched with $H_2O$ (30 mL), extracted with EA (30 mLx3). The organic layers were combined, dried over $Na_2SO_4$, filtered, and concentrated in vacuo to afford crude product. The crude product was purified by flash chromatography (silica, solvent gradient: PE/EtOAc 3:1) to give tert-butyl (3-((5-(trifluoromethyl) isoxazol-3-yl)oxy) cyclopentyl)carbamate (210 mg) as a yellow gum, yield: 15.9%. MS Calcd.: 336.1, MS Found: 358.8 $[M+Na]^+$.

Preparation of 3-((5-(trifluoromethyl)isoxazol-3-yl)oxy) cyclopentan-1-amine (46-3). To a solution tert-butyl (3-((5-(trifluoromethyl)isoxazol-3-yl)oxy) cyclopentyl)carbamate (190 mg, 0.56 mmol) in DCM (5 mL) was added trifluoroacetic acid (321 mg, 2.81 mmol) dropwise at 0° C. The mixture was stirred at room temperature under N2 for 2 hours. The mixture was concentrated in vacuo to afford crude product. The crude product was purified by flash chromatography (silica, DCM/MeOH, 10/1, v/v) to give 3-((5-(trifluoromethyl)isoxazol-3-yl)oxy) cyclopentan-1-amine (130 mg, TFA salt) as a yellow gum, yield: 68.2%. MS Calcd.: 236.2, MS Found: 237.2 [M+H]$^+$.

Preparation of N-(3-((5-(trifluoromethyl)isoxazol-3-yl) oxy)cyclopentyl) acrylamide (compound 46). To a solution of 3-((5-(trifluoromethyl)isoxazol-3-yl)oxy)cyclopentan-1-amine (130 mg, 0.38 mmol) in DCM (10 mL) was added prop-2-enoyl chloride (70 mg, 0.77 mmol) followed by TEA (120 mg, 1.18 mmol). The mixture was stirred at room temperature for 15 hours. The reaction mixture diluted with water (30 mL), extracted with DCM (3x30 mL). The organic layers were washed with brine (2x30 mL), dried over anhydrous $Na_2SO_4$ and concentrated under vacuum to afford crude product, which was purified by silica gel chromatography (elution gradient: ethyl acetate/petroleum ether, 1/1, v/v) to afford N-(3-((5-(trifluoromethyl) isoxazol-3-yl)oxy) cyclopentyl)acrylamide (62 mg) as a white solid, yield: 56.2%. $^1$H NMR (400 MHz, $CDCl_3$) δ ppm 6.27-6.25 (m, 1H). 6.10-6.09 (m, 1H). 6.06-5.98 (m, 1H). 5.66-5.65 (m, 1H). 5.48-5.45 (m, 1H). 5.00-4.98 (m, 1H). 4.56-4.53 (m, 1H). 2.46-2.44 (m, 1H). 2.34-2.16 (m, 2H). 2.04-1.94 (m, 2H). 1.83-1.63 (m, 1H). MS Calcd.: 290.2, MS Found: 290.8 [M+H]$^+$.

Example 45

Synthesis of Compound 47

((E)-N-(5-(ethoxyimino)-5,6,7,8-tetrahydronaphthalen-2-yl)acrylamide)

Scheme 47. Synthesis of compound 47.

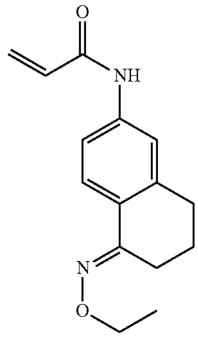

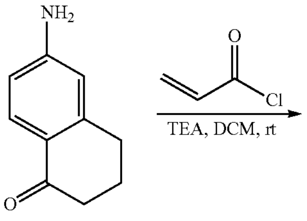

-continued

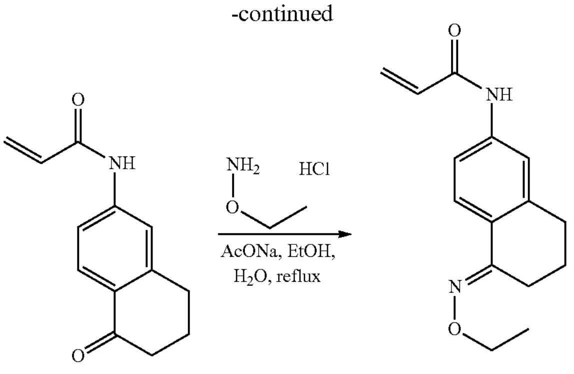

47-1 compound 47

Preparation of N-(5-oxo-5,6,7,8-tetrahydronaphthalen-2-yl)acrylamide (47-1). To a solution of 6-amino-3,4-dihydronaphthalen-1(2H)-one (2.0 g, 12.4 mmol) and triethylamine (2.51 g, 24.8 mmol) in DCM (30 mL) was added prop-2-enoyl chloride (1.68 g, 18.6 mmol) dropwise at 0° C. The reaction mixture was stirred at room temperature for 2 hours. The mixture was diluted with DCM (30 mL), washed with $NaHCO_3$ (2x30 mL), water (30 mL) and brine (30 mL). The organic layer was dried over anhydrous $Na_2SO_4$ and concentrated under vacuum to afford N-(5-oxo-5,6,7,8-tetrahydronaphthalen-2-yl)acrylamide (2.6 g) as an off-white solid, yield: 97.6%. MS Calcd.: 215.1, MS Found: 215.9 [M+H]$^+$.

Preparation of (E)-N-(5-(ethoxyimino)-5,6,7,8-tetrahydronaphthalen-2-yl)acrylamide (compound 47). To a solution of N-(5-oxo-5,6,7,8-tetrahydronaphthalen-2-yl)acrylamide (0.2 g, 0.93 mmol) and O-ethylhydroxylamine (181 mg, 1.86 mmol) in EtOH (10 mL) was added AcONa (381 mg, 4.65 mmol). The reaction mixture was stirred at 70° C. for 6 hours. The reaction mixture was cooled to room temperature, poured into water (50 mL), and acidified with 1N HCl. The mixture was extracted with EtOAc (3x30 mL). The organic layers were washed with brine (2x30 mL), dried over anhydrous Na2SO4 and concentrated under vacuum to afford crude product, which was purified by silica gel chromatography (elution gradient: ethyl acetate/petroleum ether, 2/1, v/v) to afford (E)-N-(5-(ethoxyimino)-5,6,7,8-tetrahydronaphthalen-2-yl)acrylamide (75 mg) as a white solid, yield: 31.2%. $^1$H NMR (400 MHz, CDCl3) δ ppm 7.95 (d, J=8.6 Hz, 1H), 7.60 (s, 1H), 7.33 (s, 1H), 7.22 (d, J=8.1 Hz, 1H), 6.44 (dd, J=16.8, 1.1 Hz, 1H), 6.28-6.21 (m, 1H), 5.78 (dd, J=10.2, 1.1 Hz, 1H), 4.22 (q, J=7.1 Hz, 2H), 2.73 (t, J=6.5 Hz, 4H), 1.94-1.72 (m, 2H), 1.32 (t, J=7.1 Hz, 3H). MS Calcd.: 258.1, MS Found: 258.9 [M+H]$^+$.

Example 46

Synthesis of Compound 48

((E)-N-(5-((2-ethoxyethoxy)imino)-5,6,7,8-tetrahydronaphthalen-2-yl)acrylamide)

Scheme 48. Synthesis of compound 48.

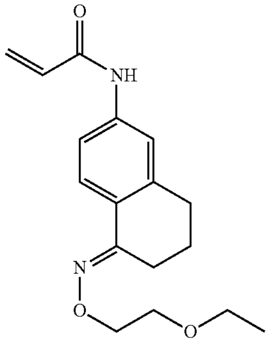

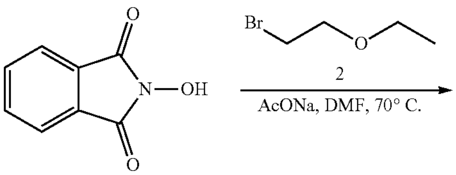

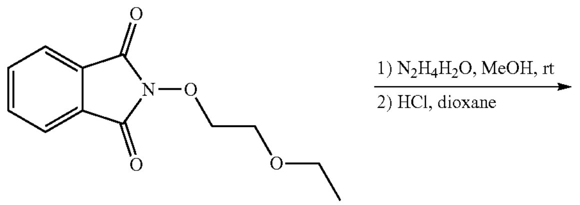

48-1

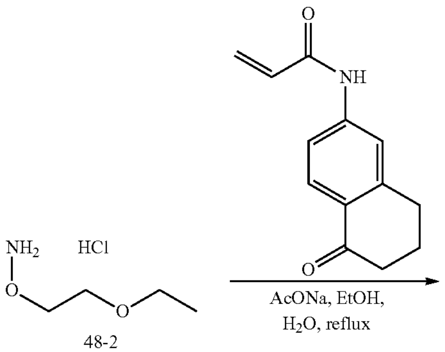

48-2

-continued

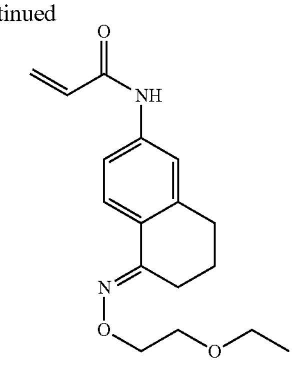

compound 48

Preparation of 2-(2-ethoxyethoxy)isoindoline-1,3-dione (48-1). To a solution of N-hydroxyphthalimide (2.0 g, 12.3 mmol) and 2-ethoxybromoethane (5.65 g, 36.9 mmol) in DMF (30 mL) was added AcONa (4.03 g, 49.2 mmol). The reaction mixture was stirred at 70° C. for 5 hours. The reaction mixture was cooled to room temperature, poured into water (100 mL), and extracted with EtOAc (3×50 mL). The organic layers were washed with brine (2×50 mL), dried over anhydrous Na2SO4 and concentrated under vacuum to afford crude product, which was purified by silica gel chromatography (elution gradient: ethyl acetate/petroleum ether, 1/3, v/v) to afford 2-(2-ethoxyethoxy)isoindoline-1,3-dione (2.6 g) as a colorless oil, yield: 90.2%. MS Calcd.: 235.1, MS Found: 235.9 $[M+H]^+$.

Preparation of O-(2-ethoxyethyl)hydroxylamine hydrochloride (48-2). To a solution of 2-(2-ethoxyethoxy)isoindoline-1,3-dione (2.6 g, 11.1 mmol) in MeOH (10 mL) was added 98% hydrazine hydrate (0.83 g, 13.3 mmol). The reaction mixture was stirred at room temperature for 1 hour. The reaction mixture was filtered to remove insoluble by-product. The filtrate was concentrated under reduced pressure at lower temperature and triturated with ether (20 mL). The insoluble was removed by filtration again. Then, to the filtrate, 4N HCl in dioxane (10 mL) was added dropwise and the precipitated salt was collected by filtration and dried under vacuum to afford O-(2-ethoxyethyl)hydroxylamine (0.9 g, HCl salt) as a white solid, yield: 57.7%. MS Calcd.: 105.1, MS Found: 106.0 $[M+H]^+$.

Example 47

Synthesis of Compound 49

((E)-N-(5-(isobutoxyimino)-5,6,7,8-tetrahydronaphthalen-2-yl)acrylamide)

Scheme 49. Synthesis of compound 49.

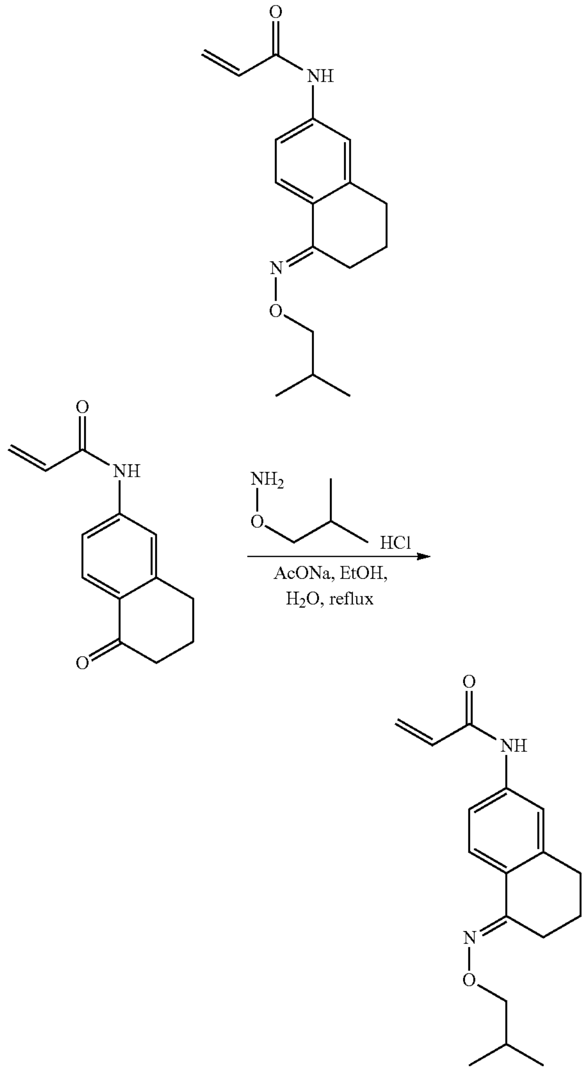

compound 49

Preparation of (E)-N-(5-(isobutoxyimino)-5,6,7,8-tetrahydronaphthalen-2-yl) acrylamide (compound 49). To a solution of N-(5-oxo-5,6,7,8-tetrahydronaphthalen-2-yl) acrylamide (0.3 g, 1.39 mmol) and O-isobutylhydroxylamine HCl (437.62 mg, 3.48 mmol) in EtOH (15 mL) was added AcONa (571.42 mg, 6.97 mmol). The reaction mixture was stirred at 70° C. for 6 hours. The reaction mixture was cooled to room temperature, poured into water (50 mL), and acidified with 1N HCl. The mixture was extracted with EtOAc (3x30 mL). The organic layers were washed with brine (2x30 mL), dried over anhydrous Na2SO4 and concentrated under vacuum to afford crude product, which was purified by silica gel chromatography (elution gradient:

ethyl acetate/petroleum ether, 1/1, v/v) to afford (E)-N-(5-(isobutoxyimino)-5,6,7,8-tetrahydronaphthalen-2-yl)acrylamide (75 mg) as a white solid, yield: 18.8%. $^1$H NMR (400 MHz, CDCl3) δ ppm 7.94 (d, J=8.6 Hz, 1H), 7.61 (s, 1H), 7.31 (s, 1H), 7.22 (d, J=8.4 Hz, 1H), 6.44 (dd, J=16.8, 1.0 Hz, 1H), 6.28-6.21 (m, 1H), 5.78 (dd, J=10.2, 1.1 Hz, 1H), 3.95 (d, J=6.8 Hz, 2H), 2.76-2.71 (m, 4H), 2.10-2.00 (m, 1H), 1.92-1.74 (m, 2H), 0.96 (d, J=6.7 Hz, 6H). Calcd.: 286.2, MS Found: 286.9 [M+H]$^+$.

Example 48

Synthesis of Compound 50

(N-(1-oxo-2-pentyl-1,2,3,4-tetrahydroisoquinolin-6-yl)acrylamide)

Scheme 50. Synthesis of compound 50.

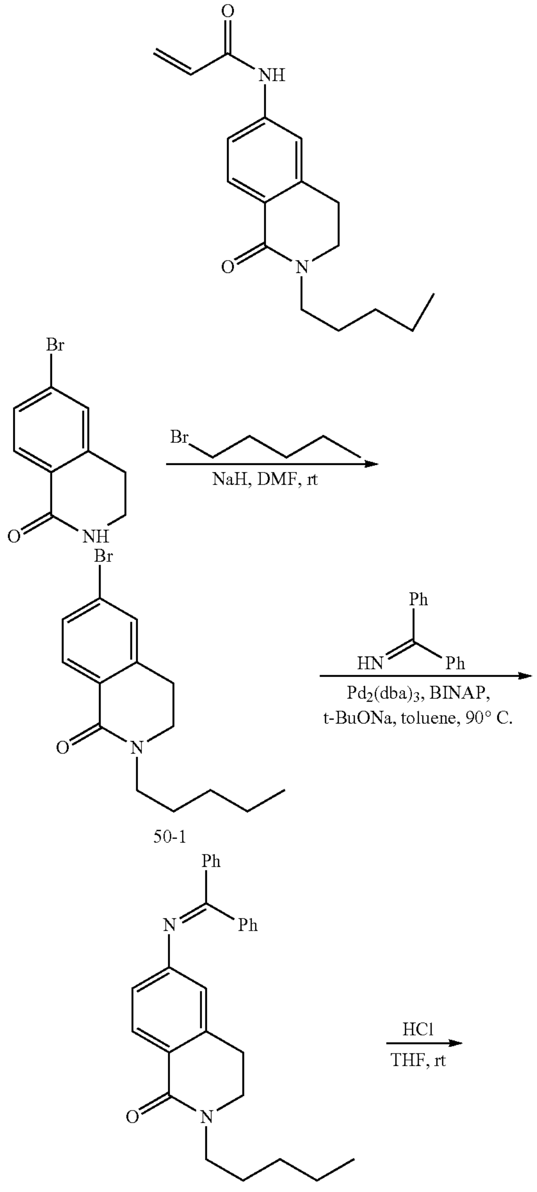

50-1

50-2

-continued

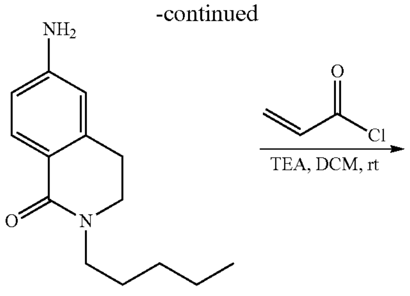

50-3

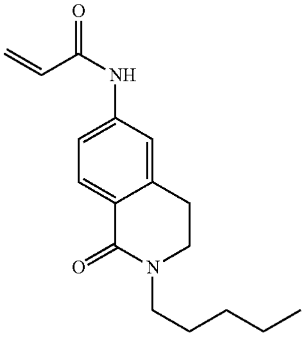

compound 50

Preparation of 6-bromo-2-pentyl-3,4-dihydroisoquinolin-1(2H)-one (50-1). To a solution of 6-bromo-3,4-dihydroisoquinolin-1(2H)-one (1 g, 4.4 mmol) in DMF (20 mL) was added NaH (60%, 506 mg, 13.2 mmol) at 0° C. The mixture was stirred at 0° C. for 1 hour. To this 1-bromopentane (0.86 g, 5.7 mmol) was added dropwise. The resulting mixture was stirred at room temperature for 3 hours. The mixture was quenched with $H_2O$ (30 mL), extracted with EA (30 mL×3). The organic layers were combined, dried over $Na_2SO_4$, filtered, and concentrated in vacuo to afford crude product. The crude product was purified by flash chromatography (silica, solvent gradient: PE/EtOAc 2:1) to give 6-bromo-2-pentyl-3,4-dihydroisoquinolin-1(2H)-one (1.2 g) as a yellow solid, yield: 90.9%. $^1H$ NMR (400 MHz, DMSO-$d_6$) δ ppm 7.77 (d, J=8.1 Hz, 1H), 7.60-7.47 (m, 2H), 3.52 (t, J=6.6 Hz, 2H), 3.44 (t, J=7.3 Hz, 2H), 2.96 (t, J=6.5 Hz, 2H), 1.64-1.44 (m, 2H), 1.36-1.21 (m, 4H), 0.87 (t, J=7.1 Hz, 3H). MS Calcd.: 295.1/297.1, MS Found: 295.7/297.8 $[M+H]^+$.

Preparation of 6-((diphenylmethylene)amino)-2-pentyl-3,4-dihydroisoquinolin-1(2H)-one (50-2). To a solution of 6-bromo-2-pentyl-3,4-dihydroisoquinolin-1(2H)-one (1.1 g, 3.7 mmol) in toluene (20 mL) was added diphenylmethanimine (0.8 g, 4.4 mmol), $Pd_2(dba)_3$ (0.34 g, 0.3 mmol) and t-BuONa (1.07 g, 11.1 mmol). The mixture was stirred at 90° C. under $N_2$ for 2 hours. The solution was evaporated and diluted with $H_2O$ (30 mL), extracted with EA (30×3). The organic layers were combined, dried over $Na_2SO_4$, filtered, and concentrated in vacuo to afford crude product. The crude product was purified by flash chromatography (silica, solvent gradient: PE/EtOAc 5:1) to give 6-((diphenylmethylene)amino)-2-pentyl-3,4-dihydroisoquinolin-1(2H)-one (800 mg) as a yellow solid, yield: 54.1%. MS Calcd.: 396.2, MS Found: 396.8 $[M+H]^+$.

Preparation of 6-amino-2-pentyl-3,4-dihydroisoquinolin-1(2H)-one (50-3). To a solution of 6-((diphenylmethylene)amino)-2-pentyl-3,4-dihydroisoquinolin-1(2H)-one (300 mg, 0.76 mmol) in THF (10 mL) was added 2N HCl (5 mL). The mixture was stirred at room temperature for 2 hours. The solution was evaporated and diluted with $H_2O$ (30 mL), extracted with EA (30×3). The organic layers were combined, dried over $Na_2SO_4$, filtered, and concentrated in vacuo to afford crude product. The crude product was purified by flash chromatography (silica, solvent gradient: PE/EtOAc 2:1) to give 6-amino-2-pentyl-3,4-dihydroisoquinolin-1(2H)-one (160 mg) as a yellow solid, yield: 91%. MS Calcd.: 232.2, MS Found: 232.9 $[M+H]^+$.

Preparation of N-(1-oxo-2-pentyl-1,2,3,4-tetrahydroisoquinolin-6-yl)acrylamide (compound 50). To a solution of 6-amino-2-pentyl-3,4-dihydroisoquinolin-1(2H)-one (160 mg, 0.69 mmol) in DCM (10 mL) was added prop-2-enoyl chloride (74 mg, 0.83 mmol) followed by TEA (209 mg, 1.01 mmol). The mixture was stirred at room temperature for 2 hours. The reaction mixture diluted with water (50 mL), extracted with DCM (3×30 mL). The organic layers were washed with brine (2×30 mL), dried over anhydrous $Na_2SO_4$ and concentrated under vacuum to afford crude product, which was purified by silica gel chromatography (elution gradient: ethyl acetate/petroleum ether, 1/1, v/v) to afford N-(1-oxo-2-pentyl-1,2,3,4-tetrahydroisoquinolin-6-yl)acrylamide (60 mg) as a yellow solid, yield: 30.2%. $^1H$ NMR (400 MHz, $CDCl_3$) δ ppm 8.23 (s, 1H), 7.95 (d, J=8.4 Hz, 1H), 7.86 (s, 1H), 7.19 (dd, J=8.4, 2.1 Hz, 1H), 6.45 (dd, J=16.9, 1.5 Hz, 1H), 6.34 (dd, J=16.9, 10.0 Hz, 1H), 5.76 (dd, J=9.9, 1.5 Hz, 1H), 3.53 (td, J=7.2, 2.0 Hz, 4H), 2.94 (t, J=6.6 Hz, 2H), 1.70-1.48 (m, 2H), 1.42-1.19 (m, 4H), 0.87 (dd, J=8.9, 4.9 Hz, 3H). Calcd.: 286.2, MS Found: 286.8 $[M+H]^+$.

Example 49

Synthesis of Compound 51

(N-(4-(4-(trifluoromethyl)pyridin-2-yl)phenyl)acrylamide)

Scheme 51. Synthesis of compound 51.

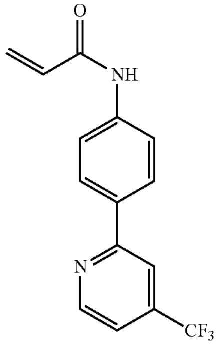

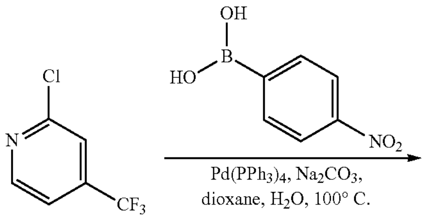

-continued

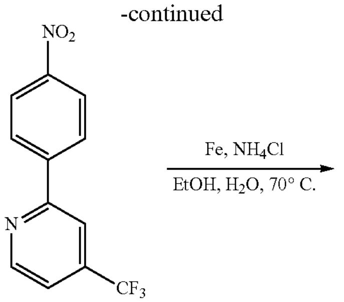

51-1

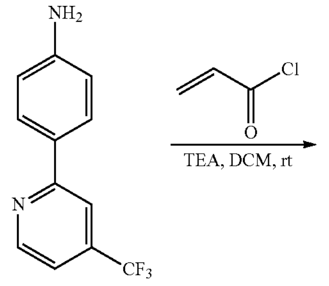

51-2

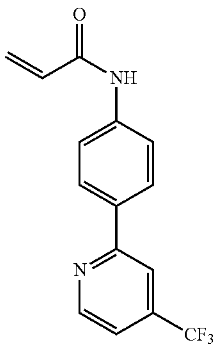

compound 51

Preparation of 2-(4-nitrophenyl)-4-(trifluoromethyl)pyridine (51-1). To a solution of 2-chloro-4-(trifluoromethyl) pyridine (500 mg, 2.75 mmol) in 1,4-dioxane/$H_2O$ (25 mL, 4:1) was added 4-nitrophenylboronic acid (552 mg, 3.30 mmol), $Pd(PPh_3)_4$ (318 mg, 0.27 mmol) and $Na_2CO_3$ (876 mg, 8.26 mmol). The mixture was stirred at 100° C. for 2 hours. The mixture was diluted with $H_2O$ (20 mL), extracted with EA (30 mL×2). The organic layers were combined, dried over $Na_2SO_4$, filtered, and concentrated in vacuo to afford crude product. The crude product was purified by flash chromatography (silica, solvent gradient: PE/EtOAc 2:1) to give 2-(4-nitrophenyl)-4-(trifluoromethyl)pyridine (600 mg) as a yellow oil, yield: 73.1%. $^1H$ NMR (400 MHz, DMSO-$d_6$) δ ppm 9.03 (d, J=5.0 Hz, 1H), 8.50 (d, J=9.1 Hz, 3H), 8.37 (d, J=9.0 Hz, 2H), 7.88 (d, J=4.5 Hz, 1H). MS Calcd.: 268.1, MS Found: 268.8 $[M+H]^+$.

Preparation of 4-(4-(trifluoromethyl)pyridin-2-yl)aniline (51-2). To a solution of 2-(4-nitrophenyl)-4-(trifluoromethyl)pyridine (300 mg, 1.12 mmol) in EtOH (9 mL) and $H_2O$ (3 mL) was added iron powder (312 mg, 5.59 mmol) and ammonium chloride (299 mg, 5.59 mmol). The mixture was stirred at 70° C. for 2 hours. The solution was evaporated and diluted with $H_2O$ (10 mL), extracted with EA (30×3). The organic layers were combined, dried over $Na_2SO_4$, filtered, and concentrated in vacuo to afford crude product. The crude product was purified by flash chromatography (silica, solvent gradient: PE/EtOAc 2:1) to give 4-(4-(trifluoromethyl)pyridin-2-yl)aniline (240 mg) as a yellow solid, yield: 92.8%. $^1H$ NMR (400 MHz, DMSO-$d_6$) δ ppm 8.77 (d, J=5.0 Hz, 1H), 8.03 (s, 1H), 7.92 (d, J=8.7 Hz, 2H), 7.48 (d, J=4.4 Hz, 1H), 6.65 (d, J=8.7 Hz, 2H), 5.62 (s, 2H). MS Calcd.: 238.1, MS Found: 238.9 $[M+H]^+$.

Preparation of N-(4-(4-(trifluoromethyl)pyridin-2-yl)phenyl)acrylamide (compound 51). To a solution of 4-(4-(trifluoromethyl)pyridin-2-yl)aniline (240 mg, 1.00 mmol) in DCM (10 mL) was added prop-2-enoyl chloride (109 mg, 1.21 mmol) followed by TEA (366 mg, 3.63 mmol). The mixture was stirred at room temperature for 2 hours. The reaction mixture diluted with water (50 mL), extracted with DCM (3×30 mL). The organic layers were washed with brine (2×30 mL), dried over anhydrous $Na_2SO_4$ and concentrated under vacuum to afford crude product, which was purified by silica gel chromatography (elution gradient: ethyl acetate/petroleum ether, 1/1, v/v) to afford N-(4-(4-(trifluoromethyl)pyridin-2-yl)phenyl)acrylamide (55 mg) as a yellow solid, yield: 18.8%. $^1H$ NMR (400 MHz, $CDCl_3$) δ ppm 8.84 (d, J=5.0 Hz, 1H), 8.04 (d, J=8.7 Hz, 2H), 7.91 (s, 1H), 7.76 (d, J=8.4 Hz, 2H), 7.50 (s, 1H), 7.43 (d, J=4.5 Hz, 1H), 6.48 (dd, J=16.8, 1.1 Hz, 1H), 6.29 (dd, J=16.8, 10.2 Hz, 1H), 5.82 (dd, J=10.2, 1.1 Hz, 1H). MS Calcd.: 292.1, MS Found: 293.1 $[M+H]^+$.

Example 50

Synthesis of Compound 52

(N-(4-(5-(trifluoromethyl)pyridin-3-yl)phenyl)acrylamide)

Scheme 52. Synthesis of compound 52.

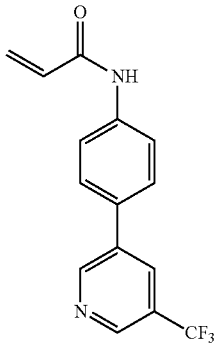

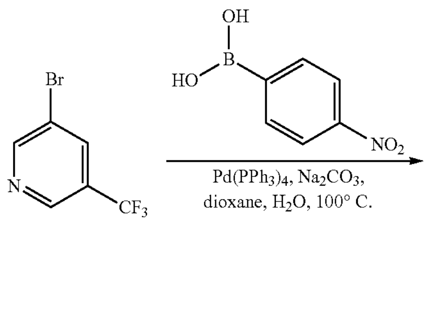

-continued

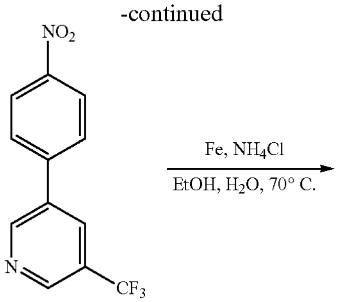

52-1

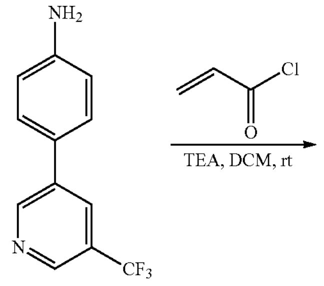

52-2

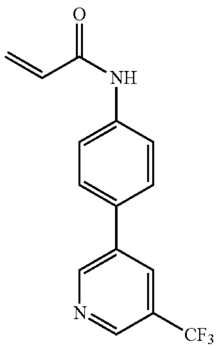

compound 52

Preparation of 3-(4-nitrophenyl)-5-(trifluoromethyl)pyridine (52-1). To a solution of 3-bromo-5-(trifluoromethyl)pyridine (500 mg, 2.21 mmol) in 1,4-dioxane/$H_2O$ (25 mL, 4:1) was added 4-nitrophenylboronic acid (443 mg, 2.65 mmol), $Pd(PPh_3)_4$ (256 mg, 0.22 mmol) and $Na_2CO_3$ (703 mg, 6.64 mmol). The mixture was stirred at 100° C. for 2 hours. The mixture was diluted with $H_2O$ (20 mL), extracted with EA (30 mL×2). The organic layers were combined, dried over $Na_2SO_4$, filtered, and concentrated in vacuo to afford crude product. The crude product was purified by flash chromatography (silica, solvent gradient: PE/EtOAc 2:1) to give 3-(4-nitrophenyl)-5-(trifluoromethyl)pyridine (400 mg) as a yellow solid, yield: 67.4%. MS Calcd.: 268.1, MS Found: 268.7 $[M+H]^+$.

Preparation of 4-(5-(trifluoromethyl)pyridin-3-yl)aniline (52-2). To a solution of 3-(4-nitrophenyl)-5-(trifluoromethyl)pyridine (400 mg, 1.49 mmol) in EtOH (9 mL) and $H_2O$ (3 mL) was added iron powder (416.5 mg, 7.46 mmol) and ammonium chloride (399 mg, 7.46 mmol). The mixture was stirred at 70° C. for 2 hours. The solution was evaporated and diluted with $H_2O$ (10 mL), extracted with EA (30×3). The organic layers were combined, dried over $Na_2SO_4$, filtered, and concentrated in vacuo to afford crude product. The crude product was purified by flash chromatography (silica, solvent gradient: PE/EtOAc 2:1) to give 4-(5-(trifluoromethyl)pyridin-3-yl)aniline (260 mg) as a yellow solid, yield: 73.15%. $^1$H NMR (400 MHz, DMSO-$d_6$) δ ppm 9.09 (d, J=1.8 Hz, 1H), 8.78 (d, J=0.9 Hz, 1H), 8.26 (s, 1H), 7.56 (d, J=8.6 Hz, 2H), 6.68 (d, J=8.6 Hz, 2H), 5.50 (s, 2H). MS Calcd.: 238.1, MS Found: 238.8 $[M+H]^+$.

Preparation of N-(4-(5-(trifluoromethyl)pyridin-3-yl)phenyl)acrylamide (compound 52). To a solution of 4-(5-(trifluoromethyl)pyridin-3-yl)aniline (260 mg, 1.21 mmol) in DCM (10 mL) was added prop-2-enoyl chloride (118.6 mg, 1.31 mmol) followed by TEA (331 mg, 3.27 mmol). The mixture was stirred at room temperature for 2 hours. The reaction mixture diluted with water (50 mL), extracted with DCM (3×30 mL). The organic layers were washed with brine (2×30 mL), dried over anhydrous $Na_2SO_4$ and concentrated under vacuum to afford crude product, which was purified by silica gel chromatography (elution gradient: ethyl acetate/petroleum ether, 1/1, v/v) to afford N-(4-(5-(trifluoromethyl)pyridin-3-yl)phenyl)acrylamide (60 mg) as a yellow solid, yield: 18.7%. $^1$H NMR (400 MHz, $CDCl_3$) δ ppm 9.01 (d, J=1.7 Hz, 1H), 8.85 (s, 1H), 8.09 (s, 1H), 7.77 (d, J=8.4 Hz, 2H), 7.60 (d, J=8.6 Hz, 2H), 7.50 (s, 1H), 6.49 (dd, J=16.8, 1.0 Hz, 1H), 6.29 (dd, J=16.8, 10.2 Hz, 1H), 5.83 (dd, J=10.2, 1.0 Hz, 1H). MS Calcd.: 292.1, MS Found: 293.1 $[M+H]^+$.

Example 51

Synthesis of Compound 53

(N-(4-(5-(trifluoromethyl)pyridazin-3-yl)phenyl)acrylamide)

Scheme 53. Synthesis of compound 53.

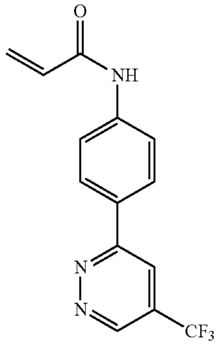

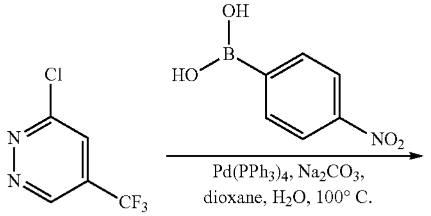

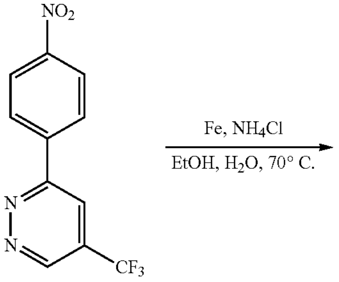

53-1

-continued

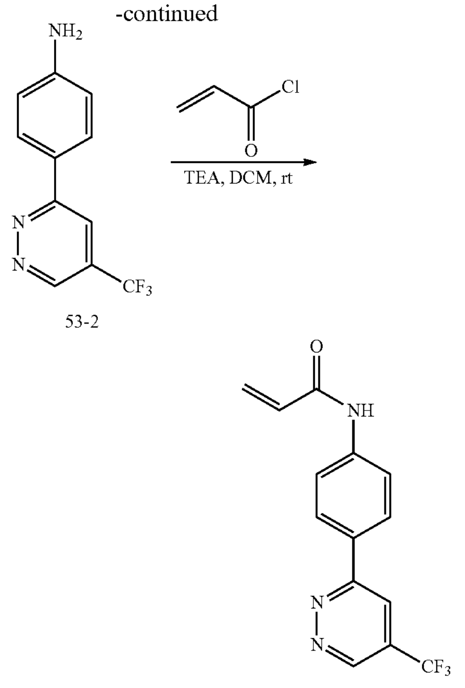

53-2 compound 53

Preparation of 3-(4-nitrophenyl)-5-(trifluoromethyl) pyridazine (53-1). To a solution of 3-chloro-5-(trifluoromethyl)pyridazine (500 mg, 2.74 mmol) in 1,4-dioxane/$H_2O$ (25 mL, 4:1) was added 4-nitrophenylboronic acid (549 mg, 3.29 mmol), $Pd(PPh_3)_4$ (317 mg, 0.27 mmol) and $Na_2CO_3$ (871 mg, 8.22 mmol). The mixture was stirred at 100° C. for 2 hours. The mixture was diluted with $H_2O$ (20 mL), extracted with EA (30 mL×2). The organic layers were combined, dried over $Na_2SO_4$, filtered, and concentrated in vacuo to afford crude product. The crude product was purified by flash chromatography (silica, solvent gradient: PE/EtOAc 2:1) to give compound 3 (450 mg) as a yellow oil, yield: 60.9%. $^1H$ NMR (400 MHz, DMSO-$d_6$) δ ppm 9.79-9.73 (m, 1H), 8.83 (dd, J=2.0, 0.9 Hz, 1H), 8.61-8.50 (m, 2H), 8.44-8.37 (m, 2H), 8.37-8.29 (m, 1H), 8.11-7.98 (m, 1H). MS Calcd.: 269.1, MS Found: 269.8 $[M+H]^+$.

Preparation of 4-(5-(trifluoromethyl)pyridazin-3-yl)aniline (53-2). To a solution of 3-(4-nitrophenyl)-5-(trifluoromethyl)pyridazine (450 mg, 2.46 mmol) in EtOH (12 mL) and $H_2O$ (4 mL) was added iron powder (688 mg, 12.3 mmol) and ammonium chloride (659 mg, 12.3 mmol). The mixture was stirred at 70° C. for 2 hours. The solution was evaporated and diluted with $H_2O$ (10 mL), extracted with EA (30×3). The organic layers were combined, dried over $Na_2SO_4$, filtered, and concentrated in vacuo to afford crude product. The crude product was purified by flash chromatography (silica, solvent gradient: PE/EtOAc 2:1) to give 4-(5-(trifluoromethyl)pyridazin-3-yl)aniline (290 mg) as a yellow solid, yield: 43.7%. $^1H$ NMR (400 MHz, DMSO-$d_6$) δ ppm 9.42 (d, J=1.4 Hz, 1H), 8.40 (d, J=0.9 Hz, 1H), 8.03 (d, J=8.7 Hz, 2H), 6.71 (d, J=8.7 Hz, 2H), 5.81 (s, 2H). MS Calcd.: 239.1, MS Found: 240.1 $[M+H]^+$.

Preparation of N-(4-(5-(trifluoromethyl)pyridazin-3-yl) phenyl)acrylamide (compound 53). To a solution of 4-(5-(trifluoromethyl)pyridazin-3-yl)aniline (290 mg, 1.21 mmol) in DCM (10 mL) was added prop-2-enoyl chloride (109 mg, 1.21 mmol) followed by TEA (366 mg, 3.63 mmol). The mixture was stirred at room temperature for 2 hours. The reaction mixture diluted with water (50 mL), extracted with DCM (3×30 mL). The organic layers were washed with brine (2×30 mL), dried over anhydrous $Na_2SO_4$ and concentrated under vacuum to afford crude product, which was purified by silica gel chromatography (elution gradient: ethyl acetate/petroleum ether, 1/1, v/v) to afford N-(4-(5-(trifluoromethyl)pyridazin-3-yl)phenyl)acrylamide (60 mg) as a yellow solid, yield: 16.9%. $^1H$ NMR (400 MHz, $CDCl_3$) δ ppm 9.36 (s, 1H), 8.14 (d, J=8.7 Hz, 2H), 8.03 (s, 1H), 7.84 (d, J=8.6 Hz, 2H), 7.68 (s, 1H), 6.50 (dd, J=16.8, 0.9 Hz, 1H), 6.32 (dd, J=16.8, 10.2 Hz, 1H), 5.91-5.73 (m, 1H). MS Calcd.: 293.1, MS Found: 293.8 $[M+H]^+$.

Example 52

Synthesis of Compound 54

(N-(4-(5-(trifluoromethyl)isothiazol-3-yl)phenyl) acrylamide)

Scheme 54. Synthesis of compound 54.

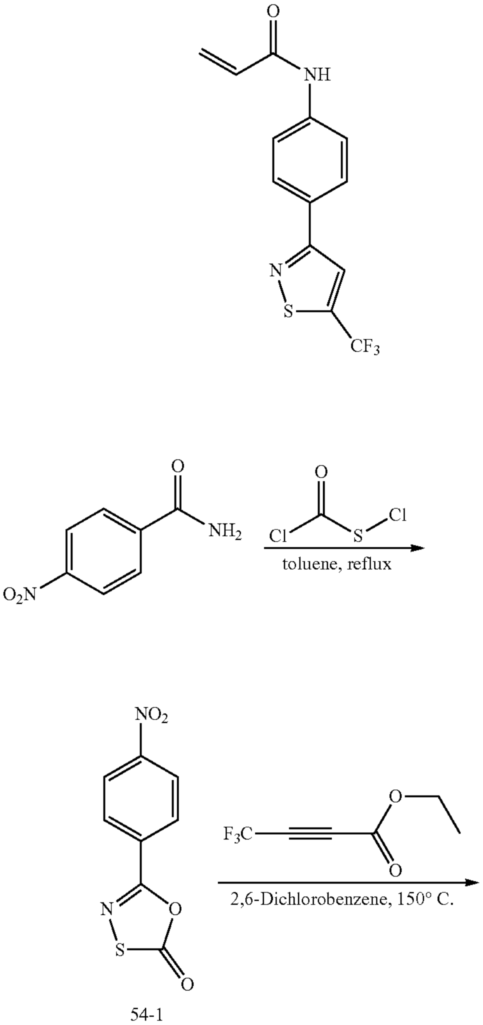

54-1

-continued

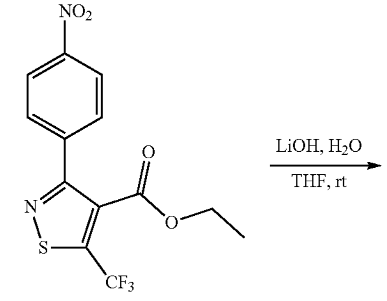

54-2

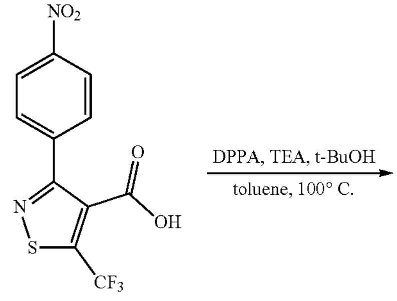

54-3

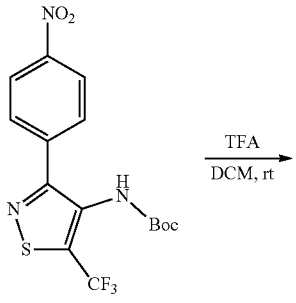

54-4

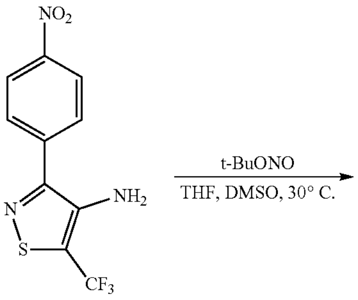

54-5

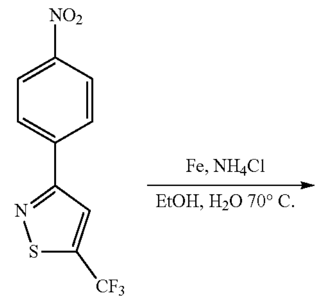

54-6

-continued

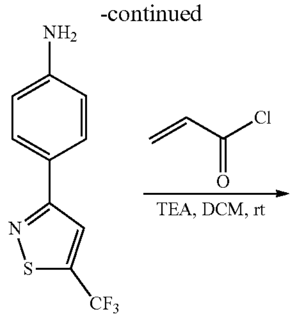

54-7

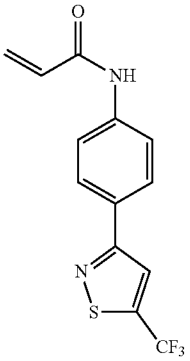

compound 54

Preparation of 5-(4-nitrophenyl)-1,3,4-oxathiazol-2-one (54-1). To a solution of 4-nitrobenzamide (6.5 g, 39.16 mmol) in toluene (100 mL) was added chloro(chlorosulfanyl)methanone (10.2 g, 78.31 mmol). The mixture was stirred overnight at 100° C. under N2 for 16 hours. The resulting mixture was concentrated in vacuo. The resulting residue was purified by column chromatography on silica gel (EtOAc/PE=1:20) to give 5-(4-nitrophenyl)-1,3,4-oxathiazol-2-one (2.8 g) as a yellow solid, yield: 31.9%. MS Calcd.: 224.0, MS Found: 224.9 $[M+H]^+$.

Preparation of ethyl 3-(4-nitrophenyl)-5-(trifluoromethyl)isothiazole-4-carboxylate (54-2). Into a 100 mL sealed tube was placed 5-(4-nitrophenyl)-1,3,4-oxathiazol-2-one (2.8 g, 12.5 mmol), ethyl 4,4,4-trifluorobut-2-ynoate (3.1 g, 18.75 mmol) and 2,6-dichlorobenzene (30 mL). The resulting solution was stirred for 18 h at 150° C. The resulting mixture was concentrated in vacuo. The resulting residue was purified by silica gel column chromatography (EtOAc/PE=1:50) to give ethyl 3-(4-nitrophenyl)-5-(trifluoromethyl)isothiazole-4-carboxylate (1.5 g) as a yellow oil, yield: 34.4%. MS Calcd.: 346.0, MS Found: 346.7 $[M+H]^+$.

Preparation of 3-(4-nitrophenyl)-5-(trifluoromethyl)isothiazole-4-carboxylic acid (54-3). To a solution of ethyl 3-(4-nitrophenyl)-5-(trifluoromethyl)isothiazole-4-carboxylate (1.5 g, 4.3 mmol) in THF (10 mL) and water (5 mL) was added LiOH hydrate (0.889 g, 21.7 mmol). Then the mixture was stirred at rt for 18 h. After acidification with IN HCl to pH=2, the solvent was removed in vacuo. The residue was purified by silica gel column chromatography (EtOAc/PE=10:1 to 1:1) to give 3-(4-nitrophenyl)-5-(trifluoromethyl)isothiazole-4-carboxylic acid (1.1 g) as a yellow solid, yield: 79.9%. MS Calcd.: 318.0, MS Found: 318.7 $[M+H]^+$.

Preparation of tert-butyl (3-(4-nitrophenyl)-5-(trifluoromethyl)isothiazol-4-yl)carbamate (54-4). To a solution of 3-(4-nitrophenyl)-5-(trifluoromethyl)isothiazole-4-carboxylic acid (1.1 g, 3.46 mmol) in toluene (10 mL) and t-BuOH (10 mL) was added DPPA (1.9 g, 6.92 mmol) and TEA (1.05 g, 10.38 mmol). The mixture was stirred at 100° C. for 16 hours. The solution was evaporated and diluted with $H_2O$ (30 mL), extracted with EA (30 mL×3). The organic layers were combined, dried over $Na_2SO_4$, filtered, and concentrated in vacuo to afford crude product. The crude product was purified by flash chromatography (silica, solvent gradient: PE/EtOAc 50:1) to give tert-butyl (3-(4-nitrophenyl)-5-(trifluoromethyl)isothiazol-4-yl)carbamate (750 mg) as a yellow gum, yield: 55.8%. MS Calcd.: 389.1, MS Found: 389.7 $[M+H]^+$.

Preparation of 3-(4-nitrophenyl)-5-(trifluoromethyl)isothiazol-4-amine (54-5). To a solution of tert-butyl (3-(4-nitrophenyl)-5-(trifluoromethyl)isothiazol-4-yl)carbamate (750 mg, 1.93 mmol) in DCM (10 mL) was added TFA (2 mL). The mixture was stirred at room temperature for 2 hours. The solution was evaporated and diluted with saturated $NaHCO_3$ aqueous solution (20 mL), extracted with EA (30 mL×3). The organic layers were combined, dried over $Na_2SO_4$, filtered, and concentrated in vacuo to afford crude product. The crude product was purified by flash chromatography (silica, solvent gradient: PE/EtOAc 5:1) to give 3-(4-nitrophenyl)-5-(trifluoromethyl)isothiazol-4-amine (600 mg, crude) as an off-white solid. MS Calcd.: 289.1, MS Found: 289.7 $[M+H]^+$.

Preparation of 3-(4-nitrophenyl)-5-(trifluoromethyl)isothiazole (54-6). To a solution of 3-(4-nitrophenyl)-5-(trifluoromethyl)isothiazol-4-amine (600 mg, crude) in THF (10 mL) and DMSO (2 mL) was added t-BuONO (428 mg, 4.15 mmol). The mixture was stirred at 30° C. for 16 hours. The solution was diluted with $H_2O$ (30 mL), extracted with EA (30 mL×3). The organic layers were combined, dried over $Na_2SO_4$, filtered, and concentrated in vacuo to afford crude product. The crude product was purified by flash chromatography (silica, solvent gradient: PE/EtOAc 10:1) to give 3-(4-nitrophenyl)-5-(trifluoromethyl)isothiazole (330 mg) as a yellow solid, overall yield of two steps: 62.2%. MS Calcd.: 274.0, MS Found: 274.7 $[M+H]^+$.

Preparation of 4-(5-(trifluoromethyl)isothiazol-3-yl)aniline (54-7). To a solution of 3-(4-nitrophenyl)-5-(trifluoromethyl)isothiazole (330 mg, 1.20 mmol) in EtOH (12 mL) and $H_2O$ (4 mL) was added iron powder (337 mg, 6.02 mmol) and ammonium chloride (325 mg, 6.02 mmol). The mixture was stirred at 70° C. for 2 hours. The solution was evaporated and diluted with $H_2O$ (10 mL), extracted with EA (30 mL×3). The organic layers were combined, dried over $Na_2SO_4$, filtered, and concentrated in vacuo to afford crude product. The crude product was purified by flash chromatography (silica, solvent gradient: PE/EtOAc 1:1) to give 4-(5-(trifluoromethyl)isothiazol-3-yl)aniline (220 mg) as an off-white solid, yield: 75.0%. MS Calcd.: 244.0, MS Found: 244.8 $[M+H]^+$.

Preparation of N-(4-(5-(trifluoromethyl)isothiazol-3-yl)phenyl)acrylamide (compound 54). To a solution of 4-(5-(trifluoromethyl)isothiazol-3-yl)aniline (220 mg, 0.9 mmol) in DCM (10 mL) was added prop-2-enoyl chloride (97 mg, 1.08 mmol) followed by TEA (273 mg, 2.7 mmol). The mixture was stirred at room temperature for 2 hours. The reaction mixture diluted with water (30 mL), extracted with DCM (3×30 mL). The organic layers were washed with brine (2×30 mL), dried over anhydrous $Na_2SO_4$ and concentrated under vacuum to afford crude product, which was purified by silica gel chromatography (elution gradient: ethyl acetate/petroleum ether, 1/1, v/v) to afford N-(4-(5-(trifluoromethyl)isothiazol-3-yl)phenyl)acrylamide (75 mg) as an off-white solid, yield: 27.8%. $^1H$ NMR (400 MHz, $CDCl_3$) δ ppm 8.00-7.87 (m, 2H), 7.84 (d, J=0.9 Hz, 1H), 7.71 (d, J=8.5 Hz, 2H), 7.42 (s, 1H), 6.47 (dd, J=16.8, 1.2 Hz, 1H), 6.26 (dd, J=16.8, 10.2 Hz, 1H), 5.81 (dd, J=10.2, 1.1 Hz, 1H). MS Calcd.: 298.0, MS Found: 298.7 $[M+H]^+$.

Example 53

Synthesis of Compound 55

(N-(4-(1-(2,2,2-trifluoroethyl)-1H-pyrazol-3-yl)phenyl)acrylamide)

Scheme 55. Synthesis of compound 55.

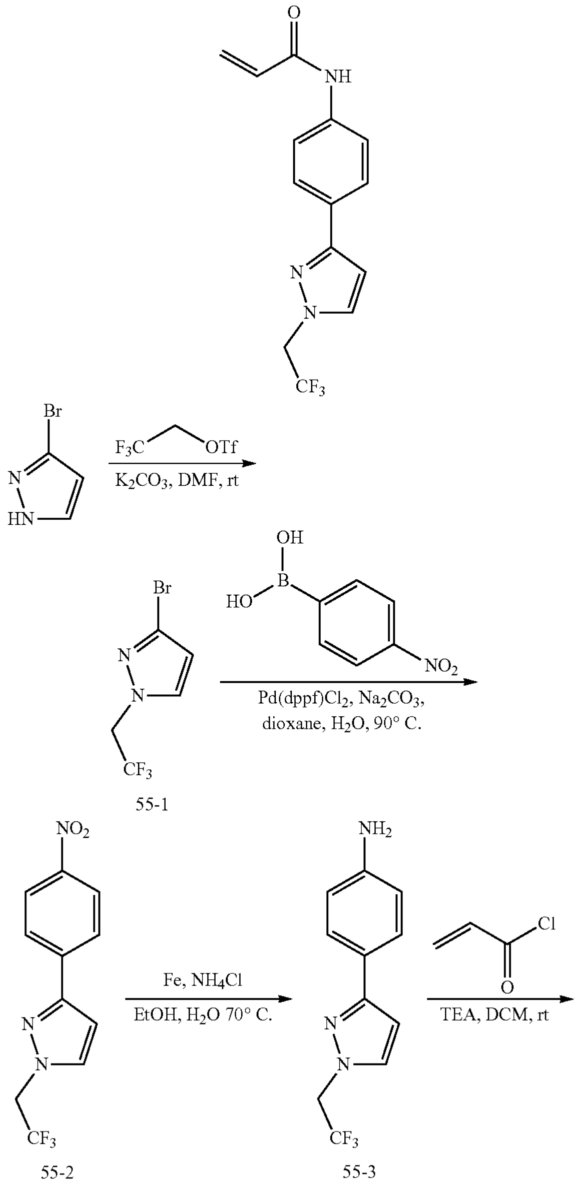

-continued

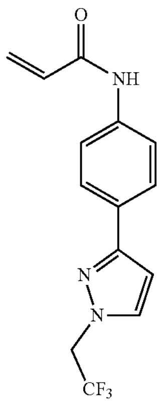

compound 55

Preparation of 3-bromo-1-(2,2,2-trifluoroethyl)-1H-pyrazole (55-1). To a solution of 3-bromopyrazole (2 g, 13.7 mmol) and $K_2CO_3$ (3.8 g, 27.4 mmol) in DMF (30 mL) was added 2,2,2-trifluoroethyl trifluoromethanesulfonate (4.77 g, 20.55 mmol). The mixture was stirred at room temperature under N2 for 16 hours. The mixture was diluted with $H_2O$ (50 mL), extracted with EA (50 mL×3). The organic layers were combined, dried over $Na_2SO_4$, filtered, and concentrated in vacuo to afford crude product. The crude product was purified by flash chromatography (silica, solvent gradient: PE/EtOAc 1:1) to give 3-bromo-1-(2,2,2-trifluoroethyl)-1H-pyrazole (1.5 g) as a yellow oil, yield: 48.2%. MS Calcd.: 228.0/229.0, MS Found: 250.7/251.7 $[M+Na]^+$.

Preparation of 3-(4-nitrophenyl)-1-(2,2,2-trifluoroethyl)-1H-pyrazole (55-2). To a solution of 3-bromo-1-(2,2,2-trifluoroethyl)-1H-pyrazole (500 mg, 2.19 mmol) in 1,4-dioxane/$H_2O$ (25 mL, 4:1) was added 4-nitrophenylboronic acid (440 mg, 2.63 mmol), Pd(dppf)$Cl_2$—$CH_2Cl_2$ (180 mg, 0.22 mmol) and $Na_2CO_3$ (703 mg, 6.64 mmol). The mixture was stirred at 90° C. under $N_2$ for 2 hours. The mixture was diluted with $H_2O$ (30 mL), extracted with EA (30 mL×2). The organic layers were combined, dried over $Na_2SO_4$, filtered, and concentrated in vacuo to afford crude product. The crude product was purified by flash chromatography (silica, solvent gradient: PE/EtOAc 2:1) to give 3-(4-nitrophenyl)-1-(2,2,2-trifluoroethyl)-1H-pyrazole (350 mg) as a yellow solid, yield: 58.9%. MS Calcd.: 270.8, MS Found: 271.8 $[M+H]^+$.

Preparation of 4-(1-(2,2,2-trifluoroethyl)-1H-pyrazol-3-yl)aniline (55-3). To a solution of 3-(4-nitrophenyl)-1-(2,2,2-trifluoroethyl)-1H-pyrazole (350 mg, 1.29 mmol) in EtOH (12 mL) and $H_2O$ (4 mL) was added iron powder (362 mg, 6.46 mmol) and ammonium chloride (349 mg, 6.46 mmol). The mixture was stirred at 70° C. for 2 hours. The solution was evaporated and diluted with $H_2O$ (10 mL), extracted with EA (30×3). The organic layers were combined, dried over $Na_2SO_4$, filtered, and concentrated in vacuo to afford crude product. The crude product was purified by flash chromatography (silica, solvent gradient: PE/EtOAc 1:1) to give 4-(1-(2,2,2-trifluoroethyl)-1H-pyrazol-3-yl)aniline (200 mg) as an off-white solid, yield: 64.3%. MS Calcd.: 241.1, MS Found: 241.9 $[M+H]^+$.

Preparation of N-(4-(1-(2,2,2-trifluoroethyl)-1H-pyrazol-3-yl)phenyl)acrylamide (compound 55). To a solution of 4-(1-(2,2,2-trifluoroethyl)-1H-pyrazol-3-yl)aniline (200 mg, 0.83 mmol) in DCM (10 mL) was added prop-2-enoyl chloride (100 mg, 1.00 mmol) followed by TEA (251 mg, 2.49 mmol). The mixture was stirred at room temperature for 2 hours. The reaction mixture diluted with water (30 mL), extracted with DCM (3×30 mL). The organic layers were washed with brine (2×30 mL), dried over anhydrous $Na_2SO_4$ and concentrated under vacuum to afford crude product, which was purified by silica gel chromatography (elution gradient: ethyl acetate/petroleum ether, 1/1, v/v) to afford N-(4-(1-(2,2,2-trifluoroethyl)-1H-pyrazol-3-yl)phenyl)acrylamide (68 mg) as an off-white solid, yield: 27.7%. $^1H$ NMR (400 MHz, $CDCl_3$) δ ppm 7.82-7.71 (m, 2H), 7.64 (d, J=8.3 Hz, 2H), 7.52-7.47 (m, 2H), 6.62 (d, J=2.5 Hz, 1H), 6.44 (dd, J=16.8, 1.2 Hz, 1H), 6.25 (dd, J=16.8, 10.2 Hz, 1H), 5.76 (dd, J=10.2, 1.3 Hz, 1H), 4.73 (q, J=8.4 Hz, 2H). MS Calcd.: 295.1, MS Found: 295.8 $[M+H]^+$.

Example 54

Synthesis of Compound 56

(1-(3-(4-(trifluoromethyl)phenoxy)azetidin-1-yl) prop-2-en-1-one)

Scheme 56. Synthesis of compound 56.

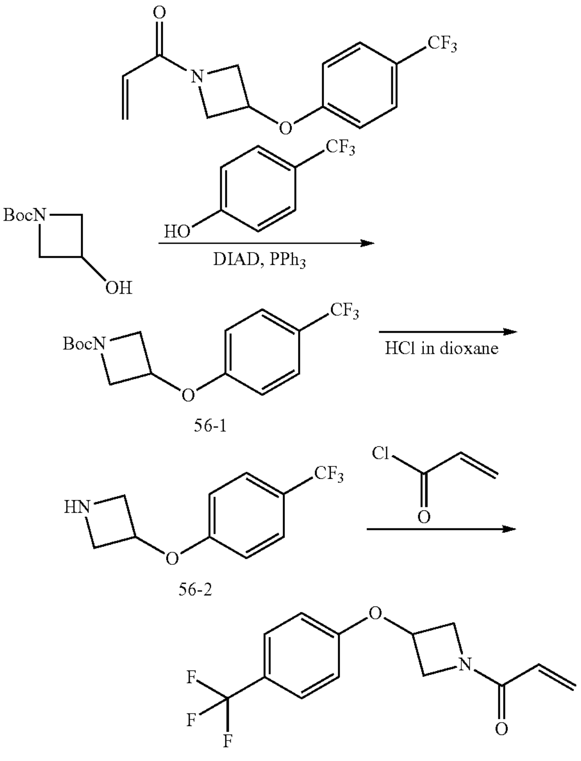

56-1

56-2 compound 56

Preparation of tert-butyl 3-(4-(trifluoromethyl)phenoxy) azetidine-1-carboxylate (56-1). The mixture of tert-butyl 3-hydroxyazetidine-1-carboxylate (500 mg, 2.89 mmol), 4-(trifluoromethyl)phenol (471 mg, 2.89 mmol), DIAD (876 mg, 4.33 mmol) and triphenylphosphine (1136 mg, 4.33 mmol) were stirred in THF (10 mL) at 70° C. under $N_2$ for 3 h. LCMS showed the reaction was completed. The reaction solution was concentrated to afford the crude product. The residue was purified by Flash Chromatography (PE/EtOAc=1:1) to give the product tert-butyl 3-(4-(trifluoromethyl)phenoxy)azetidine-1-carboxylate (450 mg, 1.4 mmol, 49.0%) as yellow solid. Mass Spectrum (ESI) m/z=262 (M+1).

Preparation of 3-(4-(trifluoromethyl)phenoxy)azetidine (56-2). The mixture of tert-butyl 3-(4-(trifluoromethyl)phenoxy)azetidine-1-carboxylate (450 mg, 1.4 mmol) and HCl in dioxane (3 mL) were stirred in DCM (5 mL) at 25° C. overnight. LCMS showed the reaction was completed. The reaction solution was concentrated to afford the crude 3-(4-(trifluoromethyl)phenoxy)azetidine. Which was used for next step without purification. Mass Spectrum (ESI) m/z=218 (M+1).

Preparation of 1-(3-(4-(trifluoromethyl)phenoxy)azetidin-1-yl)prop-2-en-1-one (compound 56). To a solution of 3-(4-(trifluoromethyl)phenoxy)azetidine (350 mg, 1.60 mmol) and $NaHCO_3$ (337 mg, 4.01 mmol) in THF/$H_2O$=5:1 (5 mL) was added prop-2-enoyl chloride (174 mg, 1.92 mmol) at 0° C. The mixture was stirred at rt overnight. LCMS showed the reaction was completed. The mixture was evaporated to afford the crude product. The residue was purified by Flash Chromatography (PE/EtOAc=3:1) to give 1-(3-(4-(trifluoromethyl)phenoxy)azetidin-1-yl)prop-2-en-1-one (220 mg, 0.811 mmol, 50.6% yield) as a white solid. (ESI) m/z=272 (M+1), $^1$H NMR (400 MHz, MeOD) δ 7.52 (d, J=8.6 Hz, 2H), 6.90 (d, J=8.6 Hz, 1H), 6.31-6.13 (m, 1H), 5.69-5.63 (m, 1H), 5.10-5.01 (m, 1H), 4.68-4.61 (m, 1H), 4.46-4.36 (m, 1H), 4.23-4.16 (m, 1H), 3.99-3.90 (m, 1H).

Example 55

Synthesis of Compound 57

(1-(3-((3-(trifluoromethyl)benzyl)oxy)azetidin-1-yl) prop-2-en-1-one)

Scheme 57. Synthesis of compound 57.

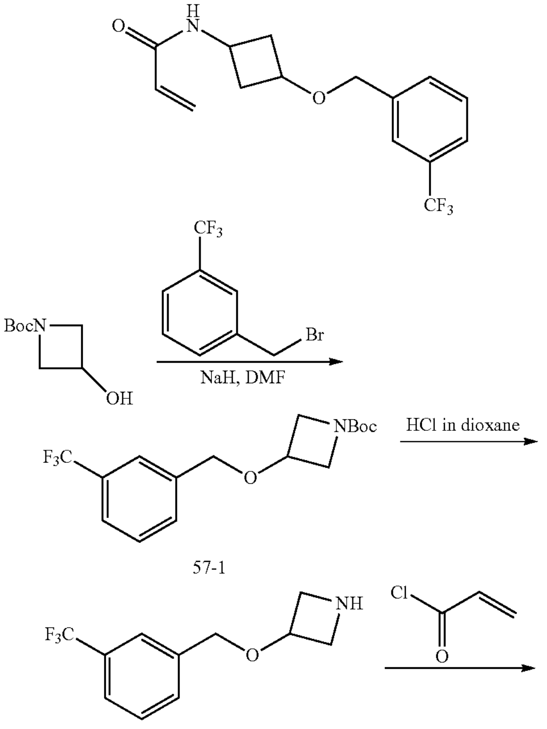

57-1

57-2

-continued

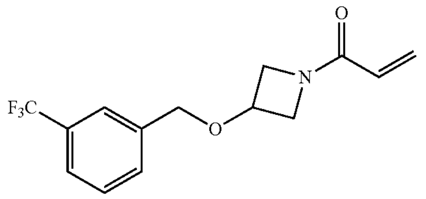

compound 57

Preparation of tert-butyl 3-((3-(trifluoromethyl)benzyl)oxy)azetidine-1-carboxylate (57-1). To a solution of tert-butyl 3-hydroxyazetidine-1-carboxylate (500 mg, 2.887 mmol) in DMF (10 mL) at 0° C. was added 60% NaH (173.20 mg, 4.330 mmol). The reaction mixture was stirred at the room temperature for 0.5 h, Then added 1-(bromomethyl)-3-(trifluoromethyl)benzene (762.22 mg, 3.175 mmol) and stirred at the room temperature for 1.5 h. LCMS showed the reaction was completed. The reaction solution was quenched with sat. $NH_4Cl$ (20 mL) and extracted with EA (20 mL*3), the organic phase was dried over $Na_2SO_4$, filtered, and concentrated to afford the crude product. The residue was purified by Flash Chromatography (PE/EtOAc=5:2) to give the product tert-butyl 3-((3-(trifluoromethyl)benzyl)oxy)azetidine-1-carboxylate (717 mg, 2.16 mmol, 74.7%) as light-yellow oil. Mass Spectrum (ESI) m/z=354.0 (M+23).

Preparation of 3-((3-(trifluoromethyl)benzyl)oxy)azetidine (57-2). To a solution of tert-butyl 3-((3-(trifluoromethyl)benzyl)oxy)azetidine-1-carboxylate (717 mg, 2.157 mmol) in DCM (15 mL) was added a solution of 4 M HCl in dioxane (2.2 mL, 8.630 mmol). The reaction mixture was stirred at the room temperature for 16 h. LCMS showed the reaction was completed. The reaction solution was concentrated to afford the crude product 3-((3-(trifluoromethyl)benzyl)oxy)azetidine (600 mg, 2.07 mmol, 95.8% yield, 80% purity) as a yellow solid. Which was used for next step without purification. Mass Spectrum (ESI) m/z=232.1 (M+1).

Preparation of 1-(3-((3-(trifluoromethyl)benzyl)oxy)azetidin-1-yl)prop-2-en-1-one (compound 57). To a solution of 3-((3-(trifluoromethyl)benzyl)oxy)azetidine (600 mg, 2.584 mmol) and $NaHCO_3$ (651.17 mg, 7.751 mmol) in THF/$H_2O$ (20 mL, V/V=4/1) at 0° C. was added prop-2-enoyl chloride (350.77 mg, 3.876 mmol). The reaction mixture was stirred at the room temperature for 2 h. LCMS showed the reaction was completed. The reaction solution was diluted with $H_2O$ (20 mL) and extracted with EA (10 mL*3), the organic phase was dried over $Na_2SO_4$, filtered, and concentrated to afford the crude product. The residue was purified by Flash Chromatography (PE/EtOAc=5:4) and prep-TLC (PE/EtOAc=1:4) to give the product 1-(3-((3-(trifluoromethyl)benzyl)oxy)azetidin-1-yl)prop-2-en-1-one (71.1 mg, 0.24 mmol, 9.28% yield) as a light-yellow oil. Mass Spectrum (ESI) m/z=286.0 (M+1). $^1$H NMR (400 MHz, MeOD) δ 7.69-7.50 (m, 4H), 6.34-6.18 (m, 2H), 5.72-5.69 (m, 1H), 4.58 (s, 2H), 4.51-4.44 (m, 2H), 4.25-4.13 (m, 2H), 3.92-3.89 (m, 1H).

Example 56

Synthesis of Compound 58 (N-(3-((3-(trifluoromethyl)phenoxy)methyl)cyclobutyl)acrylamide)

Scheme 58. Synthesis of compound 58.

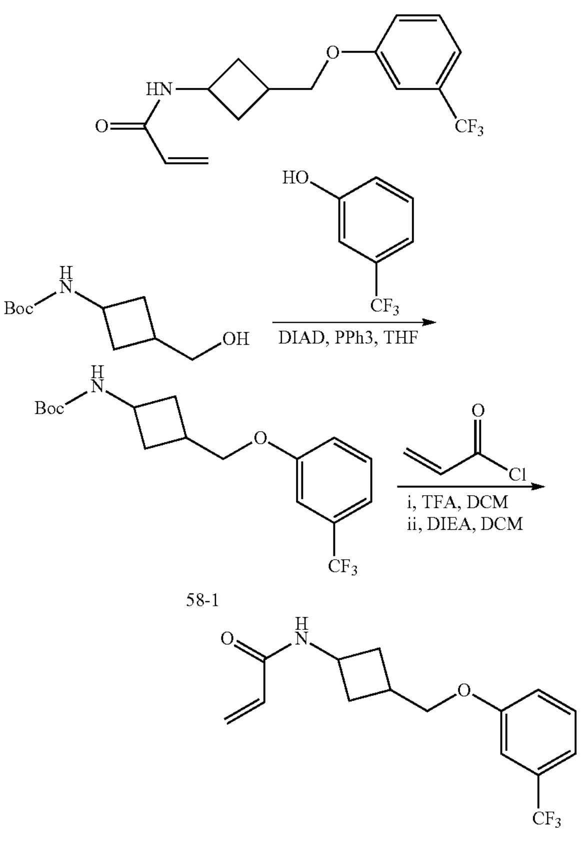

58-1 compound 58

Preparation of tert-butyl (3-((3-(trifluoromethyl)phenoxy) methyl) cyclobutyl) carbamate (58-1). A solution of tert-butyl (3-(hydroxymethyl)cyclobutyl)carbamate (500 mg, 2.48 mmol), 3-(trifluoromethyl)phenol (402 mg, 2.48 mmol) and PPh3 (782 mg, 2.98 mmol) in THF (20 mL) was added DIAD (603 mg, 2.98 mmol) at 0° C. for 10 min. Then the mixture was stirred at 0° C. for 30 min. LCMS showed the reaction was completed. The reaction solution was concentrated in vacuo to give a crude product. The crude product was purified by prep-HPLC to obtain tert-butyl (3-((3-(trifluoromethyl)phenoxy)methyl) cyclobutyl) carbamate 480 mg. (ESI) m/z=346 (M+1).

Preparation of 3-((3-(trifluoromethyl)phenoxy)methyl) cyclobutylamine. To a solution of tert-butyl (3-((3-(trifluoromethyl)phenoxy)methyl)cyclobutyl)carbamate (480 mg, 1.4 mmol) in DCM (6 ml) was added TFA (3 ml). The mixture was stirred at room temperate. for 1.0 hr. LCMS showed the reaction was completed. The reaction solution was concentrated in vacuo to give a crude 3-((3-(trifluoromethyl)phenoxy)methyl)cyclobutylamine. Which was used for next step without purification. (ESI) m/z=246 (M+1).

Preparation of N-(3-((3-(trifluoromethyl)phenoxy) methyl)cyclobutyl)acrylamide (compound 58). To a solution of 3-((3-(trifluoromethyl)phenoxy)methyl)cyclobutan-1-amine (300 mg, 1.22 mmol) and DIEA (474 mg, 3.67 mmol) in DCM (10 mL) was added acryloyl chloride (110 mg, 1.22 mmol), then the mixture was stirred at rt for 30 min. LCMS showed the reaction was completed. The mixture was concentrated to afford the crude N-(3-((3-(trifluoromethyl)phenoxy)methyl)cyclobutyl)acrylamide. The residue was purified by Prep-HPLC (column: Xbridge-C18 150×19 mm, 5 um. mobile phase: ACN-$H_2O$ (0.05% FA), B %: 25-60) to give N-(3-((3-(trifluoromethyl)phenoxy)methyl)cyclobutyl) acrylamide (53.0 mg, 0.18 mmol, 14.5% yield) as a white solid. (ESI) m/z=300 (M+1). $^1$H NMR (400 MHz, DMSO) δ 8.38 (dd, J=42.2, 7.5 Hz, 1H), 7.52 (t, J=8.0 Hz, 1H), 7.31-7.20 (m, 3H), 6.18 (ddd, J=17.1, 9.9, 4.5 Hz, 1H), 6.07 (dd, J=17.1, 2.4 Hz, 1H), 5.58 (dd, J=9.9, 2.4 Hz, 1H), 4.43 (d, J=7.7 Hz, 1H), 4.21 (d, J=7.6 Hz, 1H), 4.13 (d, J=7.2 Hz, 1H), 4.01 (d, J=5.6 Hz, 1H), 2.37 (dt, J=10.9, 8.9 Hz, 2H), 2.13 (ddd, J=21.8, 11.6, 7.5 Hz, 2H), 1.79 (dd, J=13.3, 6.5 Hz, 1H).

Example 57

Synthesis of Compound 59

(1-(3-(4-(trifluoromethyl)benzyl)azetidin-1-yl)prop-2-en-1-one)

Scheme 59. Synthesis of compound 59.

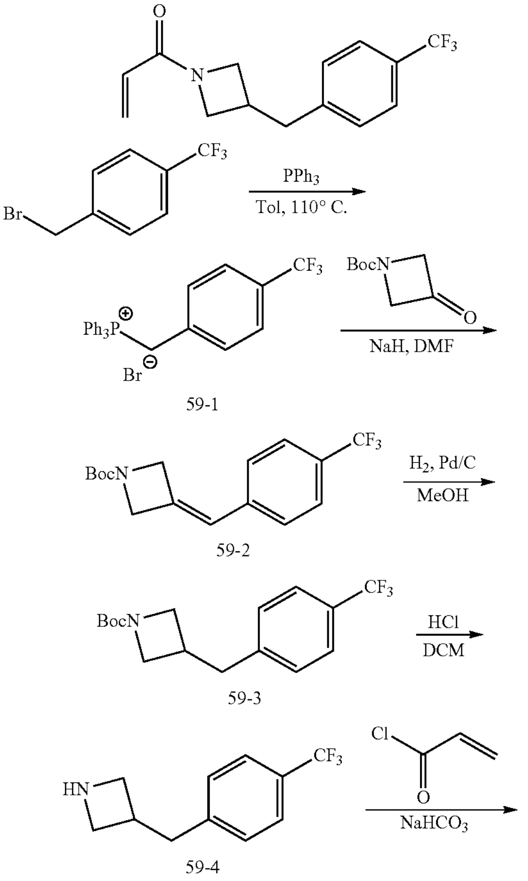

59-1

59-2

59-3

59-4

-continued

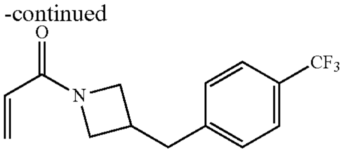

compound 59

Preparation of triphenyl(4-(trifluoromethyl)benzyl)phosphonium bromide (59-1). A mixture of 1-(bromomethyl)-4-(trifluoromethyl)benzene (1 g, 4.2 mmol, 1 eq) and $PPh_3$ (1.3 g, 5 mmol, 1.2 eq) in toluene (20 mL) was stirred at 110° C. for 3 h. LCMS showed the reaction was completed. The mixture was diluted with $Et_2O$ and filtered, and the filter cake was dried to give triphenyl(4-(trifluoromethyl)benzyl) phosphonium bromide (2.2 g, crude) as a white solid, which was used for next step without purification. Mass Spectrum (ESI) m/z=420.9 (M+1).

Preparation of tert-butyl 3-(4-(trifluoromethyl)benzylidene)azetidine-1-carboxylate (59-2). To a solution of triphenyl(4-(trifluoromethyl)benzyl)phosphonium bromide (2.2 g, 4.4 mmol) in DMF (15 mL) was added NaH (211 mg, 5.2 mmol, 60% purity) at 0° C. under N2. The reaction was stirred at 0° C. for 30 min. A solution of tert-butyl 3-oxoazetidine-1-carboxylate (900 mg, 5.2 mmol) in DMF (5 mL) was added to the above mixture. The resulting mixture was stirred at rt for 3 hrs. LCMS showed the reaction was completed. The reaction was quenched by ice water, extracted with ethyl acetate (10 mL*3). The combined organic layers were washed with brine, dried over anhydrous $Na_2SO_4$, filtered and concentrated. The residue was purified by Flash Chromatography (PE/EtOAc=0-20%) to give the product tert-butyl 3-(4-(trifluoromethyl)benzylidene)azetidine-1-carboxylate (950 mg, 61.8%) as a white solid. Mass Spectrum (ESI) m/z=258.0 (M−55)

Preparation of tert-butyl 3-(4-(trifluoromethyl)benzyl) azetidine-1-carboxylate (59-3). To a solution of tert-butyl 3-(4-(trifluoromethyl)benzylidene)azetidine-1-carboxylate (950 mg, 3 mmol) in MeOH (10 mL) was added Pd/C (95 mg). The mixture was stirred at rt for 16 h. LCMS showed the reaction was completed. The reaction solution was filtered to get the filter and concentrated to get the product tert-butyl 3-(4-(trifluoromethyl)benzyl)azetidine-1-carboxylate (940 mg, crude) as a white solid, Which was used for next step without purification. Mass Spectrum (ESI) m/z=260.0 (M−55). $^1$H NMR (400 MHz, $CDCl_3$) δ 7.55 (d, J=8.0 Hz, 2H), 7.26 (t, J=4.0 Hz, 2H), 4.00 (t, J=8.4 Hz, 2H), 3.64 (dd, J=8.7, 5.3 Hz, 2H), 2.97 (d, J=8.0 Hz, 2H), 2.88-2.76 (m, 1H), 1.44 (s, 9H).

Preparation of 3-(4-(trifluoromethyl)benzyl)azetidine (59-4). To a solution of tert-butyl 3-(4-(trifluoromethyl) benzyl)azetidine-1-carboxylate (940 mg, 3 mmol) in DCM (10 mL) was added HCl/dioxane (5 mL) and stirred for 3 h at rt. LCMS showed the reaction was completed. The mixture was evaporated to afford the product 3-(4-(trifluoromethyl)benzyl)azetidine (900 mg, crude) as a yellow oil. Mass Spectrum (ESI) m/z=216.0 (M+1).

Preparation of 1-(3-(4-(trifluoromethyl)benzyl)azetidin-1-yl)prop-2-en-1-one (compound 59). A mixture of 3-(4-(trifluoromethyl)benzyl)azetidine (500 mg, 2.3 mmol) and $NaHCO_3$ (582 mg, 7 mmol) in THF/$H_2O$=4:1 (5 mL) was added prop-2-enoyl chloride (251 mg, 2.7 mmol) at 0° C. The mixture was stirred at 0° C. for 30 min. LCMS showed the reaction was completed. The mixture was diluted with water (20 mL), extracted with EA (20 mL×3). The combined organic layers were washed with brine (20 mL), dried over $Na_2SO_4$, concentrated under vacuum, and purified by Flash Chromatography (PE/EtOAc=0-30%) to give the product 1-(3-(4-(trifluoromethyl)benzyl)azetidin-1-yl)prop-2-en-1-one (87.7 mg, 19.01%) as a white solid. Mass Spectrum (ESI) m/z=270.0 (M+1). $^1$H NMR (400 MHz, $CDCl_3$) δ 7.57 (d, J=8.0 Hz, 2H), 7.27 (d, J=7.5 Hz, 2H), 6.35 (dd, J=17.0, 1.8 Hz, 1H), 6.17 (dd, J=17.0, 10.3 Hz, 1H), 5.68 (dd, J=10.3, 1.8 Hz, 1H), 4.23 (t, J=8.3 Hz, 2H), 3.86 (dd, J=9.4, 4.8 Hz, 2H), 2.99 (q, J=7.0 Hz, 3H).

Example 58

Synthesis of Compound 60

(1-(3-((3-(trifluoromethyl)benzyl)amino)azetidin-1-yl)prop-2-en-1-one)

Scheme 60. Synthesis of compound 30.

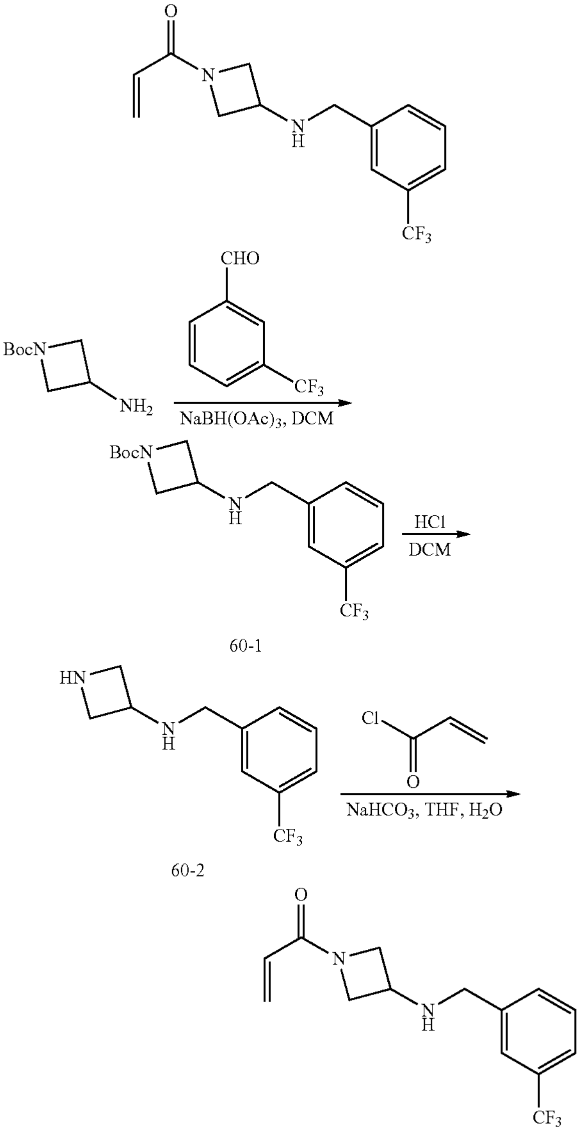

compound 60

Preparation of tert-butyl 3-((3-(trifluoromethyl)benzyl) amino)azetidine-1-carboxylate (60-1). To a solution of tert-butyl 3-aminoazetidine-1-carboxylate (500 mg, 2.9 mmol) in DCM (30 mL) was added 3(trifluoromethyl)benzaldehyde (508 mg, 2.9 mmol) and sodium triacetoxyborohydride (1.2 g, 5.8 mmol). The reaction mixture was stirred at rt for 16 hours. The reaction mixture was washed by water (20 mL), then concentrated under vacuum and purified by silica gel column chromatography to obtain tert-butyl 3-((3-(trifluoromethyl)benzyl)amino)azetidine-1-carboxylate (800 mg, 79%) as a colorless oil. Mass Spectrum (ESI) m/z=275.0 (M−55).

Preparation of 3-((3-(trifluoromethyl)benzyl)amino)azetidine (60-2). To a solution of tert-butyl 3-((3-(trifluoromethyl)benzyl)amino)azetidine-1-carboxylate (800 mg, 2.4 mmol) in DCM (10 mL) stirred at RT was added 1,4-dioxane/4M HCl (5 mL), The reaction mixture was stirred at 25° C. for 14 hours. The mixture was concentrated to obtained 3-((3-(trifluoromethyl)benzyl)amino)azetidine (600 mg, 64.5%) as white solid. Mass Spectrum (ESI) m/z=231.0 (M+1).

Preparation of 1-(3-((3-(trifluoromethyl)benzyl)amino)azetidin-1-yl)prop-2-en-1-one (compound 60). To a solution of 3-((3-(trifluoromethyl)benzyl)amino)azetidine (600 mg, 2.6 mmol) and triethylamine (525 mg, 5.2 mmol) in DCM (20 mL) was added prop-2-enoyl chloride (235 mg, 2.6 mmol) at 0° C. The reaction mixture was stirred at 0° C. for 1 hour. The reaction mixture was concentrated under vacuum and purified by silica gel column chromatography to obtain product 1-(3-((3-(trifluoromethyl)benzyl)amino)azetidin-1-yl)prop-2-en-1-one (100 mg, 12.8%) as a colorless oil. Mass Spectrum (ESI) m/z=245.9 (M+1). HNMR (ENB190595-033-1, 400 MHz, $CDCl_3$) δ 7.63-7.40 (m, 4H), 6.32 (dd, J=17.0, 1.9 Hz, 1H), 6.17 (dd, J=17.0, 10.3 Hz, 1H), 5.67 (dd, J=10.3, 1.9 Hz, 1H), 4.42-4.31 (m, 1H), 4.25 (dd, J=10.1, 7.5 Hz, 1H), 3.91 (dd, J=8.9, 4.7 Hz, 1H), 3.86-3.70 (m, 4H), 1.98 (s, 1H).

Example 59

Synthesis of Compound 61

(N-(3-((3-(trifluoromethyl)benzyl)oxy)cyclobutyl) acrylamide)

Scheme 61. Synthesis of compound 61.

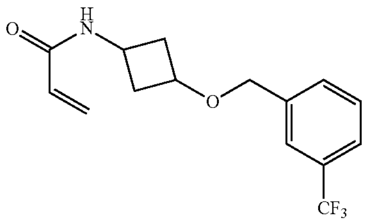

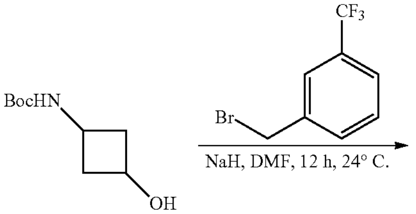

-continued

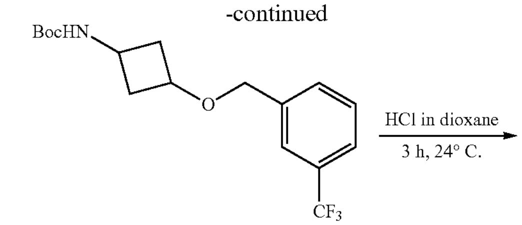

61-1

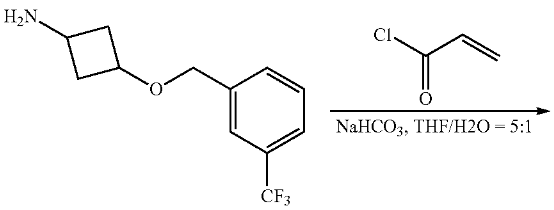

61-2

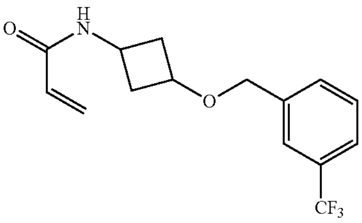

compound 61

Preparation of tert-butyl (3-((3-(trifluoromethyl)benzyl)oxy)cyclobutyl)carbamate (61-1). The mixture of tert-butyl N-(3-hydroxycyclobutyl)carbamate (500 mg, 2.670 mmol), 1-(bromomethyl)-3-(trifluoromethyl)benzene (641 mg, 2.670 mmol) and Sodium hydride (73.9 mg, 3.204 mmol) in DMF (10 mL) was stirred at 24° C. for 12 h with $N_2$. Water (30 mL) was added. The mixture was extracted with EtOAc (30 mL×3). The combined organic layers were washed with brine (30 mL), dried over $Na_2SO_4$, filtered, and concentrated to yield a crude material which was purified by flash silica gel chromatography (AcOEt/PE=1/4) to give tert-butyl (3-((3-(trifluoromethyl)benzyl)oxy)cyclobutyl)carbamate (800 mg, 90% purity) as a white oil. Mass Spectrum (ESI) m/z=368.0 (M+23).

Preparation of 3-((3-(trifluoromethyl)benzyl)oxy)cyclobutan-1-amine (61-2). A solution of tert-butyl (3-((3-(trifluoromethyl)benzyl)oxy)cyclobutyl)carbamate (800 mg, 2.309 mmol) and HCl in dioxane (3 mL) in DCM (10 mL) was stirred at 24° C. for 3 h with $N_2$. Upon completion of the reaction, The resulting mixture was concentrated to give crude 3-((3-(trifluoromethyl)benzyl)oxy)cyclobutan-1-amine (400 mg, 99% purity) as white oil. Mass Spectrum (ESI) m/z=245.9 (M+1).

Preparation of N-(3-((3-(trifluoromethyl)benzyl)oxy)cyclobutyl)acrylamide (compound 61). A solution of 3-((3-(trifluoromethyl)benzyl)oxy)cyclobutan-1-amine (400 mg, 1.624 mmol), prop-2-enoyl chloride (176 mg, 1.94 mmol) and $Na_2CO_3$ (341 mg, 4.06 mmol) in THF/$H_2O$=5:1 (6 mL) and $H_2O$ (1 mL) were stirred at 24° C. for 12 h under $N_2$. The reaction mixture was concentrated under vacuum and purified by flash silica gel chromatography (AcOEt/PE=1/4) to get N-(3-((3-(trifluoromethyl)benzyl)oxy)cyclobutyl)acrylamide (283.5 mg, 99% purity) as as white solid. Mass Spectrum (ESI) m/z=234 (M+1). $^1H$ NMR (400 MHz, $CO_3OD$) δ 7.62 (s, 1H), 7.60-7.47 (m, 3H), 6.21-6.15 (m, 2H), 5.62 (dd, J=6.6, 5.4 Hz, 1H), 4.49 (s, 2H), 4.44-4.38 (m, 0.25H), 4.25-4.21 (m, 0.21H), 3.96 (tt, J=9.0, 7.4 Hz, 1H), 3.85 (tt, J=7.7, 6.6 Hz, 1H), 2.74-2.35 (m, 2H), 2.30-1.82 (m, 2H).

Example 60

Synthesis of Compound 62

(N-(3-((3-(trifluoromethyl)phenoxy)methyl)bicyclo[1.1.1]pentan-1-yl)acrylamide)

Scheme 62. Synthesis of compound 62.

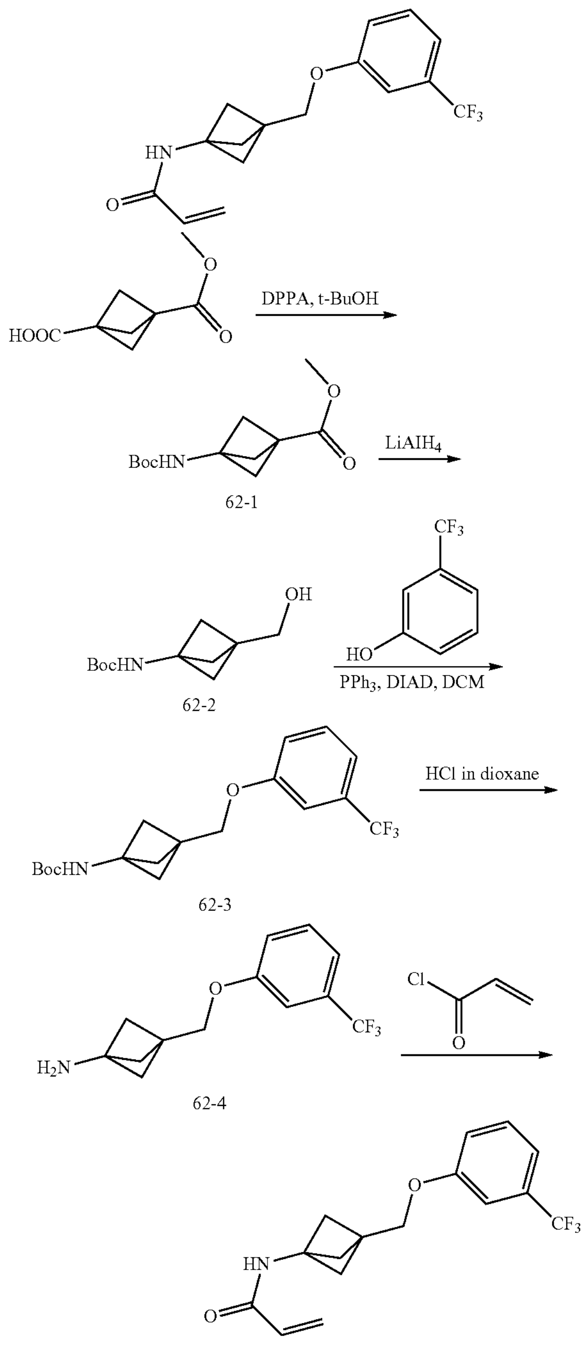

Compound 62

Preparation of methyl 3-{[(tert-butoxy)carbonyl]amino}bicyclo[1.1.1]pentane-1-carboxylate (62-1). A mixture of 3-(methoxycarbonyl)bicyclo[1.1.1]pentane-1-carboxylic acid (2.5 g, 14.7 mmol), DPPA (6.07 g, 22.0 mmol) and trimethylamine (5.95 g, 58.8 mmol) in t-BuOH (30 mL) was stirred at 80° C. for 16 h. Upon completion of the reaction, the mixture was diluted with H2O. The aqueous layer was separated and extracted with EtOAc. The organic layers were combined, dried over MgSO4, and concentrated under reduced pressure. The residue was purified by flash column chromatography (AcOEt/PE=1/4) to give methyl 3-{[(tert-butoxy)carbonyl]amino}bicyclo[1.1.1]pentane-1-carboxylate. Mass Spectrum (ESI) m/z=186.0 (M−55). $^1H$ NMR (400 MHz, $CDCl_3$) δ 5.01 (s, 1H), 3.68 (s, 3H), 2.29 (s, 6H), 1.45 (s, 9H).

Preparation of tert-butyl (3-(hydroxymethyl)bicyclo[1.1.1]pentan-1-yl)carbamate (62-2). A mixture of methyl 3-{[(tert-butoxy)carbonyl]amino}bicyclo[1.1.1]pentane-1-carboxylate (1.5 g, 6.2 mmol) and $LiAlH_4$ (470 mg, 12.4 mmol) in THF (25 mL) was stirred at 0° C. for 3 h. Upon completion of the reaction, the mixture was diluted with H2O (0.5 mL), NaOH (0.5 mL, 15% Wt) and H2O (1.5 mL), the resulting mixture was filtered, the filtrate was concentrated to give tert-butyl (3-(hydroxymethyl)bicyclo[1.1.1]pentan-1-yl)carbamate. Mass Spectrum (ESI) m/z=158.1 (M−55).

Preparation of tert-butyl (3-((3-(trifluoromethyl)phenoxy)methyl)bicyclo[1.1.1]pentan-1-yl)carbamate (62-3). To a solution of tert-butyl (3-(hydroxymethyl)bicyclo[1.1.1]pentan-1-yl)carbamate (1 g, 4.7 mmol) 3-(trifluoromethyl)phenol (770 mg, 4.7 mmol) and triphenylphosphine (1.85 mg, 7.05 mmol) Diisopropyl azodicarboxylate (1.43 g, 7.05 mmol) in THF (10 mL) stirred under nitrogen at 50° C. for 16 h. The reaction was quenched by ice water, extracted with ethyl acetate (10 mL*3). The combined organic layers were washed with brine, dried over anhydrous Na2SO4, filtered and concentrated. The residue was purified by Flash Chromatography (PE/EtOAc=30-40%) to give tert-butyl (3-((3-(trifluoromethyl)phenoxy)methyl)bicyclo[1.1.1]pentan-1-yl)carbamate (700 mg, 38.3%) as yellow oil. Mass Spectrum (ESI) m/z=302.0 (M+1).

Preparation of 3-((3-(trifluoromethyl)phenoxy)methyl)bicyclo[1.1.1]pentan-1-amine (62-4). To a solution of tert-butyl (3-((3-(trifluoromethyl)phenoxy)methyl)bicyclo[1.1.1]pentan-1-yl)carbamate (700 mg, 1.95 mmol) in HCl in dioxane/DCM (10 mL) stirred at r.t. for 16 h. The mixture concentrated and used next step (700 mg crude 3-((3-(trifluoromethyl)phenoxy)methyl)bicyclo[1.1.1]pentan-1-amine). Mass Spectrum (ESI) m/z=258.0 (M+1).

Preparation of N-(3-((3-(trifluoromethyl)phenoxy)methyl)bicyclo[1.1.1]pentan-1-yl)acrylamide (compound 62). To a solution of 3-((3-(trifluoromethyl)phenoxy)methyl)bicyclo[1.1.1]pentan-1-amine (200 mg, 0.77 mmol), $NaHCO_3$ (162 mg, 1.9 mmol) and prop-2-enoyl chloride (84 mg, 0.92 mmol) in THF/H2O=5:1 (24 mL) stirred at 0-r.t. for 2 h. The reaction was quenched by water (10 mL), extracted with ethyl acetate (10 mL*3). The combined organic layers were washed with brine, dried over anhydrous $Na_2SO_4$, filtered and concentrated. The residue was purified by Flash Chromatography (PE/EtOAc=30-40%) to give N-(3-((3-(trifluoromethyl)phenoxy)methyl)bicyclo[1.1.1]pentan-1-yl)acrylamide (104.7 mg, 42.8%) as white solid. Mass Spectrum (ESI) m/z=312.0 (M+1). $^1H$NMR (400 MHz, $CD_3OD$) δ 7.35 (t, J=8.0 Hz, 1H), 7.18 (d, J=7.7 Hz, 1H), 7.10 (s, 1H), 7.03 (dd, J=8.3, 2.5 Hz, 1H), 6.27 (dd, J=16.9, 1.3 Hz, 1H), 6.09-5.85 (m, 2H), 5.63 (dd, J=10.3, 1.3 Hz, 1H), 4.11 (s, 2H), 2.16 (s, 6H).

Example 61

Synthesis of Compound 63

(N-(6-((3-(trifluoromethyl)benzyl)amino)spiro[3.3]heptan-2-yl)acrylamide)

Scheme 63. Synthesis of compound 63.

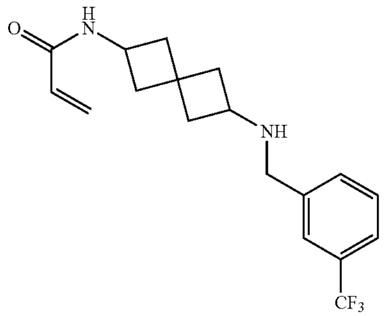

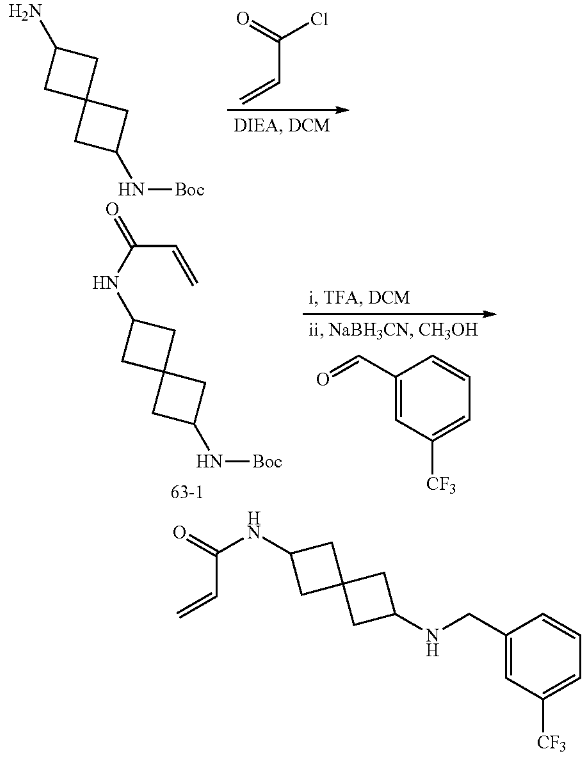

63-1

Compound 63

Preparation of tert-butyl (6-acrylamidospiro[3.3]heptan-2-yl)carbamate (63-1). To a solution of tert-butyl (6-aminospiro[3.3]heptan-2-yl)carbamate (400 mg, 1.77 mmol) in DCM (10 ml) was added DIAD (680 mg, 5.27 mmol), the mixture was stirred at 0° C., acryloyl chloride (200 mg, 2.22 mmol) was added, then the mixture was stirred at 0° C. for 30 min. product was confirmed by LCMS, The solvent was removed to afford the crude tert-butyl (6-acrylamidospiro[3.3]heptan-2-yl)carbamate, which was used for next step without purification. Mass Spectrum (ESI) m/z=281 (M+1).

Preparation of N-(6-aminospiro[3.3]heptan-2-yl)acrylamide. To a solution of tert-butyl (6-acrylamidospiro[3.3]heptan-2-yl)carbamate in DCM (5 ml) was added TFA (1 ml). The reaction mixture was stirred at room temperate for 1.0 h. LCMS showed the reaction was completed. The reaction solution was concentrated in vacuo to give crude N-(6-aminospiro[3.3]heptan-2-yl)acrylamide. Mass Spectrum (ESI) m/z=181 (M+1).

Preparation of N-(6-((3-(trifluoromethyl)benzyl)amino)spiro[3.3]heptan-2-yl)acrylamide (compound 63). To a solution of N-(6-aminospiro[3.3]heptan-2-yl)acrylamide (450 mg, 2.48 mmol) in CH3OH (10 mL) was added 3-(trifluoromethyl)benzaldehyde (500 mg, 2.87 mmol), then the mixture was stirred at rt for 30 min, NaBH3CN (450 mg, 7.14 mmol), and AcOH (0.5 ml) were added, the mixture was stirred at rt for 2 hours. product was confirmed by LCMS, The residue was purified by Pre-HPLC (column:-Xbridge-C18 150×19 mm, 5 um. mobile phase: ACN-H2O (0.05% FA), B %: 25-60) to give N-(6-((3-(trifluoromethyl)benzyl)amino) spiro[3.3]heptan-2-yl)acrylamide (190.0 mg, 0.56 mmol, 22.4% yield). Mass Spectrum (ESI) m/z=339 (M+1). $^1$H NMR (400 MHz, DMSO) δ 8.95 (s, 1H), 8.30 (d, J=7.1 Hz, 1H), 7.88 (s, 1H), 7.76 (t, J=7.0 Hz, 2H), 7.68 (d, J=7.7 Hz, 1H), 6.14 (dd, J=17.1, 9.8 Hz, 1H), 6.05 (dd, J=17.1, 2.5 Hz, 1H), 5.57 (dd, J=9.8, 2.5 Hz, 1H), 4.14 (d, J=7.9 Hz, 1H), 4.08 (s, 2H), 3.58 (s, 1H), 2.42-2.34 (m, 2H), 2.29-2.08 (m, 4H), 1.99-1.88 (m, 2H).

Example 62

Synthesis of Compound 64

(N-(6-(3-(trifluoromethyl)phenoxy)spiro[3.3]heptan-2-yl)acrylamide)

Scheme 64. Synthesis of compound 64.

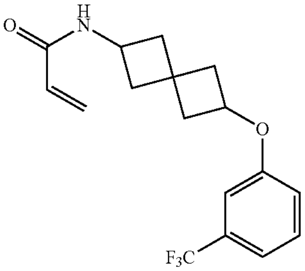

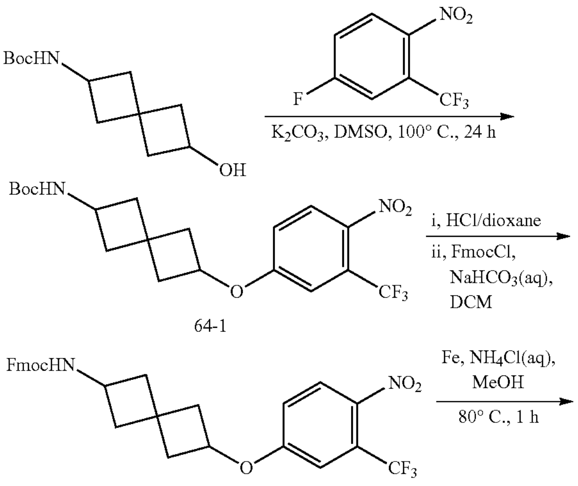

64-1

64-2

-continued

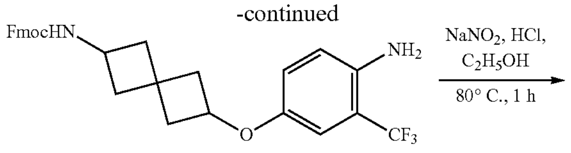

64-3

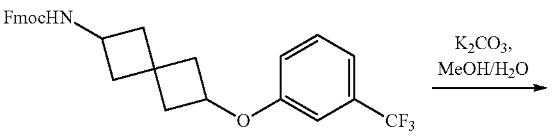

64-4

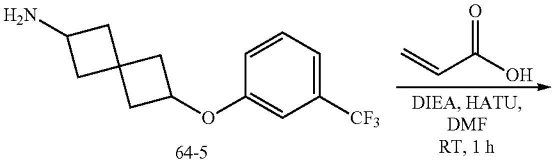

64-5

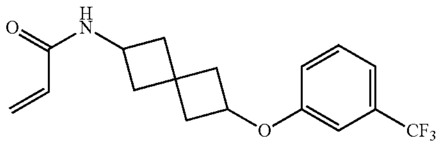

Compound 64

Preparation of tert-butyl (6-(4-nitro-3-(trifluoromethyl) phenoxy) spiro[3.3]heptan-2-yl)carbamate (64-1). A solution of tert-butyl (6-hydroxyspiro[3.3]heptan-2-yl)carbamate (150 mg, 0.66 mmol), 4-fluoro-1-nitro-2-(trifluoromethyl)benzene (138 mg, 0.66 mmol) and $K_2CO_3$ (273 mg, 1.98 mmol) in DMSO (3 mL) was stirred at 100° C. for 24 hrs. LCMS showed the reaction was completed. Water (50 mL) was added, the mixture was extracted with EtOAc (50 mL×3). The combined organic layers were washed with brine (50 mL), dried over $Na_2SO_4$, filtered, and concentrated to yield a crude material which was purified by flash silica gel chromatography (from PE/EtOAc=100/1 to 1/1) to yield tert-butyl (6-(4-nitro-3-(trifluoromethyl)phenoxy) spiro[3.3]heptan-2-yl)carbamate (220 mg, 80% yield, 95% purity) as yellow oil. Mass Spectrum (ESI) m/z=417 (M+1).

Preparation of 6-(4-nitro-3-(trifluoromethyl)phenoxy) spiro[3.3]heptan-2-amine. A solution of tert-butyl (6-(4-nitro-3-(trifluoromethyl)phenoxy)spiro[3.3]heptan-2-yl)carbamate (210 mg, 0.50 mmol) in HCl (4M in dioxane, 3 mL) was stirred at RT for 1 hr. The solution was concentrated to yield 6-(4-nitro-3-(trifluoromethyl)phenoxy)spiro[3.3]heptan-2-amine (160 mg, crude) as yellow oil. Mass Spectrum (ESI) m/z=317 (M+1).

Preparation of (9H-fluoren-9-yl)methyl (6-(4-nitro-3-(trifluoromethyl)phenoxy)spiro[3.3]heptan-2-yl)carbamate (64-2). A solution of 6-(4-nitro-3-(trifluoromethyl)phenoxy) spiro[3.3]heptan-2-amine (160 mg, 0.50 mmol), $NaHCO_3$ (126 mg, 1.50 mmol) and FmocCl (155 mg, 0.6 mmol) in DCM (4 mL) and $H_2O$ (1 mL) was stirred at RT for 1 hr. The reaction mixture was concentrated under vacuum and purified by flash silica gel chromatography (from PE/EtOAc=100/1 to 3/1) to get (9H-fluoren-9-yl)methyl (6-(4-nitro-3-(trifluoromethyl)phenoxy)spiro[3.3]heptan-2-yl)carbamate (240 mg, 88% yield, 95% purity) as a colorless oil. Mass Spectrum (ESI) m/z=561 (M+23).

Preparation of (9H-fluoren-9-yl)methyl (6-(4-amino-3-(trifluoromethyl) phenoxy)spiro[3.3]heptan-2-yl)carbamate (64-3). A solution of (9H-fluoren-9-yl)methyl (6-(4-nitro-3-(trifluoromethyl)phenoxy)spiro[3.3]heptan-2-yl)carbamate (230 mg, 0.43 mmol), Fe (240 mg, 4.30 mmol) and $NH_4Cl$ (120 mg, 2.15 mmol) in MeOH (4 mL) and $H_2O$ (1 mL) was stirred at 80° C. for 1 hr. The solid was filter out and concentrated under vacuum to get (9H-fluoren-9-yl)methyl (6-(4-amino-3-(trifluoromethyl)phenoxy)spiro[3.3]heptan-2-yl)carbamate (210 mg, crude) as a yellow solid. Mass Spectrum (ESI) m/z=509 (M+1).

Preparation of (9H-fluoren-9-yl)methyl (6-(3-(trifluoromethyl)phenoxy)spiro[3.3]heptan-2-yl)carbamate (64-4). A solution of (9H-fluoren-9-yl)methyl (6-(4-amino-3-(trifluoromethyl)phenoxy)spiro[3.3]heptan-2-yl)carbamate (200 mg, 0.39 mmol), $NaNO_2$ (55 mg, 0.78 mmol) in EtOH (4 mL) and HCl (0.2 mL) was stirred at 80° C. for 1 hr. The reaction mixture was concentrated under vacuum and purified by flash silica gel chromatography (from PE/EtOAc=100/1 to 2/1) to get (9H-fluoren-9-yl)methyl (6-(3-(trifluoromethyl)phenoxy)spiro[3.3]heptan-2-yl)carbamate (170 mg, 88% yield, 95% purity) as a colorless oil. Mass Spectrum (ESI) m/z=516 (M+23).

Preparation of 6-(3-(trifluoromethyl)phenoxy) spiro[3.3] heptan-2-amine (64-5). A solution of (9H-fluoren-9-yl) methyl (6-(3-(trifluoromethyl)phenoxy)spiro[3.3]heptan-2-yl)carbamate (160 mg, 0.32 mmol) and $K_2CO_3$ (132 mg, 0.96 mmol) in MeOH (4 mL) and $H_2O$ (1 mL) was stirred at RT for 1 hr. The residue was diluted with MeOH (10 mL), The MeOH layers were washed with PE (10 mL*3). The MeOH layers was concentrated under vacuum. The residue was diluted with water (10 mL), then extracted with EA (10 mL*3). The organic layers were combined, dried, and concentrated under vacuum to get 6-(3-(trifluoromethyl)phenoxy) spiro[3.3]heptan-2-amine (75 mg, crude) as a white solid. Mass Spectrum (ESI) m/z=272 (M+1).

Preparation of N-(6-(3-(trifluoromethyl)phenoxy)spiro[3.3]heptan-2-yl)acrylamide (compound 64). A solution of 6-(3-(trifluoromethyl)phenoxy)spiro[3.3]heptan-2-amine (70 mg, 0.26 mmol), acrylic acid (56 mg, 0.78 mmol), DIEA (201 mg, 1.56 mmol) and HATU (296 mg, 0.78 mmol) in DMF (3 mL) was stirred at RT for 1 hr. The reaction mixture was diluted with water (20 mL), then extracted with EA (20 mL*3). The organic layers were combined, dried, and concentrated under vacuum. The crude product was purified by flash silica gel chromatography (from PE/EtOAc=100/1 to 1/1) to get N-(6-(3-(trifluoromethyl)phenoxy)spiro[3.3]heptan-2-yl)acrylamide (25.9 mg, 0.08 mmol, 31% yield) as a white semi-solid. Mass Spectrum (ESI) m/z=326 (M+1). $^1H$ NMR (400 MHz, DMSO) δ 8.31 (d, J=7.6 Hz, 1H), 7.50 (t, J=8.0 Hz, 1H), 7.27 (d, J=7.7 Hz, 1H), 7.15 (dd, J=8.3, 2.3 Hz, 1H), 7.10 (s, 1H), 6.15 (dd, J=17.1, 9.9 Hz, 1H), 6.05 (dd, J=17.1, 2.5 Hz, 1H), 5.57 (dd, J=9.8, 2.5 Hz, 1H), 4.73 (t, J=6.9 Hz, 1H), 4.18 (d, J=7.7 Hz, 1H), 2.72-2.63 (m, 1H), 2.49-2.38 (m, 2H), 2.27 (dd, J=7.9, 3.2 Hz, 1H), 2.15-1.94 (m, 4H).

Example 63

Synthesis of Compound 65

(N-(4-(5-(tert-butyl)isoxazol-3-yl)phenyl)acrylamide)

Scheme 65. Synthesis of compound 65.

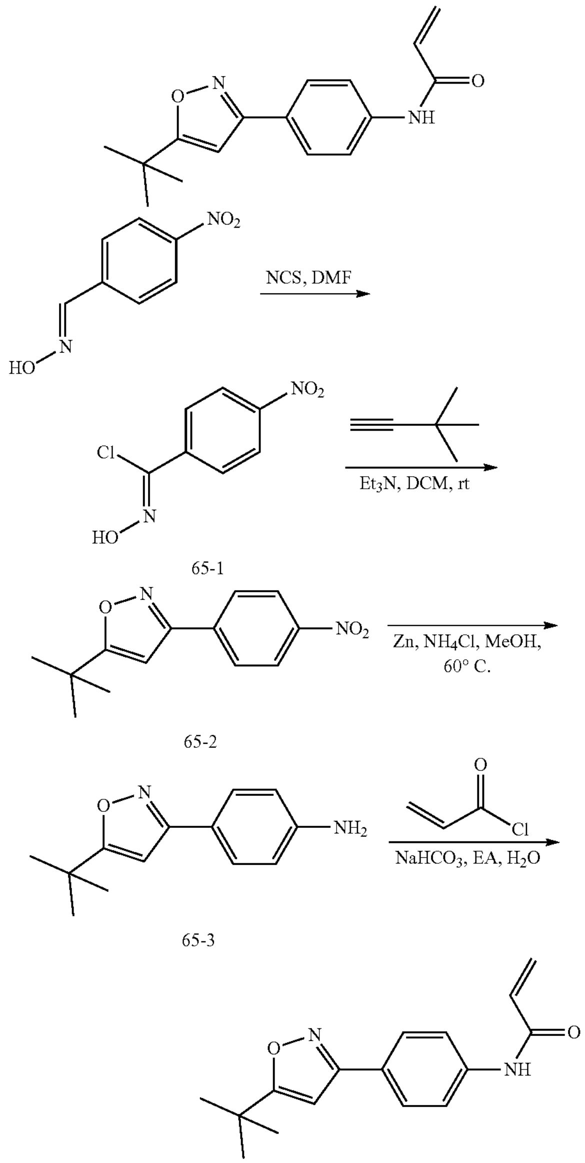

65-1

65-2

65-3

Compound 65

Preparation of (Z)—N-hydroxy-4-nitrobenzimidoyl chloride (65-1). To a solution of (E)-4-nitrobenzaldehyde oxime (8.00 g, 48.19 mmol) in DMF (80 mL) was added NCS (7.08 g, 53.00 mmol)portion wise at 0° C. The resulting mixture was warmed to room temperature naturally and stirred at this temperature for 16 h. It was quenched with sat. $Na_2S_2O_3$ (20 mL) and water (80 mL), then extracted with EA (3x50 mL). The organic layers were combined, washed with brine, dried over $Na_2SO_4$, and concentrated under reduced pressure. This produced (Z)—N-hydroxy-4-nitrobenzimidoyl chloride as a yellow solid (8.00 g, crude), which was used directly for the next step. LC-MS: (ESI) m/z (M+1), 201.

Preparation of 5-(tert-butyl)-3-(4-nitrophenyl)isoxazole (65-2). To a solution of (Z)—N-hydroxy-4-nitrobenzimidoyl chloride (2.00 g, 10.00 mmol) in DCM (20 mL) was added 3,3-dimethylbut-1-yne (1.23 g, 15.00 mmol) and triethylamine (1.5 g, 15.00 mmol). The resulting mixture was stirred at rt for 1 h. It was quenched with $H_2O$ (20 mL) and extracted with DCM (3x30 mL). The organic layers were combined, washed with brine, dried over $Na_2SO_4$ and concentrated under reduced pressure. The residue was purified by silica gel chromatography (PE/EtOAc=5/1) to afford 5-(tert-butyl)-3-(4-nitrophenyl)isoxazole as a yellow solid (0.25 g, 90%, 10.00% yield). LC-MS: (ESI) m/z (M+1), 247.

Preparation of 4-(5-(tert-butyl)isoxazol-3-yl)aniline (65-3). To a mixture of 5-(tert-butyl)-3-(4-nitrophenyl)isoxazole (250 mg, 1.01 mmol) in MeOH (3 mL) and $NH_4Cl$ sat (3 mL) was added Zn dust (169 mg, 3.03 mmol) in one charge. The resulting mixture was stirred at 60° C. for 1 h. The solid was filtrated off and washed with DCM (10 mL) and $H_2O$ (10 mL). The filtrate was extracted with DCM (3x20 mL). The organic layers were combined, washed with brine, dried over $Na_2SO_4$, and concentrated under reduced pressure. The crude 4-(5-(tert-butyl)isoxazol-3-yl)aniline was obtained as a yellow oil (180 mg, 90%, 81.81% yield) and used in the next step without further purification. LC-MS: (ESI) m/z (M+1), 217.

Preparation of N-(4-(5-(tert-butyl)isoxazol-3-yl)phenyl) acrylamide (compound 65). To a solution of 4-(5-cyclopropylisoxazol-3-yl)aniline (180 mg, 0.83 mmol) in EA (2 mL) and sat. $NaHCO_3$ (2 mL) was added acryloyl chloride (90 mg, 0.99 mmol) at 0° C. The resulting mixture was stirred at this temperature for 0.5 h. It was quenched with $H_2O$ (10 mL) and extracted with EA (3x30 mL). The organic layers were combined, washed with brine, dried over $Na_2SO_4$ and concentrated under reduced pressure. The residue was purified by silica gel chromatography (PE/EtOAc=1/1) to afford the product as a white solid (87.5 mg, 99.79%, 38.88% yield). LC-MS: (ESI) m/z (M+1), 271. $^1H$ NMR (400 MHz, DMSO) δ 10.35 (s, 1H), 7.83-7.78 (m, 4H), 6.76 (s, 1H), 6.46 (dd, J=17.0, 10.1 Hz, 1H), 6.29 (dd, J=17.0, 2.0 Hz, 1H), 5.79 (dd, J=10.1, 2.0 Hz, 1H), 1.35 (s, 9H).

Example 64

TEAD1-Luciferase Reporter Assay to Characterize the Pharmacological Properties of the Tead1 Covalent Inhibitors FIG. 1 is a schematic illustration of the mechanism of TEAD1 inhibition by the disclosed compounds, which is the theoretical basis for the development of a TEAD-YAP/TAZ cell-based functional assay to characterize the pharmacological properties of the synthesized inhibitor compounds. The MCF-7 cell-based TEAD1-Luc assay for the $IC_{50}$ measurement was performed as below. Compounds 2, 4, 5, and 7, representing different chemical scaffolds, were characterized. About 200 μL of culture medium was placed in each of the $10^4$ cell/well in a 96-well plate. The next day the cells were treated with the synthesized compounds for overnight. The luciferase activity was measured with a chemiluminescent assay kit. Specifically, the plate was equilibrated at room temperature. About 100 μL of the medium was discarded and 50 μL of the medium was left inside. To each well was added 50 μL Luciferase reagents. The plates were gently rocked for more than about 15 minutes at room temperature. The luminescence signal was then read and recorded. Table 2 below summarizes the measured $IC_{50}$ values for the disclosed compounds.

TABLE 2

The pharmacological data obtained from the TEAD1-Luciferase reporter assay.

| Compounds | $IC_{50}$ |
|---|---|
| Compound 1 | − |
| Compound 2 | + |
| Compound 3 | − |
| Compound 4 | ++ |
| Compound 5 | − |
| Compound 6 | − |
| Compound 7 | − |
| Compound 8 | − |
| Compound 9 | ++ |
| Compound 10 | ++ |
| Compound 11 | ++ |
| Compound 12 | ++ |
| Compound 13 | ++ |
| Compound 14 | ++ |
| Compound 15 | ++ |
| Compound 16 | ++ |
| Compound 17 | ++ |
| Compound 18 | ++ |
| Compound 19 | ++ |
| Compound 20 | ++ |
| Compound 21 | ++ |
| Compound 22 | ++ |
| Compound 23 | ++ |
| Compound 24 | ++ |
| Compound 25 | + |
| Compound 26 | ++ |
| Compound 27 | + |
| Compound 28 | ++ |
| Compound 29 | + |
| Compound 30 | + |
| Compound 31 | ++ |
| Compound 32 | ++ |
| Compound 33 | ++ |
| Compound 34 | ++ |
| Compound 35 | ++ |
| Compound 36 | ++ |
| Compound 37 | ++ |
| Compound 38 | ++ |
| Compound 39 | + |
| Compound 40 | ++ |
| Compound 41 | ++ |
| Compound 42 | + |
| Compound 43 | + |
| Compound 44 | + |
| Compound 45 | + |
| Compound 46 | + |
| Compound 47 | ++ |
| Compound 48 | ++ |
| Compound 49 | ++ |
| Compound 50 | + |
| Compound 51 | + |
| Compound 52 | ++ |
| Compound 53 | + |
| Compound 54 | ++ |
| Compound 55 | + |
| Compound 56 | + |
| Compound 57 | ++ |
| Compound 58 | ++ |
| Compound 59 | + |
| Compound 60 | + |
| Compound 61 | ++ |
| Compound 62 | ++ |
| Compound 63 | ++ |
| Compound 64 | − |
| Compound 65 | + |

Note:
++ ≤ 100 nM
+ 100 nM-5000 nM
− ≥ 5000 nM

Although the invention has been described with reference to the above examples, it will be understood that modifications and variations are encompassed within the spirit and scope of the invention. Accordingly, the invention is limited only by the following claims.

What is claimed is:

1. A compound according to Formula (I):

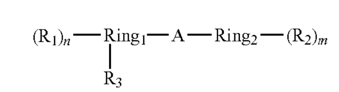

Formula (I)

or an optically pure stereoisomer, pharmaceutically acceptable salt, or solvate thereof, wherein $Ring_1$ is phenyl

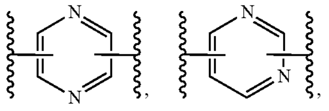

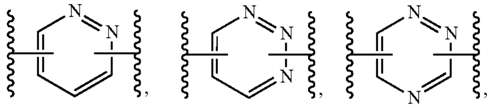

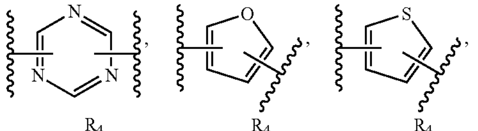

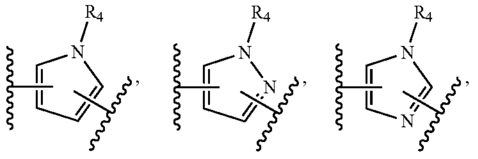

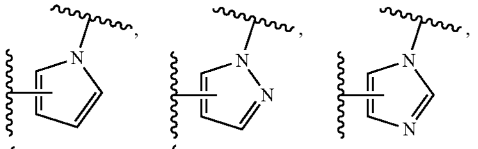

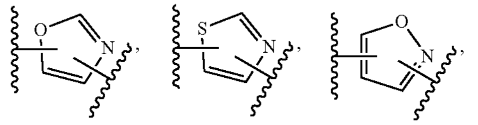

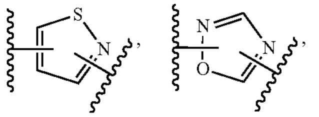

$Ring_2$ is selected from the group consisting of

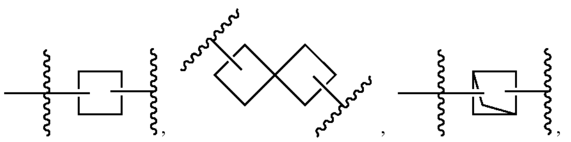

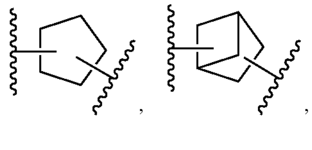

and

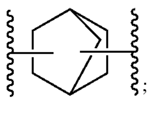

A is —O—$(CH_2)_p$—;
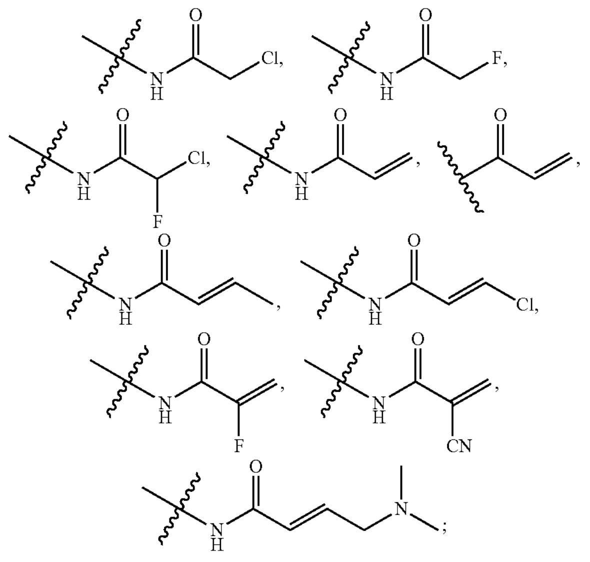
$R_2$ is $NHCOCH{=}CH_2$;
$R_3$ is $CF_3$;
n is 0;
m is 1; and
p is an integer selected from 0 to 3.
2. The compound of claim 1, selected from the group consisting of
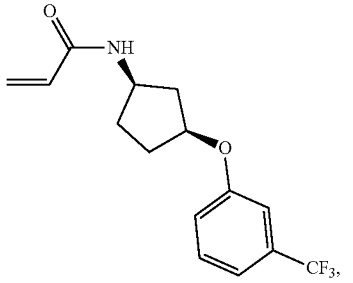
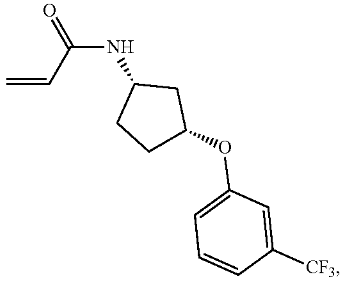
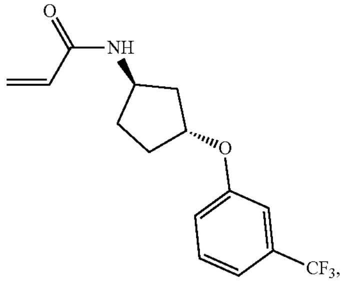
-continued
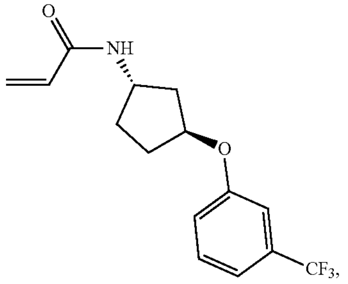
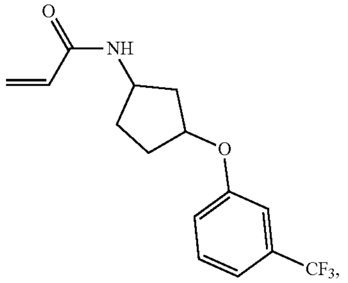
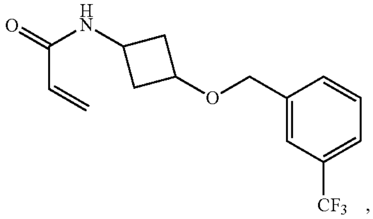
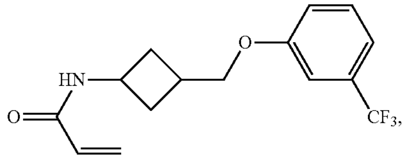
and
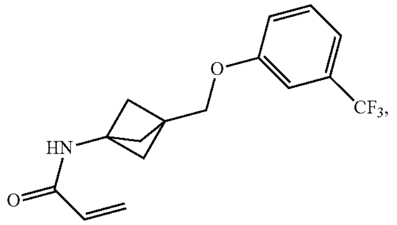
[[
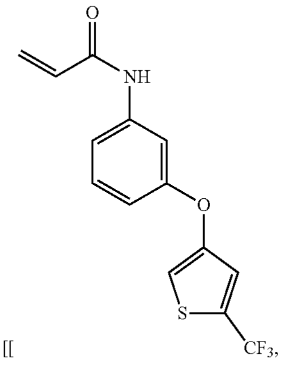

-continued
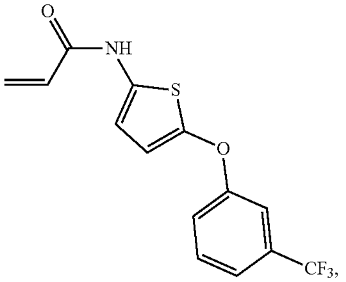
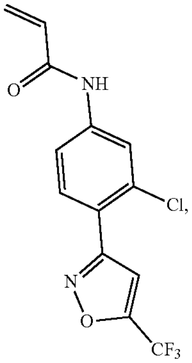
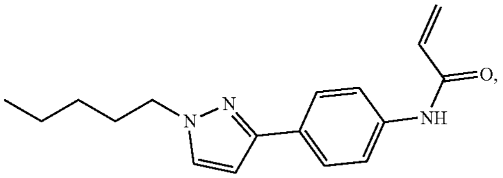
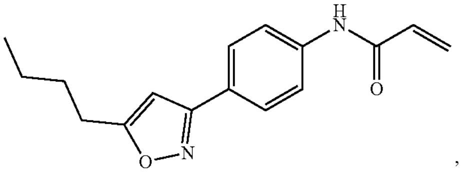
,
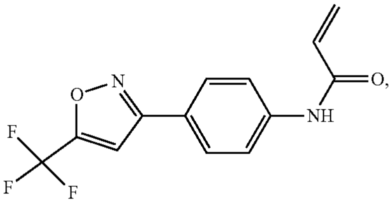
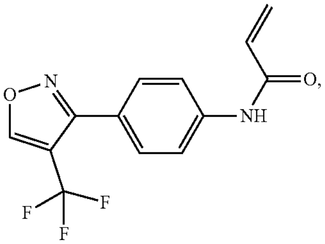
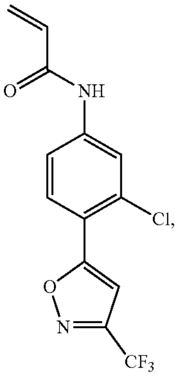
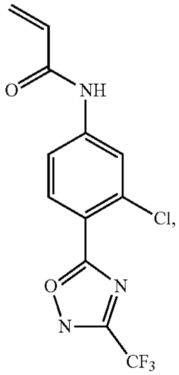
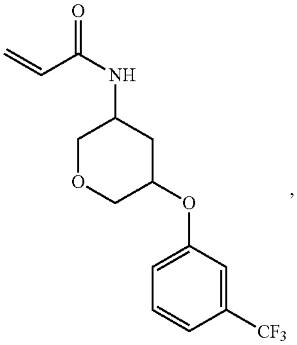
,
-continued
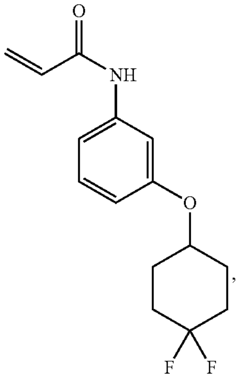
,
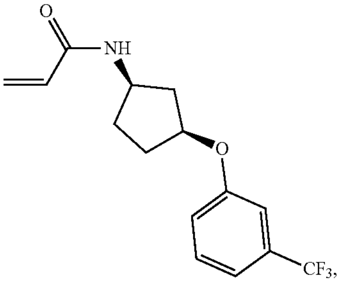
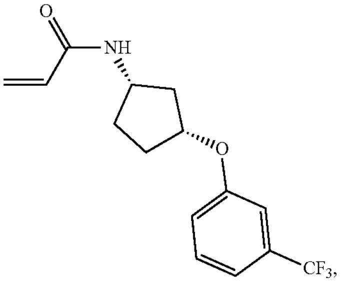
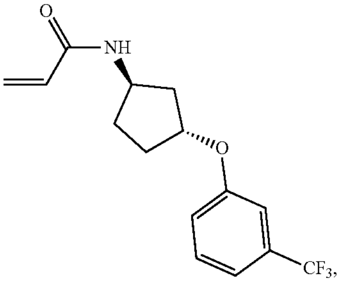
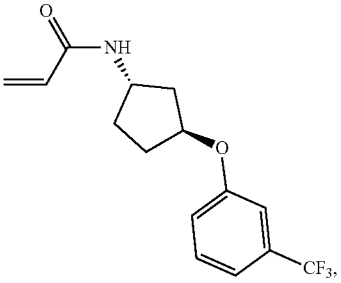

-continued

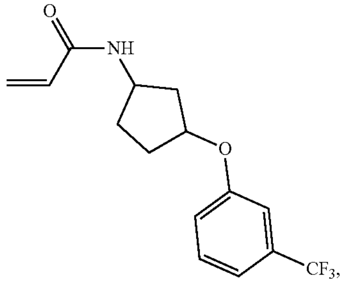

,

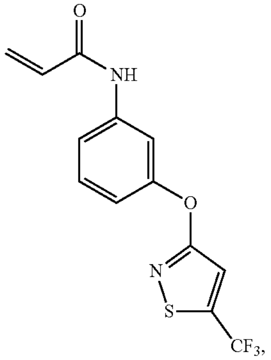

,

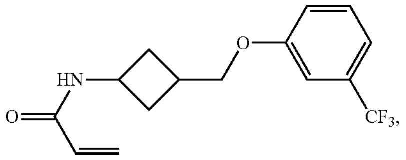

,

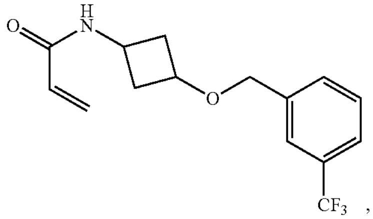

,

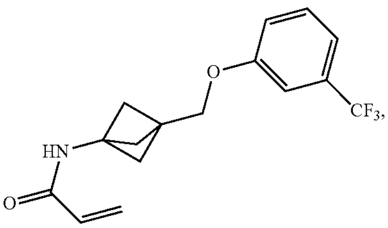

,

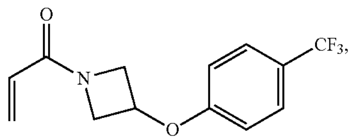

,

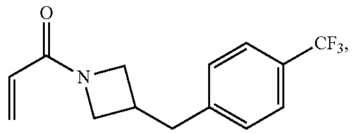

,

-continued

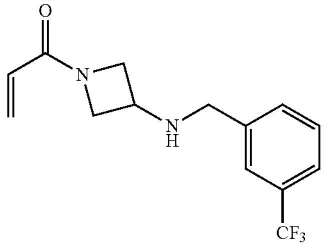

,

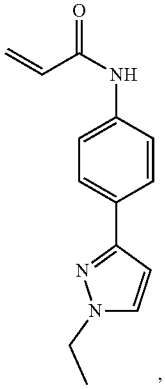

,

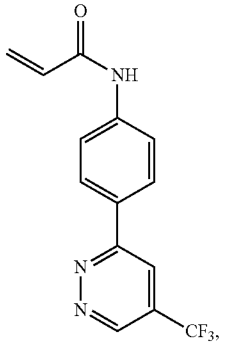

, and

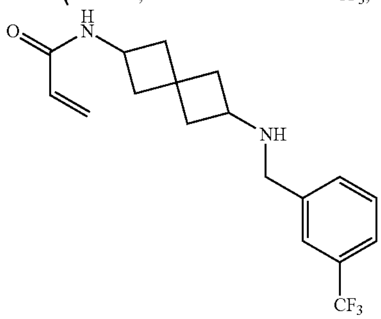

,]]

3. A pharmaceutical formulation, comprising the compound according to claim 1 and a pharmaceutically acceptable carrier.

4. A method of treating cancer in a subject, comprising administering to the subject an effective amount of the compound according to claim 1.

5. The method of claim 4, wherein the cancer is selected from the group consisting of bladder cancer, breast cancer, ovarian cancer, pancreatic ductal adenocarcinoma (PDAC), glioblastoma, gastric cancer, cervical cancer, colon cancer, endometrial cancer, head and neck cancer, lung cancer, melanoma, multiple myeloma, leukemia, non-hodgkin's lymphoma, prostate cancer, rectal cancer, malignant melanomas, alimentary/gastrointestinal tract cancer, liver cancer, skin cancer, lymphoma, malignant pleural mesothelioma (MPM), kidney cancer, muscle cancer, bone cancer, brain cancer, eye or ocular cancer, rectal cancer, colorectal cancer, cervical cancer, oral cancer, benign and malignant tumors, stomach cancer, corpus uteri, testicular cancer, renal cancer, throat cancer, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, neurofibromatosis, tuberous sclerosis, hemangiomas, and lymphangiogenesis.

6. The method of claim 4, wherein the cancer is selected from the group consisting of glioblastoma, gastric cancer, colorectal cancer, pancreatic ductal adenocarcinoma (PDAC), and malignant pleural mesothelioma (MPM).

7. The method of claim 4, further comprising administering a chemotherapeutic agent wherein the compound is administered prior to, simultaneously with, or following the administration of the chemotherapeutic agent.

8. The method of claim 4, wherein the compound is administered following resection of a tumor.

* * * * *